US012721905B2

(12) United States Patent
Mettetal, II et al.

(10) Patent No.: US 12,721,905 B2
(45) Date of Patent: Sep. 1, 2026

(54) COMBINATION OF ANTI-HER2 ANTIBODY-DRUG CONJUGATE AND PARP1 SELECTIVE INHIBITOR

(71) Applicants: AstraZeneca UK Limited, Cambridge (GB); Daiichi Sankyo Company, Limited, Tokyo (JP)

(72) Inventors: Jerome Thomas Mettetal, II, Wilmington, DE (US); Azadeh Cheraghchi Bashi Astaneh, Cambridge (GB); Elisabetta Leo, Cambridge (GB); Yann Wallez, Cambridge (GB)

(73) Assignees: AstraZeneca UK Limited, Cambridge (GB); Daiichi Sankyo Company, Limited, Tokyo (JP)

( * ) Notice: Subject to any disclaimer, the term of this patent is extended or adjusted under 35 U.S.C. 154(b) by 684 days.

(21) Appl. No.: 18/248,283

(22) PCT Filed: Oct. 8, 2021

(86) PCT No.: PCT/IB2021/059232
§ 371 (c)(1),
(2) Date: Apr. 7, 2023

(87) PCT Pub. No.: WO2022/074617
PCT Pub. Date: Apr. 14, 2022

(65) Prior Publication Data

US 2023/0372527 A1 Nov. 23, 2023

Related U.S. Application Data

(60) Provisional application No. 63/089,859, filed on Oct. 9, 2020.

(51) Int. Cl.
*A61K 47/68* (2017.01)
*A61K 31/4375* (2006.01)
*A61K 47/54* (2017.01)
*A61P 35/00* (2006.01)
*C07K 16/32* (2006.01)

(52) U.S. Cl.
CPC ...... *A61K 47/6889* (2017.08); *A61K 31/4375* (2013.01); *A61K 47/545* (2017.08); *A61P 35/00* (2018.01); *C07K 16/32* (2013.01)

(58) Field of Classification Search
CPC ............ A61K 47/6889; A61K 31/4375; A61K 47/545; A61K 47/68037; A61K 47/6855; A61P 35/00; C07K 16/32
See application file for complete search history.

(56) References Cited

U.S. PATENT DOCUMENTS

| | | | |
|---|---|---|---|
| 2010/0222348 A1 | 9/2010 | Angibaud et al. |
| 2016/0333112 A1 | 11/2016 | Naito et al. |
| 2017/0209594 A1 | 7/2017 | Goldenberg et al. |

(Continued)

FOREIGN PATENT DOCUMENTS

| | | | |
|---|---|---|---|
| TW | 202034959 A | 10/2020 |
| WO | WO-2020/022363 A1 | 1/2020 |

(Continued)

OTHER PUBLICATIONS

Anonymous https://en.wikipedia.org/wiki/List_of_cancer_types. May 22, 2020. (Year: 2020).*

(Continued)

*Primary Examiner* — Elly-Gerald Stoica
(74) *Attorney, Agent, or Firm* — Foley & Lardner LLP

(57) ABSTRACT

A pharmaceutical product for administration of an anti-HER2 antibody-drug conjugate in combination with a PARP1 selective inhibitor is provided. The anti-HER2 antibody drug conjugate is an antibody-drug conjugate in which a drug-linker represented by the following formula (wherein A represents the connecting position to an antibody) is conjugated to an anti-HER2 antibody via a thioether bond. Also provided is a therapeutic use and method wherein the antibody-drug conjugate and the PARP1 selective inhibitor are administered in combination to a subject: Formula (I).

(I)

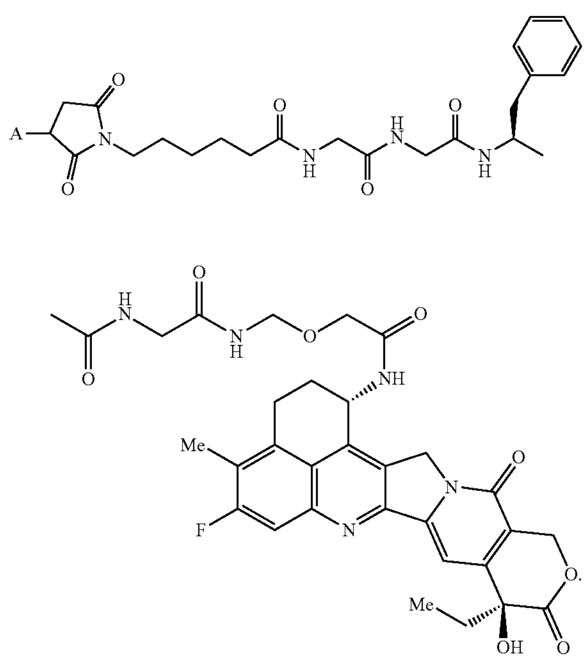

34 Claims, 17 Drawing Sheets

Specification includes a Sequence Listing.

(56) References Cited

U.S. PATENT DOCUMENTS

| | | | |
|---|---|---|---|
| 2017/0274093 A1 | 9/2017 | Goldenberg et al. |
| 2022/0023436 A1 | 1/2022 | Ogitani et al. |

FOREIGN PATENT DOCUMENTS

| | | |
|---|---|---|
| WO | WO-2020/031936 A1 | 2/2020 |
| WO | WO-2021/013735 A1 | 1/2021 |

OTHER PUBLICATIONS

Anonymous-https://www.cancer.gov/about-cancer/understanding/what-is-cancer. May 22, 2020. (Year: 2020).*

Garcia-Parra et al., Poly (ADP-ribose) polymerase inhibition enhances trastuzumab antitumor activity in HER2 overexpressing breast cancer. Eur. J. Cancer, 50, 2725-2734, 2014. (Year: 2014).*

Takegawa et al. ([fam-] trastuzumab deruxtecan, antitumor activity is dependent on HER2 expression level rather than on HER2 amplification. Int. J. Cancer. 145, 3414-3424, 2019. (Year: 2019).*

Nowsheen et al. (HER2 overexpression renders human breast cancers sensitive to PARP inhibition independently of any defect in homologous recombination DNA repair. Cancer Res. 72, 4796-4806, 2012. (Year: 2012).*

Non-Final Office Action issued in connection with U.S. Appl. No. 17/312,084 dated May 8, 2024.

Office Action issued in corresponding Taiwanese Patent Application No. 110137529 dated May 9, 2025.

International Search Report and Written Opinion issued in connection with PCT Appl. Ser. No. PCT/IB2021/059232 dated Dec. 23, 2021 (18 pages).

International Preliminary Report on Patentability issued in corresponding International Patent Application No. PCT/IB2021/059232, dated Mar. 28, 2023.

Office Action issued in corresponding Japanese Patent Application No. 2023-521678 dated Nov. 11, 2025.

Illuzzi et al.; "Preclinical characterization of AZD5305, a next generation, highly selective PARP1 inhibitor and trapper" Submitted Manuscript: Confidential, Template updated: Feb. 2021.

Office Action issued in corresponding Taiwanese Patent Application No. 110137529 received Nov. 20, 2025.

* cited by examiner

[Figure 1]

SEQ ID NO: 1 - Amino acid sequence of a heavy chain of anti-HER2 antibody

SEQ ID NO: 2 - Amino acid sequence of a light chain of anti-HER2 antibody

SEQ ID NO: 3 - Amino acid sequence of heavy chain CDRH1

SEQ ID NO: 4 - Amino acid sequence of heavy chain CDRH2

SEQ ID NO: 5 - Amino acid sequence of heavy chain CDRH3

SEQ ID NO: 6 - Amino acid sequence of light chain CDRL1

SEQ ID NO: 7 - Amino acid sequence comprising amino acid sequence of light chain CDRL2 (SAS)

SEQ ID NO: 8 - Amino acid sequence of light chain CDRL3

SEQ ID NO: 9 - Amino acid sequence of heavy chain variable region

SEQ ID NO: 10 - Amino acid sequence of light chain variable region

SEQ ID NO: 11 - Amino acid sequence of heavy chain

E V Q L V E S G G G L V Q P G G S L R L S C A A S G F N I K D T Y I H W V R
Q A P G K G L E W V A R I Y P T N G Y T R Y A D S V K G R F T I S A D T S K
N T A Y L Q M N S L R A E D T A V Y Y C S R W G G D G F Y A M D Y W G Q G T
L V T V S S A S T K G P S V F P L A P S S K S T S G G T A A L G C L V K D Y
F P E P V T V S W N S G A L T S G V H T F P A V L Q S S G L Y S L S S V V T
V P S S S L G T Q T Y I C N V N H K P S N T K V D K K V E P K S C D K T H T
C P P C P A P E L L G G P S V F L F P P K P K D T L M I S R T P E V T C V V
V D V S H E D P E V K F N W Y V D G V E V H N A K T K P R E E Q Y N S T Y R
V V S V L T V L H Q D W L N G K E Y K C K V S N K A L P A P I E K T I S K A
K G Q P R E P Q V Y T L P P S R E E M T K N Q V S L T C L V K G F Y P S D I
A V E W E S N G Q P E N N Y K T T P P V L D S D G S F F L Y S K L T V D K S
R W Q Q G N V F S C S V M H E A L H N H Y T Q K S L S L S P G

[Figure 12A]
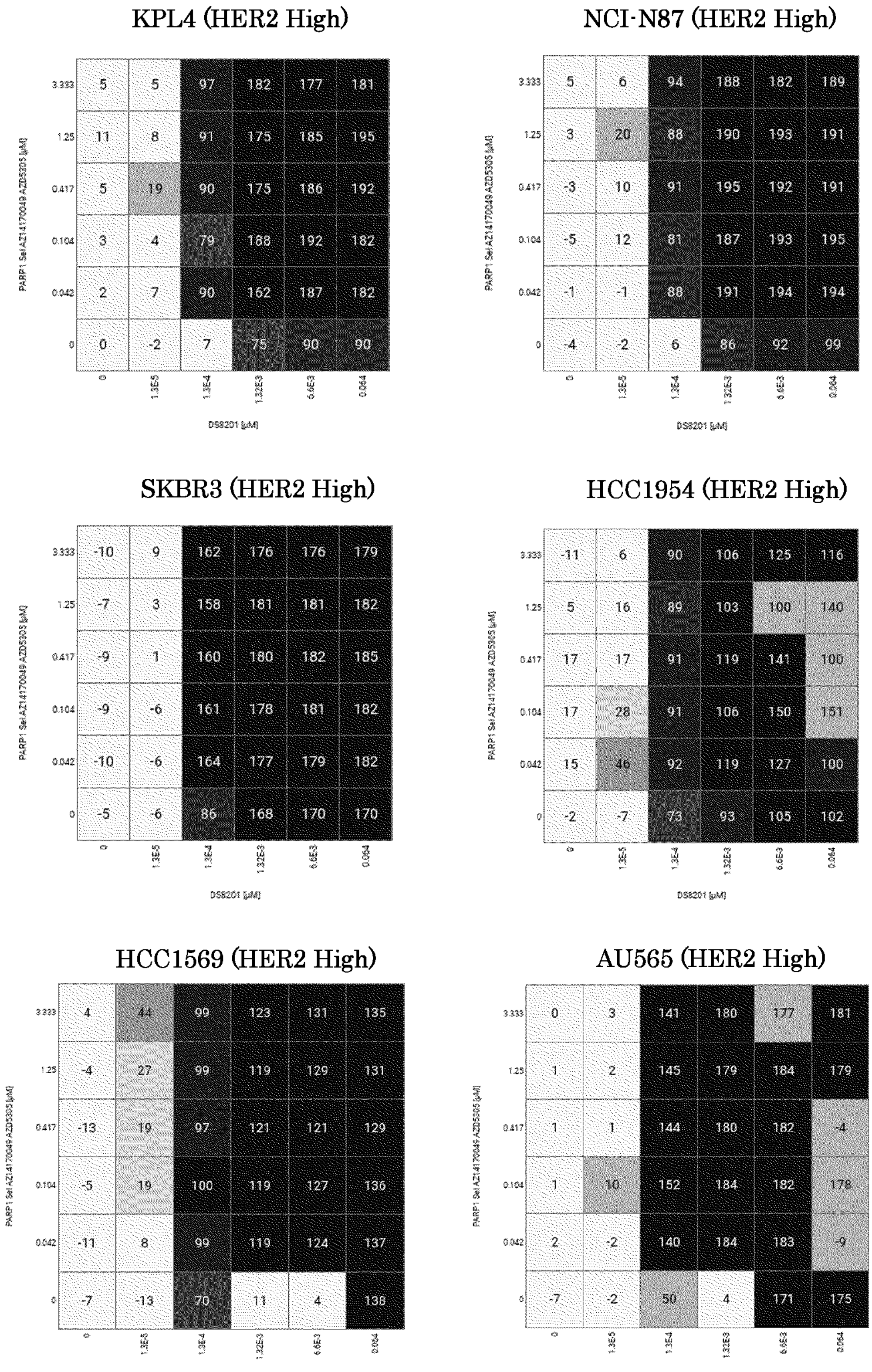

[Figure 12B]
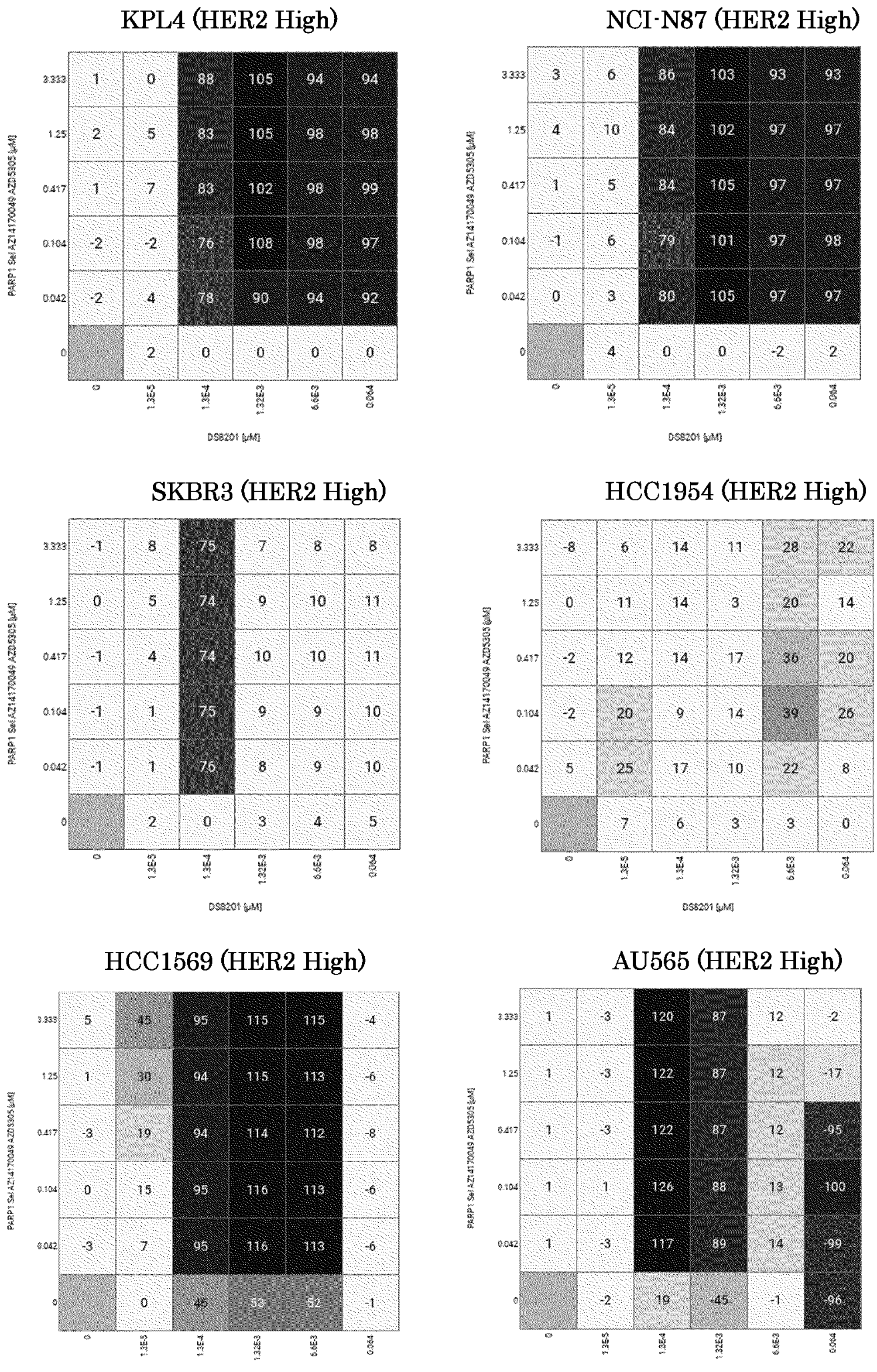

[Figure 13A]
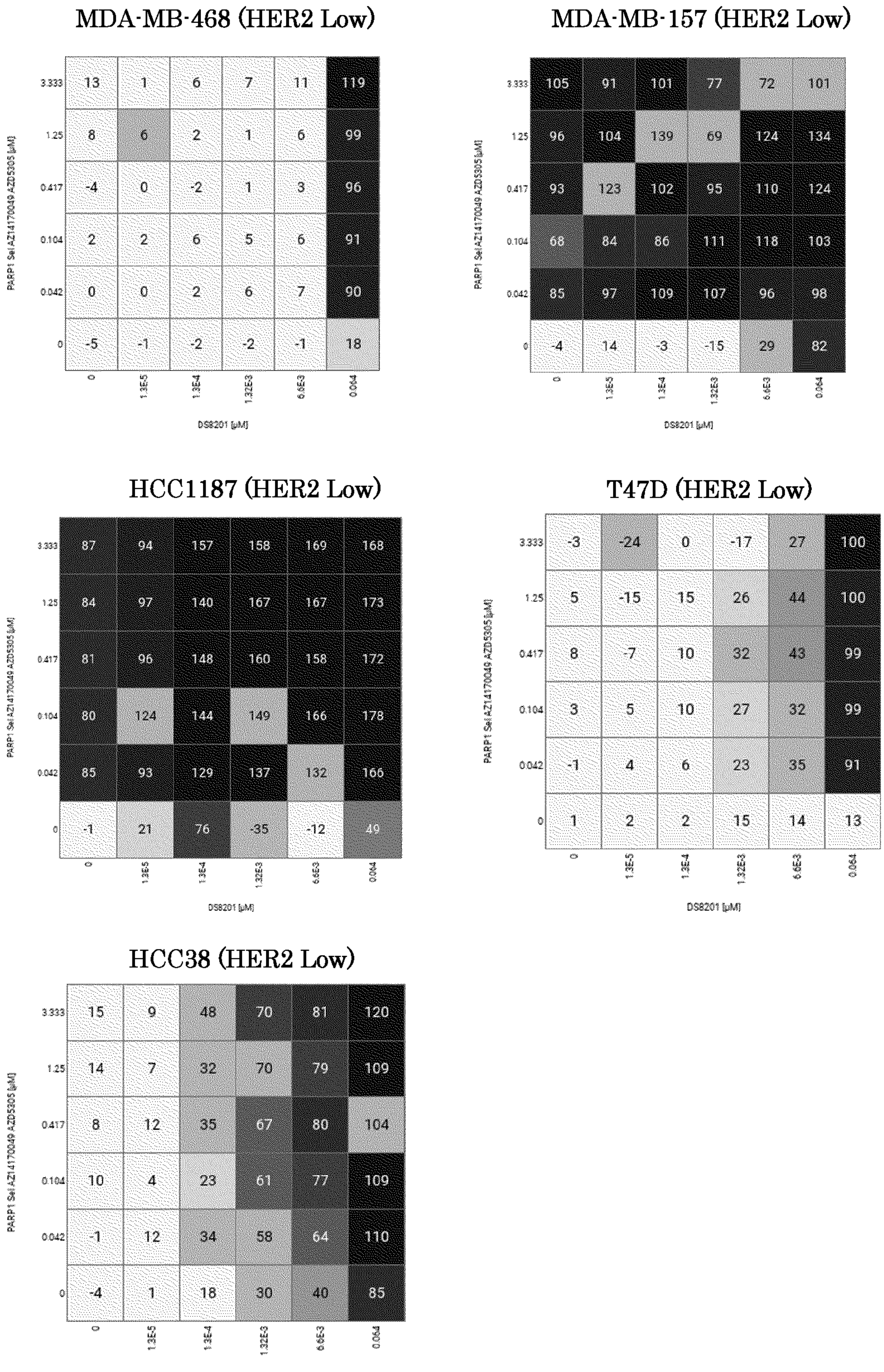

[Figure 13B]
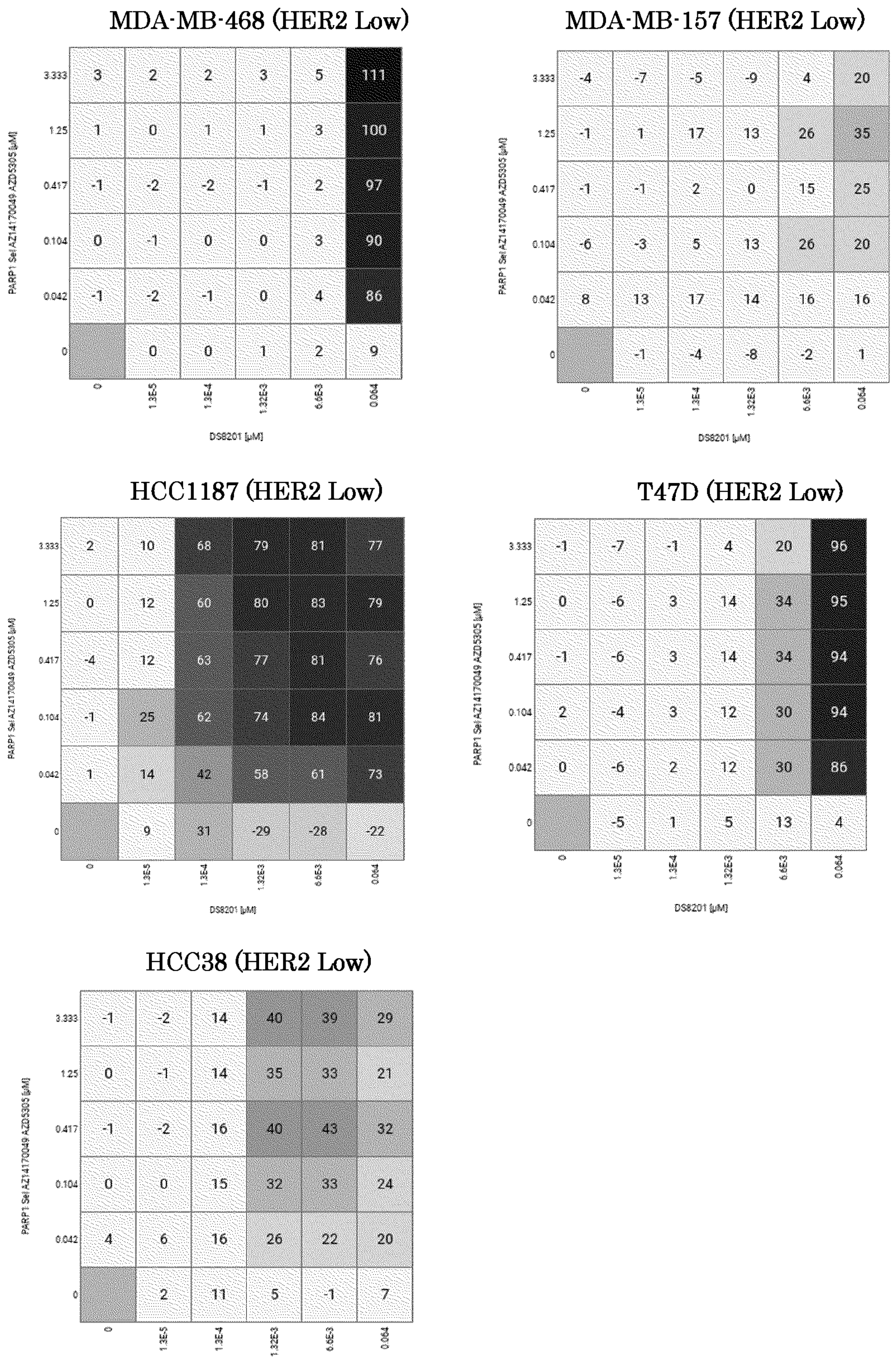

[Figure 14]
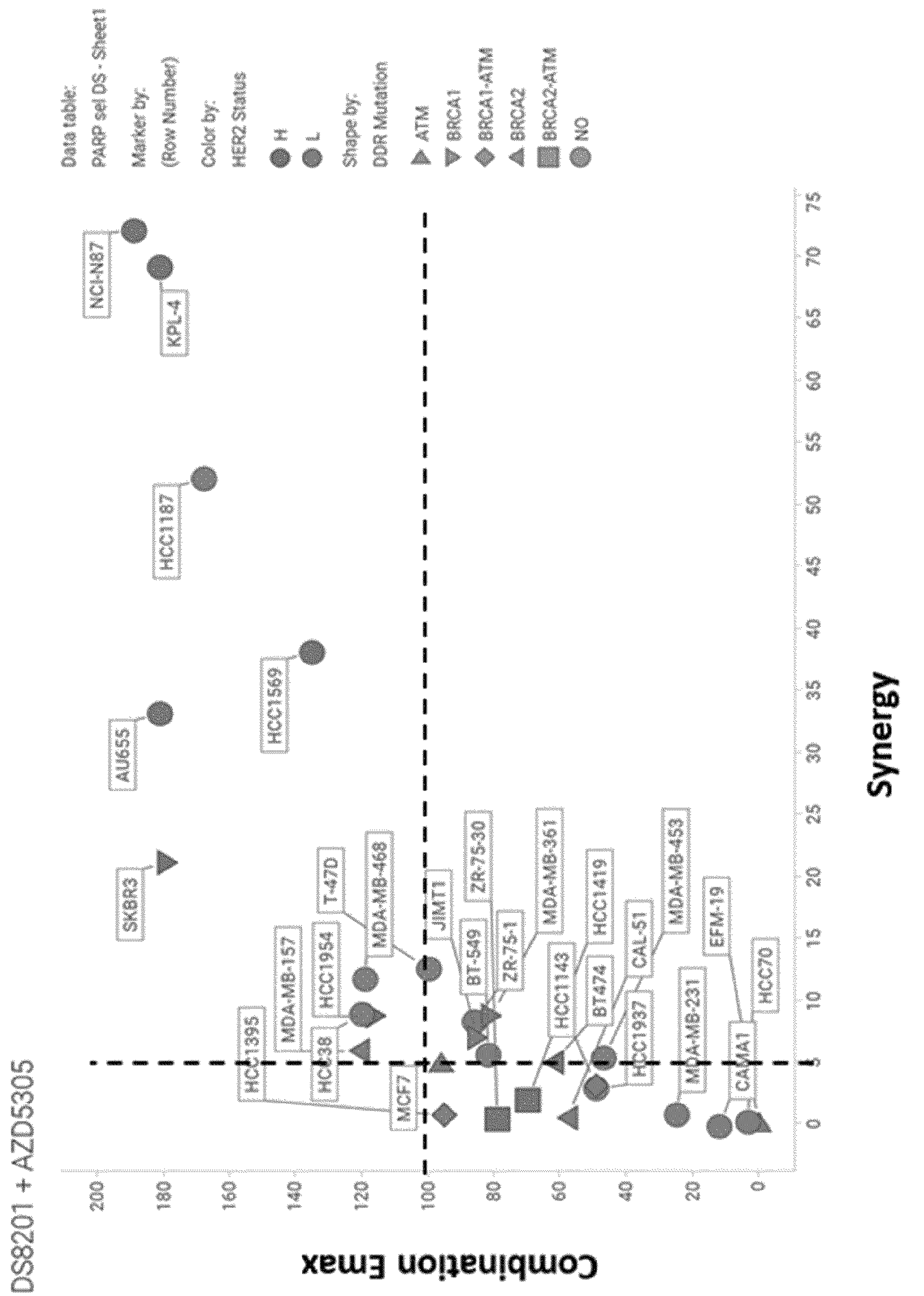

[Figure 15A]
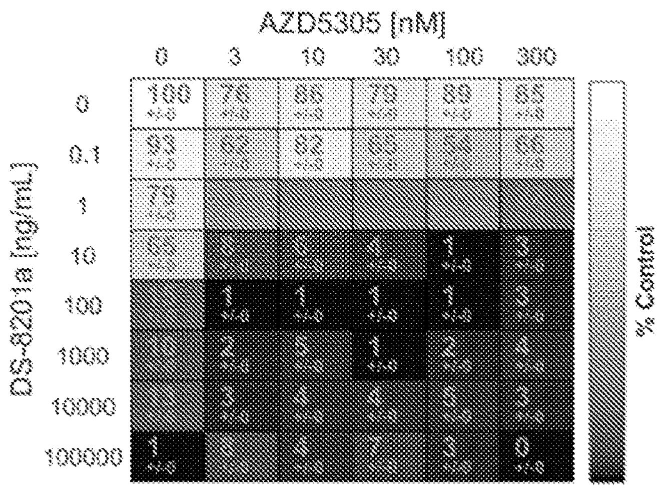
DS-8201a v AZD5305 in KPL4
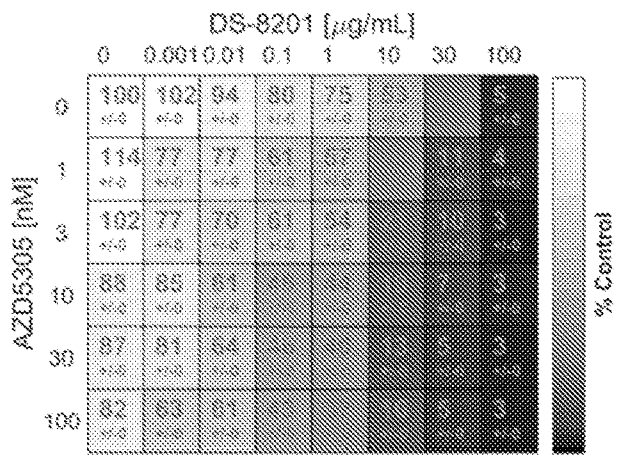
AZD5305 + DS-8201 in JIMT1 cells
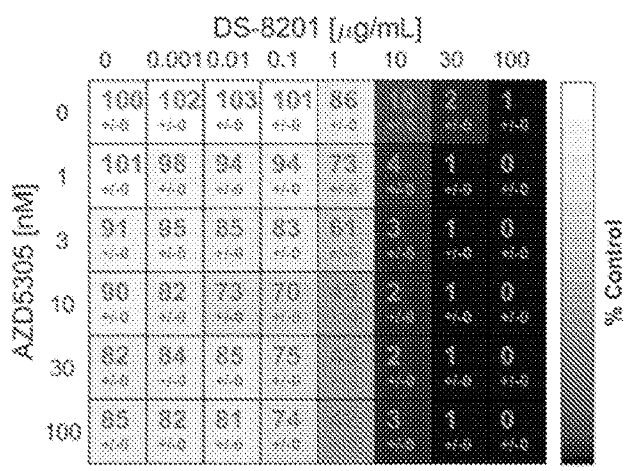
AZD5305 + DS-8201 in MDA-MB-468 cells

[Figure 15B]
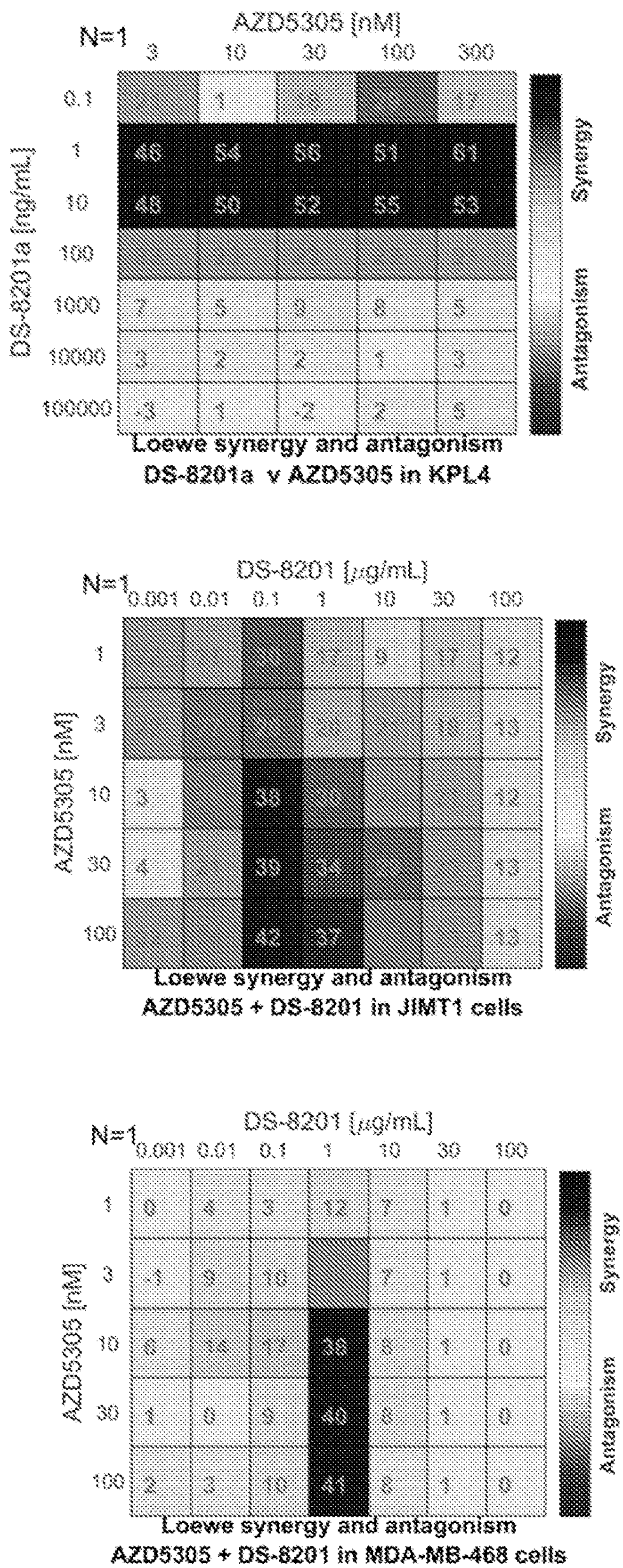

[Figure 16A]
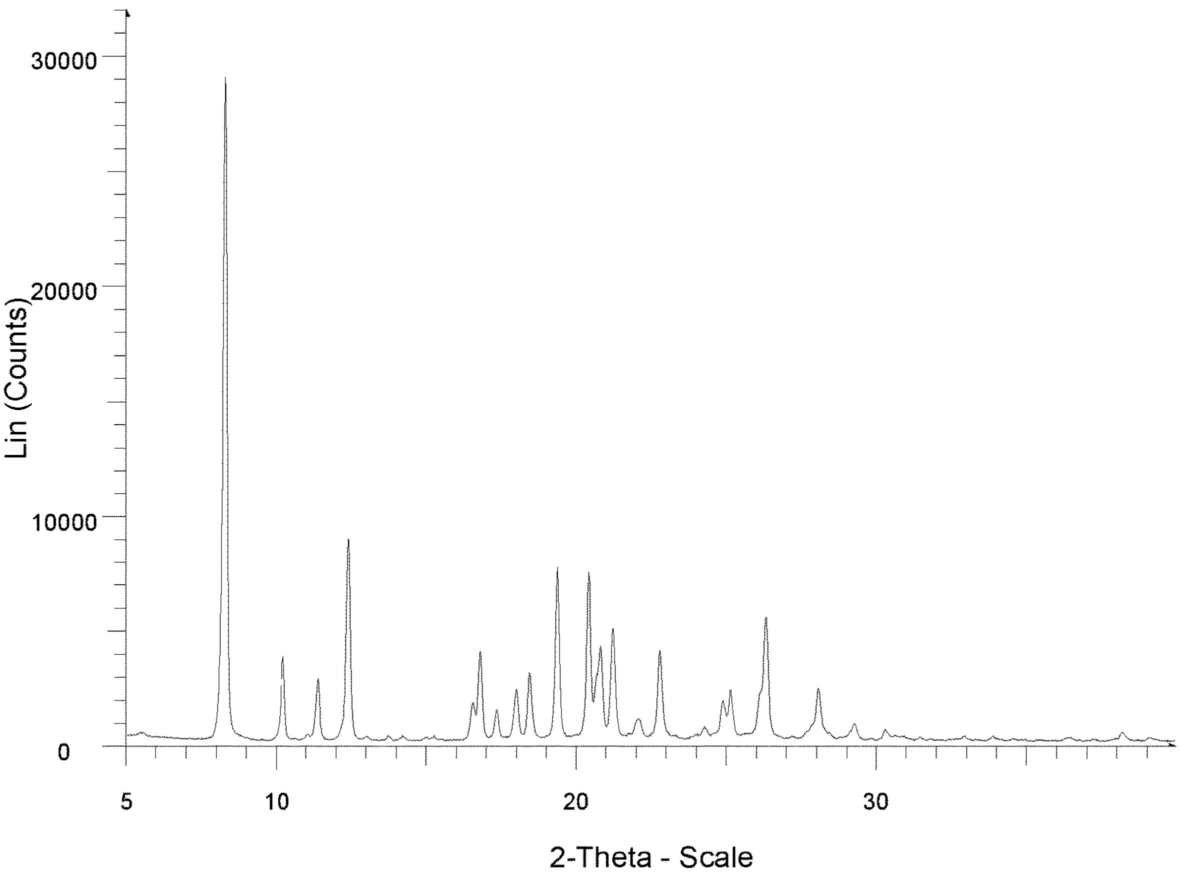

[Figure 16B]
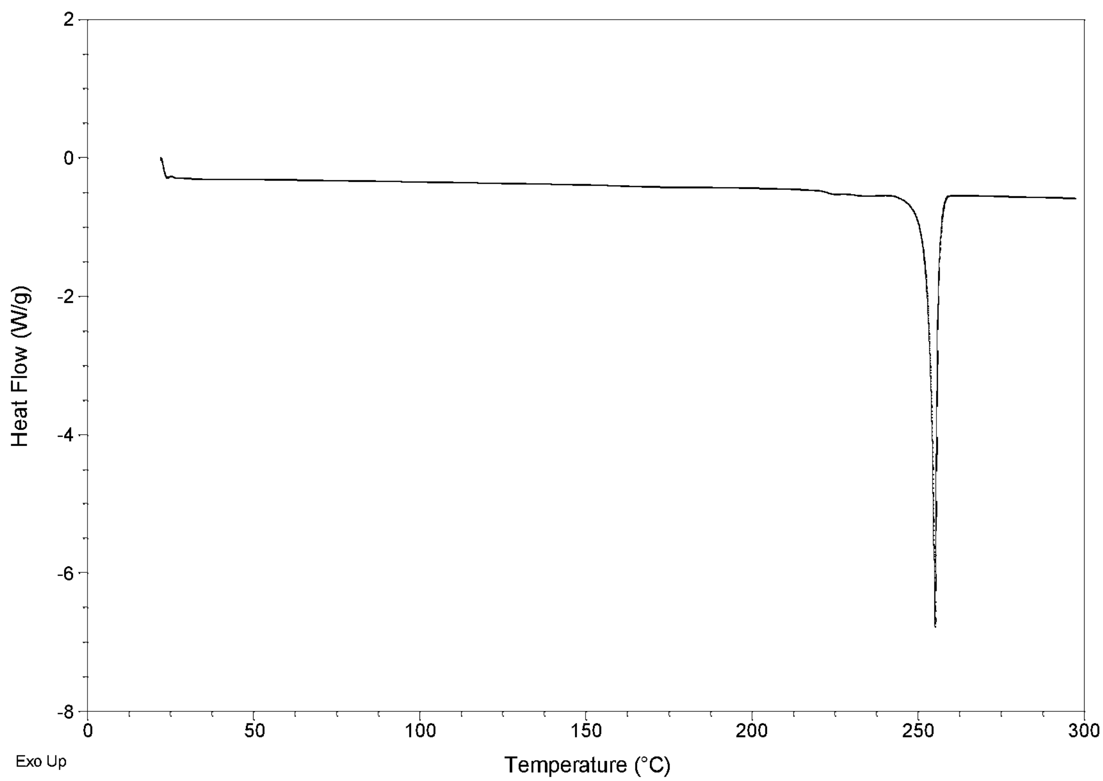

[Figure 17]
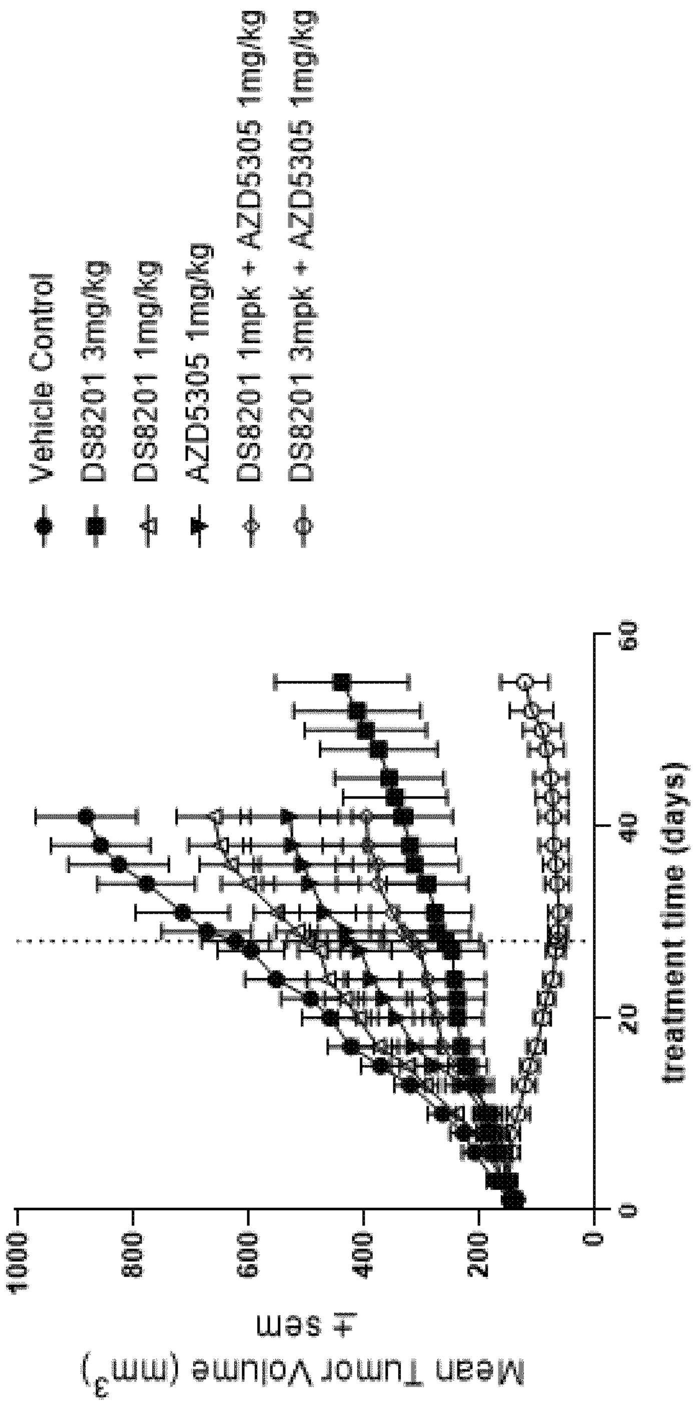

[Figure 18A]
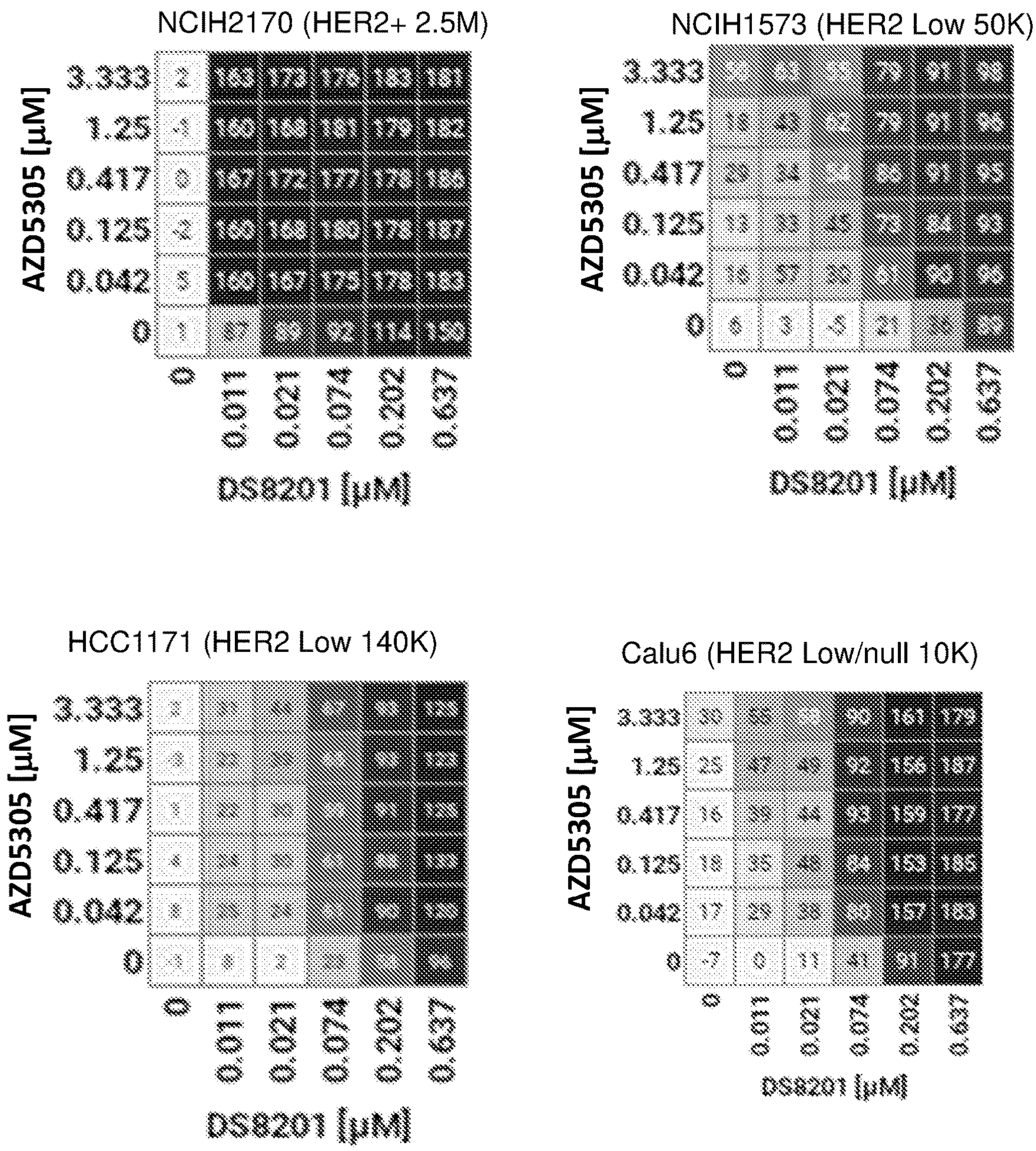

[Figure 18B]
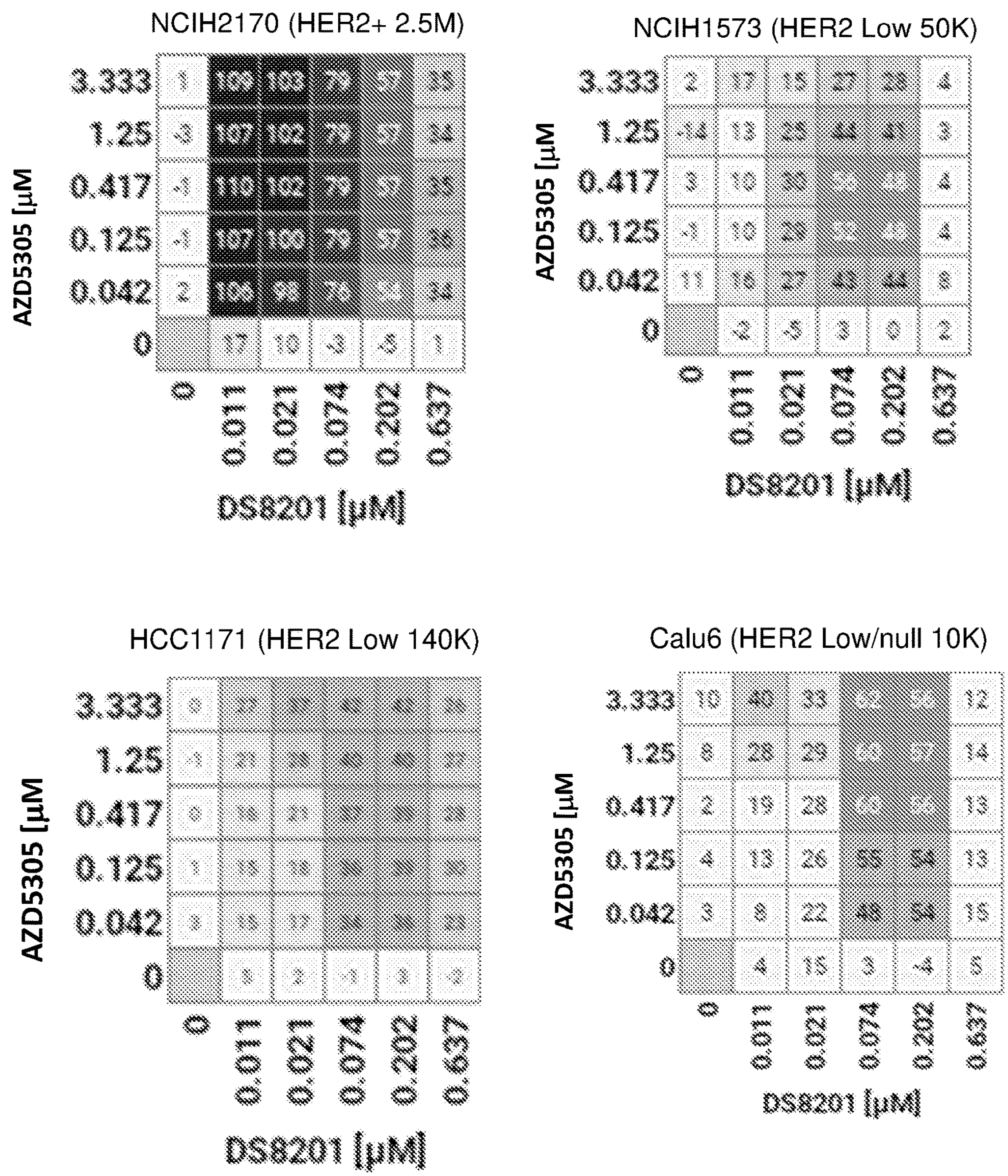

[Figure 18C]
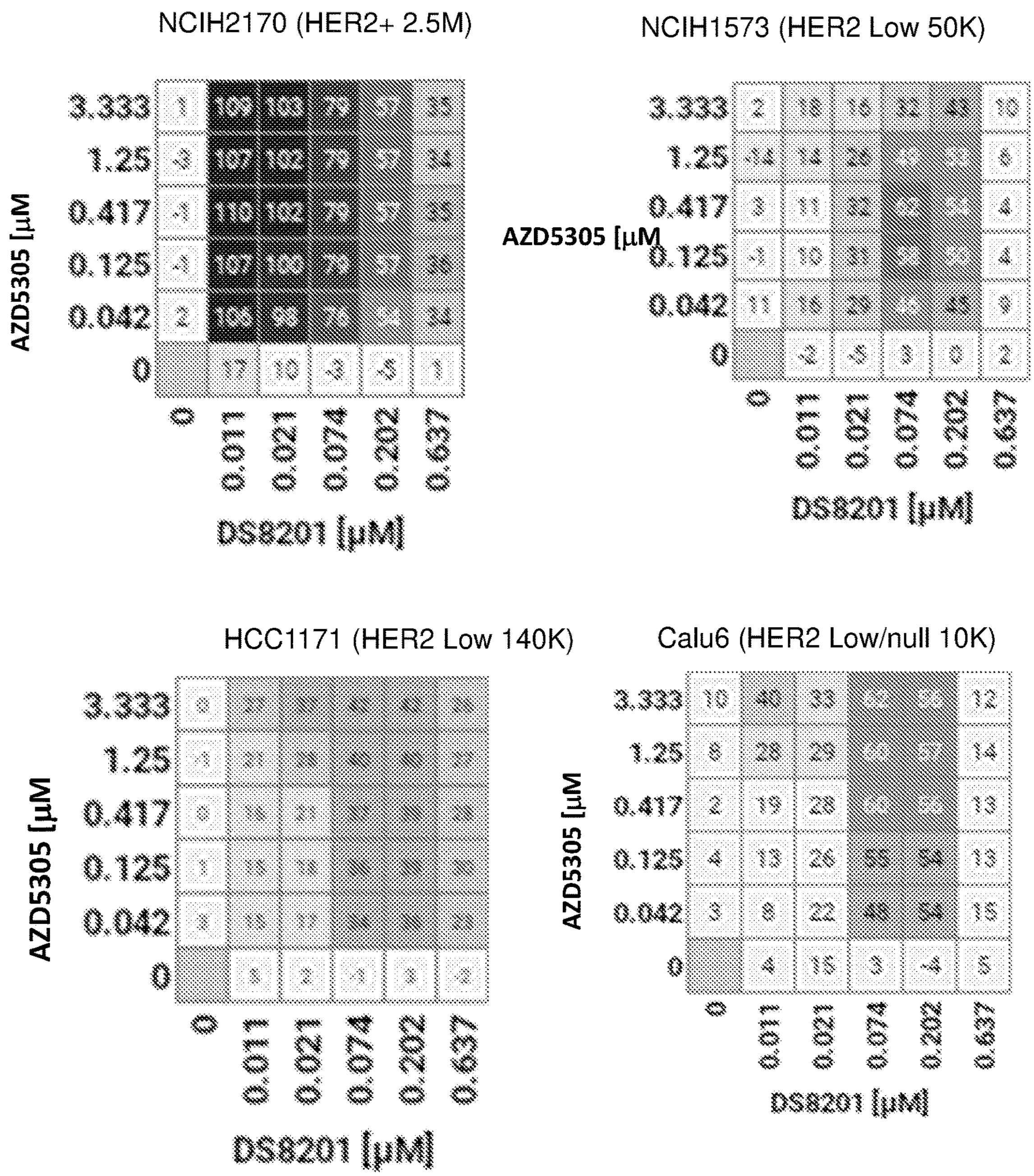

[Figure 19A]
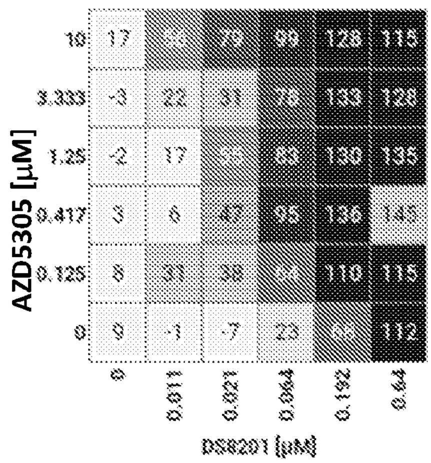
[Figure 19B]
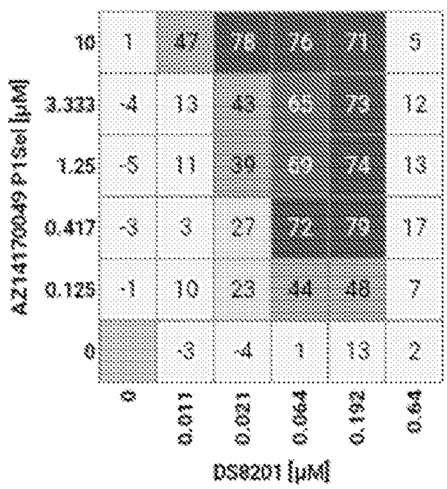
[Figure 19C]
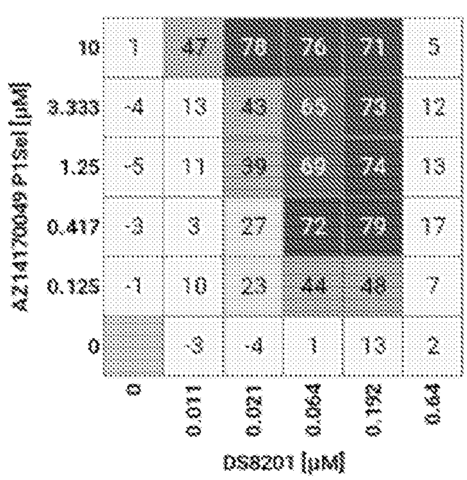

COMBINATION OF ANTI-HER2 ANTIBODY-DRUG CONJUGATE AND PARP1 SELECTIVE INHIBITOR

CROSS-REFERENCE TO RELATED APPLICATIONS

The present application claims priority under 35 U.S.C. § 371 to International Patent Application No. PCT/IB2021/059232, filed Oct. 8, 2021, which claims priority to and the benefit of U.S. Provisional Patent Application No. 63/089,859, filed on Oct. 9, 2020. The contents of these applications are hereby incorporated by reference in their entireties.

SEQUENCE LISTING

The instant application contains a Sequence Listing which has been submitted in ASCII format via EFS-Web and is hereby incorporated by reference in its entirety. This ASCII copy is named 122622-0161 SL.txt and is 14 kb in size.

TECHNICAL FIELD

The present disclosure relates to a pharmaceutical product for administration of a specific antibody-drug conjugate, having an antitumor drug conjugated to an anti-HER2 antibody via a linker structure, in combination with a PARP1 selective inhibitor, and to a therapeutic use and method wherein the specific antibody-drug conjugate and the PARP1 selective inhibitor are administered in combination to a subject.

BACKGROUND

The Poly (ADP-ribose) polymerase (PARP) family of enzymes plays an important role in a number of cellular processes, such as replication, recombination, chromatin remodeling, and DNA damage repair (O'Connor M J, *Mol Cell* (2015) 60(4):547-60). Examples of PARP inhibitors and their mechanism of action are taught in e.g. WO2004/080976.

PARP1 and PARP2 are the most extensively studied PARPs for their role in DNA damage repair. PARP1 is activated by DNA damage breaks and functions to catalyse the addition of poly (ADP-ribose) (PAR) chains to target proteins. This post-translational modification, known as PARylation, mediates the recruitment of additional DNA repair factors to DNA lesions. Following completion of this recruitment role, PARP auto-PARylation triggers the release of bound PARP from DNA to allow access to other DNA repair proteins to complete repair. Thus, the binding of PARP to damaged sites, its catalytic activity, and its eventual release from DNA are all important steps for a cancer cell to respond to DNA damage caused by chemotherapeutic agents and radiation therapy (Bai P. *Biology of poly(ADP-ribose) polymerases: the factotums of cell maintenance. Mol Cell* 2015; 58:947-58).

Inhibition of PARP family enzymes has been exploited as a strategy to selectively kill cancer cells by inactivating complementary DNA repair pathways. A number of pre-clinical and clinical studies have demonstrated that tumor cells bearing deleterious alterations of BRCA1 or BRCA2, key tumor suppressor proteins involved in double-strand DNA break (DSB) repair by homologous recombination (HR), are selectively sensitive to small molecule inhibitors of the PARP family of DNA repair enzymes. Such tumors have deficient homologous recombination repair (HRR) pathways and are dependent on PARP enzymes function for survival. Although PARP inhibitor therapy has predominantly targeted BRCA-mutated cancers, PARP inhibitors have been tested clinically in non-BRCA-mutant tumors, those which exhibit homologous recombination deficiency (HRD) (Turner N, Tutt A, Ashworth A. *Hallmarks of 'BRCAness' in sporadic cancers. Nat Rev Cancer* 2004; 4: 814-9).

It is believed that PARP inhibitors having improved selectivity for PARP1 may possess improved efficacy and reduced toxicity compared to non-selective PARP inhibitors. It is believed also that selective strong inhibition of PARP1 would lead to trapping of PARP1 on DNA, resulting in DNA double-strand breaks (DSBs) through collapse of replication forks in S-phase. It is believed also that PARP1-DNA trapping is an effective mechanism for selectively killing tumor cells having HRD.

Antibody-drug conjugates (ADCs) which are composed of a cytotoxic drug conjugated to an antibody, can deliver the drug selectively to cancer cells, and are therefore expected to cause accumulation of the drug within cancer cells and to kill the cancer cells (Ducry, L., et al., Bioconjugate Chem. (2010) 21, 5-13; Alley, S. C., et al., Current Opinion in Chemical Biology (2010) 14, 529-537; Damle N. K. Expert Opin. Biol. Ther. (2004) 4, 1445-1452; Senter P. D., et al., Nature Biotechnology (2012) 30, 631-637; Burris H A., et al., J. Clin. Oncol. (2011) 29(4): 398-405).

One such antibody-drug conjugate is trastuzumab deruxtecan, which is composed of a HER2-targeting antibody and a derivative of exatecan (Ogitani Y. et al., Clinical Cancer Research (2016) 22(20), 5097-5108; Ogitani Y. et al., Cancer Science (2016) 107, 1039-1046). Trastuzumab deruxtecan (Enhertu®, DS-8201) has shown significant clinical efficacy in HER2-expressing solid tumors, including breast cancer, gastric cancer, colorectal cancer and non-small cell lung cancer. Significantly, DS-8201 has demonstrated promising activity in HER2 low tumors in the above indications. There is a need to identify combination partners for DS-8201 to enhance efficacy, increase durability of therapeutic response, improve tolerance to patients and/or reduce dose-dependent toxicity.

Despite the therapeutic potential of antibody-drug conjugates such as trastuzumab deruxtecan, and of PARP1 inhibitors, no literature is published that describes a test result demonstrating an excellent effect of combined use of an antibody-drug conjugate and a PARP1 selective inhibitor.

Accordingly, a need remains for improved therapeutic compositions and methods, that can enhance efficacy of existing cancer treating agents, increase durability of therapeutic response, improve tolerance to patients and/or reduce dose-dependent toxicity.

SUMMARY OF DISCLOSURE

The antibody-drug conjugate used in the present disclosure (an anti-HER2 antibody-drug conjugate that includes a derivative of the topoisomerase I inhibitor exatecan, as a component) has been confirmed to exhibit an excellent antitumor effect in the treatment of certain cancers such as breast cancer and gastric cancer, when administered singly. Furthermore, a PARP1 inhibitor has been confirmed to exhibit an antitumor effect in the treatment of certain cancers. However, it is desired to provide a medicine and treatment which can obtain a superior antitumor effect in the treatment of cancers, such as enhanced efficacy, increased durability of therapeutic response and/or reduced dose-dependent toxicity.

The present disclosure provides a pharmaceutical product which can exhibit an excellent antitumor effect in the treatment of cancers, through administration of an anti-HER2 antibody-drug conjugate in combination with a PARP1 selective inhibitor. The present disclosure also provides a therapeutic use and method wherein the anti-HER2 antibody-drug conjugate and PARP1 selective inhibitor are administered in combination to a subject.

Specifically, the present disclosure relates to the following [1] to [54]:

[1] a pharmaceutical product comprising an anti-HER2 antibody-drug conjugate and a PARP1 selective inhibitor for administration in combination, wherein the anti-HER2 antibody-drug conjugate is an antibody-drug conjugate in which a drug-linker represented by the following formula:

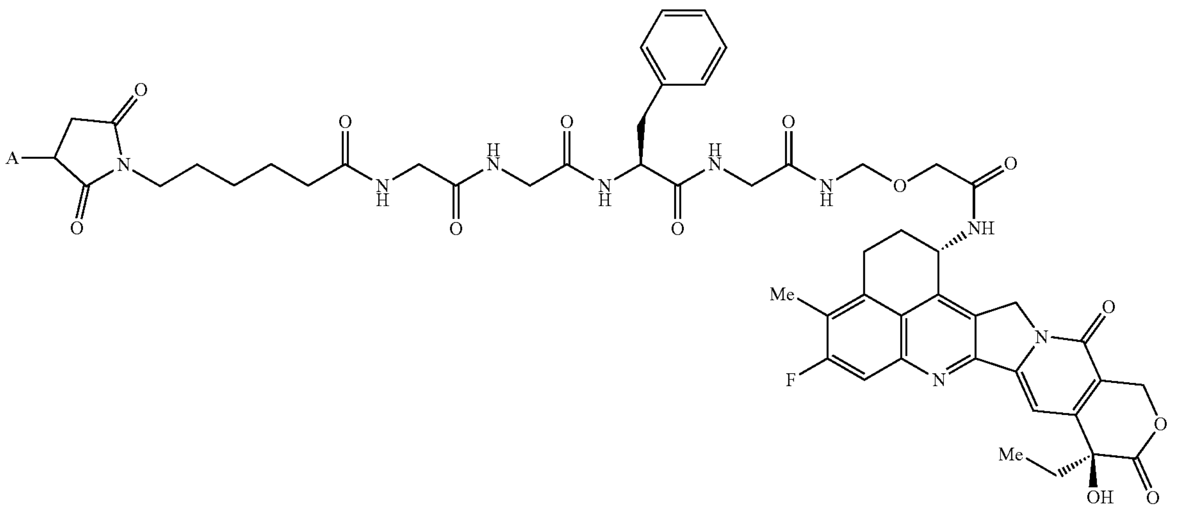

wherein A represents the connecting position to an antibody, is conjugated to an anti-HER2 antibody via a thioether bond;

[2] the pharmaceutical product according to [1], wherein the PARP1 selective is a compound represented by the following formula (I):

(I)

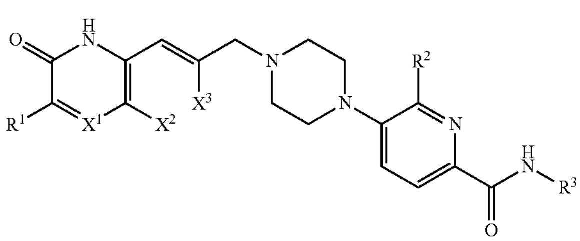

wherein:

$X^1$ and $X^2$ are each independently selected from N and C(H), $X^3$ is independently selected from N and C($R^4$), wherein $R^4$ is H or fluoro, $R^1$ is $C_{1-4}$ alkyl or $C_{1-4}$ fluoroalkyl, $R^2$ is independently selected from H, halo, $C_{1-4}$ alkyl, and $C_{1-4}$ fluoroalkyl, and $R^3$ is H or $C_{1-4}$ alkyl, or a pharmaceutically acceptable salt thereof provided that:

when $X^1$ is N, then $X^2$ is C(H), and $X^3$ is C($R^4$), when $X^2$ is N, then $X^1$=C(H), and $X^3$ is C($R^4$), and when $X^3$ is N, then $X^1$ and $X^2$ are both C(H);

[3] the pharmaceutical product according to [2] wherein, in formula (I), $R^3$ is $C_{1-4}$ alkyl;

[4] the pharmaceutical product according to [3] wherein, in formula (I), $R^3$ is methyl;

[5] the pharmaceutical product according to any one of [2] to [4] wherein, in formula (I), $R^1$ is ethyl;

[6] the pharmaceutical product according to [1], wherein the PARP1 selective inhibitor is a compound represented by the following formula (Ia):

(Ia)

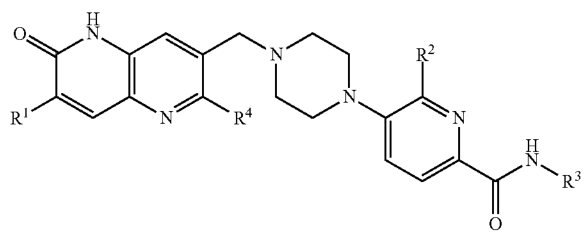

wherein $R^1$ is $C_{1-4}$ alkyl, $R^2$ is selected from H, halo, $C_{1-4}$ alkyl, and $C_{1-4}$ fluoroalkyl, $R^3$ is H or $C_{1-4}$ alkyl, and $R^4$ is H, or a pharmaceutically acceptable salt thereof;

[7] the pharmaceutical product according to [6] wherein, in formula (Ia), $R^2$ is H or halo;

[8] the pharmaceutical product according to [6] wherein in formula (Ia), $R^1$ is ethyl, $R^2$ is selected from H, chloro and fluoro, and $R^3$ is methyl;

[9] the pharmaceutical product according to [1], wherein the PARP1 selective inhibitor is AZD5305, also known as AZ14170049, represented by the following formula:

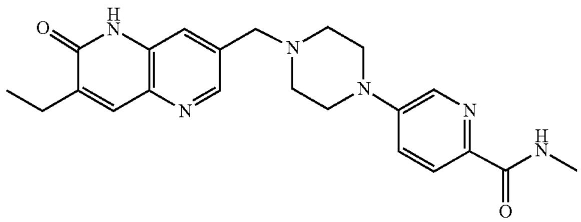 [SMILES: CCc1cc2ncc(CN3CCN(c4ccc(C(=O)NC)nc4)CC3)cc2[nH]c1=O]

or a pharmaceutically acceptable salt thereof;

a light chain consisting of an amino acid sequence represented by SEQ ID NO: 2;

[13] the pharmaceutical product according to any one of [1] to [9], wherein the anti-HER2 antibody is an antibody comprising a heavy chain consisting of an amino acid sequence represented by SEQ ID NO: 11 [=amino acid residues 1 to 449 of SEQ ID NO: 1] and a light chain consisting of an amino acid sequence represented by SEQ ID NO: 2;

[14] the pharmaceutical product according to any one of [1] to [13], wherein the anti-HER2 antibody-drug conjugate is represented by the following formula:

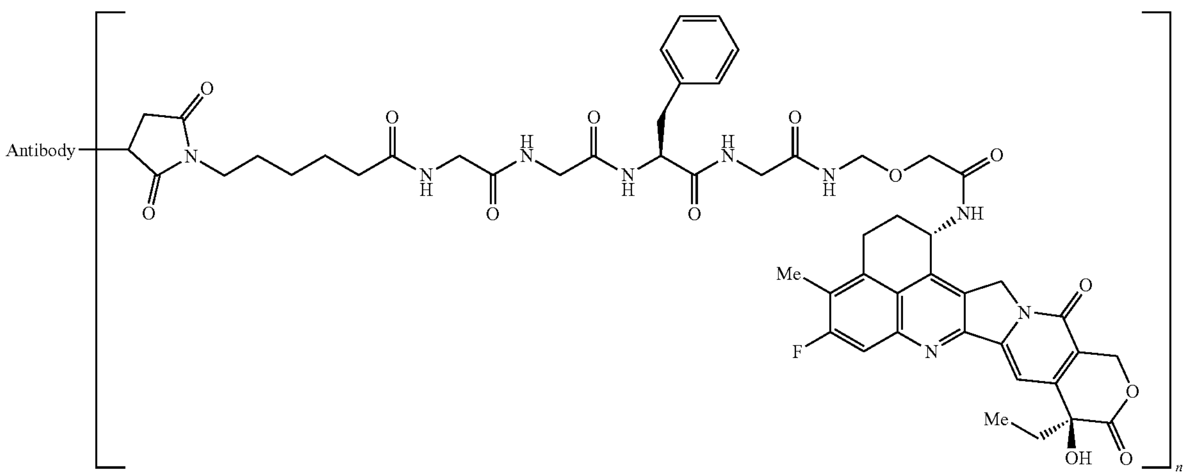

[10] the pharmaceutical product according to any one of [1] to [9], wherein the anti-HER2 antibody is an antibody comprising a heavy chain comprising CDRH1 consisting of an amino acid sequence represented by SEQ ID NO: 3 [=amino acid residues 26 to 33 of SEQ ID NO: 1], CDRH2 consisting of an amino acid sequence represented by SEQ ID NO: 4 [=amino acid residues 51 to 58 of SEQ ID NO: 1] and CDRH3 consisting of an amino acid sequence represented by SEQ ID NO: 5 [=amino acid residues 97 to 109 of SEQ ID NO: 1], and a light chain comprising CDRL1 consisting of an amino acid sequence represented by SEQ ID NO: 6 [=amino acid residues 27 to 32 of SEQ ID NO: 2], CDRL2 consisting of an amino acid sequence consisting of amino acid residues 1 to 3 of SEQ ID NO: 7 [=amino acid residues 50 to 52 of SEQ ID NO: 2] and CDRL3 consisting of an amino acid sequence represented by SEQ ID NO: 8 [=amino acid residues 89 to 97 of SEQ ID NO: 2];

[11] the pharmaceutical product according to any one of [1] to [9], wherein the anti-HER2 antibody is an antibody comprising a heavy chain comprising a heavy chain variable region consisting of an amino acid sequence represented by SEQ ID NO: 9 [=amino acid residues 1 to 120 of SEQ ID NO: 1] and a light chain comprising a light chain variable region consisting of an amino acid sequence represented by SEQ ID NO: 10 [=amino acid residues 1 to 107 of SEQ ID NO: 2];

[12] the pharmaceutical product according to any one of [1] to [9], wherein the anti-HER2 antibody is an antibody comprising a heavy chain consisting of an amino acid sequence represented by SEQ ID NO: 1 and wherein 'Antibody' indicates the anti-HER2 antibody conjugated to the drug-linker via a thioether bond, and n indicates an average number of units of the drug-linker conjugated per antibody molecule in the antibody-drug conjugate, wherein n is in the range of from 7 to 8;

[15] the pharmaceutical product according to any one of [1] to [14], wherein the anti-HER2 antibody-drug conjugate is trastuzumab deruxtecan (DS-8201);

[16] the pharmaceutical product according to any one of [1] to [15] wherein the product is a composition comprising the anti-HER2 antibody-drug conjugate and the PARP1 selective inhibitor, for simultaneous administration;

[17] the pharmaceutical product according to any one of [1] to [15] wherein the product is a combined preparation comprising the anti-HER2 antibody-drug conjugate and the PARP1 selective inhibitor, for sequential or simultaneous administration;

[18] the pharmaceutical product according to any one of [1] to [17], wherein the product is for treating cancer;

[19] the pharmaceutical product according to [18], wherein the cancer is at least one selected from the group consisting of breast cancer, gastric cancer, colorectal cancer, lung cancer, esophageal cancer, head-and-neck cancer, esophagogastric junction adenocarcinoma, biliary tract cancer, Paget's disease, pancreatic cancer, ovarian cancer, uterine carcinosarcoma, urothelial cancer, prostate cancer, bladder cancer, gastrointestinal stromal tumor, digestive tract stromal tumor, uterine cervix cancer, squamous cell carcinoma, peritoneal cancer, liver cancer, hepatocellular cancer, corpus uteri carcinoma, kidney cancer, vulval cancer, thyroid cancer, penis cancer, leukemia, malignant lymphoma, plasmacytoma, myeloma, glioblastoma multiforme, osteosarcoma, sarcoma, and melanoma;

[20] the pharmaceutical product according to [19], wherein the cancer is breast cancer;

[21] the pharmaceutical product according to [20], wherein the breast cancer has a HER2 status score of IHC 3+;

[22] the pharmaceutical product according to [20], wherein the breast cancer is HER2 low-expressing breast cancer;

[23] the pharmaceutical product according to [20], wherein the breast cancer has a HER2 status score of IHC 2+;

[24] the pharmaceutical product according to [20], wherein the breast cancer has a HER2 status score of IHC 1+;

[25] the pharmaceutical product according to [20], wherein the breast cancer has a HER2 status score of IHC>0 and <1+;

[26] the pharmaceutical product according to [20], wherein the breast cancer is triple-negative breast cancer;

[27] the pharmaceutical product according to [18], wherein the cancer is gastric cancer;

[28] the pharmaceutical product according to [18], wherein the cancer is colorectal cancer;

[29] the pharmaceutical product according to [18], wherein the cancer is lung cancer;

[30] the pharmaceutical product according to [29], wherein the lung cancer is non-small cell lung cancer;

[31] the pharmaceutical product according to [18], wherein the cancer is pancreatic cancer;

[32] the pharmaceutical product according to [18], wherein the cancer is ovarian cancer;

[33] the pharmaceutical product according to [18], wherein the cancer is prostate cancer;

[34] the pharmaceutical product according to [18], wherein the cancer is kidney cancer;

[35] a pharmaceutical product as defined in any one of [1] to [17], for use in treating cancer;

[36] the pharmaceutical product for the use according to [25], wherein the cancer is as defined in any one of [19] to [34];

[37] use of an anti-HER2 antibody-drug conjugate or a PARP1 selective inhibitor in the manufacture of a medicament for administration of the anti-HER2 antibody-drug conjugate and the PARP1 selective inhibitor in combination, wherein the anti-HER2 antibody-drug conjugate and the PARP1 selective inhibitor are as defined in any one of [1] to [15], for treating cancer;

[38] the use according to [37], wherein the cancer is as defined in any one of [19] to [34];

[39] the use according to [37] or [38] wherein the medicament is a composition comprising the anti-HER2 antibody-drug conjugate and the PARP1 selective inhibitor, for simultaneous administration;

[40] the use according to [37] or [38] wherein the medicament is a combined preparation comprising the anti-HER2 antibody-drug conjugate and the PARP1 selective inhibitor, for sequential or simultaneous administration;

[41] an anti-HER2 antibody-drug conjugate for use, in combination with a PARP1 selective inhibitor, in the treatment of cancer, wherein the anti-HER2 antibody-drug conjugate and the PARP1 selective inhibitor are as defined in any one of [1] to [15];

[42] the anti-HER2 antibody-drug conjugate for the use according to [41], wherein the cancer is as defined in any one of [19] to [34];

[43] the anti-HER2 antibody-drug conjugate for the use according to [41] or [42], wherein the use comprises administration of the anti-HER2 antibody-drug conjugate and the PARP1 selective inhibitor sequentially;

[44] the anti-HER2 antibody-drug conjugate for the use according to [41] or [42], wherein the use comprises administration of the anti-HER2 antibody-drug conjugate and the PARP1 selective inhibitor simultaneously;

[45] An anti-HER2 antibody-drug conjugate for use in the treatment of cancer in a subject, wherein said treatment comprises the separate, sequential or simultaneous administration of i) said anti-HER2 antibody-drug conjugate, and ii) a PARP1 selective inhibitor to said subject, wherein said anti-HER2 antibody-drug conjugate and said PARP1 selective inhibitor are as defined in any one of [1] to [15];

[46] a PARP1 selective inhibitor for use, in combination with an anti-HER2 antibody-drug conjugate, in the treatment of cancer, wherein the anti-HER2 antibody-drug conjugate and the PARP1 selective inhibitor are as defined in any one of [1] to [15];

[47] the PARP1 selective inhibitor for the use according to [46], wherein the cancer is as defined in any one of [19] to [34];

[48] the PARP1 selective inhibitor for the use according to [46] or [47], wherein the use comprises administration of the anti-HER2 antibody-drug conjugate and the PARP1 selective inhibitor sequentially;

[49] the PARP1 selective inhibitor for the use according to [46] or [47], wherein the use comprises administration of the anti-HER2 antibody-drug conjugate and the PARP1 selective inhibitor simultaneously;

[50] A PARP1 selective inhibitor for use in the treatment of cancer in a subject, wherein said treatment comprises the separate, sequential or simultaneous administration of i) said PARP1 selective inhibitor, and ii) an anti-HER2 antibody-drug conjugate to said subject, wherein said PARP1 selective inhibitor and said anti-HER2 antibody-drug conjugate are as defined in any one of [1] to [15];

[51] a method of treating cancer comprising administering an anti-HER2 antibody-drug conjugate and a PARP1 selective inhibitor as defined in any one of [1] to [15] in combination to a subject in need thereof;

[52] the method according to [51], wherein the cancer is as defined in any one of [19] to [34];

[53] the method according to [51] or [52], wherein the method comprises administering the anti-HER2 antibody-drug conjugate and the PARP1 selective inhibitor sequentially; and

[54] the method according to [51] or [52], wherein the method comprises administering the anti-HER2 antibody-drug conjugate and the PARP1 selective inhibitor simultaneously.

Advantageous Effects of Disclosure

The present disclosure provides a pharmaceutical product wherein an anti-HER2 antibody-drug conjugate, having an antitumor drug conjugated to an anti-HER2 antibody via a linker structure, and a PARP1 selective inhibitor are administered in combination, and a therapeutic use and method wherein the specific antibody-drug conjugate and the PARP1 selective inhibitor are administered in combination to a subject. Thus, the present disclosure can provide a medicine and treatment which can obtain a superior antitumor effect in the treatment of cancers.

BRIEF DESCRIPTION OF DRAWINGS

FIG. 1 is a diagram showing the amino acid sequence of a heavy chain of an anti-HER2 antibody (SEQ ID NO: 1).

FIG. 2 is a diagram showing the amino acid sequence of a light chain of an anti-HER2 antibody (SEQ ID NO: 2).

FIG. 3 is a diagram showing the amino acid sequence of a heavy chain CDRH1 (SEQ ID NO: 3 [=amino acid residues 26 to 33 of SEQ ID NO: 1]).

FIG. 4 is a diagram showing the amino acid sequence of a heavy chain CDRH2 (SEQ ID NO: 4 [=amino acid residues 51 to 58 of SEQ ID NO: 1]).

FIG. 5 is a diagram showing the amino acid sequence of a heavy chain CDRH3 (SEQ ID NO: 5 [=amino acid residues 97 to 109 of SEQ ID NO: 1]).

FIG. 6 is a diagram showing the amino acid sequence of a light chain CDRL1 (SEQ ID NO: 6 [=amino acid residues 27 to 32 of SEQ ID NO: 2]).

FIG. 7 is a diagram showing an amino acid sequence comprising the amino acid sequence of a light chain CDRL2 (SAS) (SEQ ID NO: 7 [=amino acid residues 50 to 56 of SEQ ID NO: 2]).

FIG. 8 is a diagram showing the amino acid sequence of a light chain CDRL3 (SEQ ID NO: 8 [=amino acid residues 89 to 97 of SEQ ID NO: 2]).

FIG. 9 is a diagram showing the amino acid sequence of a heavy chain variable region (SEQ ID NO: 9 [=amino acid residues 1 to 120 of SEQ ID NO: 1]).

FIG. 10 is a diagram showing the amino acid sequence of a light chain variable region (SEQ ID NO: 10 [=amino acid residues 1 to 107 of SEQ ID NO: 2]).

FIG. 11 is a diagram showing the amino acid sequence of a heavy chain (SEQ ID NO: 11 [=amino acid residues 1 to 449 of SEQ ID NO: 1]).

FIGS. 12A and 12B are diagrams showing combination matrices obtained with high-throughput screens combining DS-8201 with AZD5305 (AZ14170049; PARP1 selective inhibitor) in cell lines with high HER2 expression.

FIGS. 13A and 13B are diagrams showing combination matrices obtained with high-throughput screens combining DS-8201 with AZD5305 in cell lines with low HER2 expression.

FIG. 14 is a diagram showing combination Emax and Loewe synergy scores in cell lines treated with DS-8201 combined with AZD5305.

FIGS. 15A and 15B are diagrams showing combination matrices for combining DS-8201 with AZD5305 in cell lines with low or high HER2 expression.

FIGS. 16A and 16B show respectively an X-ray diffraction pattern and a representative DSC trace, of Synthesis Example 4 Form A.

FIG. 17 is a graph showing tumour volumes for in vivo treatments with DS-8201 or AZD5305 alone or with DS-8201 in combination with AZD5305. The dotted line represents the end of the AZD5305 dosing period.

FIGS. 18A, 18B and 18C are diagrams showing combination matrices obtained with high-throughput screens combining DS-8201 with AZD5305 in NSCLC cell lines with low or high HER2 expression.

FIGS. 19A, 19B and 19C are diagrams showing combination matrices obtained with high-throughput screens combining DS-8201 with AZD5305 in a urinary tract cancer cell line with HER2-mutant expression.

In order that the present disclosure can be more readily understood, certain terms are first defined. Additional definitions are set forth throughout the detailed description.

Before describing the present disclosure in detail, it is to be understood that this disclosure is not limited to specific compositions or method steps, as such can vary. As used in this specification and the appended claims, the singular forms “a”, “an” and “the” include plural referents unless the context clearly dictates otherwise. The terms “a” (or “an”), as well as the terms “one or more,” and “at least one” can be used interchangeably herein.

Furthermore, “and/or” where used herein is to be taken as specific disclosure of each of the two specified features or components with or without the other. Thus, the term “and/or” as used in a phrase such as “A and/or B” herein is intended to include “A and B,” “A or B,” “A” (alone), and “B” (alone). Likewise, the term “and/or” as used in a phrase such as “A, B, and/or C” is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range.

It is understood that wherever aspects are described herein with the language “comprising”, otherwise analogous aspects described in terms of “consisting of” and/or “consisting essentially of” are also provided.

The terms “inhibit”, “block”, and “suppress” are used interchangeably herein and refer to any statistically significant decrease in biological activity, including full blocking of the activity. For example, “inhibition” can refer to a decrease of about 10%, 20%, 30%, 40%, 50%, 60%, 70%, 80%, 90% or 100% in biological activity. Cellular proliferation can be assayed using art recognized techniques which measure rate of cell division, and/or the fraction of cells within a cell population undergoing cell division, and/or rate of cell loss from a cell population due to terminal differentiation or cell death (e.g., thymidine incorporation).

The term “subject” refers to any animal (e.g., a mammal), including, but not limited to humans, non-human primates, rodents, and the like, which is to be the recipient of a particular treatment. Typically, the terms “subject” and “patient” are used interchangeably herein in reference to a human subject.

The term “pharmaceutical product” refers to a preparation which is in such form as to permit the biological activity of the active ingredients, either as a composition containing all the active ingredients (for simultaneous administration), or as a combination of separate compositions (a combined preparation) each containing at least one but not all of the active ingredients (for administration sequentially or simultaneously), and which contains no additional components which are unacceptably toxic to a subject to which the product would be administered. Such product can be sterile. By “simultaneous administration” is meant that the active ingredients are administered at the same time. By "sequential administration" is meant that the active ingredients are administered one after the other, in either order, at a time interval between the individual administrations. The time interval can be, for example, less than 24 hours, preferably less than 6 hours, more preferably less than 2 hours.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a subject is successfully "treated" for cancer according to the methods of the present disclosure if the patient shows, e.g., total, partial, or transient remission of a certain type of cancer.

The terms "cancer", "tumor", "cancerous", and "malignant" refer to or describe the physiological condition in mammals that is typically characterized by unregulated cell growth. Examples of cancers include but are not limited to, breast cancer, gastric cancer, colorectal cancer, lung cancer, esophageal cancer, head-and-neck cancer, esophagogastric junction adenocarcinoma, biliary tract cancer, Paget's disease, pancreatic cancer, ovarian cancer, uterine carcinosarcoma, urothelial cancer, prostate cancer, bladder cancer, gastrointestinal stromal tumor, digestive tract stromal tumor, uterine cervix cancer, squamous cell carcinoma, peritoneal cancer, liver cancer, hepatocellular cancer, corpus uteri carcinoma, kidney cancer, vulval cancer, thyroid cancer, penis cancer, leukemia, malignant lymphoma, plasmacytoma, myeloma, glioblastoma multiforme, osteosarcoma, sarcoma, and melanoma. Cancers include hematological malignancies such as acute myeloid leukemia, multiple myeloma, chronic lymphocytic leukemia, diffuse large B cell lymphoma, Burkitt's lymphoma, follicular lymphoma and solid tumors such as breast cancer, lung cancer, neuroblastoma and colon cancer.

The term "cytotoxic agent" as used herein is defined broadly and refers to a substance that inhibits or prevents the function of cells and/or causes destruction of cells (cell death), and/or exerts anti-neoplastic/anti-proliferative effects. For example, a cytotoxic agent prevents directly or indirectly the development, maturation, or spread of neoplastic tumor cells. The term includes also such agents that cause a cytostatic effect only and not a mere cytotoxic effect. The term includes chemotherapeutic agents as specified below, as well as other HER2 antagonists, anti-angiogenic agents, tyrosine kinase inhibitors, protein kinase A inhibitors, members of the cytokine family, radioactive isotopes, and toxins such as enzymatically active toxins of bacterial, fungal, plant or animal origin. The term "chemotherapeutic agent" is a subset of the term "cytotoxic agent" comprising natural or synthetic chemical compounds.

In accordance with the methods or uses of the present disclosure, compounds of the present disclosure may be administered to a patient to promote a positive therapeutic response with respect to cancer. The term "positive therapeutic response" with respect to cancer treatment refers to an improvement in the symptoms associated with the disease. For example, an improvement in the disease can be characterized as a complete response. The term "complete response" refers to an absence of clinically detectable disease with normalization of any previous test results. Alternatively, an improvement in the disease can be categorized as being a partial response. A "positive therapeutic response" encompasses a reduction or inhibition of the progression and/or duration of cancer, the reduction or amelioration of the severity of cancer, and/or the amelioration of one or more symptoms thereof resulting from the administration of compounds of the present disclosure. In specific aspects, such terms refer to one, two or three or more results following the administration of compounds of the instant disclosure:

(1) a stabilization, reduction or elimination of the cancer cell population;
(2) a stabilization or reduction in cancer growth; (3) an impairment in the formation of cancer;
(4) eradication, removal, or control of primary, regional and/or metastatic cancer;
(5) a reduction in mortality;
(6) an increase in disease-free, relapse-free, progression-free, and/or overall survival, duration, or rate;
(7) an increase in the response rate, the durability of response, or number of patients who respond or are in remission;
(8) a decrease in hospitalization rate,
(9) a decrease in hospitalization lengths,
(10) the size of the cancer is maintained and does not increase or increases by less than 10%, preferably less than 5%, preferably less than 4%, preferably less than 2%, and
(11) an increase in the number of patients in remission.
(12) a decrease in the number of adjuvant therapies (e.g., chemotherapy or hormonal therapy) that would otherwise be required to treat the cancer.

Clinical response can be assessed using screening techniques such as PET, magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like.

In addition to these positive therapeutic responses, the subject undergoing therapy can experience the beneficial effect of an improvement in the symptoms associated with the disease.

Alkyl groups and moieties are straight or branched chain, e.g. $C_{1-8}$ alkyl, $C_{1-6}$ alkyl, $C_{1-4}$ alkyl or $C_{5-6}$ alkyl. Examples of alkyl groups are methyl, ethyl, n-propyl, iso-propyl, n-butyl, t-butyl, n-pentyl, n-hexyl, n-heptyl and n-octyl, such as methyl or n-hexyl.

Fluoroalkyl groups are alkyl groups in which one or more H atoms is replaced with one or more fluoro atoms, e.g. $C_{1-8}$ fluoroalkyl, $C_{1-6}$ fluoroalkyl, $C_{1-4}$ fluoroalkyl or $C_{5-6}$ fluoroalkyl. Examples include fluoromethyl ($CH_2F$—), difluromethyl ($CHF_2$—), trifluoromethyl ($CF_3$—), 2,2,2-trifluoroethyl ($CF_3CH_2$—), 1,1-difluoroethyl ($CH_3CHF_2$—), 2,2-difluoroethyl ($CHF_2CH_2$—), and 2-fluoroethyl ($CH_2FCH_2$—).

Halo means fluoro, chloro, bromo, and iodo. In an embodiment, halo is fluoro or chloro.

As used herein, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical product will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician. In particular, an effective amount of a compound for use in the treatment of cancer in combination with the antibody-drug conjugate is an amount such that the combination is sufficient to symptomatically relieve in a warm-blooded animal such as man, the symptoms of cancer, to slow the progression of cancer, or to reduce in patients with symptoms of cancer the risk of getting worse.

In this specification, unless otherwise stated, the term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

It will be understood that compounds of formula (I) may form stable pharmaceutically acceptable acid or base salts, and in such cases administration of a compound as a salt may be appropriate. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Non-toxic physiologically-acceptable salts are preferred, although other salts may be useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

Compounds of formula (I) may have more than one chiral center, and it is to be understood that the application encompasses all individual stereoisomers, enantiomers and diastereoisomers and mixtures thereof. Thus, it is to be understood that, insofar as the compounds of formula (I) can exist in optically active or racemic forms by virtue of one or more asymmetric carbon atoms, the application includes in its definition any such optically active or racemic form which possesses the above-mentioned activity. The present application encompasses all such stereoisomers having activity as herein defined.

Thus, throughout the specification, where reference is made to the compound of formula (I) it is to be understood that the term compound includes diastereoisomers, mixtures of diastereoisomers, and enantiomers that are PARP1 inhibitors.

It is also to be understood that certain compounds of formula (I), and pharmaceutically salts thereof, can exist in solvated as well as unsolvated forms such as, for example, hydrated and anhydrous forms. It is to be understood that the compounds herein encompass all such solvated forms. For the sake of clarity, this includes both solvated (e.g., hydrated) forms of the free form of the compound, as well as solvated (e.g., hydrated) forms of the salt of the compound.

Some of the compounds of formula (I) may be crystalline and may have more than one crystalline form. It is to be understood that the disclosure encompasses any crystalline or amorphous form, or mixtures thereof, which have PARP1 selective inhibitory activity. It is generally known that crystalline materials may be analysed using conventional techniques such as, for example, X-Ray Powder Diffraction (hereinafter XRPD) analysis and Differential Scanning Calorimetry (DSC).

Formula (I) as described herein is intended to encompass all isotopes of its constituent atoms. For example, H (or hydrogen) includes any isotopic form of hydrogen including $^{1}H$, $^{2}H$ (D), and $^{3}H$ (T); C includes any isotopic form of carbon including $^{12}C$, $^{13}C$, and $^{14}C$; O includes any isotopic form of oxygen including $^{16}O$, $^{17}O$ and $^{18}O$; N includes any isotopic form of nitrogen including $^{13}N$, $^{14}N$ and $^{15}N$; F includes any isotopic form of fluorine including $^{19}F$ and $^{18}F$; and the like. In one aspect, the compounds of formula (I) include isotopes of the atoms covered therein in amounts corresponding to their naturally occurring abundance. However, in certain instances, it may be desirable to enrich one or more atom in a particular isotope which would normally be present in a lower abundance. For example, $^{1}H$ would normally be present in greater than 99.98% abundance; however, in one aspect, a compound of any formula presented herein may be enriched in $^{2}H$ or $^{3}H$ at one or more positions where H is present. In another aspect, when a compound of any formula presented herein is enriched in a radioactive isotope, for example $^{3}H$ and $^{14}C$, the compound may be useful in drug and/or substrate tissue distribution assays. It is to be understood that the present application encompasses all such isotopic forms.

DESCRIPTION OF EMBODIMENTS

Hereinafter, preferred modes for carrying out the present disclosure are described. The embodiments described below are given merely for illustrating one example of a typical embodiment of the present disclosure and are not intended to limit the scope of the present disclosure.

1. Antibody-Drug Conjugate

The antibody-drug conjugate used in the present disclosure is an antibody-drug conjugate in which a drug-linker represented by the following formula:

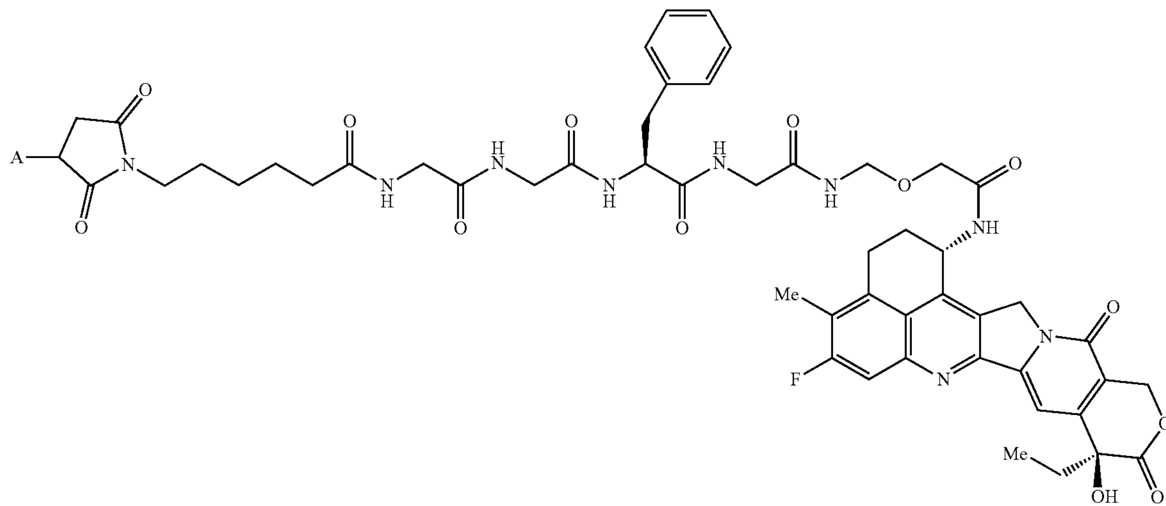

wherein A represents the connecting position to an antibody, is conjugated to an anti-HER2 antibody via a thioether bond.

In the present disclosure, the partial structure consisting of a linker and a drug in the antibody-drug conjugate is referred to as a "drug-linker". The drug-linker is connected to a thiol group (in other words, the sulfur atom of a cysteine residue) formed at an interchain disulfide bond site (two sites between heavy chains, and two sites between a heavy chain and a light chain) in the antibody.

The drug-linker of the present disclosure includes exatecan (IUPAC name: (1S,9S)-1-amino-9-ethyl-5-fluoro-1,2,3,9,12,15-hexahydro-9-hydroxy-4-methyl-10H,13H-benzo[de]pyrano[3',4':6,7]indolizino[1,2-b]quinolin-10,13-dione, (also expressed as chemical name: (1S,9S)-1-amino-9-ethyl-5-fluoro-2,3-dihydro-9-hydroxy-4-methyl-1H,12H-benzo[de]pyrano[3',4':6,7] indolizino[1,2-b]quinolin-10,13(9H,15H)-dione)), which is a topoisomerase I inhibitor, as a component. Exatecan is a camptothecin derivative having an antitumor effect, represented by the following formula:

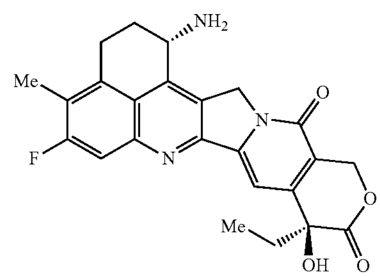 [SMILES: CC[C@@]1(O)C(=O)OCc2c1cc1n(c2=O)Cc2c-1nc1cc(F)c(C)c3c1c2[C@@H](N)CC3]

The anti-HER2 antibody-drug conjugate used in the present disclosure can be also represented by the following formula:

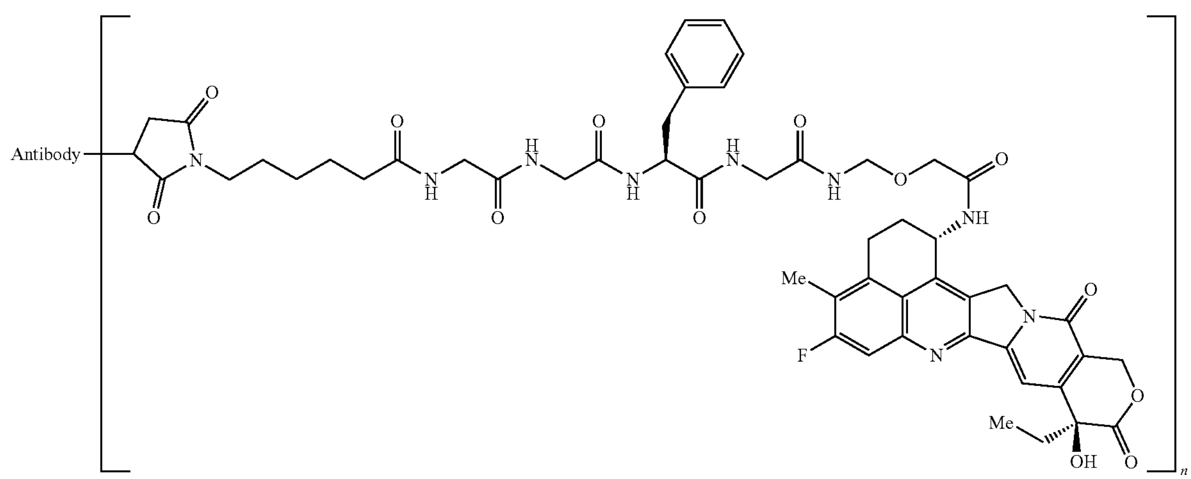

Here, the drug-linker is conjugated to an anti-HER2 antibody ('Antibody-') via a thioether bond. The meaning of n is the same as that of what is called the average number of conjugated drug molecules (DAR; Drug-to-Antibody Ratio), and indicates the average number of units of the drug-linker conjugated per antibody molecule.

After migrating into cancer cells, the anti-HER2 antibody-drug conjugate used in the present disclosure is cleaved at the linker portion to release a compound represented by the following formula:

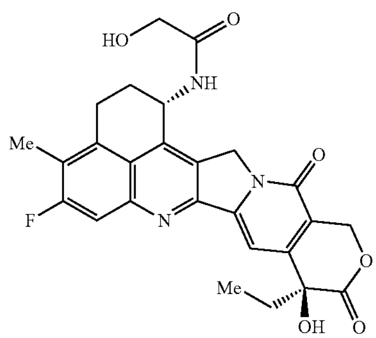 [SMILES: CC[C@@]1(O)C(=O)OCc2c1cc1n(c2=O)Cc2c-1nc1cc(F)c(C)c3c1c2[C@@H](NC(=O)CO)CC3]

This compound is inferred to be the original source of the antitumor activity of the antibody-drug conjugate used in the present disclosure, and has been confirmed to have a topoisomerase I inhibitory effect (Ogitani Y. et al., Clinical Cancer Research, 2016, Oct. 15; 22(20):5097-5108, Epub 2016 Mar. 29).

The anti-HER2 antibody-drug conjugate used in the present disclosure is known to have a bystander effect (Ogitani Y. et al., Cancer Science (2016) 107, 1039-1046). The bystander effect is exerted through a process whereby the antibody-drug conjugate used in the present disclosure is internalized in cancer cells expressing the target and the compound released then exerts an antitumor effect also on cancer cells which are present therearound and not expressing the target. This bystander effect is exerted as an excellent antitumor effect even when the anti-HER2 antibody-drug conjugate is used in combination with a PARP1 selective inhibitor according to the present disclosure.

2. Antibody in Antibody-Drug Conjugate

The anti-HER2 antibody in the antibody-drug conjugate used in the present disclosure may be derived from any species, and is preferably an anti-HER2 antibody derived from a human, a rat, a mouse, or a rabbit. In cases when the antibody is derived from species other than human species, it is preferably chimerized or humanized using a well known technique. The anti-HER2 antibody may be a polyclonal antibody or a monoclonal antibody and is preferably a monoclonal antibody.

The antibody in the antibody-drug conjugate used in the present disclosure is an anti-HER2 antibody preferably having a characteristic of being capable of targeting cancer cells, and is preferably an antibody possessing, for example, a property of recognizing a cancer cell, a property of binding to a cancer cell, a property of internalizing in a cancer cell, and/or cytocidal activity against cancer cells.

The binding activity of the anti-HER2 antibody against cancer cells can be confirmed using flow cytometry. The internalization of the antibody into cancer cells can be confirmed using (1) an assay of visualizing an antibody incorporated in cells under a fluorescence microscope using a secondary antibody (fluorescently labeled) binding to the therapeutic antibody (Cell Death and Differentiation (2008) 15, 751-761), (2) an assay of measuring a fluorescence intensity incorporated in cells using a secondary antibody (fluorescently labeled) binding to the therapeutic antibody (Molecular Biology of the Cell, Vol. 15, 5268-5282, December 2004), or (3) a Mab-ZAP assay using an immunotoxin binding to the therapeutic antibody wherein the toxin is released upon incorporation into cells to inhibit cell growth (Bio Techniques 28: 162-165, January 2000). As the immunotoxin, a recombinant complex protein of a diphtheria toxin catalytic domain and protein G may be used.

The antitumor activity of the anti-HER2 antibody can be confirmed in vitro by determining inhibitory activity against cell growth. For example, a cancer cell line overexpressing HER2 as a target protein for the antibody is cultured, and the antibody is added at varying concentrations into the culture system to determine inhibitory activity against focus formation, colony formation, and spheroid growth. The antitumor activity can be confirmed in vivo, for example, by administering the antibody to a nude mouse with a transplanted cancer cell line highly expressing the target protein, and determining change in the cancer cell.

Since the compound conjugated in the anti-HER2 antibody-drug conjugate exerts an antitumor effect, it is preferred but not essential that the anti-HER2 antibody itself should have an antitumor effect. For the purpose of specifically and selectively exerting the cytotoxic activity of the antitumor compound against cancer cells, it is important and also preferred that the anti-HER2 antibody should have the property of internalizing to migrate into cancer cells.

The anti-HER2 antibody in the antibody-drug conjugate used in the present disclosure can be obtained by a procedure known in the art. For example, the antibody of the present disclosure can be obtained using a method usually carried out in the art, which involves immunizing animals with an antigenic polypeptide and collecting and purifying antibodies produced in vivo. The origin of the antigen is not limited to humans, and the animals may be immunized with an antigen derived from a non-human animal such as a mouse, a rat and the like. In this case, the cross-reactivity of antibodies binding to the obtained heterologous antigen with human antigens can be tested to screen for an antibody applicable to a human disease.

Alternatively, antibody-producing cells which produce antibodies against the antigen are fused with myeloma cells according to a method known in the art (e.g., Kohler and Milstein, Nature (1975) 256, p. 495-497; and Kennet, R. ed., Monoclonal Antibodies, p. 365-367, Plenum Press, N.Y. (1980)) to establish hybridomas, from which monoclonal antibodies can in turn be obtained.

The antigen can be obtained by genetically engineering host cells to produce a gene encoding the antigenic protein. Specifically, vectors that permit expression of the antigen gene are prepared and transferred to host cells so that the gene is expressed. The antigen thus expressed can be purified. The antibody can also be obtained by a method of immunizing animals with the above-described genetically engineered antigen-expressing cells or a cell line expressing the antigen.

The anti-HER2 antibody in the antibody-drug conjugate used the present disclosure is preferably a recombinant antibody obtained by artificial modification for the purpose of decreasing heterologous antigenicity to humans such as a chimeric antibody or a humanized antibody, or is preferably an antibody having only the gene sequence of an antibody derived from a human, that is, a human antibody. These antibodies can be produced using a known method.

As the chimeric antibody, an antibody in which antibody variable and constant regions are derived from different species, for example, a chimeric antibody in which a mouse- or rat-derived antibody variable region is connected to a human-derived antibody constant region can be exemplified (Proc. Natl. Acad. Sci. USA, 81, 6851-6855, (1984)).

As the humanized antibody, an antibody obtained by integrating only the complementarity determining region (CDR) of a heterologous antibody into a human-derived antibody (Nature (1986) 321, pp. 522-525), and an antibody obtained by grafting a part of the amino acid residues of the framework of a heterologous antibody as well as the CDR sequence of the heterologous antibody to a human antibody by a CDR-grafting method (WO 90/07861), and an antibody humanized using a gene conversion mutagenesis strategy (U.S. Pat. No. 5,821,337) can be exemplified.

As the human antibody, an antibody generated by using a human antibody-producing mouse having a human chromosome fragment including genes of a heavy chain and light chain of a human antibody (see Tomizuka, K. et al., Nature Genetics (1997) 16, p. 133-143; Kuroiwa, Y. et. al., Nucl. Acids Res. (1998) 26, p. 3447-3448; Yoshida, H. et. al., Animal Cell Technology: Basic and Applied Aspects vol. 10, p. 69-73 (Kitagawa, Y., Matsuda, T. and Iijima, S. eds.), Kluwer Academic Publishers, 1999; Tomizuka, K. et. al., Proc. Natl. Acad. Sci. USA (2000) 97, p. 722-727, etc.) can be exemplified. As an alternative, an antibody obtained by phage display, the antibody being selected from a human antibody library (see Wormstone, I. M. et. al, Investigative Ophthalmology & Visual Science. (2002)43 (7), p. 2301-2308; Carmen, S. et. al., Briefings in Functional Genomics and Proteomics (2002), 1(2), p. 189-203; Siriwardena, D. et. al., Ophthalmology (2002) 109(3), p. 427-431, etc.) can be exemplified.

In the present disclosure, modified variants of the anti-HER2 antibody in the antibody-drug conjugate used in the present disclosure are also included. The modified variant refers to a variant obtained by subjecting the antibody according to the present disclosure to chemical or biological modification. Examples of the chemically modified variant include variants including a linkage of a chemical moiety to an amino acid skeleton, variants including a linkage of a chemical moiety to an N-linked or O-linked carbohydrate chain, etc. Examples of the biologically modified variant include variants obtained by post-translational modification (such as N-linked or O-linked glycosylation, N- or C-terminal processing, deamidation, isomerization of aspartic acid, or oxidation of methionine), and variants in which a methionine residue has been added to the N terminus by being expressed in a prokaryotic host cell. Further, an antibody labeled so as to enable the detection or isolation of the antibody or an antigen according to the present disclosure, for example, an enzyme-labeled antibody, a fluorescence-labeled antibody, and an affinity-labeled antibody are also included in the meaning of the modified variant. Such a modified variant of the antibody according to the present disclosure is useful for improving the stability and blood retention of the antibody, reducing the antigenicity thereof, detecting or isolating an antibody or an antigen, and so on.

Further, by regulating the modification of a glycan which is linked to the antibody according to the present disclosure (glycosylation, defucosylation, etc.), it is possible to enhance antibody-dependent cellular cytotoxic activity. As the technique for regulating the modification of a glycan of antibodies, those disclosed in WO99/54342, WO00/61739, WO02/31140, WO2007/133855, WO2013/120066, etc. are known. However, the technique is not limited thereto. In the anti-HER2 antibody according to the present disclosure, antibodies in which the modification of a glycan is regulated are also included.

It is known that a lysine residue at the carboxyl terminus of the heavy chain of an antibody produced in a cultured mammalian cell is deleted (Journal of Chromatography A, 705: 129-134 (1995)), and it is also known that two amino acid residues (glycine and lysine) at the carboxyl terminus of the heavy chain of an antibody produced in a cultured mammalian cell are deleted and a proline residue newly located at the carboxyl terminus is amidated (Analytical Biochemistry, 360: 75-83 (2007)). However, such deletion and modification of the heavy chain sequence do not affect the antigen-binding affinity and the effector function (the activation of complement, antibody-dependent cellular cytotoxicity, etc.) of the antibody. Therefore, in the anti-HER2 antibody according to the present disclosure, antibodies subjected to such modification and functional fragments of the antibody are also included, and deletion variants in which one or two amino acids have been deleted at the carboxyl terminus of the heavy chain, variants obtained by amidation of deletion variants (for example, a heavy chain in which the carboxyl terminal proline residue has been amidated), and the like are also included. The type of deletion variant having a deletion at the carboxyl terminus of the heavy chain of the anti-HER2 antibody according to the present disclosure is not limited to the above variants as long as the antigen-binding affinity and the effector function are conserved. The two heavy chains constituting the antibody according to the present disclosure may be of one type selected from the group consisting of a full-length heavy chain and the above-described deletion variant, or may be of two types in combination selected therefrom. The ratio of the amount of each deletion variant can be affected by the type of cultured mammalian cells which produce the anti-HER2 antibody according to the present disclosure and the culture conditions; however, an antibody in which one amino acid residue at the carboxyl terminus has been deleted in both of the two heavy chains in the antibody according to the present disclosure can be exemplified as preferred.

As isotypes of the anti-HER2 antibody according to the present disclosure, for example, IgG (IgG1, IgG2, IgG3, IgG4) can be exemplified, and IgG1 or IgG2 can be exemplified as preferred.

In the present disclosure, the term "anti-HER2 antibody" refers to an antibody which specifically binds to HER2 (Human Epidermal Growth Factor Receptor Type 2; ErbB-2), and preferably has an activity of internalizing in HER2-expressing cells by binding to HER2.

Examples of the anti-HER2 antibody include trastuzumab (U.S. Pat. No. 5,821,337) and pertuzumab (WO01/00245), and trastuzumab can be exemplified as preferred.

3. Production of Antibody-Drug Conjugate

A drug-linker intermediate for use in production of the anti-HER2 antibody-drug conjugate according to the present disclosure is represented by the following formula:

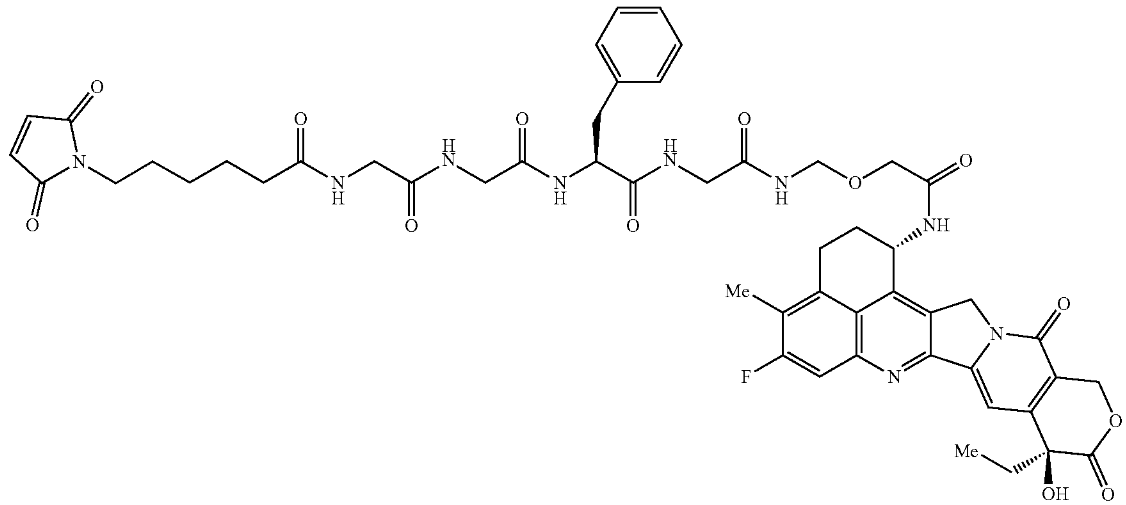 [SMILES: CC[C@@]1(O)C(=O)OCc2c1cc1n(c2=O)Cc2c-1nc1cc(F)c(C)c3c1c2[C@@H](NC(=O)COCNC(=O)CNC(=O)[C@H](Cc1ccccc1)NC(=O)CNC(=O)CNC(=O)CCCCCN1C(=O)C=CC1=O)CC3]

The drug-linker intermediate can be expressed as the chemical name N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide, and can be produced with reference to descriptions in WO2014/057687, WO2015/098099, WO2015/115091, WO2015/155998, WO2019/044947 and so on.

The anti-HER2 antibody-drug conjugate used in the present disclosure can be produced by reacting the above-described drug-linker intermediate and an anti-HER2 antibody having a thiol group (also referred to as a sulfhydryl group).

The anti-HER2 antibody having a sulfhydryl group can be obtained by a method well known in the art (Hermanson, G. T, Bioconjugate Techniques, pp. 56-136, pp. 456-493, Academic Press (1996)). For example, by using 0.3 to 3 molar equivalents of a reducing agent such as tris(2-carboxyethyl) phosphine hydrochloride (TCEP) per interchain disulfide within the antibody and reacting with the antibody in a buffer solution containing a chelating agent such as ethylenediamine tetraacetic acid (EDTA), an anti-HER2 antibody having a sulfhydryl group with partially or completely reduced interchain disulfides within the antibody can be obtained.

Further, by using 2 to 20 molar equivalents of the drug-linker intermediate per anti-HER2 antibody having a sulfhydryl group, an anti-HER2 antibody-drug conjugate in which 2 to 8 drug molecules are conjugated per antibody molecule can be produced.

The average number of conjugated drug molecules per anti-HER2 antibody molecule of the antibody-drug conjugate produced can be determined, for example, by a method of calculation based on measurement of UV absorbance for the antibody-drug conjugate and the conjugation precursor thereof at two wavelengths of 280 nm and 370 nm (UV method), or a method of calculation based on quantification through HPLC measurement for fragments obtained by treating the antibody-drug conjugate with a reducing agent (HPLC method).

Conjugation between the anti-HER2 antibody and the drug-linker intermediate and calculation of the average number of conjugated drug molecules per antibody molecule of the antibody-drug conjugate can be performed with reference to descriptions in WO2014/057687, WO2015/098099, WO2015/115091, WO2015/155998, WO2017/002776, WO2018/212136, and so on.

In the present disclosure, the term "anti-HER2 antibody-drug conjugate" refers to an antibody-drug conjugate such that the antibody in the antibody-drug conjugate according to the present disclosure is an anti-HER2 antibody.

The anti-HER2 antibody is preferably an antibody comprising a heavy chain comprising CDRH1 consisting of an amino acid sequence consisting of amino acid residues 26 to 33 of SEQ ID NO: 1, CDRH2 consisting of an amino acid sequence consisting of amino acid residues 51 to 58 of SEQ ID NO: 1 and CDRH3 consisting of an amino acid sequence consisting of amino acid residues 97 to 109 of SEQ ID NO: 1, and a light chain comprising CDRL1 consisting of an amino acid sequence consisting of amino acid residues 27 to 32 of SEQ ID NO: 2, CDRL2 consisting of an amino acid sequence consisting of amino acid residues 50 to 52 of SEQ ID NO: 2 and CDRL3 consisting of an amino acid sequence consisting of amino acid residues 89 to 97 of SEQ ID NO: 2, and more preferably an antibody comprising a heavy chain comprising a heavy chain variable region consisting of an amino acid sequence consisting of amino acid residues 1 to 120 of SEQ ID NO: 1 and a light chain comprising a light chain variable region consisting of an amino acid sequence consisting of amino acid residues 1 to 107 of SEQ ID NO: 2, and even more preferably an antibody comprising a heavy chain consisting of an amino acid sequence represented by SEQ ID NO: 1 and a light chain consisting of the amino acid sequence represented by SEQ ID NO: 2, or an antibody comprising a heavy chain consisting of amino acid residues 1 to 449 of SEQ ID NO: 1 and a light chain consisting of an amino acid sequence consisting of all amino acid residues 1 to 214 of SEQ ID NO: 2.

The average number of units of the drug-linker conjugated per antibody molecule in the anti-HER2 antibody-drug conjugate is preferably 2 to 8, more preferably 3 to 8, even more preferably 7 to 8, even more preferably 7.5 to 8, and even more preferably about 8.

The anti-HER2 antibody-drug conjugate used in the present disclosure can be produced with reference to descriptions in WO2015/115091 and so on.

In preferred embodiments, the anti-HER2 antibody-drug conjugate is trastuzumab deruxtecan (DS-8201).

4. PARP1 Selective Inhibitor

In the present disclosure, the term “PARP1 selective inhibitor” refers to a PARP inhibitor that exhibits selectivity for PARP1 over other PARP family members such as PARP2, PARP3, PARP5a, and PARP6, advantageously selectivity for PARP1 over PARP2, preferably at least 10-fold selectivity for PARP1 over PARP2, and more preferably at least 100-fold selectivity for PARP1 over PARP2. Preferred examples of PARP1 selective inhibitors can include those disclosed herein.

Examples of PARP1 selective inhibitors which may be used according to the present disclosure include azaquinolone compounds of formula (I). Azaquinolone compounds of formula (I) described herein have surprisingly high selectivity for PARP1 over other PARP family members such as PARP2, PARP3, PARP5a, and PARP6. Advantageously, compounds of formula (I) described herein have low hERG activity. It is well known that blockade of the cardiac ion channel coded by human ether-à-gogo-related gene (hERG) is a risk factor in drug discovery and development, and that blockage of hERG can cause safety problems such as cardiac arrhythmia.

Accordingly, in preferred embodiments of the PARP1 selective inhibitor used in the present disclosure, the PARP1 selective inhibitor is a compound represented by the following formula (I):

(I)

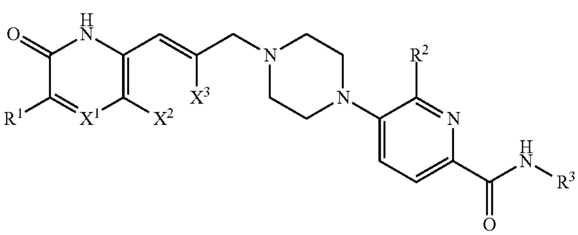

wherein:

$X^1$ and $X^2$ are each independently selected from N and C(H), $X^3$ is independently selected from N and C($R^4$), wherein $R^4$ is H or fluoro, $R^1$ is $C_{1-4}$ alkyl or $C_{1-4}$ fluoroalkyl (preferably is ethyl), $R^2$ is independently selected from H, halo, $C_{1-4}$ alkyl, and $C_{1-4}$ fluoroalkyl, and $R^3$ is H or $C_{1-4}$ alkyl (preferably is $C_{1-4}$ alkyl, more preferably methyl), or a pharmaceutically acceptable salt thereof provided that:

when $X^1$ is N, then $X^2$ is C(H), and $X^3$ is C($R^4$), when $X^2$ is N, then $X^1$=C(H), and $X^3$ is C($R^4$), and when $X^3$ is N, then $X^1$ and $X^2$ are both C(H).

In one embodiment the PARP1 selective inhibitor used in the disclosure is a compound of formula (Ia):

(Ia)

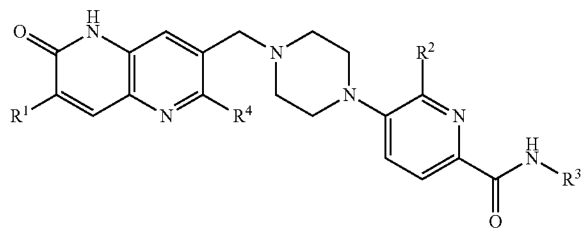

wherein $R^1$ is $C_{1-4}$ alkyl, $R^2$ is selected from H, halo, $C_{1-4}$ alkyl, and $C_{1-4}$ fluoroalkyl (preferably is selected from difluoromethyl, trifluoromethyl, and methyl, or is H or halo), $R^3$ is H or $C_{1-4}$ alkyl, and $R^4$ is H. In the compound of formula (Ia), preferably $R^1$ is ethyl, $R^2$ is selected from H, chloro and fluoro, $R^3$ is methyl, and $R^4$ is H.

In another embodiment the PARP1 selective inhibitor used in the disclosure is a compound of formula (Ib):

(Ib)

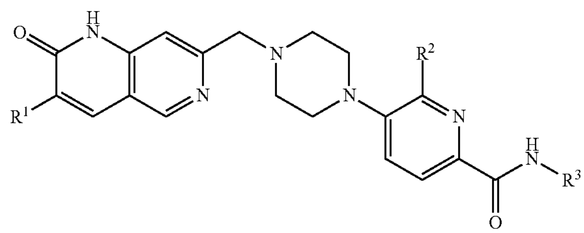

wherein $R^1$ is $C_{1-4}$ alkyl, $R^2$ is H or halo, and $R^3$ is H or $C_{1-4}$ alkyl. In the compound of formula (Ib), preferably $R^1$ is ethyl, $R^2$ is selected from H, chloro and fluoro, and $R^3$ is methyl.

In another embodiment the PARP1 selective inhibitor used in the disclosure is a compound of formula (Ic):

(Ic)

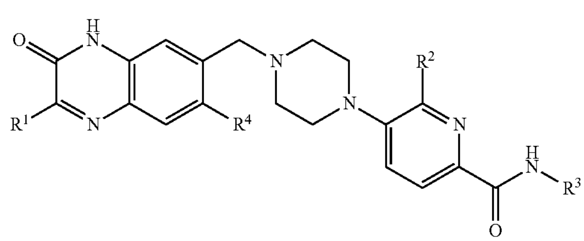

wherein $R^1$ is $C_{1-4}$ alkyl or $C_{1-4}$ fluoroalkyl, $R^2$ is independently selected from H, halo, $C_{1-4}$ alkyl, and $C_{1-4}$ fluoroalkyl, $R^3$ is H or $C_{1-4}$ alkyl, and $R^4$ is H or fluoro.

In another embodiment the PARP1 selective inhibitor is a compound of formula (Ic) wherein:

$R^1$ is independently selected from ethyl, n-propyl, trifluoromethyl, 1,1-difluoroethyl, 2,2-difluoroethyl, 2-fluoroethyl, and 2,2,2-trifluoroethyl; $R^2$ is independently selected from H, methyl, ethyl, trifluoromethyl, difluoromethyl, fluoromethyl, fluoro, and chloro; $R^3$ is H or methyl, and $R^4$ is H.

In another embodiment the PARP1 selective inhibitor is a compound of formula (I), or of formula (Ia), (Ib) or (Ic), having selectivity for PARP1 over PARP2, preferably at least 10-fold selectivity for PARP1 over PARP2, and more preferably at least 100-fold selectivity for PARP1 over PARP2.

In other embodiments the PARP1 selective inhibitor used in the disclosure is a compound selected from:

5-[4-[(3-ethyl-2-oxo-1H-1,6-naphthyridin-7-yl)methyl]piperazin-1-yl]-N-methyl-pyridine-2-carboxamide, 5-[4-[(3-ethyl-2-oxo-1H-1,6-naphthyridin-7-yl)methyl]piperazin-1-yl]-6-fluoro-N-methyl-pyridine-2-carboxamide, 6-chloro-5-[4-[(3-ethyl-2-oxo-1H-1,6-naphthyridin-7-yl)methyl]piperazin-1-yl]-N-methyl-pyridine-2-carboxamide, 5-[4-[(7-ethyl-6-oxo-5H-1,5-naphthyridin-3-yl)methyl]piperazin-1-yl]-N-methyl-pyridine-2-carboxamide, 5-[4-[(7-ethyl-6-oxo-5H-1,5-naphthyridin-3-yl)methyl]piperazin-1-yl]-6-fluoro-N-methyl-pyridine-2-carboxamide, 6-chloro-5-[4-[(7-ethyl-6-oxo-5H-1,5-naphthyridin-3-yl)methyl]piperazin-1-yl]-N-methyl-pyridine-2-carboxamide, 5-[4-[(7-ethyl-6-oxo-5H-1,5-naphthyridin-3-yl)methyl]piperazin-1-yl]pyridine-2-carboxamide 6-ethyl-5-[4-[(2-ethyl-3-oxo-4H-quinoxalin-6-yl)methyl]piperazin-1-yl]-N-methyl-pyridine-2-carboxamide, 5-[4-[(2-ethyl-3-oxo-4H-quinoxalin-6-yl)methyl]piperazin-1-yl]-N-methyl-6-(trifluoromethyl)pyridine-2-carboxamide, 6-(difluoromethyl)-5-[4-[(2-ethyl-3-oxo-4H-quinoxalin-6-yl)methyl]piperazin-1-yl]-N-methyl-pyridine-2-carboxamide, 5-[4-[(2-ethyl-3-oxo-4H-quinoxalin-6-yl)methyl]piperazin-1-yl]-N-methyl-pyridine-2-carboxamide, 5-[4-[(2-ethyl-3-oxo-4H-quinoxalin-6-yl)methyl]piperazin-1-yl]-6-fluoro-N-methyl-pyridine-2-carboxamide, 5-[4-[(2-ethyl-3-oxo-4H-quinoxalin-6-yl)methyl]piperazin-1-yl]-N,6-dimethyl-pyridine-2-carboxamide, 6-chloro-5-[4-[(2-ethyl-3-oxo-4H-quinoxalin-6-yl)methyl]piperazin-1-yl]-N-methyl-pyridine-2-carboxamide, N-methyl-5-[4-[[3-oxo-2-(trifluoromethyl)-4H-quinoxalin-6-yl]methyl]piperazin-1-yl]pyridine-2-carboxamide, 6-chloro-N-methyl-5-[4-[[3-oxo-2-(trifluoromethyl)-4H-quinoxalin-6-yl]methyl]piperazin-1-yl]pyridine-2-carboxamide, 6-fluoro-N-methyl-5-[4-[[3-oxo-2-(trifluoromethyl)-4H-quinoxalin-6-yl]methyl]piperazin-1-yl]pyridine-2-carboxamide, N-methyl-5-[4-[(3-oxo-2-propyl-4H-quinoxalin-6-yl)methyl]piperazin-1-yl]pyridine-2-carboxamide, 6-chloro-N-methyl-5-[4-[(3-oxo-2-propyl-4H-quinoxalin-6-yl)methyl]piperazin-1-yl]pyridine-2-carboxamide, 6-fluoro-N-methyl-5-[4-[(3-oxo-2-propyl-4H-quinoxalin-6-yl)methyl]piperazin-1-yl]pyridine-2-carboxamide, 5-[4-[(2-ethyl-7-fluoro-3-oxo-4H-quinoxalin-6-yl)methyl]piperazin-1-yl]-6-fluoro-N-methyl-pyridine-2-carboxamide, 5-[4-[[2-(1,1-difluoroethyl)-3-oxo-4H-quinoxalin-6-yl]methyl]piperazin-1-yl]-N-methyl-pyridine-2-carboxamide, 5-[4-[[2-(2,2-difluoroethyl)-3-oxo-4H-quinoxalin-6-yl]methyl]piperazin-1-yl]-N-methyl-pyridine-2-carboxamide, 5-[4-[[2-(2,2-difluoroethyl)-3-oxo-4H-quinoxalin-6-yl]methyl]piperazin-1-yl]-6-fluoro-N-methyl-pyridine-2-carboxamide, 5-[4-[[2-(2-fluoroethyl)-3-oxo-4H-quinoxalin-6-yl]methyl]piperazin-1-yl]-N-methyl-pyridine-2-carboxamide, 6-fluoro-5-[4-[[2-(2-fluoroethyl)-3-oxo-4H-quinoxalin-6-yl]methyl]piperazin-1-yl]-N-methyl-pyridine-2-carboxamide, N-methyl-5-[4-[[3-oxo-2-(2,2,2-trifluoroethyl)-4H-quinoxalin-6-yl]methyl]piperazin-1-yl]pyridine-2-carboxamide, and 6-fluoro-N-methyl-5-(4-((3-oxo-2-(2,2,2-trifluoroethyl)-3,4-dihydroquinoxalin-6-yl)methyl)piperazin-1-yl)picolinamide, or a pharmaceutically acceptable salt thereof.

In another embodiment the PARP1 selective inhibitor used in the disclosure is a compound selected from:

6-(difluoromethyl)-5-[4-[(7-ethyl-6-oxo-5H-1,5-naphthyridin-3-yl)methyl]piperazin-1-yl]-N-methyl-pyridine-2-carboxamide, 5-[4-[(7-ethyl-6-oxo-5H-1,5-naphthyridin-3-yl)methyl]piperazin-1-yl]-N-methyl-6(trifluoromethyl)pyridine-2-carboxamide, 5-[4-[(7-ethyl-6-oxo-5H-1,5-naphthyridin-3-yl)methyl]piperazin-1-yl]-N,6-dimethyl-pyridine-2-carboxamide, and N-ethyl-5-[4-[(7-ethyl-6-oxo-5H-1,5-naphthyridin-3-yl)methyl]piperazin-1-yl]pyridine-2-carboxamide, or a pharmaceutically acceptable salt thereof.

In a preferred embodiment the PARP1 selective inhibitor used in the disclosure is the compound AZD5305 (5-[4-[(7-ethyl-6-oxo-5H-1,5-naphthyridin-3-yl)methyl]piperazin-1-yl]-N-methyl-pyridine-2-carboxamide) represented by the following formula:

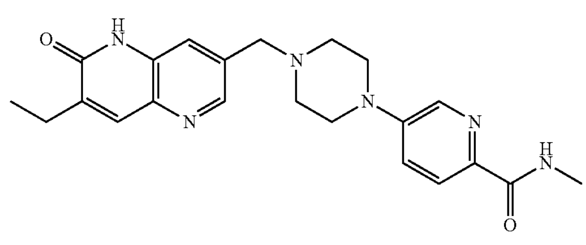 [SMILES: CCc1cc2ncc(CN3CCN(c4ccc(C(=O)NC)nc4)CC3)cc2[nH]c1=O]

or a pharmaceutically acceptable salt thereof.

5. Combination of Antibody-Drug Conjugate and PARP1 Selective Inhibitor

In a first combination embodiment of the disclosure, the anti-HER2 antibody-drug conjugate which is combined with the PARP1 selective inhibitor is an antibody-drug conjugate in which a drug-linker represented by the following formula:

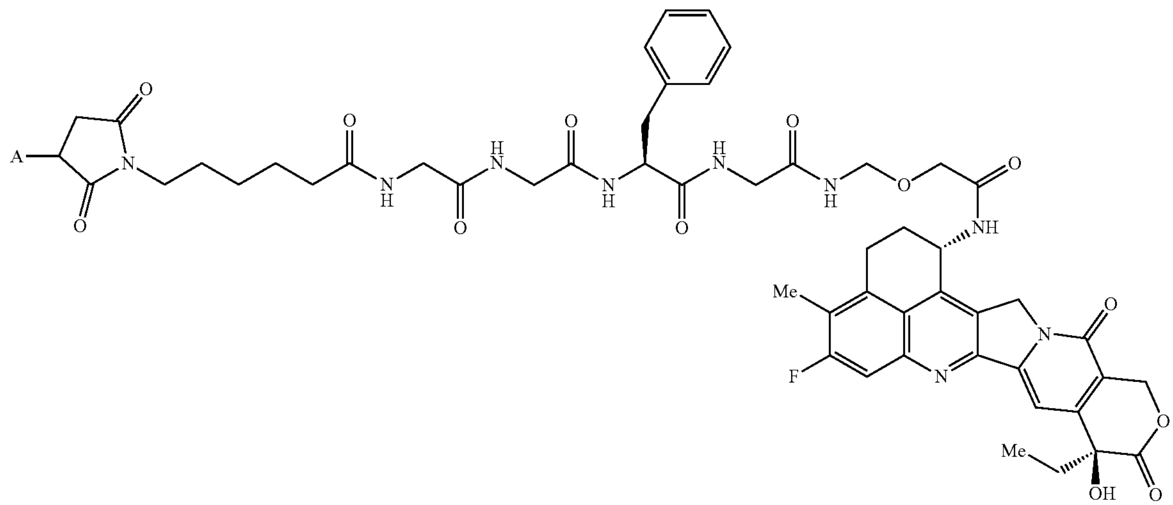

wherein A represents the connecting position to an antibody, is conjugated to an anti-HER2 antibody via a thioether bond.

In another combination embodiment, the anti-HER2 antibody-drug conjugate as defined above for the first combination embodiment is combined with a PARP1 selective inhibitor which is a compound represented by the following formula (I):

(I)

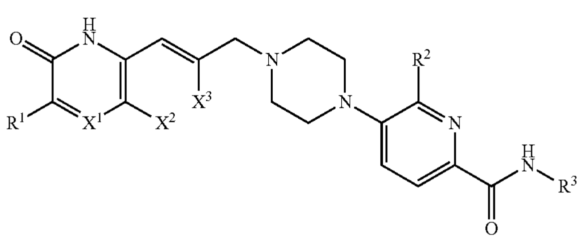

wherein:

$X^1$ and $X^2$ are each independently selected from N and C(H), $X^3$ is independently selected from N and C($R^4$), wherein $R^4$ is H or fluoro, $R^1$ is $C_{1-4}$ alkyl or $C_{1-4}$ fluoroalkyl, $R^2$ is independently selected from H, halo, $C_{1-4}$ alkyl, and $C_{1-4}$ fluoroalkyl, and $R^3$ is H or $C_{1-4}$ alkyl, or a pharmaceutically acceptable salt thereof provided that:

when $X^1$ is N, then $X^2$ is C(H), and $X^3$ is C($R^4$), when $X^2$ is N, then $X^1$=C(H), and $X^3$ is C($R^4$), and when $X^3$ is N, then $X^1$ and $X^2$ are both C(H).

In another combination embodiment, the anti-HER2 antibody-drug conjugate as defined above is combined with a PARP1 selective inhibitor as defined above wherein, in formula (I), $R^3$ is $C_{1-4}$ alkyl.

In another combination embodiment, the anti-HER2 antibody-drug conjugate as defined above is combined with a PARP1 selective inhibitor as defined above wherein, in formula (I), $R^3$ is methyl.

In another combination embodiment, the anti-HER2 antibody-drug conjugate as defined above is combined with a PARP1 selective inhibitor as defined above wherein, in formula (I), $R^1$ is ethyl.

In another combination embodiment, the anti-HER2 antibody-drug conjugate as defined above is combined with a PARP1 selective inhibitor which is a compound represented by the following formula (Ia):

(Ia)

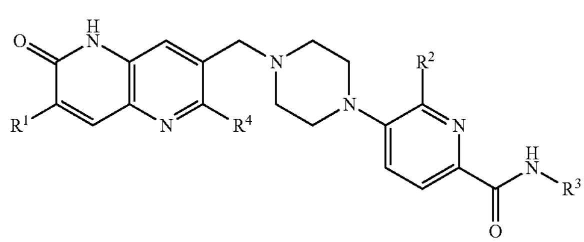

wherein $R^1$ is $C_{1-4}$ alkyl, $R^2$ is selected from H, halo, $C_{1-4}$ alkyl, and $C_{1-4}$ fluoroalkyl, $R^3$ is H or $C_{1-4}$ alkyl, and $R^4$ is H, or a pharmaceutically acceptable salt thereof.

In another combination embodiment, the anti-HER2 antibody-drug conjugate as defined above is combined with a PARP1 selective inhibitor as defined above wherein, in formula (Ia), $R^2$ is H or halo.

In another combination embodiment, the anti-HER2 antibody-drug conjugate as defined above is combined with a PARP1 selective inhibitor as defined above wherein, in formula (Ia), $R^1$ is ethyl, $R^2$ is selected from H, chloro and fluoro, and $R^3$ is methyl.

In another combination embodiment, the anti-HER2 antibody-drug conjugate as defined above is combined with a PARP1 selective inhibitor wherein the PARP1 selective inhibitor is AZD5305 represented by the following formula:

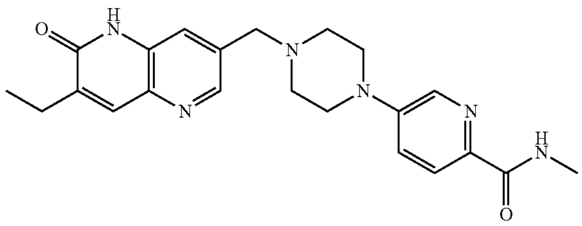 [SMILES: CCc1cc2ncc(CN3CCN(c4ccc(C(=O)NC)nc4)CC3)cc2[nH]c1=O]

or a pharmaceutically acceptable salt thereof.

In an embodiment of each of the combination embodiments described above, the anti-HER2 antibody comprises a heavy chain comprising CDRH1 consisting of an amino acid sequence represented by SEQ ID NO: 3, CDRH2 consisting of an amino acid sequence represented by SEQ ID NO: 4 and CDRH3 consisting of an amino acid sequence represented by SEQ ID NO: 5, and a light chain comprising CDRL1 consisting of an amino acid sequence represented by SEQ ID NO: 6, CDRL2 consisting of an amino acid sequence consisting of amino acid residues 1 to 3 of SEQ ID NO: 7 and CDRL3 consisting of an amino acid sequence represented by SEQ ID NO: 8. In another embodiment of each of the combination embodiments described above, the anti-HER2 antibody comprises a heavy chain comprising a heavy chain variable region consisting of an amino acid sequence represented by SEQ ID NO: 9 and a light chain comprising a light chain variable region consisting of an amino acid sequence represented by SEQ ID NO: 10. In another embodiment of each of the combination embodiments described above, the anti-HER2 antibody comprises a heavy chain consisting of an amino acid sequence represented by SEQ ID NO: 1 and a light chain consisting of an amino acid sequence represented by SEQ ID NO: 2. In another embodiment of each of the combination embodiments described above, the anti-HER2 antibody comprises a heavy chain consisting of an amino acid sequence represented by SEQ ID NO: 11 and a light chain consisting of an amino acid sequence represented by SEQ ID NO: 2.

In a particularly preferred combination embodiment of the disclosure, the anti-HER2 antibody-drug conjugate is trastuzumab deruxtecan (DS-8201) and the PARP1 selective inhibitor is the compound represented by the following formula:

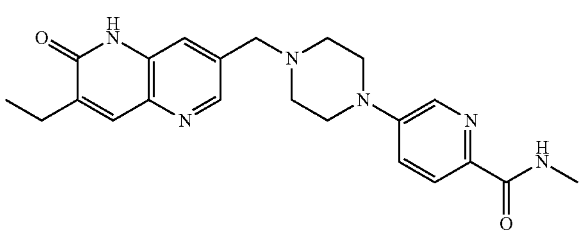 [SMILES: CCc1cc2ncc(CN3CCN(c4ccc(C(=O)NC)nc4)CC3)cc2[nH]c1=O]

also identified as AZD5305.

6. Therapeutic Combined Use and Method

Described in the following are a pharmaceutical product and a therapeutic use and method wherein the anti-HER2 antibody-drug conjugate according to the present disclosure and a PARP1 selective inhibitor are administered in combination.

The pharmaceutical product and therapeutic use and method of the present disclosure may be characterized in that the anti-HER2 antibody-drug conjugate and the PARP1 selective inhibitor are separately contained as active components in different formulations, and are administered simultaneously or at different times, or characterized in that the antibody-drug conjugate and the PARP1 selective inhibitor are contained as active components in a single formulation and administered.

In the pharmaceutical product and therapeutic method of the present disclosure, a single PARP1 selective inhibitor used in the present disclosure can be administered in combination with the anti-HER2 antibody-drug conjugate, or two or more different PARP1 selective inhibitors can be administered in combination with the antibody-drug conjugate.

The pharmaceutical product and therapeutic method of the present disclosure can be used for treating cancer, and can be preferably used for treating at least one cancer selected from the group consisting of breast cancer (including triple negative breast cancer and luminal breast cancer), gastric cancer (also called gastric adenocarcinoma), colorectal cancer (also called colon and rectal cancer, and including colon cancer and rectal cancer), lung cancer (including small cell lung cancer and non-small cell lung cancer), esophageal cancer, head-and-neck cancer (including salivary gland cancer and pharyngeal cancer), esophagogastric junction adenocarcinoma, biliary tract cancer (including bile duct cancer), Paget's disease, pancreatic cancer, ovarian cancer, uterine carcinosarcoma, urothelial cancer, prostate cancer, bladder cancer, gastrointestinal stromal tumor, uterine cervix cancer, squamous cell carcinoma, peritoneal cancer, liver cancer, hepatocellular cancer, corpus uteri carcinoma, kidney cancer, vulval cancer, thyroid cancer, penis cancer, leukemia, malignant lymphoma, plasmacytoma, myeloma, glioblastoma multiforme, osteosarcoma, sarcoma, and melanoma, and can be more preferably used for treating at least one cancer selected from the group consisting of breast cancer, gastric cancer, colorectal cancer, lung cancer (preferably non-small cell lung cancer), pancreatic cancer, ovarian cancer, prostate cancer, and kidney cancer.

The presence or absence of HER2 tumor markers can be determined, for example, by collecting tumor tissue from a cancer patient to prepare a formalin-fixed, paraffin-embedded (FFPE) specimen and subjecting the specimen to a test for gene products (proteins), for example, with an immunohistochemical (IHC) method, a flow cytometer, or Western blotting, or to a test for gene transcription, for example, with an in situ hybridization (ISH) method, a quantitative PCR method (q-PCR), or microarray analysis, or by collecting cell-free circulating tumor DNA (ctDNA) from a cancer patient and subjecting the ctDNA to a test with a method such as next-generation sequencing (NGS).

The pharmaceutical product and therapeutic method of the present disclosure can be used for HER2-expressing cancer, which may be HER2-overexpressing cancer (high or moderate) or may be HER2 low-expressing cancer.

In the present disclosure, the term "HER2-overexpressing cancer" is not particularly limited as long as it is recognized as HER2-overexpressing cancer by those skilled in the art. Preferred examples of the HER2-overexpressing cancer can include cancer given a score of 3+ for the expression of HER2 in an IHC method, and cancer given a score of 2+ for the expression of HER2 in an IHC method and determined as positive for the expression of HER2 in an in situ hybridization method (ISH). The in situ hybridization method of the present disclosure includes a fluorescence in situ hybridization method (FISH) and a dual color in situ hybridization method (DISH).

In the present disclosure, the term "HER2 low-expressing cancer" is not particularly limited as long as it is recognized as HER2 low-expressing cancer by those skilled in the art. Preferred examples of the HER2 low-expressing cancer can include cancer given a score of 2+ for the expression of HER2 in an IHC method and determined as negative for the expression of HER2 in an in situ hybridization method, and cancer given a score of 1+ for the expression of HER2 in an IHC method.

The method for scoring the degree of HER2 expression by the IHC method, or the method for determining positivity or negativity to HER2 expression by the in situ hybridization method is not particularly limited as long as it is recognized by those skilled in the art. Examples of the method can include a method described in the 4th edition of the guidelines for HER2 testing, breast cancer (developed by the Japanese Pathology Board for Optimal Use of HER2 for Breast Cancer).

The cancer, particularly in regard to the treatment of breast cancer, may be HER2-overexpressing (high or moderate) or low-expressing breast cancer, or triple-negative breast cancer, and/or may have a HER2 status score of IHC 3+, IHC 2+, IHC 1+ or IHC>0 and <1+.

The pharmaceutical product and therapeutic method of the present disclosure can be preferably used for a mammal, but are more preferably used for a human.

The antitumor effect of the pharmaceutical product and therapeutic method of the present disclosure can be confirmed by transplanting cancer cells to a test subject animal to prepare a model and measuring reduction in tumor volume or life-prolonging effect by application of the pharmaceutical product and therapeutic method of the present disclosure. And then, the effect of combined use of the antibody-drug conjugate used in the present disclosure and a PARP1 selective inhibitor can be confirmed by comparing antitumor effect with single administration of the antibody-drug conjugate used in the present disclosure and that of the PARP1 selective inhibitor.

The antitumor effect of the pharmaceutical product and therapeutic method of the present disclosure can be confirmed in a clinical trial using any of an evaluation method with Response Evaluation Criteria in Solid Tumors (RECIST), a WHO evaluation method, a Macdonald evaluation method, body weight measurement, and other approaches, and can be determined on the basis of indexes of complete response (CR), partial response (PR); progressive disease (PD), objective response rate (ORR), duration of response (DoR), progression-free survival (PFS), overall survival (OS), and so on.

By using the above methods, the superiority in antitumor effect of the pharmaceutical product and therapeutic method of the present disclosure to existing pharmaceutical products and therapeutic methods for cancer treatment can be confirmed.

The pharmaceutical product and therapeutic method of the present disclosure can delay development of cancer cells, inhibit growth thereof, and further kill cancer cells. These effects can allow cancer patients to be free from symptoms caused by cancer or achieve improvement in quality of life (QOL) of cancer patients and attain a therapeutic effect by sustaining the lives of the cancer patients. Even if the pharmaceutical product and therapeutic method of the present disclosure do not accomplish killing cancer cells, they can achieve higher QOL of cancer patients while achieving longer-term survival, by inhibiting or controlling the growth of cancer cells.

The pharmaceutical product of the present disclosure can be expected to exert a therapeutic effect by application as systemic therapy to patients, and additionally, by local application to cancer tissues.

The pharmaceutical product and therapeutic method of the present disclosure, in another aspect, provides for use as an adjunct in cancer therapy with ionizing radiation or other chemotherapeutic agents. For example, in the treatment of cancer, the treatment may comprise administering to a subject in need of treatment a therapeutically-effective amount of the pharmaceutical product, simultaneously or sequentially with ionizing radiation or other chemotherapeutic agents.

The pharmaceutical product and therapeutic method of the present disclosure can be used as adjuvant chemotherapy combined with surgery operation. The pharmaceutical product of the present disclosure may be administered for the purpose of reducing tumor size before surgical operation (referred to as preoperative adjuvant chemotherapy or neoadjuvant therapy), or may be administered for the purpose of preventing recurrence of tumor after surgical operation (referred to as postoperative adjuvant chemotherapy or adjuvant therapy).

In further aspects, the pharmaceutical product of the present disclosure may be used for the treatment of cancer which is deficient in Homologous Recombination (HR) dependent DNA DSB repair activity. The HR dependent DNA DSB repair pathway repairs double-strand breaks (DSBs) in DNA via homologous mechanisms to reform a continuous DNA helix (K. K. Khanna and S. P. Jackson, Nat. Genet. 27(3): 247-254 (2001)). The components of the HR dependent DNA DSB repair pathway include, but are not limited to, ATM (NM_000051), RAD51 (NM_002875), RAD51L1 (NM_002877), RAD51C (NM_002876), RAD51L3 (NM_002878), DMC1 (NM_007068), XRCC2 (NM_005431), XRCC3 (NM_005432), RAD52 (NM_002879), RAD54L (NM_003579), RAD54B (NM_012415), BRCA1 (NM_007295), BRCA2 (NM_000059), RAD50 (NM_005732), MRE11A (NM_005590) and NBS1 (NM_002485). Other proteins involved in the HR dependent DNA DSB repair pathway include regulatory factors such as EMSY (Hughes-Davies, et al., *Cell,* 115, pp 523-535). HR components are also described in Wood, et al., *Science,* 291, 1284-1289 (2001). A cancer which is deficient in HR dependent DNA DSB repair may comprise or consist of one or more cancer cells which have a reduced or abrogated ability to repair DNA DSBs through that pathway, relative to normal cells i.e. the activity of the HR dependent DNA DSB repair pathway may be reduced or abolished in the one or more cancer cells. The activity of one or more components of the HR dependent DNA DSB repair pathway may be abolished in the one or more cancer cells of an individual having a cancer which is deficient in HR dependent DNA DSB repair. Components of the HR dependent DNA DSB repair pathway are well characterised in the art (see for example, Wood, et al., *Science,* 291, 1284-1289 (2001)) and include the components listed above.

In some embodiments, the cancer cells may have a BRCA1 and/or a BRCA2 deficient phenotype i.e. BRCA1 and/or BRCA2 activity is reduced or abolished in the cancer cells. Cancer cells with this phenotype may be deficient in BRCA1 and/or BRCA2, i.e. expression and/or activity of BRCA1 and/or BRCA2 may be reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor (Hughes-Davies, et al., *Cell,* 115, 523-535). BRCA1 and BRCA2 are known tumour suppressors whose wild-type alleles are frequently lost in tumours of heterozygous carriers (Jasin M., Oncogene, 21(58), 8981-93 (2002); Tutt, et al., *Trends Mol Med.,* 8 (12), 571-6, (2002)). The association of BRCA1 and/or BRCA2 mutations with breast cancer is well-characterised in the art (Radice, P. J., *Exp Clin Cancer Res.,* 21(3 Suppl), 9-12 (2002)). Amplification of the EMSY gene, which encodes a BRCA2 binding factor, is also known to be associated with breast and ovarian cancer. Carriers of mutations in BRCA1 and/or BRCA2 are also at elevated risk of certain cancers, including breast, ovary, pancreas, prostate, hematological, gastrointestinal and lung cancer. In some embodiments, the individual is heterozygous for one or more variations, such as mutations and polymorphisms, in BRCA1 and/or BRCA2 or a regulator thereof. The detection of variation in BRCA1 and BRCA2 is well-known in the art and is described, for example in EP 699 754, EP 705 903, Neuhausen, S. L. and Ostrander, E. A., Genet. Test, 1, 75-83 (1992); Chappnis, P. O. and Foulkes, W. O., *Cancer Treat Res,* 107, 29-59 (2002); Janatova M., et al., *Neoplasma,* 50(4), 246-505 (2003); Jancarkova, N., *Ceska Gynekol.,* 68{1), 11-6 (2003)). Determination of amplification of the BRCA2 binding factor EMSY is described in Hughes-Davies, et al., *Cell,* 115, 523-535).

Mutations and polymorphisms associated with cancer may be detected at the nucleic acid level by detecting the presence of a variant nucleic acid sequence or at the protein level by detecting the presence of a variant (i.e. a mutant or allelic variant) polypeptide.

The pharmaceutical product of the present disclosure can be administered containing at least one pharmaceutically suitable ingredient. Pharmaceutically suitable ingredients can be suitably selected and applied from formulation additives or the like that are generally used in the art, in accordance with the dosage, administration concentration, or the like of the antibody-drug conjugate used in the present disclosure and a PARP1 selective inhibitor. The anti-HER2 antibody-drug conjugate used in the present disclosure can be administered, for example, as a pharmaceutical product containing a buffer such as histidine buffer, a vehicle such as sucrose and trehalose, and a surfactant such as Polysorbates 80 and 20. The pharmaceutical product containing the antibody-drug conjugate used in the present disclosure can be preferably used as an injection, can be more preferably used as an aqueous injection or a lyophilized injection, and can be even more preferably used as a lyophilized injection. In the case that the pharmaceutical product containing the anti-HER2 antibody-drug conjugate used in the present disclosure is an aqueous injection, the aqueous injection can be preferably diluted with a suitable diluent and then given as an intravenous infusion. Examples of the diluent can include dextrose solution and physiological saline, dextrose solution can be preferably exemplified, and 5% dextrose solution can be more preferably exemplified. In the case that the pharmaceutical product of the present disclosure is a lyophilized injection, a required amount of the lyophilized injection dissolved in advance in water for injection can be preferably diluted with a suitable diluent and then given as an intravenous infusion. Examples of the diluent can include dextrose solution and physiological saline, dextrose solution can be preferably exemplified, and 5% dextrose solution can be more preferably exemplified.

Examples of the administration route applicable to administration of the pharmaceutical product of the present disclosure can include intravenous, intradermal, subcutaneous, intramuscular, and intraperitoneal routes, and intravenous routes are preferred.

The anti-HER2 antibody-drug conjugate used in the present disclosure can be administered to a human with intervals of 1 to 180 days, can be preferably administered with intervals of a week, two weeks, three weeks, or four weeks, and can be more preferably administered with intervals of three weeks. The anti-HER2 antibody-drug conjugate used in the present disclosure can be administered in a dose of about 0.001 to 100 mg/kg per administration, and can be preferably administered in a dose of 0.8 to 12.4 mg/kg per administration. For example, the anti-HER2 antibody-drug conjugate can be administered once every three weeks at a dose of 0.8 mg/kg, 1.6 mg/kg, 3.2 mg/kg, 5.4 mg/kg, 6.4 mg/kg, 7.4 mg/kg, or 8 mg/kg, and can be preferably administered once every three weeks at a dose of 5.4 mg/kg or 6.4 mg/kg.

The PARP1 selective inhibitor may be administered in a suitable dose by any suitable route of administration. The size of the dose required for the therapeutic treatment of a particular disease state will necessarily be varied depending on the subject treated, the route of administration and the severity of the illness being treated. For further information on routes of administration and dosage regimes, reference may be made to Chapter 25.3 in Volume 5 of Comprehensive Medicinal Chemistry (Corwin Hansch; Chairman of Editorial Board), Pergamon Press 1990.

Compounds of formula (I), or pharmaceutically acceptable salts thereof, will normally be administered via the oral route in the form of pharmaceutical preparations comprising the active ingredient or a pharmaceutically acceptable salt or solvate thereof, or a solvate of such a salt, in a pharmaceutically acceptable dosage form. Depending upon the disorder and patient to be treated, the compositions may be administered at varying doses.

The pharmaceutical formulations of the compound of formula (I) described above may be prepared for oral administration, particularly in the form of tablets or capsules, and especially involving technologies aimed at furnishing colon-targeted drug release (Patel, M. M. Expert Opin. Drug Deliv. 2011, 8 (10), 1247-1258).

The pharmaceutical formulations of the compound of formula (I) described above may conveniently be administered in unit dosage form and may be prepared by any of the methods well-known in the pharmaceutical art, for example as described in Remington's Pharmaceutical Sciences, 17th ed., Mack Publishing Company, Easton, PA., (1985).

Pharmaceutical formulations of a compound of formula (I) suitable for oral administration may comprise one or more physiologically compatible carriers and/or excipients and may be in solid or liquid form. Tablets and capsules may be prepared with binding agents, fillers, lubricants and/or surfactants, such as sodium lauryl sulfate. Liquid compositions may contain conventional additives such as suspending agents, emulsifying agents and/or preservatives. Liquid compositions may be encapsulated in, for example, gelatin to provide a unit dosage form. Solid oral dosage forms include tablets, two-piece hard shell capsules and soft elastic gelatin (SEG) capsules. Such two-piece hard shell capsules may be made for example by filling a compound of formula (I) into a gelatin or hydroxypropyl methylcellulose (HPMC) shell.

A dry shell formulation of a compound of formula (I) typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitable daily doses of the compounds of formula (I), or a pharmaceutically acceptable salt thereof, in therapeutic treatment of humans are about 0.0001-100 mg/kg body weight. Oral formulations are preferred, particularly tablets or capsules which may be formulated by methods known to those skilled in the art to provide doses of the active compound in the range of 0.1 mg to 1000 mg.

EXAMPLES

The present disclosure is specifically described in view of the examples shown below. However, the present disclosure is not limited to these. Further, it is by no means to be interpreted in a limited way.

Synthesis Examples of PARP1 Selective Inhibitor

Synthesis Examples 1 to 32 described below, of PARP1 selective inhibitors, are as described in Examples 1 to 32 of WO2021/013735.

General Experimental Conditions $^1$H NMR spectra were obtained using a Bruker 300 MHz, 400 MHz or 500 MHz spectrometer at 27° C. unless otherwise noted; chemical shifts are expressed in parts per million (ppm, δ units) and are referenced to the residual mono-$^1$H isotopologue of the solvent ($CHCl_3$: 7.24 ppm; $CHDCl_2$: 5.32 ppm; $CD_3S({=}O)CD_2H$: 2.49 ppm). Coupling constants are given in units of hertz (Hz). Splitting patterns describe apparent multiplicities and are designated as s (singlet), d (doublet), t (triplet), q (quartet), m (multiplet) and br s (broad singlet). LC-MS was carried out using a Waters UPLC fitted with a Waters SQD mass spectrometer or Shimadzu LC-20AD LC-20XR LC-30AD with a Shimadzu 2020 mass spectrometer. Reported molecular ions correspond to [M+H]+ unless otherwise noted; for molecules with multiple isotopic patterns (Br, Cl, etc.) the reported value is the one obtained for the lowest isotope mass unless otherwise specified.

Flash chromatography was performed using straight phase flash chromatography on a SP1™ Purification system from Biotage™, CombiFlash®Rf from ISCO or on Gilson system from Thermo Fisher using normal phase silica FLASH+™ (40M, 25M or 12 M) or SNAP™ KP-Sil Cartridges (340, 100, 50 or 10), Flash Column silica-CS columns from Agela, with C18-flash columns or standard flash chromatography. In general, all solvents used were commercially available and of analytical grade. Anhydrous solvents were routinely used for reactions. Phase Separators used in the examples are ISOLUTE® Phase Separator columns. The intermediates and examples named below were named using ACD/Name 12.01 from Advanced Chemistry Development, Inc. (ACD/Labs). The starting materials were obtained from commercial sources or made via literature routes.

X-Ray Powder Diffraction (XRPD) Analysis

XRPD analysis was performed using a Bruker D8 diffractometer, which is commercially available from Bruker AXS Inc™ (Madison, Wisconsin). The XRPD spectra were obtained by mounting a sample (approximately 10 mg) of the material for analysis on a single silicon crystal wafer mount (e.g., a Bruker silicon zero background X-ray diffraction sample holder) and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 angstroms (i.e., about 1.54 angstroms). The sample was exposed for 1 second per 0.02 degree 2-theta increment (continuous scan mode) over the range 5 degrees to 40 degrees 2-theta in theta-theta mode. The running time was ~15 min for D8. XRPD 2θ values may vary with a reasonable range, e.g., in the range±0.2° and that XRPD intensities may vary when measured for essentially the same crystalline form for a variety of reasons including, for example, preferred orientation. Principles of XRPD are described in publications, such as, for example, Giacovazzo, C. et al. (1995), Fundamentals of Crystallography, Oxford University Press; Jenkins, R. and Snyder, R. L. (1996), Introduction to X-Ray Powder Diffractometry, John Wiley & Sons, New York; and Klug, H. P. & Alexander, L. E. (1974), X-ray Diffraction Procedures, John Wiley and Sons, New York.

DSC Analysis

DSC analysis was performed on samples prepared according to standard methods using a Q SERIES™ Q1000 DSC calorimeter available from TA INSTRUMENTS® (New Castle, Delaware). A sample (approximately 2 mg) was weighed into an aluminum sample pan and transferred to the DSC. The instrument was purged with nitrogen at 50 mL/min and data collected between 22° C. and 300° C., using a dynamic heating rate of 10° C./minute. Thermal data was analyzed using standard software, e.g., Universal v.4.5A from TA INSTRUMENTS®.

The following abbreviations are used: AcOH=acetic acid; aq=aqueous; BAST=Bis(2-methoxyethyl)aminosulfur Trifluoride; $Boc_2O$=di-tert-butyl decarbonate; Boc=t-butyloxycarbonyl; $CDCl_3$=deuterated chloroform; $CD_3OD$=deuterated methanol; $CH_3NO_2$=nitromethane; DCE=1,2-dichloroethane; DCM=dichloromethane; DEA=diethylamine; DEAD=diethyl azodicarboxylate; Dess-martin periodinane=1,1,1-Tris(acetyloxy)-1,1-dihydro-1,2-benziodoxol-3-(1H)-one; DIPEA=N,N-diisopropylethylamine; DMAP=2,6-dimethylaminopyridine; DMF=N,N-dimethylformamide; DMSO=dimethyls- ulfoxide; DMSO-$d_6$=deuterated dimethylsulfoxide; DPPA=diphenyl phosphorazidate; dppf=1,1'-bis(diphenylphosphino)ferrocene; DIAD=Di-isopropyl (E)-diazene-1,2-dicarboxylate; DSC=differential scanning calorimetry; DTAD=Di-tert-butyl (E)-diazene-1,2-dicarboxylate; ee=enantiomeric excess; eq.=equivalent; ESI=electrospray ionization; $Et_2O$=diethyl ether; EtOAc or EA=ethylacetate; EtOH=ethanol; FA=formic acid; Grubbs catalyst (1,3-Dimesitylimidazolin-2-ylidene) (tricyclohexylphosphine)ruthenium dichloride; h=hour(s); HATU=(dimethylamino)-N, N-dimethyl(3-oxido-1H-[1,2,3]triazolo[4,5-b]pyridinyl) methaniminium hexafluorophosphate; HCl=hydrochloric acid; $H_2O_2$=hydrogen peroxide; HP=high pressure; IPA=isopropylalcohol; LC=liquid chromatography; $LiClO_4$=lithium perchlorate; mmol=millimole; mCPBA=meta-chloroperoxybenzoic acid; MeOH=methanol; min=minute(s); MeCN or CH3CN=acetonitrile; $MeNO_2$=nitromethane; MS=mass=spectrometry; NMP=N-methyl-2-pyrrolidone; NMR=nuclear magnetic resonance; Pd/C=Palladium on carbon; $Pd_2dba_3$=Tris(dibenzylideneacetone)dipalladium (0); $PdCl_2(dppf)$=1,1'-bis(di-tert-butylphosphino)ferrocene palladium dichloride; PE=Petroleum ether; $PPh_3$=Triphenylphosphine; rt=room temperature; Rt or RT=retention time; Ruphos Pd G3=(2-Dicyclohexylphosphino-2',6'-diisopropoxy-1,1'-biphenyl)[2-(2'-amino-1,1'biphenyl)]palladium(II) methanesulfonate; sat=saturated; SFC=supercritical fluid chromatography; T3P=2,4,6-tripropyl-1,3,5,2,4,6-trioxatriphosphinane 2,4,6-trioxide; TBTU=2-(1H-benzo[d][1,2,3]triazol-1-yl)-1,1,3,3-tetramethylisouronium tetrafluoroborate; TFA=trifluoroacetic acid; THF=tetrahydrofuran; TLC=thin layer chromatography; TMS=trimethylsilyl; Xantphos=4,5-bis(diphenylphosphino)-9,9-dimethylxanthene; CBr4=Carbon tetrabromide; HCl=Hydrochloric acid; HBr=Hydrobromic acid; Cs2CO3=Cesium carbonate; MgSO4=Magnesium sulfate; $NaHCO_3$=Sodium bicarbonate; DDQ=2,3-Dichloro-5,6-dicyano-1,4-benzoquinone; SOCl2=Thionyl chloride; DIBAL-H=Diisobutylaluminium hydride; NH4HCO3=Ammonium bicarbonate; BINAP=2,2'-bis(diphenylphosphino)-1,1'-binaphthyl.

Synthesis of Starting Materials and Intermediates

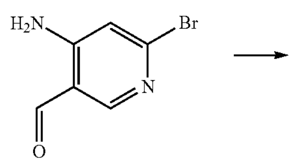

Intermediate 1

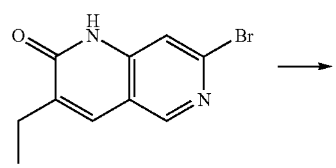

Intermediate 2

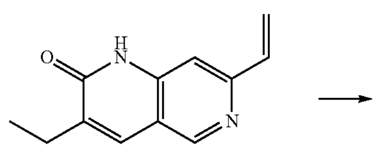

Intermediate 3

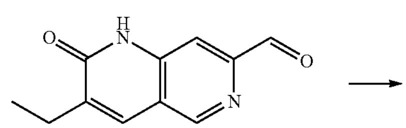

Intermediate 4

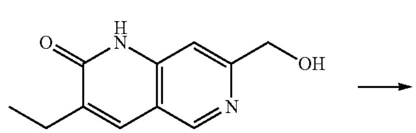

Intermediate 5

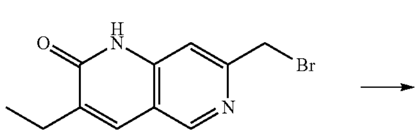

Intermediate 6

-continued

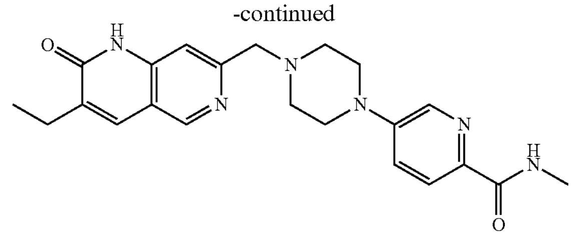

Example 1

Intermediate 2: 7-bromo-3-ethyl-1H-1,6-naphthyridin-2-one

Butyryl chloride (0.143 mL, 1.37 mmol) was added dropwise to a stirred solution of 4-amino-6-bromo-pyridine-3-carbaldehyde (Intermediate 1 250 mg, 1.24 mmol), DIPEA (1.086 mL, 6.22 mmol) and DMAP (30.4 mg, 0.25 mmol) in $CH_2Cl_2$ (5 mL) at 0° C. The resulting solution was stirred rt for 4 h. More 2 eq of butyryl chloride was added and reaction was continued for another 24 h. Reaction was diluted with water and extracted with ethyl acetate. Organic layer was dried over sodium sulphate and concentrated to give crude product. 1.5 mL MeOH was added and the solid (product) was filter off, washed with 1 mL MeOH to give 7-bromo-3-ethyl-1H-1,6-naphthyridin-2-one (Intermediate 2, 167 mg, 53.1%) as a white solid. 1H NMR (DMSO-d6) 1.17 (3H, t), 2.45-2.50 (2H, m, overlapped with solvent DMSO peak), 7.35 (1H, s), 7.82 (1H, s), 8.63 (1H, s), 12.09 (1H, br s); m/z ($ES^+$) $[M+H]^+$=252.

Intermediate 3: 3-ethyl-7-vinyl-1H-1,6-naphthyridin-2-one $PdCl_2$(dppf) (37.6 mg, 0.05 mmol) was added to a stirred mixture of 7-bromo-3-ethyl-1H-1,6-naphthyridin-2-one (Intermediate 2, 130 mg, 0.51 mmol), 4,4,5,5-tetramethyl-2-vinyl-1,3,2-dioxaborolane (0.105 mL, 0.62 mmol) and $K_2CO_3$ (213 mg, 1.54 mmol) in 1,4-dioxane (4 mL)/water (1.333 mL) and the resulting mixture was stirred at 90° C. for 1 h. The reaction mixture was diluted with water and extracted with ethyl acetate. The organic layers were combined, dried over sodium sulphate and concentrated to give crude product. The resulting residue was purified by flash silica chromatography, elution gradient 0 to 20% MeOH in DCM. Product fractions were concentrated under reduced pressure to dryness to afford 3-ethyl-7-vinyl-1H-1,6-naphthyridin-2-one (Intermediate 3, 93 mg, 90%) as a yellow solid.

1H NMR (DMSO-d6) 1.18 (3H, t), 2.53 (2H, m, overlapped with solvent DMSO peak), 5.49 (1H, dd), 6.27 (1H, dd), 6.84 (1H, dd), 7.15 (1H, s), 7.81 (1H, s), 8.78 (1H, s), 12.00 (1H, br s); m/z ($ES^+$) $[M+H]^+$=201.

Intermediate 4: 3-ethyl-2-oxo-1H-1,6-naphthyridine-7-carbaldehyde

Osmium tetroxide in $H_2O$ (0.024 mL, 3.00 μmol) was added to a solution of 3-ethyl-7-vinyl-1H-1,6-naphthyridin-2-one (Intermediate 3, 30 mg, 0.15 mmol), 2,6-lutidine (0.035 mL, 0.30 mmol) and sodium periodate (128 mg, 0.60 mmol) in THF (1 mL)/water (0.200 mL) and stirred at rt for overnight. Reaction was diluted with water and extracted with ethyl acetate and the filtrate was concentrated to dryness. The resulting residue was purified by flash silica chromatography, elution gradient 0 to 15% MeOH in DCM. Product fractions were concentrated under reduced pressure to afford 3-ethyl-2-oxo-1H-1,6-naphthyridine-7-carbaldehyde (Intermediate 4, 24.00 mg, 79%) as a light-yellow foam.

1H NMR (DMSO-d6) 1.20 (3H, t), 2.55-2.62 (2H, m, overlapped with solvent DMSO peak), 7.73 (1H, s), 7.95 (1H, s), 9.03 (1H, s), 10.00 (1H, s), 12.32 (1H, br s); m/z ($ES^+$) $[M+H]^+$=203.

Intermediate 5: 3-ethyl-7-(hydroxymethyl)-1H-1,6-naphthyridin-2-one

Sodium borohydride (61.4 mg, 1.62 mmol) was added slowly to a stirred solution of 3-ethyl-2-oxo-1H-1,6-naphthyridine-7-carbaldehyde (Intermediate 4, 82 mg, 0.41 mmol) in methanol (2 mL) at 0° C. and the resulting mixture was stirred at room temperature for 1 h. Methanol was removed under vacuum and the resulting residue was purified by flash silica chromatography, elution gradient 0 to 35% MeOH in DCM. Product fractions were concentrated under reduced pressure to afford 3-ethyl-7-(hydroxymethyl)-1H-1,6-naphthyridin-2-one (Intermediate 5, 68.0 mg, 82%) as a pale-yellow solid.

1H NMR (500 MHz, DMSO-d6) 1.18 (3H, t), 2.52-2.55 (2H, m, overlapped with solvent DMSO peak), 4.59 (2H, br s), 5.52 (1H, br s), 7.33 (1H, s), 7.80 (1H, s), 8.71 (1H, s), 12.01 (1H, br s); m/z ($ES^+$) $[M+H]^+$=205.

Intermediate 6: 7-(bromomethyl)-3-ethyl-1H-1,6-naphthyridin-2-one

CBr4 (928 mg, 2.80 mmol) was added to a stirred solution of 3-ethyl-7-(hydroxymethyl)-1H-1,6-naphthyridin-2-one (Intermediate 5, 381 mg, 1.87 mmol) and triphenylphosphine (734 mg, 2.80 mmol) in CH2Cl2 (18.656 ml) at 0° C. and the resulting solution was stirred at 0° C. for 2 hours. Reaction was concentrated, and the resulting residue was purified by flash silica chromatography, elution gradient 0 to 15% MeOH in DCM. Product fractions were concentrated under reduced pressure to afford 7-(bromomethyl)-3-ethyl-1H-1,6-naphthyridin-2-one (Intermediate 6, 386 mg, 77%) as a white solid (Contains triphenyl phosphine oxide, difficult to separate). This compound was subjected to the next step without further purification.

m/z ($ES^+$) $[M]^+$=267.

Synthesis Example 1: 5-[4-[(3-ethyl-2-oxo-1H-1,6-naphthyridin-7-yl)methyl]piperazin-1-yl]-N-methyl-pyridine-2-carboxamide

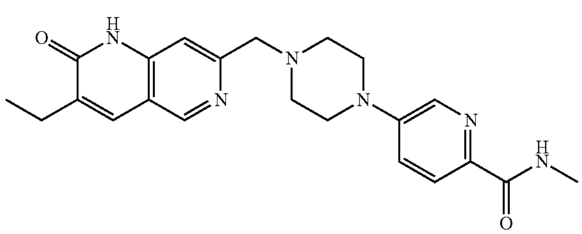 [SMILES: CCc1cc2cnc(CN3CCN(c4ccc(C(=O)NC)nc4)CC3)cc2[nH]c1=O]

DIPEA (0.059 mL, 0.34 mmol) was added to a stirred solution of 7-(bromomethyl)-3-ethyl-1H-1,6-naphthyridin-2-one (Intermediate 6, 30 mg, 0.11 mmol) and N-methyl-5-piperazin-1-yl-pyridine-2-carboxamide, 2HCl (Intermediate 13, 42.8 mg, 0.15 mmol) in acetonitrile (1 mL) at 20° C. The resulting solution was stirred at 70° C. for 2 hours. Solvent was removed under vacuum and the resulting crude material was further purified by reverse phase chromatography (RediSep Rf Gold® C18, 0 to 90% acetonitrile in water, 0.1% NH4OH as an additive).

Product fractions were concentrated under reduced pressure to dryness to afford 5-[4-[(3-ethyl-2-oxo-1H-1,6-naphthyridin-7-yl)methyl]piperazin-1-yl]-N-methyl-pyridine-2-carboxamide (Synthesis Example 1, 23.60 mg, 51.7%) as a pale-yellow solid.

1H NMR (500 MHz, DMSO-d6) 1.18 (3H, br t), 2.54 (2H, m, overlapped with solvent DMSO peak), 2.67 (4H, br s), 2.79 (3H, br d), 3.38 (4H, br s), 3.75 (2H, br s), 7.34 (1H, s), 7.42 (1H, br dd), 7.77-7.88 (2H, m), 8.29 (1H, br d), 8.40 (1H, br d), 8.75 (1H, s), 11.60-12.11 (1H, m); m/z ($ES^+$) $[M+H]^+$=407.

Synthesis Example 2: 5-[4-[(3-ethyl-2-oxo-1H-1,6-naphthyridin-7-yl)methyl]piperazin-1-yl]-6-fluoro-N-methyl-pyridine-2-carboxamide

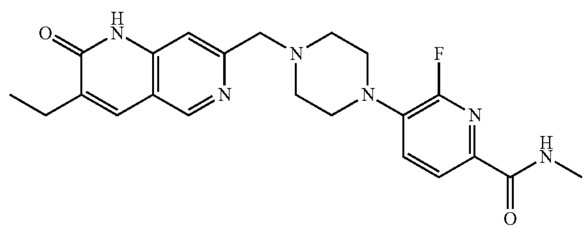

DIPEA (0.082 mL, 0.47 mmol) was added to a stirred solution of 7-(bromomethyl)-3-ethyl-1H-1,6-naphthyridin-2-one (Intermediate 6, 25 mg, 0.09 mmol) and 6-fluoro-N-methyl-5-piperazin-1-yl-pyridine-2-carboxamide, HCl (Intermediate 23, 28.3 mg, 0.10 mmol) in acetonitrile (2 mL) at 20° C. The resulting solution was stirred at 70° C. for 2 hours. Solvent was removed under vacuum. The resulting residue was purified by flash silica chromatography, elution gradient 0 to 20% MeOH in DCM. Product fractions were concentrated under reduced pressure to afford 5-[4-[(3-ethyl-2-oxo-1H-1,6-naphthyridin-7-yl)methyl]piperazin-1-yl]-6-fluoro-N-methyl-pyridine-2-carboxamide (Synthesis Example 2, 17.00 mg, 42.8%) as a pale yellow solid.

1H NMR (500 MHz, DMSO-d6) 1.18 (3H, t), 2.52-2.55 (2H, m, overlapped with solvent DMSO peak), 2.64 (4H, br s), 2.77 (3H, d), 3.20 (4H, br s), 3.70 (2H, s), 7.32 (1H, s), 7.59 (1H, dd), 7.80 (1H, s), 7.86 (1H, d), 8.31-8.49 (1H, m), 8.73 (1H, s), 11.93 (1H, br s); m/z ($ES^+$) $[M+H]^+$=425.

Synthesis Example 3: 6-chloro-5-[4-[(3-ethyl-2-oxo-1H-1,6-naphthyridin-7-yl)methyl]piperazin-1-yl]-N-methyl-pyridine-2-carboxamide

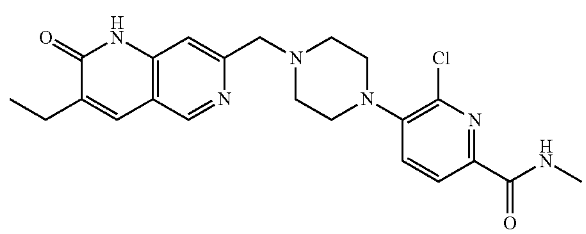 [SMILES: CCc1cc2cnc(CN3CCN(c4ccc(C(=O)NC)nc4F)CC3)cc2[nH]c1=O]

DIPEA (0.082 mL, 0.47 mmol) was added to a stirred solution of 7-(bromomethyl)-3-ethyl-1H-1,6-naphthyridin-2-one (Intermediate 6, 25 mg, 0.09 mmol) and 6-chloro-N-methyl-5-piperazin-1-yl-pyridine-2-carboxamide, 2HCl (Intermediate 47, 33.7 mg, 0.10 mmol) in acetonitrile (2 mL) at 20° C. and the resulting solution was stirred at 70° C. for 2 hours. Solvent was removed under vacuum. The resulting residue was purified by flash silica chromatography, elution gradient 0 to 20% MeOH in DCM. Product fractions were concentrated under reduced pressure to afford 6-chloro-5-[4-[(3-ethyl-2-oxo-1H-1,6-naphthyridin-7-yl)methyl]piperazin-1-yl]-N-methyl-pyridine-2-carboxamide (Synthesis Example 3, 19.20 mg, 46.5%) as a white solid.

1H NMR (500 MHz, DMSO-d6) 1.18 (3H, t), 2.53 (2H, m, overlapped with solvent DMSO peak), 2.66 (4H, br s), 2.80 (3H, d), 3.15 (4H, br s), 3.72 (2H, s), 7.33 (1H, s), 7.68 (1H, d), 7.81 (1H, s), 7.95 (1H, d), 8.43 (1H, br d), 8.74 (1H, s), 11.93 (1H, s); m/z (ES$^+$) $[M+H]^+$=441.

-continued

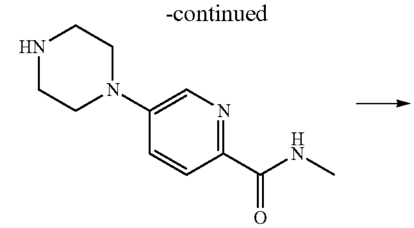

Intermediate 13

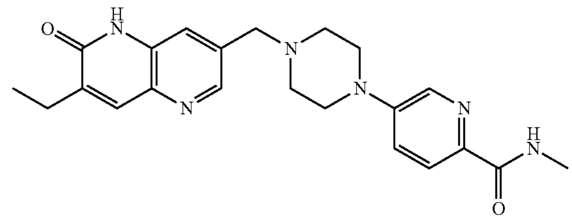

Example 4

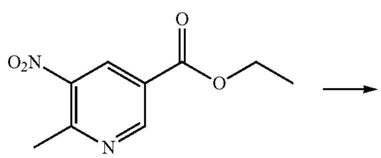

Intermediate 7

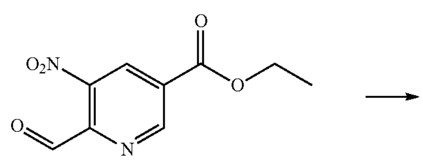

Intermediate 8

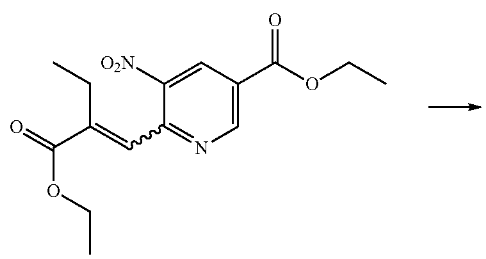

Intermediate 9

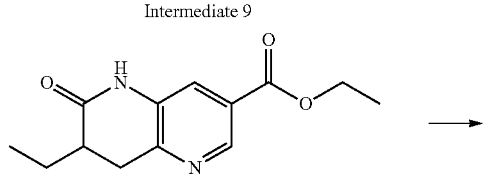

Intermediate 10

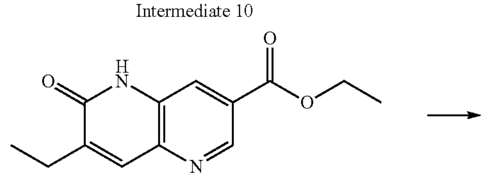

Intermediate 11

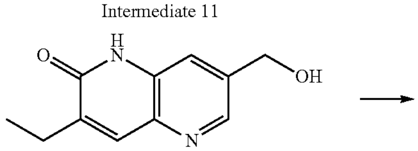

Intermediate 12

Intermediate 8: ethyl 6-formyl-5-nitro-pyridine-3-carboxylate

A mixture of ethyl 6-methyl-5-nitro-pyridine-3-carboxylate (Intermediate 7, 10 g, 47.58 mmol) and selenium dioxide (7.92 g, 71.36 mmol) in 1,4-dioxane (50 mL) was stirred at 110° C. for 20 h. The reaction mixture was cooled to room temperature, filtered through a pad of celite and the celite was washed with ethyl acetate. The combined filtrate was concentrated, and the resulting residue was purified by flash silica chromatography, elution gradient 0 to 70% ethyl acetate in hexanes. Product fractions were concentrated under reduced pressure to afford ethyl 6-formyl-5-nitro-pyridine-3-carboxylate (Intermediate 8, 9.70 g, 91%) as a brown oil. 1H NMR (500 MHz, CHLOROFORM-d) 1.48 (3H, t), 4.54 (2H, q), 8.81 (1H, d), 9.51 (1H, d), 10.32 (1H, s); m/z (ES$^+$) $[M]^+$=224.

Intermediate 9: ethyl 6-[(E)-2-ethoxycarbonylbut-1-enyl]-5-nitro-pyridine-3-carboxylate (mixture of E/Z isomers)

To a stirred solution of sodium hydride (9.63 g, 240.89 mmol) (60% in mineral oil) in anhydrous THF (100 mL) was added ethyl 2-(diethoxyphosphoryl)butanoate (60.8 g, 240.89 mmol) dropwise with an addition funnel at 0° C. to give a grey colored mixture. The resulting mixture was stirred at 0° C. for 10 min and warmed to room temperature over 10 minutes and stirred at 40° C. for 5 minutes. The reaction mixture was cooled to −78° C. and to this cooled reaction mixture was then slowly added solution of ethyl 6-formyl-5-nitro-pyridine-3-carboxylate (Intermediate 8, 22.5 g, 100.37 mmol) in 100 ml THF. The mixture was quenched with sat·$NH_4Cl$ solution, extracted with ethyl acetate. The combined the organic layers were dried over sodium $Na_2SO_4$, filtered and concentrated to give crude product. the resulting residue was purified by flash silica chromatography, elution gradient 0 to 50% ethyl acetate in hexanes. Product fractions were concentrated under reduced pressure to afford ethyl 6-[(E)-2-ethoxycarbonylbut-1-enyl]-5-nitro-pyridine-3-carboxylate (Intermediate 9, 24.30 g, 75%) as a yellow oil (1:1 and mixture of E/Z isomer). 1H NMR (500 MHz, CHLOROFORM-d) 1.13 (3H, t), 1.18 (3H, t), 1.23 (3H, t), 1.37 (3H, t), 1.45 (6H, q), 2.57 (2H, qd), 2.66 (2H, q), 4.11-4.24 (2H, m), 4.32 (2H, q), 4.45-4.56 (4H, m), 7.08 (1H, s), 7.85 (1H, s), 8.86 (2H, dd), 9.26 (1H, d), 9.43 (1H, d); m/z ($ES^+$) $[M]^+$=322.

Intermediate 10: ethyl 7-ethyl-6-oxo-7,8-dihydro-5H-1,5-naphthyridine-3-carboxylate A mixture of ethyl 6-[(E)-2-ethoxycarbonylbut-1-enyl]-5-nitro-pyridine-3-carboxylate (1:1 mixture of E/Z isomers) (Intermediate 9, 3.75 g, 11.63 mmol), Pd/C (1.857 g, 1.75 mmol) (10%) in ethanol (30 mL) was degassed, filled up with H2 (balloon), and the reaction was stirred at room temperature for overnight under H2 atmosphere. The mixture was filtered through a celite bed and the celite bed washed with ethanol. After concentration, 4M HCl in dioxanes (15 ml) was added to the resulting residue and the mixture was stirred at room temperature for 30 min. The mixture was diluted with ether and the solid was filtered off, washed with diethyl ether and dried under vacuum to afford ethyl 7-ethyl-6-oxo-7,8-dihydro-5H-1,5-naphthyridine-3-carboxylate (Intermediate 10, 2.260 g, 78%) as a white solid. 1H NMR (500 MHz, DMSO-d6) 0.94 (3H, t), 1.33 (3H, t), 1.41-1.51 (1H, m), 1.69-1.81 (1H, m), 2.41-2.48 (1H, m), 2.94 (1H, dd), 3.20 (1H, dd), 4.35 (2H, t), 7.67 (1H, d), 8.61 (1H, d), 10.32 (1H, s); m/z ($ES^+$) $[M+H]^+$=249.

Intermediate 11: ethyl 7-ethyl-6-oxo-5H-1,5-naphthyridine-3-carboxylate

Ethyl 7-ethyl-6-oxo-7,8-dihydro-5H-1,5-naphthyridine-3-carboxylate (Intermediate 10, 2.26 g, 9.10 mmol) was dissolve into 1,4-dioxane (40 mL), DDQ (2.273 g, 10.01 mmol) was added and the mixture was stirred at reflux for 3 h. Solvent was removed under reduced pressure, sat. $NaHCO_3$ solution was added and the residue stirred at room temperature for 1 hr. The solid was filtered off, washed with water followed by 10 ml of diethyl ether. The resulting solid was dried under vacuum afford ethyl 7-ethyl-6-oxo-5H-1,5-naphthyridine-3-carboxylate (Intermediate 11, 1.738 g, 78%) as a light brown solid. 1H NMR (500 MHz, DMSO-d6) 1.14-1.28 (3H, m), 1.35 (3H, t), 2.58 (2H, q), 4.38 (2H, q), 7.83 (1H, s), 8.17 (1H, s), 8.90 (1H, s), 12.05 (1H, s); m/z ($ES^+$) $[M+H]^+$=247.

Intermediate 12: 3-ethyl-7-(hydroxymethyl)-1H-1,5-naphthyridin-2-one

Lithium aluminum hydride, 2 M in THF (29.2 mL, 58.47 mmol) was added dropwise to ethyl 7-ethyl-6-oxo-5H-1,5-naphthyridine-3-carboxylate (Intermediate 11, 7.2 g, 29.24 mmol) in tetrahydrofuran (150 mL) at 0° C. over a period of 45 minutes under nitrogen. The resulting mixture was stirred at 0° C. for 1.5 hours. The reaction mixture was quenched by dropwise addition of 1 M aq HCl (29 mL). The reaction mixture was concentrated and the solid was diluted with water (~150 ml) and 29 ml of 1M HCl solution gave a yellow suspension. The solid was collected by filtration, washed with water, diethyl ether and dried to yield the crude product as a yellow solid (contaminated by some inorganic salt). This solid was suspended in a mixture of methanol and DCM (2:1) (400 ml) and heated to reflux. The solid was filtered off. This solid was resuspended in methanol/DCM mixture and repeated this procedure 5 times to get most of the product out from this mixture. The combined filtrate was then concentrated until about 100 ml and the solid was collected by filtration, washed with ether, dried under vacuum to yield 3-ethyl-7-(hydroxymethyl)-1H-1,5-naphthyridin-2-one (Intermediate 12, 4.35 g, 72.8%) as yellow solid. 1H NMR (500 MHz, DMSO-d6) 1.18 (3H, t), 2.52-2.56 (2H, m), 4.61 (2H, d), 5.44 (1H, t), 7.61 (1H, s), 7.74 (1H, s), 8.37 (1H, s), 11.87 (1H, br s); m/z (ES+) [M+H]+=205.3.

Synthesis Example 4: 5-[4-[(7-ethyl-6-oxo-5H-1,5-naphthyridin-3-yl)methyl]piperazin-1-yl]-N-methyl-pyridine-2-carboxamide

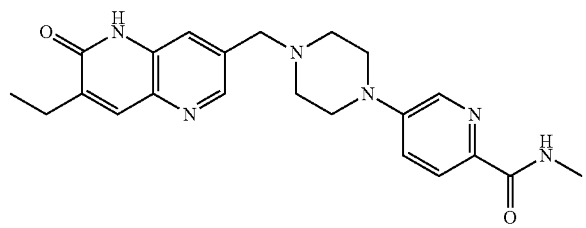 [SMILES: CCc1cc2ncc(CN3CCN(c4ccc(C(=O)NC)nc4)CC3)cc2[nH]c1=O]

Thionyl chloride (6.41 mL, 88.14 mmol) was added dropwise to a suspension of 3-ethyl-7-(hydroxymethyl)-1,5-naphthyridin-2(1H)-one (Intermediate 12, 3 g, 14.69 mmol) and N,N-dimethylformamide (0.114 mL, 1.47 mmol) in CH2Cl2 (60 mL) at 0° C. and the resulting solution was stirred at room temperature for 6 hours. The mixture was concentrated to dryness to give crude 7-(chloromethyl)-3-ethyl-1H-1,5-naphthyridin-2-one (Intermediate 17). DIPEA (12.83 mL, 73.45 mmol) was added to a stirred solution of 7-(chloromethyl)-3-ethyl-1H-1,5-naphthyridin-2-one (Intermediate 17, crude from above), potassium iodide (0.488 g, 2.94 mmol) and N-methyl-5-piperazin-1-yl-pyridine-2-carboxamide, 2HCl (Intermediate 13, 4.31 g, 14.69 mmol) in acetonitrile (50.00 mL) at 20° C. The resulting solution was stirred at 80° C. for 2 hours. Solvent was removed under vacuum. Crude material was diluted with water, basified with aq. $NaHCO_3$ solution and extracted with ethyl acetate. Organic layer was dried over sodium sulphate and concentrated to give crude product. The resulting residue was purified by flash silica chromatography, elution gradient 0 to 15% MeOH in DCM. Product fractions were concentrated under reduced pressure to afford 5-[4-[(7-ethyl-6-oxo-5H-1,5-naphthyridin-3-yl)methyl]piperazin-1-yl]-N-methyl-pyridine-2-carboxamide (Synthesis Example 4, 3.93 g, 65.8%) as an off white partially crystalline solid. 1H NMR (500 MHz, DMSO-d6) 1.19 (3H, t), 2.53-2.59 (6H, m), 2.79 (3H, d), 3.33-3.39 (4H, m), 3.66 (2H, s), 7.39 (1H, dd), 7.64 (1H, s), 7.76 (1H, s), 7.83 (1H, d), 8.27 (1H, d), 8.36-8.40 (1H, m), 8.41 (1H, d), 11.85 (1H, s); m/z ($ES^+$) $[M]^+$=406.

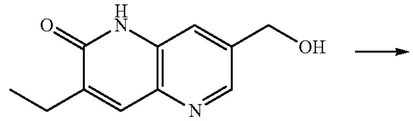

Intermediate 12

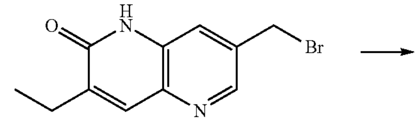

Intermediate 14

-continued

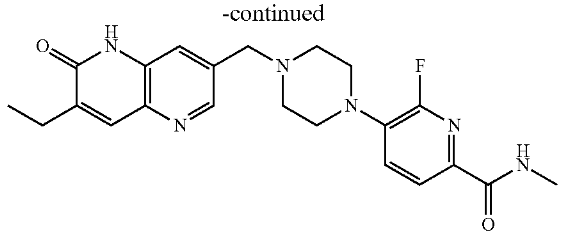

Example 5

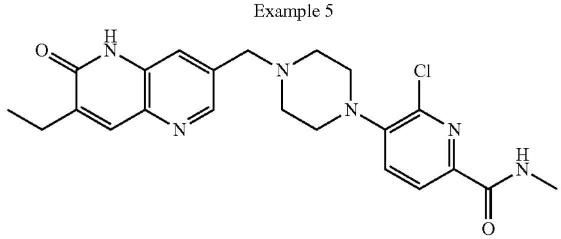

Example 6

Intermediate 14: 7-(bromomethyl)-3-ethyl-1H-1,5-naphthyridin-2-one $CBr_4$ (219 mg, 0.66 mmol) was added to a stirred solution of 3-ethyl-7-(hydroxymethyl)-1H-1,5-naphthyridin-2-one (Intermediate 12, 90 mg, 0.44 mmol) and triphenylphosphine (173 mg, 0.66 mmol) in $CH_2Cl_2$ (4 mL) at 0° C. The resulting solution was stirred at 0° C. for 2 hours. Reaction was concentrated under vacuum and the resulting residue was purified by flash silica chromatography, elution gradient 0 to 15% MeOH in DCM. Product fractions were concentrated under reduced pressure to afford 7-(bromomethyl)-3-ethyl-1H-1,5-naphthyridin-2-one (Intermediate 14, 84 mg, 71.4%) (Contains triphenyl phosphine oxide, difficult to separate). This compound was subjected to the next step without further purification.

m/z ($ES^+$) $[M]^+$=267.

Synthesis Example 5: 5-[4-[(7-ethyl-6-oxo-5H-1,5-naphthyridin-3-yl)methyl]piperazin-1-yl]-6-fluoro-N-methyl-pyridine-2-carboxamide

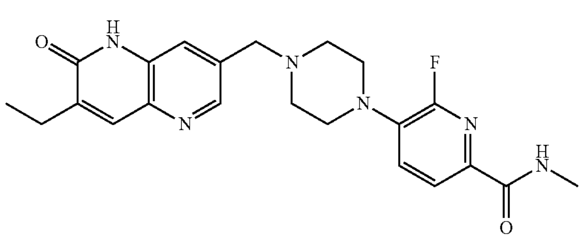

DIPEA (0.082 mL, 0.47 mmol) was added to a stirred solution of 7-(bromomethyl)-3-ethyl-1H-1,5-naphthyridin-2-one (Intermediate 14, 25 mg, 0.09 mmol) and 6-fluoro-N-methyl-5-piperazin-1-yl-pyridine-2-carboxamide, 2HCl (Intermediate 23, 32.0 mg, 0.10 mmol) in acetonitrile (2 mL) at 20° C. The resulting solution was stirred at 70° C. for 2 hours. Solvent was removed under vacuum. The resulting residue was purified by flash silica chromatography, elution gradient 0 to 20% MeOH in DCM. Product fractions were concentrated under reduced pressure to afford 5-[4-[(7-ethyl-6-oxo-5H-1,5-naphthyridin-3-yl)methyl]piperazin-1-yl]-6-fluoro-N-methyl-pyridine-2-carboxamide (Synthesis Example 5, 13.00 mg, 33%), pale yellow solid. 1H NMR (500 MHz, DMSO-d6) 1.19 (3H, t), 2.55 (2H, m, overlapped with solvent DMSO peak), 2.58 (4H, br d), 2.77 (3H, d), 3.19 (4H, br s), 3.67 (2H, s), 7.57 (1H, dd), 7.63 (1H, s), 7.76 (1H, s), 7.85 (1H, d), 8.32-8.49 (2H, m), 11.85 (1H, s); m/z ($ES^+$) $[M+H]^+$=425.

Synthesis Example 6: 6-chloro-5-[4-[(7-ethyl-6-oxo-5H-1,5-naphthyridin-3-yl)methyl]piperazin-1-yl]-N-methyl-pyridine-2-carboxamide

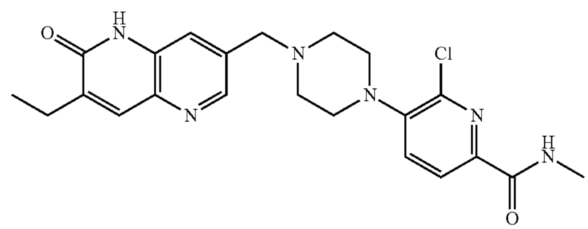 [SMILES: CCc1cc2ncc(CN3CCN(c4ccc(C(=O)NC)nc4Cl)CC3)cc2[nH]c1=O]

DIPEA (0.082 mL, 0.47 mmol) was added to a stirred solution of 7-(bromomethyl)-3-ethyl-1H-1,5-naphthyridin-2-one (Intermediate 14, 25 mg, 0.09 mmol) and 6-chloro-N-methyl-5-piperazin-1-yl-pyridine-2-carboxamide (Intermediate 48, 26.2 mg, 0.10 mmol) in acetonitrile (2 mL) at 20° C. The resulting solution was stirred at 70° C. for 2 hours. Solvent was removed under vacuum. The resulting residue was purified by flash silica chromatography, elution gradient 0 to 20% MeOH in DCM. Product fractions were concentrated under reduced pressure to afford 6-chloro-5-[4-[(7-ethyl-6-oxo-5H-1,5-naphthyridin-3-yl)methyl]piperazin-1-yl]-N-methyl-pyridine-2-carboxamide (Synthesis Example 6, 19.80 mg, 48.0%) as a pale-yellow solid. 1H NMR (500 MHz, DMSO-d6) 1.19 (3H, t), 2.55 (2H, m, overlapped with solvent DMSO peak), 2.58-2.65 (4H, m), 2.79 (3H, d), 3.13 (4H, br s), 3.68 (2H, s), 7.63 (1H, d), 7.67 (1H, d), 7.76 (1H, s), 7.94 (1H, d), 8.34-8.50 (2H, m), 11.85 (1H, s); m/z ($ES^+$) $[M+H]^+$=441.

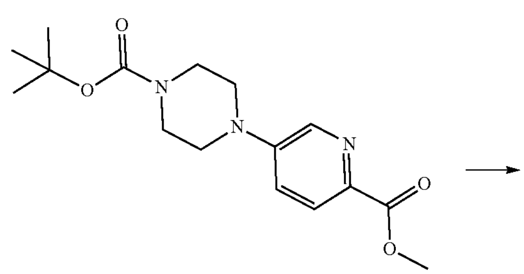

Intermediate 15

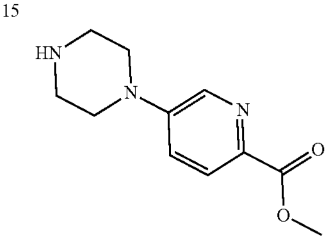

Intermediate 16

-continued

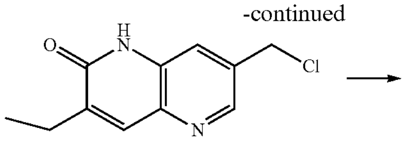

Intermediate 17

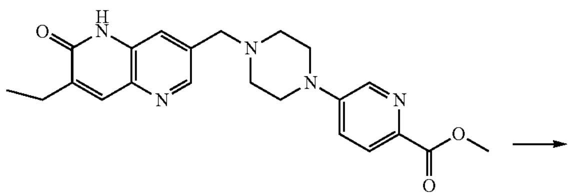

Intermediate 18

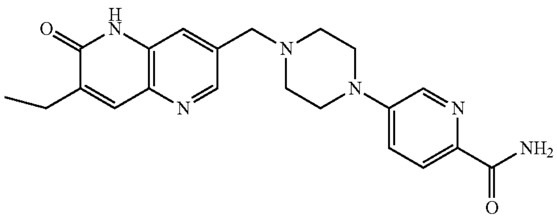

Example 7

Intermediate 16: methyl 5-piperazin-1-ylpyridine-2-carboxylate

HCl in dioxane (4.67 mL, 18.67 mmol) was added to a stirred solution of tert-butyl 4-(6-methoxycarbonyl-3-pyridyl)piperazine-1-carboxylate (Intermediate 15, 600 mg, 1.87 mmol) in MeOH (1 mL) and the resulting solution was stirred at rt for 18 hours. Solvent was removed under vacuum to give methyl 5-piperazin-1-ylpyridine-2-carboxylate, 2HCl (Intermediate 16, 543 mg, 99%) as light yellow solid.

1H NMR (500 MHz, DMSO-d6) 3.20 (4H, br s), 3.71 (4H, br s), 3.85 (3H, s), 7.58 (1H, br d), 7.99 (1H, br d), 8.43 (1H, br s), 9.73 (2H, br), 11.29-11.75 (1H, br); m/z ($ES^+$) $[M+H]^+$=222.

Intermediate 18: methyl 5-[4-[(7-ethyl-6-oxo-5H-1,5-naphthyridin-3-yl)methyl]piperazin-1-yl]pyridine-2-carboxylate DIPEA (944 μl, 5.40 mmol) was added to a stirred solution of 7-(chloromethyl)-3-ethyl-1H-1,5-naphthyridin-2-one, HCl (Intermediate 17, 200 mg, 0.77 mmol), sodium iodide (11.57 mg, 0.08 mmol) and methyl 5-piperazin-1-ylpyridine-2-carboxylate, 2HCl (Intermediate 16, 250 mg, 0.85 mmol) in acetonitrile (6774 μl) at 20° C. The resulting solution was stirred at 80° C. for 3 hours. Solvent was removed under vacuum, 0.4 mL saturated sodium bicarbonate solution and 1.5 mL acetonitrile was added and reaction was stirred for 10 min. Solid was filtered off, washed with 2 mL water followed by 1 mL acetonitrile to give methyl 5-[4-[(7-ethyl-6-oxo-5H-1,5-naphthyridin-3-yl)methyl]piperazin-1-yl]pyridine-2-carboxylate (Intermediate 18, 158 mg, 50.2%) as off white solid. 1H NMR (500 MHz, DMSO-d6) 1.19 (3H, br t), 2.54-2.61 (6H, m), 3.40 (4H, br s), 3.66 (2H, s), 3.81 (3H, s), 7.35 (1H, br dd), 7.62 (1H, s), 7.75 (1H, s), 7.88 (1H, br d), 8.28-8.47 (2H, m), 12.03 (1H, br); m/z ($ES^+$) $[M+H]^+$=408.

Synthesis Example 7: 5-[4-[(7-ethyl-6-oxo-5H-1,5-naphthyridin-3-yl)methyl]piperazin-1-yl]pyridine-2-carboxamide

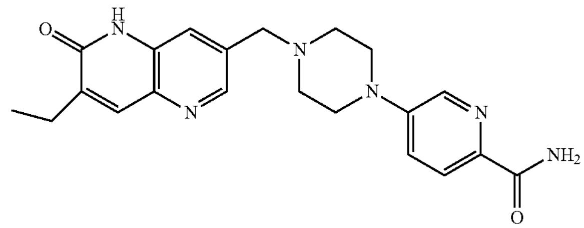 [SMILES: CCc1cc2ncc(CN3CCN(c4ccc(C(N)=O)nc4)CC3)cc2[nH]c1=O]

Ammonia in methanol (4 mL, 28.00 mmol) was added to methyl 5-[4-[(7-ethyl-6-oxo-5H-1,5-naphthyridin-3-yl)methyl]piperazin-1-yl]pyridine-2-carboxylate (Intermediate 18, 60 mg, 0.15 mmol) and The resulting solution was heated to 50° C. for 24 h (sealed tube). Reaction was cooled to room temperature and the solid was filtered off and washed with 2 mL methanol to give 5-[4-[(7-ethyl-6-oxo-5H-1,5-naphthyridin-3-yl)methyl]piperazin-1-yl]pyridine-2-carboxamide (Synthesis Example 7, 88 mg, 90%) as light brown solid. 1H NMR (500 MHz, DMSO-d6) 1.19 (3H, t), 2.56 (6H, m, overlapped with solvent DMSO peak), 3.35 (4H, br d), 3.66 (2H, s), 7.30 (1H, br s), 7.40 (1H, dd), 7.64 (1H, s), 7.76 (2H, s), 7.85 (1H, d), 8.28 (1H, d), 8.41 (1H, d), 11.61-11.98 (1H, m); m/z ($ES^+$) $[M+H]^+$=393.

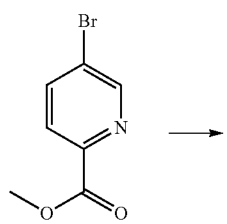

Intermediate 19

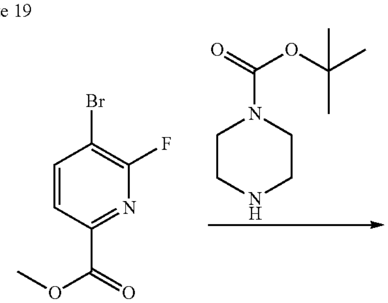

Intermediate 20

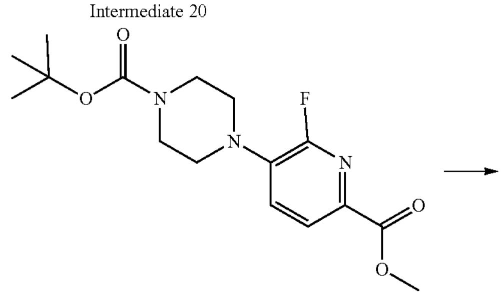

Intermediate 21

-continued

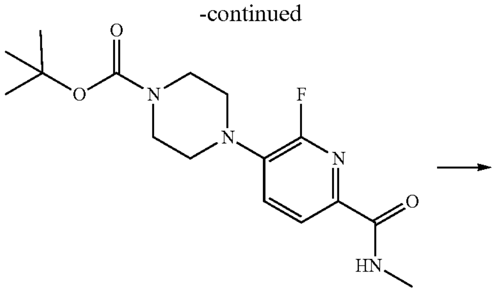

Intermediate 22

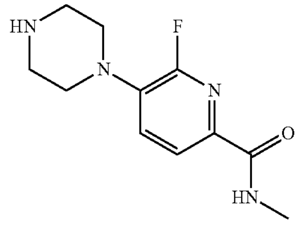

Intermediate 23

Intermediate 20: methyl 5-bromo-6-fluoro-pyridine-2-carboxylate

An oven dried flask was charged with methyl 5-bromopyridine-2-carboxylate (Intermediate 19, 6 g, 27.77 mmol) in acetonitrile (60 mL). Silver (II) fluoride (14.18 g, 97.21 mmol) was added and the mixture was stirred at room temperature for overnight. Reaction mixture was filtered through filter paper and washed with DCM. The filtrate was concentrated to give a light brown solid. The residue was suspended in a mixture of DCM and sat. $NH_4Cl$ solution and the white suspension was filtered off. The organic layer was separated, and the aqueous layer was extracted with DCM (100 ml×2). The combined organic layers were dried over $Na_2SO_4$, filtered and concentrated. The resulting residue was purified by flash silica chromatography, elution gradient 0 to 25% EtOAc in hexanes. Product fractions were concentrated under reduced pressure to dryness to afford methyl 5-bromo-6-fluoro-pyridine-2-carboxylate (Intermediate 20, 5.98 g yield 90%). $^1$H NMR (500 MHz, CHLOROFORM-d) 4.01 (3H, s), 7.93 (1H, d), 8.15 (1H, t); m/z (ES$^+$) [M]$^+$=234.

Intermediate 21: tert-butyl 4-(2-fluoro-6-methoxycarbonyl-3-pyridyl)piperazine-1-carboxylate A mixture of tert-butyl piperazine-1-carboxylate (13.11 g, 70.41 mmol), methyl 5-bromo-6-fluoro-pyridine-2-carboxylate (Intermediate 20, 10.985 g, 46.94 mmol), RuphosPd-G3 (2.5 g, 2.99 mmol) and $Cs_2CO_3$ (38 g, 116.63 mmol) in 1,4-dioxane (200 mL) was stirred at 80° C. for overnight under $N_2$. The mixture was diluted with water and ethyl acetate, the layers were separated. The aqueous layer was extracted with DCM (100 ml×2). The combined organic layers were dried over $Na_2SO_4$, filtered and concentrated. The resulting residue was purified by flash silica chromatography, elution gradient 0 to 100% EtOAc in hexanes. Product fractions were concentrated under reduced pressure to dryness to afford tert-butyl 4-(2-fluoro-6-methoxycarbonyl-3-pyridyl)piperazine-1-carboxylate (Intermediate 21, 14.00 g, 88%) as a yellow solid; 1H NMR (500 MHz, CHLOROFORM-d) 1.51 (9H, s), 3.16-3.32 (4H, m), 3.58-3.72 (4H, m), 3.98 (3H, s), 7.29-7.34 (1H, m), 8.00 (1H, d); m/z (ES$^+$) [M+H]$^+$=340.

Intermediate 22: tert-butyl 4-[2-fluoro-6-(methylcarbamoyl)-3-pyridyl]piperazine-1-carboxylate tert-butyl 4-(2-fluoro-6-methoxycarbonyl-3-pyridyl)piperazine-1-carboxylate (Intermediate 21, 12.49 g, 36.80 mmol) in methylamine (120 mL, 36.80 mmol, 33 wt % in ethanol) was stirred at r.t for 24 hrs. (sealed tube). The solvent was removed under reduced pressure. The residue was dissolved into DCM and filtered through silica gel bed and washed with ethyl acetate. The filtrate was concentrated and dried under vacuum to afford tert-butyl 4-[2-fluoro-6-(methylcarbamoyl)-3-pyridyl]piperazine-1-carboxylate (Intermediate 22, 12.45 g, 100%) as a yellow solid. 1H NMR (500 MHz, DMSO-d6) 1.42 (9H, s), 2.77 (3H, d), 3.04-3.16 (4H, m), 3.43-3.56 (4H, m), 7.59 (1H, dd), 7.80-7.93 (1H, m), 8.41 (1H, q); m/z (ES$^+$) [M+H]$^+$=340.

Intermediate 23: 6-fluoro-N-methyl-5-piperazin-1-yl-pyridine-2-carboxamide

HCl (4M in dioxane, 100 ml, 400.00 mmol) was added to a solution of tert-butyl 4-[2-fluoro-6-(methylcarbamoyl)-3-pyridyl]piperazine-1-carboxylate (Intermediate 22, 12.5 g, 36.94 mmol) in 1,4-dioxane (50 mL) at 0° C. the reaction was stirred for 5 h during which the temperature was warmed to room temperature to give a yellow suspension. The suspension was diluted with ether, solid was filtered off and washed with ether. This solid was dried under vacuum to afford 6-fluoro-N-methyl-5-piperazin-1-yl-pyridine-2-carboxamide, 2HCl (Intermediate 23, 11.42 g, 99%) as a light-yellow solid. 1H NMR (500 MHz, DMSO-d6) δ ppm 2.8 (d, J=4.6 Hz, 3H) 3.3 (br s, 4H) 3.4 (br d, J=4.4 Hz, 4H) 7.6-7.7 (m, 1H) 7.9 (d, J=8.1 Hz, 1H) 8.4 (br d, J=4.4 Hz, 1H) 9.0-9.3 (m, 2H); m/z (ES$^+$) [M+H]$^+$=239

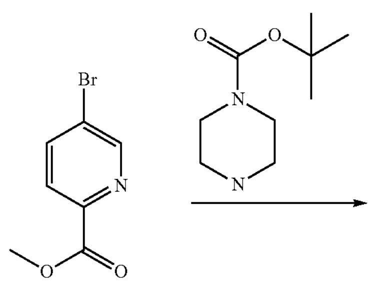

Intermediate 19

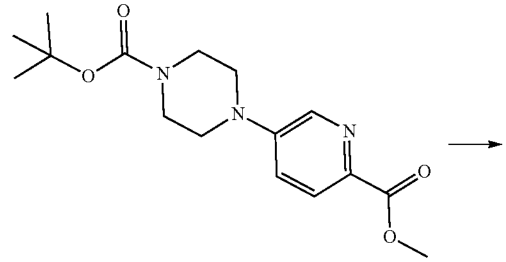

Intermediate 15

-continued

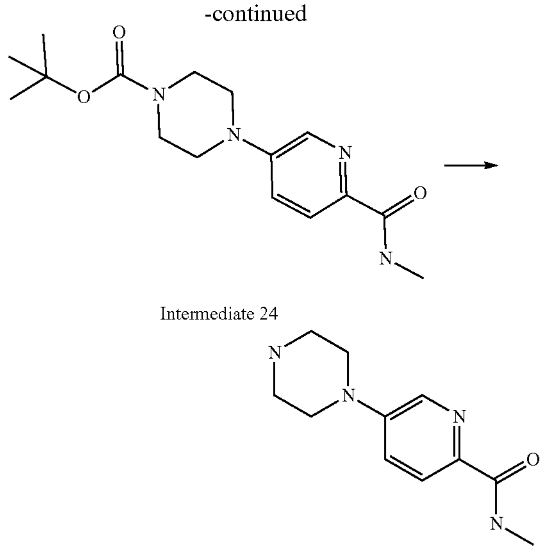

Intermediate 24

Intermediate 13

Intermediate 15: tert-butyl 4-(6-methoxycarbonyl-3-pyridyl)piperazine-1-carboxylate Ruphos Pd G3 (4.07 g, 4.86 mmol) was added to a degassed mixture of methyl 5-bromopyridine-2-carboxylate (Intermediate 19, 30 g, 138.87 mmol), tert-butyl piperazine-1-carboxylate (27.2 g, 145.81 mmol), $Cs_2CO_3$ (90 g, 277.73 mmol) in 1,4-dioxane (200 mL) and the mixture was stirred at 110° C. for 6 hrs under $N_2$ atmosphere. The mixture was then cooled to room temperature, diluted with water, extracted with ethyl acetate (150 ml×3). Combined organic layers were dried over anhydrous $Na_2SO_4$ and filtered. To this filtrate was added 3-(Diethylenetriamino)propyl-functionalized silica gel (12 g, 1.3 mmol/g loading) and the mixture was stirred at r.t for 1 hr. The mixture was filtered, and the filtrate was concentrated to ~100 ml. The crystalline yellow solid was filtered off, washed with ether and dried under vacuum to afford tert-butyl 4-(6-methoxycarbonyl-3-pyridyl)piperazine-1-carboxylate (Intermediate 15, 26.36 g, 82 mmol, 59.1%) as a yellow solid. 1H NMR (500 MHz, CHLOROFORM-d) 1.50 (9H, s), 3.31-3.42 (4H, m), 3.56-3.68 (4H, m), 3.98 (3H, s), 8.04 (1H, d), 8.37 (1H, d); m/z ($ES^+$) $[M+H]^+$=322.

Intermediate 24: tert-butyl 4-[6-(methylcarbamoyl)-3-pyridyl]piperazine-1-carboxylate Methylamine (100 ml, 1155.26 mmol, 40% in water) was added to a solution of tert-butyl 4-(6-methoxycarbonyl-3-pyridyl)piperazine-1-carboxylate (Intermediate 15, 36 g, 112.02 mmol) in MeOH (100 mL) and the reaction was stirred at room temperature for 4 hs to give a white suspension. The mixture was concentrated, the residue was partitioned between sat. $NH_4Cl$ solution and DCM, the layers were separated. The aqueous layer was extracted with DCM, the organic layers were combined, washed with brine, dried over $Na_2SO_4$, filtered and concentrated to give tert-butyl 4-[6-(methylcarbamoyl)-3-pyridyl]piperazine-1-carboxylate (Intermediate 24, 35.9 g, 100%) as a yellow solid. 1H NMR (500 MHz, CHLOROFORM-d) 1.49 (9H, s), 3.02 (3H, d), 3.26-3.35 (4H, m), 3.58-3.67 (4H, m), 7.23 (1H, dd), 7.81 (1H, br d), 8.07 (1H, d), 8.16 (1H, d); m/z ($ES^+$) $[M+H]^+$=321.

Intermediate 13: carboxylate N-methyl-5-piperazin-1-yl-pyridine-2-carboxamide HCl (4M in dioxane, 150 ml, 600.00 mmol) was added to a suspension of tert-butyl 4-[6-(methylcarbamoyl)-3-pyridyl]piperazine-1-carboxylate (Intermediate 24, 35.9 g, 112.05 mmol) in MeOH (50 mL) and the resulting orange suspension was stirred at r.t for 4 hr. About 80 ml of solvent was removed under reduced pressure and the mixture was diluted with ether and hexanes (200 ml, 1/1). The solid was collected by filtration, washed with hexanes, dried and dried under vacuum to afford N-methyl-5-piperazin-1-yl-pyridine-2-carboxamide, 2HCl salt (Intermediate 13, 37.0 g, 100%) as a yellow solid. 1H NMR (500 MHz, DMSO-d6) 2.79 (3H, d), 3.22 (4H, br s), 3.53-3.67 (4H, m), 7.51 (1H, dd), 7.91 (1H, d), 8.33 (1H, d), 8.50 (1H, br s), 9.19-9.49 (2H, m); m/z ($ES^+$) $[M+H]^+$=221

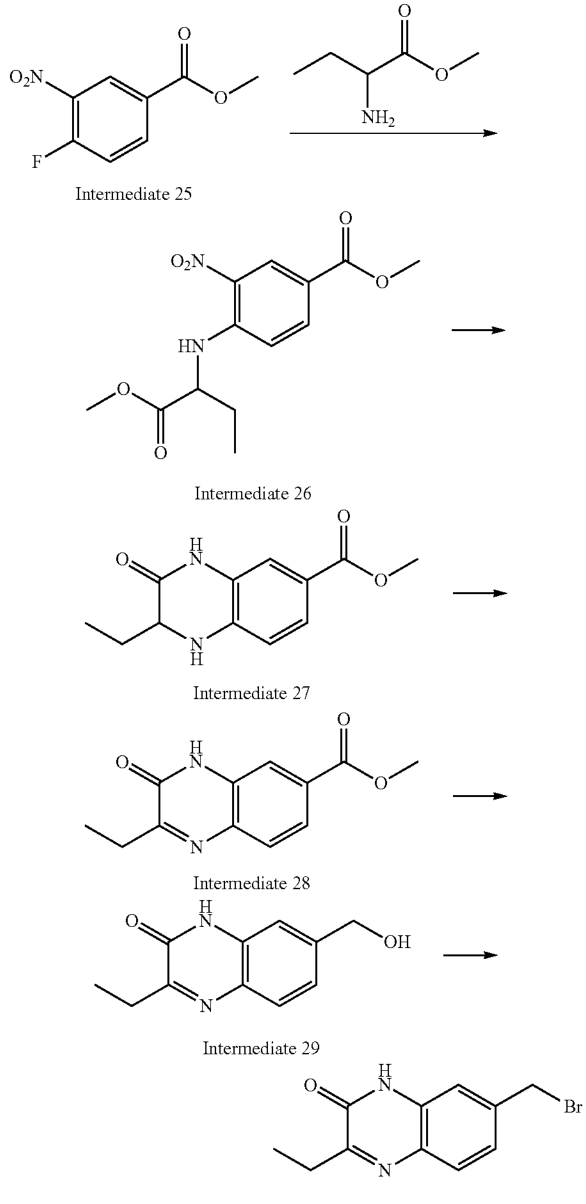

Intermediate 25

Intermediate 26

Intermediate 27

Intermediate 28

Intermediate 29

Intermediate 30

Intermediate 26: methyl 4-(1-methoxycarbonylpropylamino)-3-nitro-benzoate sodium hydrogen carbonate (27.0 g, 321.39 mmol) was added portion wise to a stirred mixture of methyl 4-fluoro-3-nitrobenzoate (Intermediate 25, 16, 80.35 mmol), and methyl 2-aminobutanoate, HCl (14.81 g, 96.42 mmol) in THF (100 mL). The reaction mixture was stirred at room temperature for overnight. The reaction was quenched by addition of water, extracted with ethyl acetate. The combined organic layer was washed with saturated aq. $NaHCO_3$ solution, organic layer was dried over $MgSO_4$ and concentrated to dryness to give methyl 4-(1-methoxycarbonylpropylamino)-3-nitro-benzoate (Intermediate 26, 22.86 g, 96%) as a bright yellow solid. 1H NMR (500 MHz, DMSO-d6) 0.91 (3H, t), 1.75-2.12 (2H, m), 3.75 (3H, s), 3.85 (3H, s), 4.63-4.82 (1H, m), 7.15 (1H, d), 8.00 (1H, dd), 8.52-8.76 (2H, m).

Intermediate 27: methyl 2-ethyl-3-oxo-2,4-dihydro-1H-quinoxaline-6-carboxylate

Pd/C (4.15 g, 3.90 mmol) was added portion wise to a stirred solution of methyl 4-(1-methoxycarbonylpropylamino)-3-nitro-benzoate (Intermediate 26, 23.1 g, 77.97 mmol) in MeOH (300 mL) and the resulting slurry was stirred under $H_2$ atmosphere at room temperature for 30 h. Methanol was removed under vacuum, 150 mL DMF was added and the mixture was stirred for 10 min. The palladium catalyst was filtered off on ceilite, washed with 50 mL of DMF (Material has very low solubility in organic solvents like MeOH/DCM/EtOAc). The filtrate was concentrated in Genevac to give methyl 2-ethyl-3-oxo-2,4-dihydro-1H-quinoxaline-6-carboxylate (Intermediate 27, 15.80 g, 87%) as a gray colored solid. Material was analyzed by NMR and subjected to the next step without purification. 1H NMR (500 MHz, DMSO-d6) 0.91 (3H, t), 1.63-1.73 (2H, m), 3.75 (3H, s), 3.90 (1H, td), 6.71 (1H, d), 6.84 (1H, s), 7.33 (1H, d), 7.41 (1H, dd), 10.39 (1H, s); m/z ($ES^+$) $[M]^+$=235.

Intermediate 28: methyl 2-ethyl-3-oxo-4H-quinoxaline-6-carboxylate

DDQ (15.87 g, 69.92 mmol) was added to a suspension of methyl 2-ethyl-3-oxo-2,4-dihydro-1H-quinoxaline-6-carboxylate (Intermediate 27, 15.6 g, 66.59 mmol) in 1,4-dioxane (150 mL). The reaction mixture was stirred for overnight at room temperature. The mixture was slowly added to saturated aq $NaHCO_3$ solution (~500 ml) and stirred at room temperature for 20 min. The precipitate was filtered, washed with water (100 ml) and dried to yield methyl 2-ethyl-3-oxo-4H-quinoxaline-6-carboxylate as an off white solid (Intermediate 28, 11.40 g, 73.7%). 1H NMR (500 MHz, DMSO-d6) 1.23 (3H, t), 2.83 (2H, q), 3.89 (3H, s), 7.73-7.86 (2H, m), 7.89 (1H, d), 12.45 (1H, s); m/z ($ES^+$) $[M+H]^+$=233.

Intermediate 29: 3-ethyl-7-(hydroxymethyl)-1H-quinoxalin-2-one

Lithium aluminum hydride, 2 M in THF (49.1 mL, 98.17 mmol) was added dropwise to a slurry of methyl 2-ethyl-3-oxo-4H-quinoxaline-6-carboxylate (Intermediate 28, 11.4 g, 49.09 mmol) in tetrahydrofuran (350 mL) at 0° C. over a period of 50 minutes under nitrogen atmosphere. The resulting mixture was stirred at 0° C. for 1.5 hours. The reaction mixture was slowly poured into 1 M aq HCl (300 mL) at 0° C. The reaction mixture was extracted with ethyl acetate (~300 ml×2) followed by extraction with DCM/methanol (5:1) (150 ml×3). The combined organic layers were concentrated to 300 ml and diluted with ether (200 ml) to give a suspension. The solid was collected by filtration, washed with ether, dried under vacuum to yield 3-ethyl-7-(hydroxymethyl)-1H-quinoxalin-2-one (Intermediate 29, 8.00 g, 80%). 1H NMR (500 MHz, DMSO-d6) 1.22 (3H, t), 2.80 (2H, q), 4.59 (2H, s), 5.19-5.61 (1H, m), 7.19 (1H, dd), 7.28 (1H, s), 7.66 (1H, d), 12.28 (1H, br s); m/z ($ES^+$) $[M+H]^+$=205.

Intermediate 30: 7-(bromomethyl)-3-ethyl-1H-quinoxalin-2-one

Hydrogen bromide (60 ml, 48 wt % in water) was added to 3-ethyl-7-(hydroxymethyl)-1H-quinoxalin-2-one (Intermediate 29, 7.8 g, 38.19 mmol) (results in clear brown solution) and the mixture was stirred at 80° C. for 8 hrs, the reaction mixture was cooled to room temperature, poured to 150 mL iced water to give an off-white precipitate. The solid was filtered under vacuum and washed with water followed by diethyl ether and dried to give 7-(bromomethyl)-3-ethyl-1H-quinoxalin-2-one as a beige solid (Intermediate 30, 11.10 g, 84%) with 80% purity. 1H NMR (500 MHz, DMSO-d6) 1.20 (3H, t), 2.79 (2H, q), 4.79 (2H, s), 7.27-7.38 (2H, m), 7.69 (1H, d), 12.34 (1H, br s); m/z ($ES^+$) $[M]^+$=267.0.

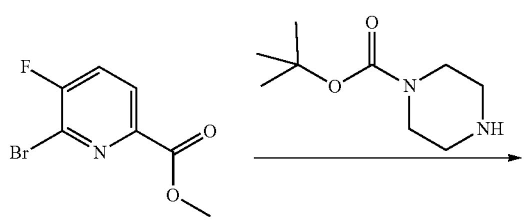

Intermediate 31

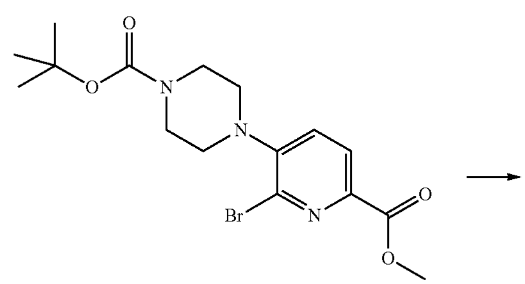

Intermediate 32

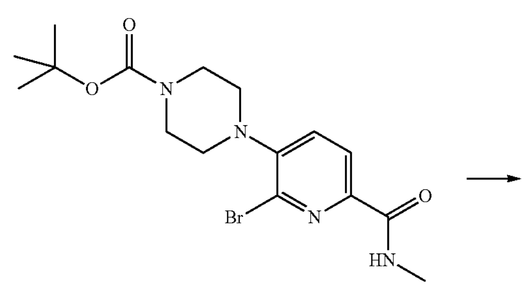

Intermediate 33

-continued

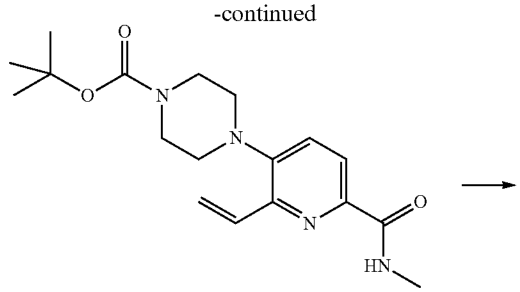

Intermediate 34

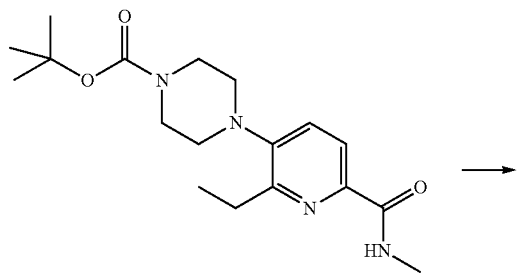

Intermediate 35

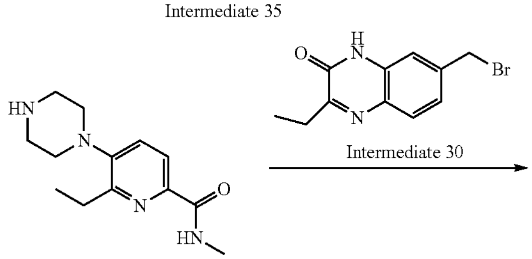

Intermediate 36

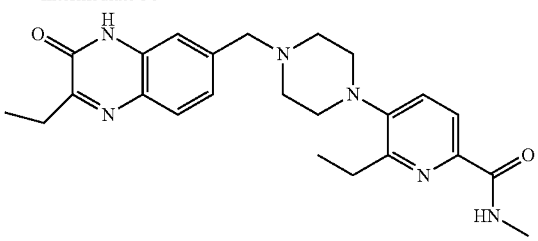

Example 8

Intermediate 32: tert-butyl 4-(2-bromo-6-methoxycarbonyl-3-pyridyl)piperazine-1-carboxylate A mixture of tert-butyl piperazine-1-carboxylate (Intermediate 31, 2.57 g, 13.80 mmol), methyl 6-bromo-5-fluoropyridine-2-carboxylate (1.9 g, 8.12 mmol) and potassium carbonate (1.459 g, 10.55 mmol) in DMF (20 mL) was stirred at 110° C. for 5 hours, LCMS indicated full conversion. The mixture was cooled to r.t, diluted with DCM and water, the layers were separated. The water layer was extracted twice with DCM and the combined organic layers were dried over anhydrous $Na_2SO_4$, filtered and concentrated. The resulting residue was purified by flash silica chromatography, elution gradient 0 to 50% EtOAc in hexanes. Product fractions were concentrated under reduced pressure to dryness to afford tert-butyl 4-(2-bromo-6-methoxycarbonyl-3-pyridyl)piperazine-1-carboxylate (Intermediate 32, 2.200 g, 67.7%) as a light-yellow solid. 1H NMR (500 MHz, CHLOROFORM-d) 1.50 (9H, s), 3.05-3.20 (4H, m), 3.58-3.72 (4H, m), 3.98 (3H, s), 7.31 (1H, d), 8.06 (1H, d); m/z ($ES^+$) $[M+H]^+$=400.

Intermediate 33: tert-butyl 4-[2-bromo-6-(methylcarbamoyl)-3-pyridyl]piperazine-1-carboxylate A sealed pressure vessel was charged with tert-butyl 4-(2-bromo-6-methoxycarbonyl-3-pyridyl)piperazine-1-carboxylate (Intermediate 32, 2.2 g, 5.50 mmol) and methylamine (22 ml, 176.72 mmol) (33 wt. % in ethanol) and the mixture was heated at 60° C. for 2 hours, LCMS indicated full conversion. The mixture was concentrated, and the resulting residue was purified by flash silica chromatography, elution gradient 0 to 80% EtOAc in hexanes. Product fractions were concentrated under reduced pressure to dryness to afford tert-butyl 4-[2-bromo-6-(methylcarbamoyl)-3-pyridyl]piperazine-1-carboxylate (Intermediate 33, 2.200 g, 100%) as a white solid. 1H NMR (500 MHz, CHLOROFORM-d) 1.50 (9H, s), 3.02 (3H, d), 3.05-3.14 (4H, m), 3.56-3.74 (4H, m), 7.36 (1H, d), 7.68 (1H, br d), 8.11 (1H, d); m/z ($ES^+$) $[M+H]^+$=399.

Intermediate 34: tert-butyl 4-[6-(methylcarbamoyl)-2-vinyl-3-pyridyl]piperazine-1-carboxylate A mixture of tert-butyl 4-[2-bromo-6-(methylcarbamoyl)-3-pyridyl]piperazine-1-carboxylate (Intermediate 33, 200 mg, 0.50 mmol), tributyl(vinyl)stannane (0.161 ml, 0.55 mmol) and 2nd gen XPhos Pd cycle (19.71 mg, 0.03 mmol) in 1,4-dioxane (5 ml) was stirred at 100° C. under N2 for 2.5 hr, LCMS indicated full conversion. The mixture was diluted with DCM, washed with sat. $NH_4Cl$, the organic layer was dried (anhydrous $Na_2SO_4$), filtered and concentrated. The resulting residue was purified by flash silica chromatography, elution gradient 0 to 80% EtOAc in hexanes. Product fractions were concentrated under reduced pressure to dryness to afford tert-butyl 4-[6-(methylcarbamoyl)-2-vinyl-3-pyridyl]piperazine-1-carboxylate (Intermediate 34, 174 mg, 100%) as a white solid. m/z ($ES^+$) $[M+H]^+$= 347

Intermediate 35: tert-butyl 4-[2-ethyl-6-(methylcarbamoyl)-3-pyridyl]piperazine-1-carboxylate Pd/C (53.5 mg, 0.05 mmol) (10 wt % dry basis, wet load) was added to a solution of tert-butyl 4-[6-(methylcarbamoyl)-2-vinyl-3-pyridyl]piperazine-1-carboxylate (Intermediate 34, 174 mg, 0.50 mmol) MeOH (6 mL). The flask was degassed and refilled with $H_2$ (balloon). The mixture was stirred at r.t for overnight. LCMS indicated the reaction was not complete. More Pd/C (53.5 mg, 0.05 mmol), was added and the resulting mixture was stirred at r.t for 5 hrs under H2 atmosphere. The mixture was filtered through a pad of celite, washed with methanol, the filtrate was concentrated to dryness to yield tert-butyl 4-[2-ethyl-6-(methylcarbamoyl)-3-pyridyl]piperazine-1-carboxylate (Intermediate 35, 172 mg, 98%) as a colorless residue. 1H NMR (500 MHz, CHLOROFORM-d) 1.37 (3H, t), 1.51 (9H, s), 2.82-2.95 (6H, m), 3.05 (3H, d), 3.57-3.73 (4H, m), 7.39 (1H, d), 7.93-8.13 (2H, m); m/z ($ES^+$) $[M]^+$=348.

Intermediate 36: 6-ethyl-N-methyl-5-piperazin-1-yl-pyridine-2-carboxamide

A mixture of tert-butyl 4-[2-ethyl-6-(methylcarbamoyl)-3-pyridyl]piperazine-1-carboxylate (Intermediate 35, 172 mg, 0.49 mmol) in HCl (4M in dioxane, 8 ml, 32.00 mmol)

was stirred at r.t for 1 hr to give a white suspension. The mixture was diluted with ether and the solid filtered off and dried under vacuum to give 6-ethyl-N-methyl-5-piperazin-1-yl-pyridine-2-carboxamide, 2HCl (Intermediate 36, 159 mg, 100%) as a light-yellow solid. 1H NMR (500 MHz, DMSO-d6) 1.31 (3H, t), 2.74-2.86 (5H, m), 3.00-3.14 (4H, m), 3.24 (4H, br s), 7.57 (1H, d), 7.82 (1H, d), 8.43 (1H, br d), 9.20 (2H, br s); m/z (ES$^+$) $[M+H]^+$=249.

Synthesis Example 8: 6-ethyl-5-[4-[(2-ethyl-3-oxo-4H-quinoxalin-6-yl)methyl]piperazin-1-yl]-N-methyl-pyridine-2-carboxamide

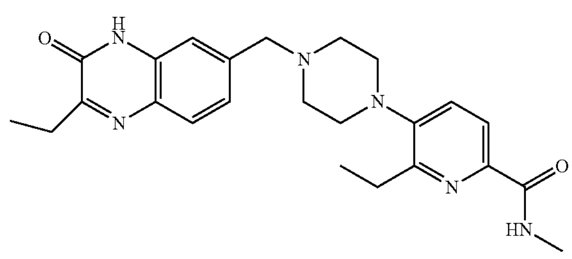 [SMILES: CCc1nc(C(=O)NC)ccc1N1CCN(Cc2ccc3nc(CC)c(=O)[nH]c3c2)CC1]

DIPEA (0.203 mL, 1.17 mmol) was added to a suspension of 6-ethyl-N-methyl-5-piperazin-1-yl-pyridine-2-carboxamide, 2HCl (Intermediate 36, 75 mg, 0.23 mmol) and 7-(bromomethyl)-3-ethyl-1H-quinoxalin-2-one (Intermediate 30, 69.3 mg, 0.23 mmol) in acetonitrile (3 mL). The resulting mixture was stirred at 60° C. for 3 hrs, LCMS indicated full conversion. The mixture was cooled to r.t, concentrated, the residue was purified on Gilson reverse phase column (eluted with 0 to 95% ACN/water/0.1% TFA, 15 min run, collected from 5 to 9 min). The product containing fractions were concentrated and the residue was then dissolved into methanol and DCM. 300 mgs of tetraalkylammonium carbonite, polymer-bound (40-90 mesh, 2.5-3.5 mmol/g) and the mixture was stirred at r.t for 10 min. The mixture was then filtered and washed with methanol. The filtrate was concentrated, redissolved into a mixture of water/CAN and this mixture was lyophilized to dryness to yield 6-ethyl-5-[4-[(2-ethyl-3-oxo-4H-quinoxalin-6-yl)methyl]piperazin-1-yl]-N-methyl-pyridine-2-carboxamide (Synthesis Example 8, 60.0 mg, 59.1%) as a light-yellow solid. 1H NMR (500 MHz, DMSO-d6) 1.22 (3H, t), 1.30 (3H, t), 2.54-2.69 (2H, m), 2.72-2.86 (7H, m), 2.93 (4H, br s), 3.26 (2H, s), 3.64 (2H, s), 7.17-7.33 (2H, m), 7.52 (1H, d), 7.69 (1H, br d), 7.80 (1H, d), 8.40 (1H, br d), 12.25 (1H, br s); m/z (ES$^+$) $[M+H]^+$=435.

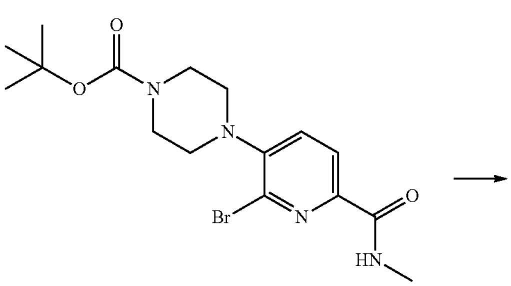

Intermediate 33

-continued

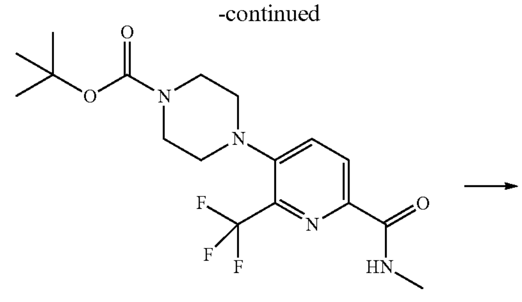

Intermediate 37

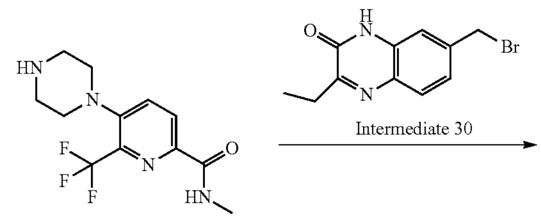

Intermediate 38

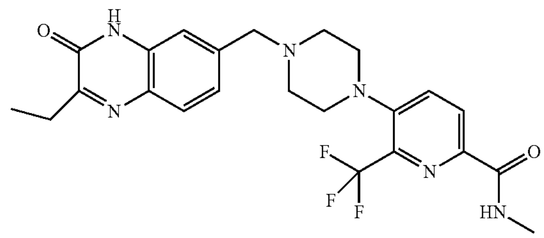

Example 9

Intermediate 37: tert-butyl 4-[6-(methylcarbamoyl)-2-(trifluoromethyl)-3-pyridyl]piperazine-1-carboxylate To a well stirred mixture of silver(I) fluoride (176 mg, 1.39 mmol) in DMF (2 mL), trimethyl(trifluoromethyl) silane (0.247 mL, 1.67 mmol) was added at room temperature. The mixture was stirred for 20 min which followed by addition of copper powder (133 mg, 2.09 mmol). After stirred for 4 h the reaction mixture turned to blue color (indicator of the formation of $CuCF_3$). tert-butyl 4-(2-bromo-6-methoxycarbonyl-3-pyridyl)piperazine-1-carboxylate (Intermediate 33, 150 mg, 0.38 mmol) was added to the mixture and the resulting dark mixture was stirred at 90° C. for 18 hrs gave a brown suspension. LCMS indicated full conversion. The mixture was diluted with ethyl acetate and the solid was filtered off. The filtrate was washed with water followed by wash with brine. The organic layer was dried over anhydrous $Na_2SO_4$, filtered and concentrated. The resulting residue was purified by flash silica chromatography, elution gradient 0 to 70% EtOAc in hexanes. Product fractions were concentrated under reduced pressure to dryness to afford tert-butyl 4-[6-(methylcarbamoyl)-2-(trifluoromethyl)-3-pyridyl]piperazine-1-carboxylate (Intermediate 37, 146 mg, 100%) as a yellow residue. 1H NMR (500 MHz, CHLOROFORM-d) 1.50 (9H, s), 2.93-3.03 (4H, m), 3.05 (3H, d), 3.55-3.69 (4H, m), 7.71 (1H, d), 7.81 (1H, br d), 8.33 (1H, d); m/z (ES$^+$) $[M+H]^+$=389.

Intermediate 38: N-methyl-5-piperazin-1-yl-6-(trifluoromethyl)pyridine-2-carboxamide A mixture of tert-butyl 4-[6-(methylcarbamoyl)-2-(trifluoromethyl)-3-pyridyl]piperazine-1-carboxylate (Intermediate 37, 146 mg, 0.38 mmol) in HCl (4M in dioxane, 8 ml, 32.00 mmol) was stirred at r.t for 2 hrs. LCMS indicated full conversion. The solvent was concentrated to the volume 2 ml, the mixture was diluted with ether/hexanes (15 ml, 5/1). The Solid was filtered off and dried under vacuum to afford N-methyl-5-piperazin-1-yl-6-(trifluoromethyl)pyridine-2-carboxamide, 2HCl (Intermediate 38, 127 mg, 94%) as a pink solid. 1H NMR (500 MHz, DMSO-d6) 2.83 (3H, d), 3.21 (8H, br s), 8.09 (1H, d), 8.23 (1H, d), 8.46 (1H, br d), 9.08 (2H, br d); m/z (ES$^+$) [M+H]$^+$=289.

Synthesis Example 9: 5-[4-[(2-ethyl-3-oxo-4H-quinoxalin-6-yl)methyl]piperazin-1-yl]-N-methyl-6-(trifluoromethyl)pyridine-2-carboxamide

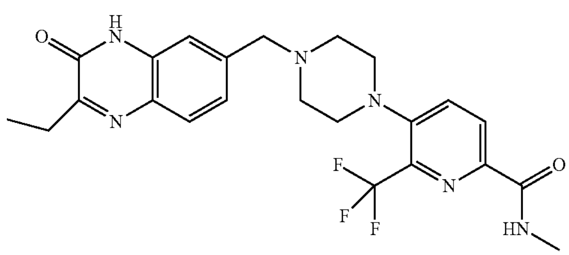 [SMILES: CCc1nc2ccc(CN3CCN(c4ccc(C(=O)NC)nc4C(F)(F)F)CC3)cc2[nH]c1=O]

DIPEA (0.121 mL, 0.69 mmol) was added to a suspension of N-methyl-5-piperazin-1-yl-6-(trifluoromethyl)pyridine-2-carboxamide, 2HCl (Intermediate 38, 50 mg, 0.14 mmol) and 7-(bromomethyl)-3-ethylquinoxalin-2(1H)-one (Intermediate 30, 46.2 mg, 0.14 mmol) in acetonitrile (3 mL) and the mixture was stirred at 60° C. for 3 hrs. The mixture was cooled to r.t, concentrated, the residue was purified on Gilson reverse phase column (eluted with 0 to 95% ACN/water/0.1% TFA). The product containing fractions were concentrated at room temperature. The reside was then dissolved into methanol and DCM followed by addition of 250 mg of tetraalkylammonium carbonite polymer-bound (40-90 mesh, 2.5-3.5 mmol/g) and the mixture was stirred at room temperature for 10 min. The solid was then filtered off, washed with methanol and the filtrate was concentrated to give solid. This solid was then redissolved into a mixture of water/CH3CN and lyophilized to dryness to afford 5-[4-[(2-ethyl-3-oxo-4H-quinoxalin-6-yl)methyl]piperazin-1-yl]-N-methyl-6-(trifluoromethyl)pyridine-2-carboxamide (Synthesis Example 9, 40.0 mg, 60.9%) as a white solid. 1H NMR (500 MHz, CHLOROFORM-d) 1.40 (3H, t), 2.70 (4H, br s), 2.98-3.08 (5H, m), 3.12 (4H, br s), 3.72 (2H, br s), 7.29-7.32 (1H, m), 7.37 (1H, dd), 7.74 (1H, d), 7.79-7.88 (2H, m), 8.33 (1H, d), 11.06 (1H, br s); m/z (ES$^+$) [M+H]$^+$=475.

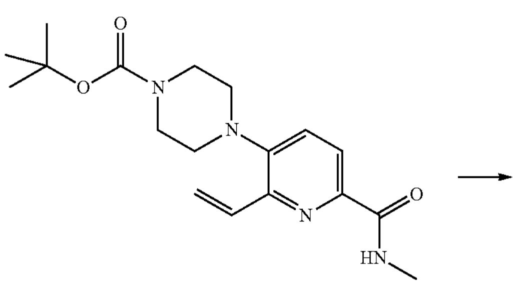

Intermediate 34

-continued

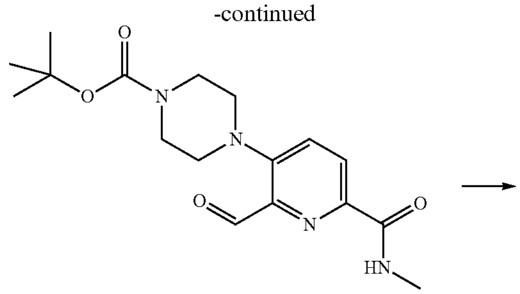

Intermediate 39

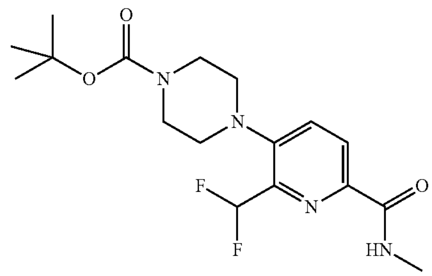

Intermediate 40

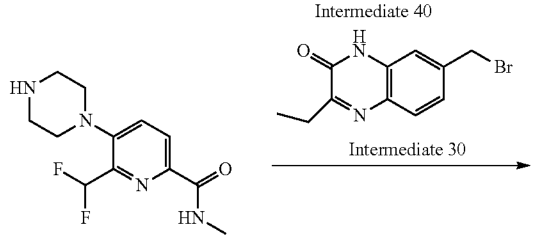

Intermediate 41

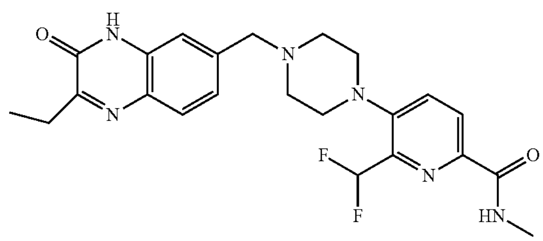

Example 10

Intermediate 39: tert-butyl 4-[2-formyl-6-(methylcarbamoyl)-3-pyridyl]piperazine-1-carboxylate Osmium tetroxide in $H_2O$ (0.050 mL, 6.35 μmol) was added to a solution of tert-butyl 4-[6-(methylcarbamoyl)-2-vinyl-3-pyridyl]piperazine-1-carboxylate (Intermediate 34, 110 mg, 0.32 mmol), 2,6-lutidine (0.074 mL, 0.64 mmol) and sodium periodate (272 mg, 1.27 mmol) in THF (5 mL)/water (1 mL)/tert-butanol (0.304 mL, 3.18 mmol) and the mixture was stirred at rt for overnight to give a yellow suspension. LCMS and TLC indicated full conversion. Reaction was diluted with water and extracted with ethyl acetate. After concentration the resulting residue was purified by flash silica chromatography, elution gradient 0 to 100% EtOAc in hexanes. Product fractions were concentrated under reduced pressure to dryness to afford tert-butyl 4-[2-formyl-6-(methylcarbamoyl)-3-pyridyl]piperazine-1-carboxylate (Intermediate 39, 100 mg, 90%) as a yellow solid. 1H NMR (500 MHz, CHLOROFORM-d) 1.50 (9H, s), 3.07 (3H, d), 3.14-3.29 (4H, m), 3.66-3.79 (4H, m), 7.49 (1H, d), 7.86 (1H, br d), 8.28 (1H, d), 10.10 (1H, s). m/z ($ES^+$) $[M+H]^+$=349.

Intermediate 40: tert-butyl 4-[2-(difluoromethyl)-6-(methylcarbamoyl)-3-pyridyl]piperazine-1-carboxylate tert-butyl 4-[2-formyl-6-(methylcarbamoyl)-3-pyridyl]piperazine-1-carboxylate (Intermediate 39, 99 mg, 0.28 mmol) in $CH_2Cl_2$ (2 mL) was cooled to 0° C., DAST (0.710 mL, 0.71 mmol) (1M in DCM) was added and the resulting mixture was stirred at room temperature for 3 hr. TLC and LCMS indicated full conversion. Reaction was quenched with dropwise addition of sat. $NaHCO_3$ solution and extracted with DCM. The combined organics were dried over anhydrous $Na_2SO_4$, filtered and concentrated to give the crude product. The resulting residue was purified by flash silica chromatography, elution gradient 0 to 100% EtOAc in hexanes. Product fractions were concentrated under reduced pressure to dryness to afford tert-butyl 4-[2-(difluoromethyl)-6-(methylcarbamoyl)-3-pyridyl]piperazine-1-carboxylate (Intermediate 40, 94 mg, 89%) as an off white solid. 1H NMR (500 MHz, CHLOROFORM-d) 1.51 (9H, s), 2.89-3.03 (4H, m), 3.06 (3H, d), 3.54-3.73 (4H, m), 6.82-7.16 (1H, m), 7.64 (1H, d), 7.94 (1H, br d), 8.29 (1H, d); m/z ($ES^+$) $[M+H]^+$=371.

Intermediate 41: 6-(difluoromethyl)-N-methyl-5-piperazin-1-yl-pyridine-2-carboxamide A mixture of tert-butyl 4-[2-(difluoromethyl)-6-(methylcarbamoyl)-3-pyridyl]piperazine-1-carboxylate (Intermediate 40, 92 mg, 0.25 mmol) in HCl 4M in 1,4-dioxane (6 ml, 24.00 mmol) was stirred at r.t for 1.5 hr gave an orange suspension, the mixture was diluted with ether, filtered, the solid was redissolved into methanol, concentrated to dryness to yield 6-(difluoromethyl)-N-methyl-5-piperazin-1-yl-pyridine-2-carboxamide, 2HCl (Intermediate 41, 56.0 mg, 65.7%) as an orange solid. 1H NMR (500 MHz, DMSO-d6) 2.83 (3H, d), 3.03-3.23 (5H, m), 3.30 (4H, br s), 7.06-7.49 (1H, m), 7.92 (1H, d), 8.13 (1H, d), 8.43 (1H, br d), 9.00 (2H, br d); m/z ($ES^+$) $[M+H]^+$=271.

Synthesis Example 10: 6-(difluoromethyl)-5-[4-[(2-ethyl-3-oxo-4H-quinoxalin-6-yl)methyl]piperazin-1-yl]-N-methyl-pyridine-2-carboxamide

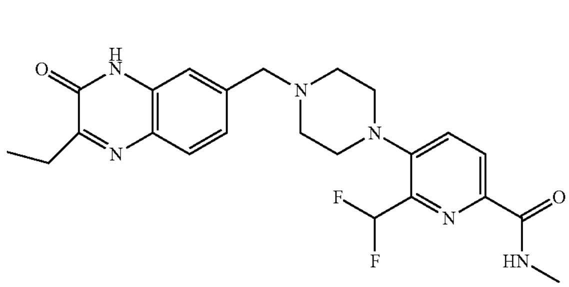 [SMILES: CCc1nc2ccc(CN3CCN(c4ccc(C(=O)NC)nc4C(F)F)CC3)cc2[nH]c1=O]

DIPEA (0.127 mL, 0.73 mmol) was added to a suspension of 6-(difluoromethyl)-N-methyl-5-piperazin-1-yl-pyridine-2-carboxamide, 2HCl (Intermediate 41, 50 mg, 0.15 mmol) and 7-(bromomethyl)-3-ethylquinoxalin-2(1H)-one (Intermediate 30, 48.6 mg, 0.15 mmol) in acetonitrile (3 mL). The resulting mixture was stirred at 60° C. for 3 hrs, LCMS indicated full conversion. The mixture was concentrated, and the residue was purified on Gilson reverse phase column (eluted with 0 to 95% ACN/water/0.1% TFA). The product contain fractions were concentrated at room temperature. The reside was then dissolved into methanol and DCM followed by addition of 250 mg of tetraalkylammonium carbonite polymer-bound (40-90 mesh, 2.5-3.5 mmol/g) and the mixture was stirred at room temperature for 10 min. The solid was then filtered off, washed with methanol and the filtrate was concentrated to give solid. This solid was then redissolved into a mixture of water/CH3CN and lyophilized to dryness to afford 6-(difluoromethyl)-5-[4-[(2-ethyl-3-oxo-4H-quinoxalin-6-yl)methyl]piperazin-1-yl]-N-methyl-pyridine-2-carboxamide (Synthesis Example 10, 50.0 mg, 75%) as a yellow solid. 1H NMR (500 MHz, CHLOROFORM-d) 1.40 (3H, t), 2.72 (4H, br s), 2.97-3.17 (9H, m), 3.73 (2H, s), 6.84-7.15 (1H, m), 7.32 (1H, s), 7.37 (1H, d), 7.64 (1H, d), 7.83 (1H, d), 7.95 (1H, br d), 8.29 (1H, d), 11.32-11.62 (1H, m); m/z ($ES^+$) $[M+H]^+$=457.

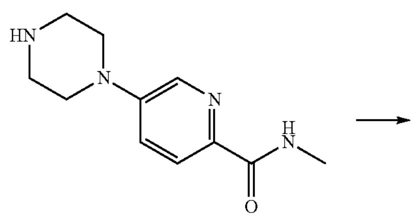

Intermediate 13

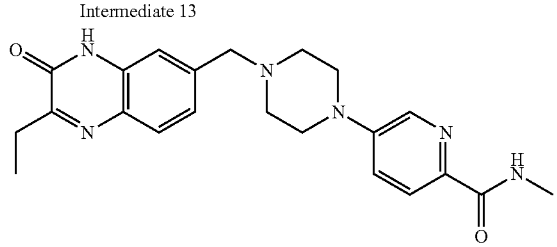

Example 11

Synthesis Example 11: 5-[4-[(2-ethyl-3-oxo-4H-quinoxalin-6-yl)methyl]piperazin-1-yl]-N-methyl-pyridine-2-carboxamide

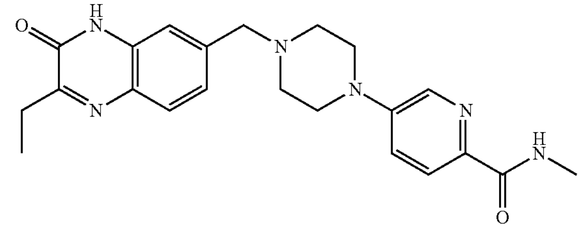 [SMILES: CCc1nc2ccc(CN3CCN(c4ccc(C(=O)NC)nc4)CC3)cc2[nH]c1=O]

In a 20 mL vial was added 7-(bromomethyl)-3-ethylquinoxalin-2(1H)-one (Intermediate 30, 0.147 g, 0.55 mmol) and N-methyl-5-piperazin-1-yl-pyridine-2-carboxamide, 2HCl (Intermediate 13, 0.161 g, 0.55 mmol). The vial was sealed, evacuated, and refilled with $N_2$. Acetonitrile (3 mL) and DIPEA (0.481 mL, 2.75 mmol) were added to the vial and placed in a heating block pre-heated to 70 C. The reaction mixture was stirred at the same temperature for 2 hours and cooled to room temperature. The volume of the reaction was reduced to ⅓ of its initial volume under vacuum and aqueous $NaHCO_3$ solution was added (2 mL). The reaction mixture was stirred for 30 mins, filtered and the solid was washed with water (50 mL). The crude product was purified by flash silica chromatography using 0-30% MeOH in DCM to yield 5-[4-[(2-ethyl-3-oxo-4H-quinoxalin-6-yl)methyl]piperazin-1-yl]-N-methyl-pyridine-2-carboxamide (Synthesis Example 11, 93.0 mg, 41.6%) as a light-yellow solid. 1H NMR (500 MHz, DMSO-$d_6$) 1.22 (3H, t), 2.52-2.60 (4H, m), 2.73-2.85 (5H, m), 3.30 (4H, m, overlapped with water peak), 3.62 (2H, s), 7.22-7.31 (2H, m), 7.39 (1H, dd), 7.69 (1H, d), 7.83 (1H, d), 8.23-8.31 (1H, m), 8.39 (1H, br d), 12.13-12.36 (1H, m); m/z ($ES^+$) $[M+H]^+$=407.

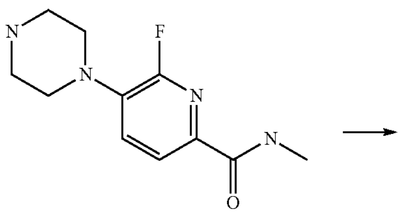

Intermediate 23

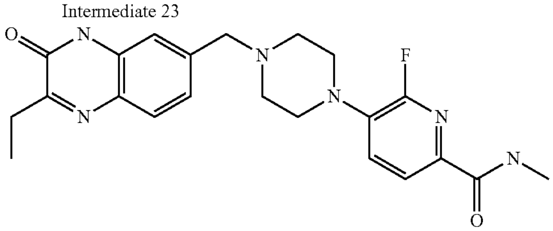

Example 12

Synthesis Example 12: 5-[4-[(2-ethyl-3-oxo-4H-quinoxalin-6-yl)methyl]piperazin-1-yl]-6-fluoro-N-methyl-pyridine-2-carboxamide

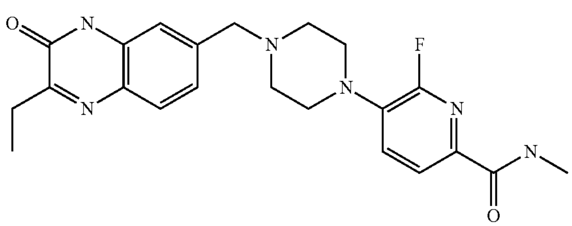 [SMILES: CCc1nc2ccc(CN3CCN(c4ccc(C(=O)NC)nc4F)CC3)cc2[nH]c1=O]

7-(bromomethyl)-3-ethylquinoxalin-2(1H)-one (Intermediate 30, 150 mg, 0.56 mmol) was added to 6-fluoro-N-methyl-5-piperazin-1-yl-pyridine-2-carboxamide (Intermediate 23, 60 mg, 0.25 mmol) and DIPEA (0.270 mL, 1.55 mmol) in NMP (2 mL). The resulting mixture was stirred at 80° C. for 2 hours. The solvent was removed under reduced pressure. The crude product was purified by preparative HPLC (Column: XBridge Shield RP18 OBD Column, 5 um, 19×150 mm; Mobile Phase A: Water (10 MMOL/L $NH_4HCO_3$, 0.1% $NH_3 \cdot H_2O$), Mobile Phase B: ACN; Flow rate: 20 mL/min; Gradient: 28% B to 38% B in 8 min; 254; 220 nm; RT: 8.02 min). Fractions containing the desired compound were evaporated to dryness to afford 5-[4-[(2-ethyl-3-oxo-4H-quinoxalin-6-yl)methyl]piperazin-1-yl]-6-fluoro-N-methyl-pyridine-2-carboxamide (Synthesis Example 12, 9 mg, 42.9%) as a white solid. 1H NMR (400 MHz, $CD_3OD$) δ 1.33 (3H, t), 2.65-2.72 (4H, m), 2.87-2.95 (5H, m), 3.26-3.30 (4H, m), 3.71 (2H, s), 7.33-7.41 (2H, m), 7.52 (1H, dd), 7.76 (1H, d), 7.90 (1H, dd); $^{19}F$ NMR (376 MHz, $CD_3OD$) δ −73.40; m/z ($ES^+$) $[M+H]^+$=425.

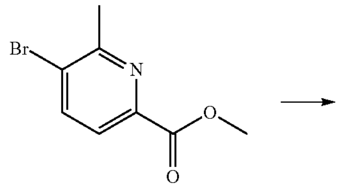

Intermediate 42

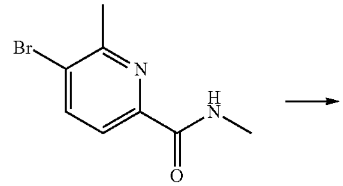

Intermediate 43

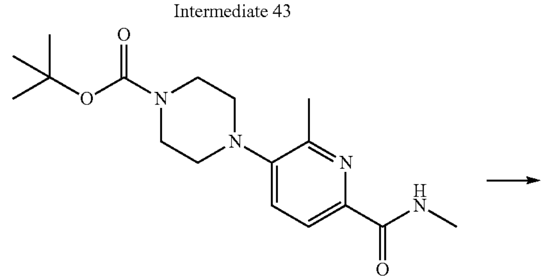

Intermediate 44

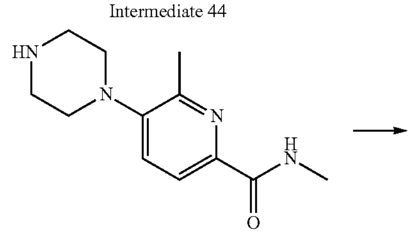

Intermediate 45

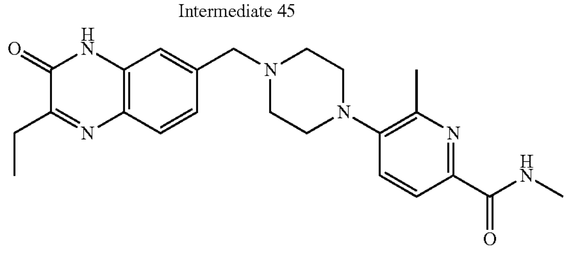

Example 13

Intermediate 43: 5-bromo-N,6-dimethylpicolinamide

A 2 M solution of methylamine in THF (20 mL, 40.00 mmol) was added to methyl 5-bromo-6-methylpicolinate (Intermediate 42, 2.0 g, 8.69 mmol) and the resulting mixture was stirred at 80° C. for 18 hours. The solvent was removed under reduced pressure. The crude product was purified by reverse phase chromatography, elution gradient 5 to 80% MeOH in water (0.1% $NH_4HCO_3$). Pure fractions were evaporated to dryness to afford 5-bromo-N,6-dimethylpicolinamide (Intermediate 43, 1.5 g, 75%) as a pale yellow solid. $^1H$ NMR (400 MHz, DMSO-$d_6$) δ 2.65 (3H, s), 2.82 (3H, d), 7.75 (1H, d), 8.17 (1H, d), 8.57-8.76 (1H, m); m/z (ES$^+$) [M+H]$^+$=229.

Intermediate 44: tert-butyl 4-(2-methyl-6-(methylcarbamoyl)pyridin-3-yl)piperazine-1-carboxylate 5-bromo-N,6-dimethylpicolinamide (Intermediate 43, 1.0 g, 4.37 mmol) was added to tert-butyl piperazine-1-carboxylate (0.894 g, 4.80 mmol), BINAP (0.272 g, 0.44 mmol), $Pd(OAc)_2$ (0.098 g, 0.44 mmol) and $Cs_2CO_3$ (3.56 g, 10.91 mmol) in toluene (20 mL) under nitrogen. The resulting mixture was stirred at 80° C. for 16 hours. The solvent was removed under reduced pressure. The crude product was purified by reverse phase chromatography, elution gradient 5 to 30% MeOH in water (0.4% $HCO_2H$). Pure fractions were evaporated to dryness to afford tert-butyl 4-(2-methyl-6-(methylcarbamoyl)pyridin-3-yl)piperazine-1-carboxylate (Intermediate 44, 1.2 g, 82%) as a brown solid. $^1H$ NMR (300 MHz, $CD_3OD$) δ 1.50 (9H, s), 2.58 (3H, s), 2.92-3.00 (7H, m), 3.62 (4H, m), 7.50 (1H, d), 7.88 (1H, d); m/z (ES$^+$) [M+H]$^+$=335.

Intermediate 45: N,6-dimethyl-5-(piperazin-1-yl)picolinamide tert-butyl 4-(2-methyl-6-(methylcarbamoyl)pyridin-3-yl) piperazine-1-carboxylate (Intermediate 44, 1.18 g, 3.53 mmol) was added to a 4 M solution of HCl in the 1,4-dioxane (10 mL, 329.15 mmol). The resulting mixture was stirred at room temperature for 1 hour. The precipitate was collected by filtration, washed with petroleum ether (5 mL×2), $Et_2O$ (5 mL×2), and dried under vacuum to afford N,6-dimethyl-5-(piperazin-1-yl)picolinamide (Intermediate 45, 0.77 g, 81%) as an yellow solid. 1H NMR (300 MHz, $CD_3OD$) δ 2.86 (3H, s), 3.02 (3H, s), 3.42-3.54 (8H, m), 8.29 (2H, d); m/z (ES$^+$) [M+H]$^+$=235.

Synthesis Example 13: 5-[4-[(2-ethyl-3-oxo-4H-quinoxalin-6-yl)methyl]piperazin-1-yl]-N, 6-dimethyl-pyridine-2-carboxamide

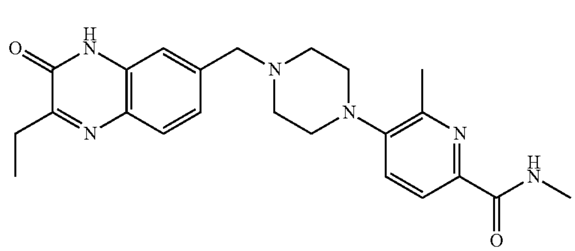 [SMILES: CCc1nc2ccc(CN3CCN(c4ccc(C(=O)NC)nc4C)CC3)cc2[nH]c1=O]

7-(bromomethyl)-3-ethylquinoxalin-2(1H)-one (Intermediate 30, 100 mg, 0.37 mmol) was added to N,6-dimethyl-5-(piperazin-1-yl)picolinamide (Intermediate 45, 90 mg, 0.33 mmol) and DIPEA (0.36 mL, 2.05 mmol) in NMP (2 mL). The resulting mixture was stirred at 80° C. for 2 hours. The solvent was removed under reduced pressure. The crude product was purified by preparative HPLC (Column: XBridge Prep OBD C18 Column 30×150 mm, 5 um; Mobile Phase A: Water (10 MMOL/L $NH_4HCO_3$), Mobile Phase B: ACN; Flow rate: 60 mL/min; Gradient: 30% B to 40% B in 7 min; 254; 220 nm; RT: 6.43 min). Fractions containing the desired compound were evaporated to dryness to afford 5-[4-[(2-ethyl-3-oxo-4H-quinoxalin-6-yl)methyl]piperazin-1-yl]-N,6-dimethyl-pyridine-2-carboxamide (Synthesis Example 13, 68.7 mg, 43.6%) as an off-white solid. $^1H$ NMR (400 MHz, $CD_3OD$) δ 1.33 (3H, t), 2.55 (3H, s), 2.71 (4H, s), 2.87-2.99 (5H, m), 3.05 (4H, t), 3.73 (2H, s), 7.35 (1H, s), 7.38 (1H, d), 7.49 (1H, d), 7.77 (1H, d), 7.87 (1H, d); m/z (ES$^+$) [M+H]$^+$=421.

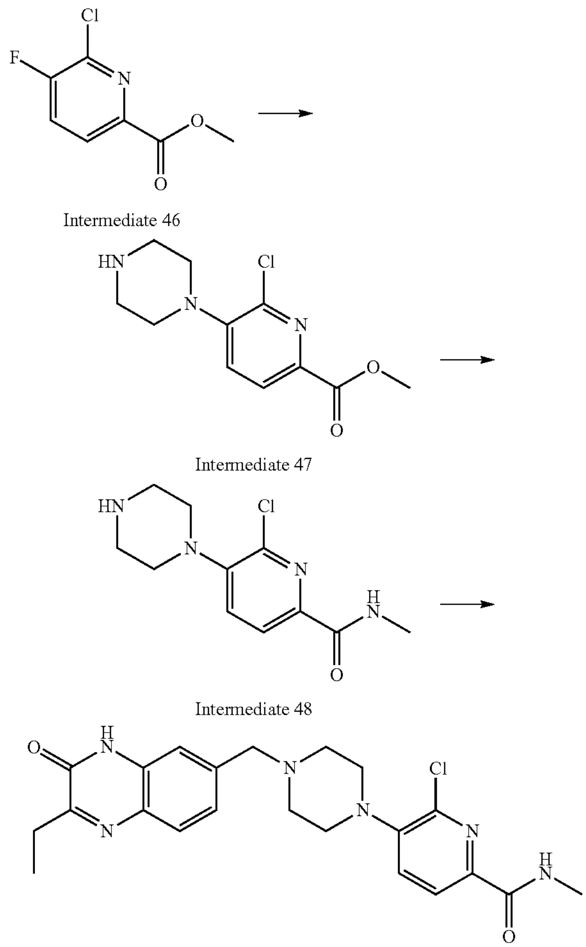

Intermediate 46

Intermediate 47

Intermediate 48

Example 14

Intermediate 47: methyl 6-chloro-5-(piperazin-1-yl)picolinate

Piperazine (1.0 g, 11.61 mmol) was added to methyl 6-chloro-5-fluoropicolinate (Intermediate 46, 1.0 g, 5.28 mmol) in MeCN (30 mL). The resulting mixture was stirred at 80° C. for 18 hours. The solvent was removed under reduced pressure. The crude product was purified by reverse phase chromatography, elution gradient 5 to 60% MeCN in water (0.1% $NH_4HCO_3$). Pure fractions were evaporated to dryness to afford methyl 6-chloro-5-(piperazin-1-yl)picolinate (Intermediate 47, 1.28 g, 95%) as a red oil. $^1H$ NMR (400 MHz, DMSO-$d_6$) δ 2.81-2.91 (4H, m), 3.04-3.08 (4H, m), 3.85 (3H, s), 7.61 (1H, d), 8.00 (1H, d) (NH proton is not shown); m/z (ES$^+$) [M+H]$^+$=256.

Intermediate 48: 6-chloro-N-methyl-5-(piperazin-1-yl)picolinamide

A 2 M solution of methylamine in THF (40 mL, 80.00 mmol) was added to methyl 6-chloro-5-(piperazin-1-yl) picolinate (Intermediate 47, 1.26 g, 4.93 mmol). The resulting mixture was stirred at 80° C. for 18 hours. The solvent was removed under reduced pressure. The crude product was purified by reverse phase chromatography, elution gradient 5 to 60% MeCN in water (0.1% $NH_4HCO_3$). Pure fractions were evaporated to dryness to afford 6-chloro-N-methyl-5-(piperazin-1-yl)picolinamide (Intermediate 48, 1.12 g, 89%) as a pale yellow oil. 1H NMR (300 MHz, DMSO-$d_6$) δ 2.79 (3H, d), 2.85-2.89 (4H, m), 2.97-3.02 (4H, m), 7.63 (1H, d), 7.94 (1H, d), 8.45 (1H, q) (Piperazine-NH proton is not shown); m/z ($ES^+$) $[M+H]^+$=255.

Synthesis Example 14: 6-chloro-5-[4-[(2-ethyl-3-oxo-4H-quinoxalin-6-yl)methyl]piperazin-1-yl]-N-methyl-pyridine-2-carboxamide

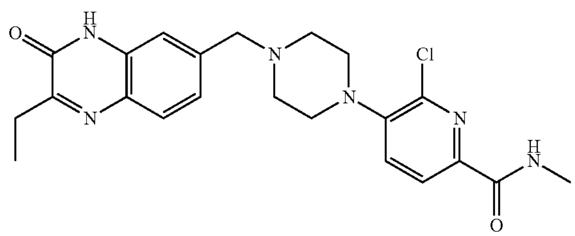 [SMILES: CCc1nc2ccc(CN3CCN(c4ccc(C(=O)NC)nc4Cl)CC3)cc2[nH]c1=O]

7-(bromomethyl)-3-ethylquinoxalin-2(1H)-one (Intermediate 30, 200 mg, 0.75 mmol) was added to 6-chloro-N-methyl-5-(piperazin-1-yl)picolinamide (Intermediate 48, 100 mg, 0.39 mmol) and DIPEA (0.358 mL, 2.05 mmol) in NMP (2 mL). The resulting mixture was stirred at 80° C. for 2 hours. The solvent was removed under reduced pressure. The crude product was purified by preparative HPLC (Column: XBridge Prep OBD C18 Column 30×150 mm 5 um; Mobile Phase A: Water (10 MMOL/L $NH_4HCO_3$), Mobile Phase B: ACN; Flow rate: 60 mL/min; Gradient: 30% B to 40% B in 8 min; 254; 220 nm; RT: 7.3 min). Fractions containing the desired compound were evaporated to dryness to afford 6-chloro-5-[4-[(2-ethyl-3-oxo-4H-quinoxalin-6-yl)methyl]piperazin-1-yl]-N-methyl-pyridine-2-carboxamide (Synthesis Example 14, 52.6 mg, 30.4%) as a white solid. 1HNMR (400 MHz, $CD_3OD$) δ 1.33 (3H, t), 2.71 (4H, s), 2.87-2.96 (5H, m), 3.23 (4H, s), 3.73 (2H, s), 7.33-7.41 (2H, m), 7.62 (1H, d), 7.77 (1H, d), 8.00 (1H, d); m/z ($ES^+$) $[M+H]^+$=441.

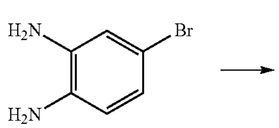

Intermediate 49

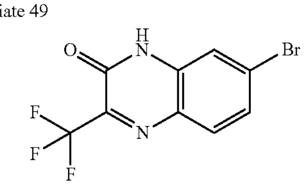

+

Intermediate 50

-continued

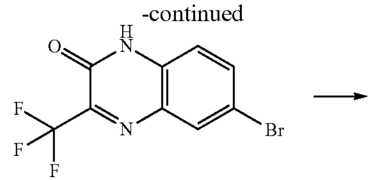

Intermediate 51

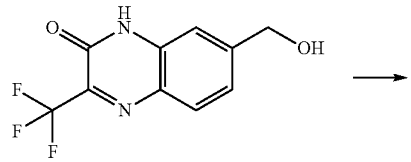

Intermediate 52

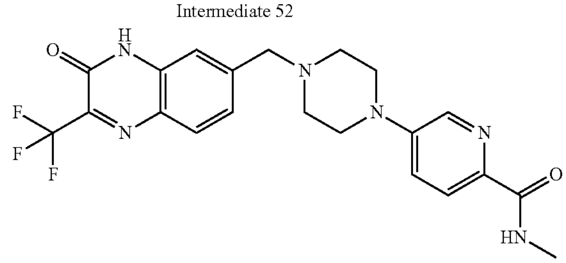

Example 15

Intermediate 50: 7-bromo-3-(trifluoromethyl)quinoxalin-2 (1H)-one 4-bromobenzene-1,2-diamine (Intermediate 49, 0.9 g, 4.81 mmol) was added to methyl 3,3,3-trifluoro-2-oxopropanoate (0.9 g, 5.77 mmol) in toluene (10 mL). The resulting mixture was stirred at 100° C. for 60 minutes. The solvent was removed under reduced pressure. The crude product was purified by flash silica chromatography, elution gradient 0 to 50% EtOAc in petroleum ether. Pure fractions were evaporated to dryness to afford regioisomeric mixture of 7-bromo-3-(trifluoromethyl)quinoxalin-2(1H)-one and 6-bromo-3-(trifluoromethyl)quinoxalin-2(1H)-one (Intermediate 50+Intermediate 51, 1.28 g, 45.4%) as an off-white solid. A mixture of regioisomers were isolated, and the 1H NMR spectrum was not interpreted; m/z ($ES^+$) $[M+H]^+$=295.

Intermediate 52: 7-(hydroxymethyl)-3-(trifluoromethyl) quinoxalin-2(1H)-one $Pd(Ph_3P)_4$ (0.3 g, 0.26 mmol) was added to a mixture of 7-bromo-3-(trifluoromethyl)quinoxalin-2(1H)-one and 6-bromo-3-(trifluoromethyl)quinoxalin-2(1H)-one (Intermediate 50+Intermediate 51, 1.2 g, 2.05 mmol) and (tributylstannyl)methanol (1.2 g, 3.74 mmol) in 1,4-dioxane (40 mL). The resulting mixture was stirred at 100° C. for 18 hours under nitrogen. The solvent was removed under reduced pressure. The crude product was purified by reverse phase chromatography, elution gradient 5 to 50% MeCN in water (0.1% $HCO_2H$). Pure fractions were evaporated to dryness to afford 7-(hydroxymethyl)-3-(trifluoromethyl)quinoxalin-2(1H)-one (Intermediate 52, 0.32 g, 64.0%) as an off-white solid. $^1H$ NMR (300 MHz, DMSO-$d_6$) δ 4.63 (2H, d), 5.52 (1H, t), 7.30 (1H, dd), 7.38 (1H, d), 7.83 (1H, d), 13.05 (1H, s); m/z ($ES^+$) $[M+H]^+$=245.

Synthesis Example 15: N-methyl-5-[4-[[3-oxo-2-(trifluoromethyl)-4H-quinoxalin-6-yl]methyl]piperazin-1-yl]pyridine-2-carboxamide

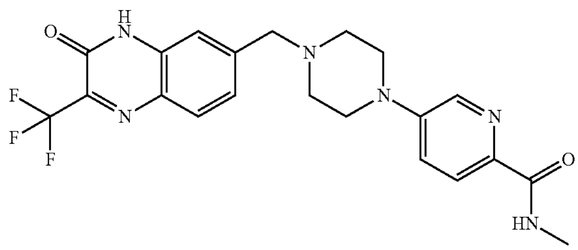 [SMILES: CNC(=O)c1ccc(N2CCN(Cc3ccc4nc(C(F)(F)F)c(=O)[nH]c4c3)CC2)cn1]

A solution of 33% HBr in AcOH (3 mL, 18.23 mmol) was added to 7-(hydroxymethyl)-3-(trifluoromethyl)quinoxalin-2(1H)-one (Intermediate 52, 111 mg, 0.45 mmol). The resulting mixture was stirred at 80° C. for 1 hour. The solvent was removed under reduced pressure. DIEA (0.5 mL, 2.86 mmol) and N-methyl-5-(piperazin-1-yl)picolinamide (Intermediate 13, 100 mg, 0.45 mmol) were added to the above mixture in NMP (3 mL). The resulting mixture was stirred at 80° C. for 1 hour. The solvent was removed under reduced pressure. The crude product was purified by preparative HPLC (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 22 B to 32 B in 7 min; 254; 220 nm; RT: 5.77. Fractions containing the desired compound were evaporated to dryness to afford N-methyl-5-[4-[[3-oxo-2-(trifluoromethyl)-4H-quinoxalin-6-yl]methyl]piperazin-1-yl]pyridine-2-carboxamide (Synthesis Example 15, 44.0 mg, 21.71%) as a white solid. 1H NMR (400 MHz, DMSO-$d_6$) δ 2.55-2.62 (m, 4H), 2.78 (d, 3H), 3.34-3.38 (t, 4H), 3.69 (s, 2H), 7.34-7.44 (m, 3H), 7.80-7.91 (m, 2H), 8.27 (d, 1H), 8.36-8.41 (m, 1H), 12.97 (s, 1H); $^{19}$F NMR (376 MHz, DMSO-$d_6$) δ −68.36; m/z ($ES^+$) $[M+H]^+$=447.

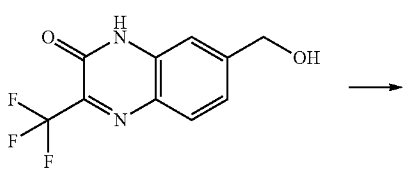

Intermediate 52

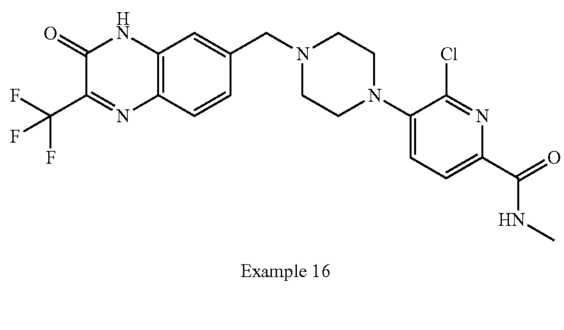

Example 16

Synthesis Example 16: 6-chloro-N-methyl-5-[4-[[3-oxo-2-(trifluoromethyl)-4H-quinoxalin-6-yl]methyl]piperazin-1-yl]pyridine-2-carboxamide

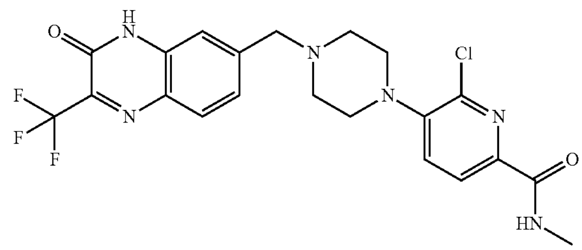 [SMILES: CNC(=O)c1ccc(N2CCN(Cc3ccc4nc(C(F)(F)F)c(=O)[nH]c4c3)CC2)c(Cl)n1]

33% HBr in AcOH (3 mL, 18.23 mmol) was added to 7-(hydroxymethyl)-3-(trifluoromethyl)quinoxalin-2(1H)-one (Intermediate 52, 43.1 mg, 0.18 mmol). The resulting mixture was stirred at 80° C. for 1 hour. The solvent was removed under reduced pressure. DIPEA (0.5 mL, 2.86 mmol) and 6-chloro-N-methyl-5-(piperazin-1-yl)picolinamide (Intermediate 48, 45 mg, 0.18 mmol) was added to the above mixture in NMP (5 mL). The resulting mixture was stirred at 80° C. for 1 hour. The solvent was removed under reduced pressure. The crude product was purified by preparative HPLC (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 10 B to 50 B in 7 min; 254; 220 nm; RT: 6.75. Fractions containing the desired compound were evaporated to dryness to afford 6-chloro-N-methyl-5-[4-[[3-oxo-2-(trifluoromethyl)-4H-quinoxalin-6-yl]methyl]piperazin-1-yl]pyridine-2-carboxamide (Synthesis Example 16, 22.00 mg, 25.9%) as an off-white solid. 1H NMR (400 MHz, DMSO-$d_6$) δ 2.56-2.64 (s, 4H), 2.79 (d, 3H), 3.09-3.17 (m, 4H), 3.71 (s, 2H), 7.36-7.42 (m, 2H), 7.67 (d, 1H), 7.88 (d, 1H), 7.94 (d, 1H), 8.39-8.44 (m, 1H), 12.89 (s, 1H); $^{19}$F NMR (376 MHz, DMSO) 5-68.41; m/z (ES+) $[M+H]^+$=481.

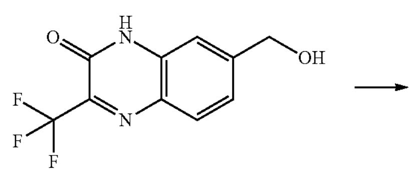

Intermediate 52

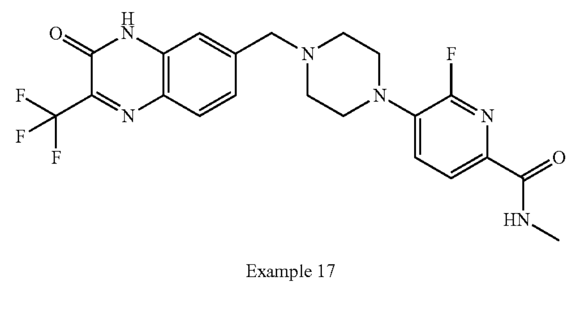

Example 17

Synthesis Example 17: 6-fluoro-N-methyl-5-[4-[[3-oxo-2-(trifluoromethyl)-4H-quinoxalin-6-yl]methyl]piperazin-1-yl]pyridine-2-carboxamide

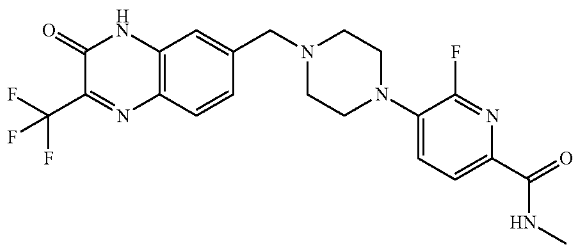 [SMILES: CNC(=O)c1ccc(N2CCN(Cc3ccc4nc(C(F)(F)F)c(=O)[nH]c4c3)CC2)c(F)n1]

33% HBr in AcOH (3 mL, 55.25 mmol) was added to 7-(hydroxymethyl)-3-(trifluoromethyl)quinoxalin-2(1H)-one (Intermediate 52, 102 mg, 0.42 mmol). The resulting mixture was stirred at 80° C. for 1 hour. The solvent was removed under reduced pressure. 6-fluoro-N-methyl-5-(piperazin-1-yl)picolinamide (Intermediate 23, 100 mg, 0.42 mmol) and DIPEA (0.5 mL, 2.86 mmol) was added to the above mixture in NMP (5 mL). The resulting mixture was stirred at 80° C. for 1 hour. The solvent was removed under reduced pressure. The crude product was purified by preparative HPLC (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 15 B to 40 B in 8 min; 254; 220 nm; RT: 7.2. Fractions containing the desired compound were evaporated to dryness to afford 6-fluoro-N-methyl-5-[4-[[3-oxo-2-(trifluoromethyl)-4H-quinoxalin-6-yl]methyl]piperazin-1-yl]pyridine-2-carboxamide (Synthesis Example 17, 66.0 mg, 33.9%) as a white solid. 1H NMR (400 MHz, DMSO-$d_6$) δ 2.55-2.69 (m, 4H), 2.77 (d, 3H), 3.15-3.23 (m, 4H), 3.69 (s, 2H), 7.33-7.46 (m, 2H), 7.58 (dd, 1H), 7.78-7.93 (m, 2H), 8.37-8.42 (m, 1H), 12.99 (s, 1H); $^{19}F$ NMR (376 MHz, DMSO-$d_6$) δ −68.36, −72.52; m/z ($ES^+$) $[M+H]^+$=465.

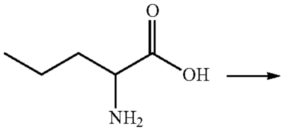

Intermediate 53

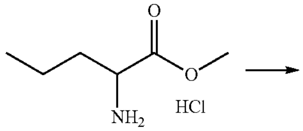

Intermediate 54

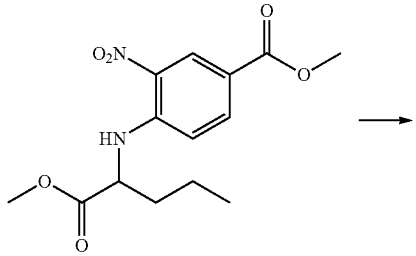

Intermediate 55

-continued

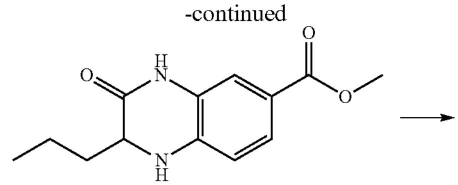

Intermediate 56

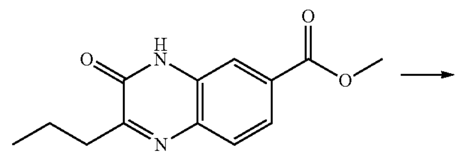

Intermediate 57

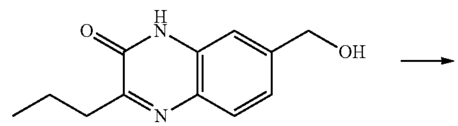

Intermediate 58

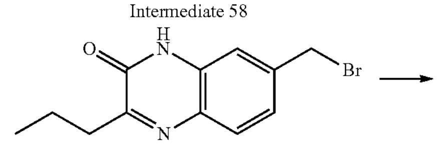

Intermediate 59

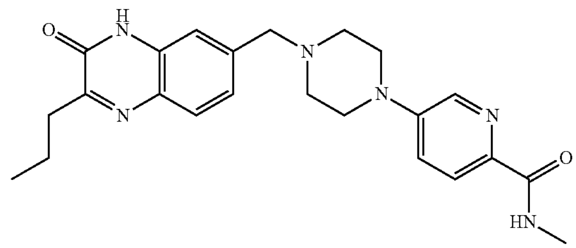 [SMILES: CCCc1nc2ccc(CN3CCN(c4ccc(C(=O)NC)nc4)CC3)cc2[nH]c1=O]

Example 18

Intermediate 54: methyl 2-aminopentanoate hydrochloride $SOCl_2$ (17 mL, 232.94 mmol) was added dropwise to 2-aminopentanoic acid (Intermediate 53, 10.0 g, 85.36 mmol) in MeOH (200 mL) at 0° C. The resulting mixture was stirred at room temperature for 18 hours. The solvent was removed under reduced pressure to afford methyl 2-aminopentanoate hydrochloride (Intermediate 54, 15.78 g, 110%) as a white solid. $^1H$ NMR (DMSO-$d_6$, 400 MHz) δ 0.88 (3H, t), 1.19-1.51 (2H, m), 1.67-1.83 (2H, m), 3.74 (3H, s), 3.89-3.93 (1H, m), 8.64 (3H, s); m/z ($ES^+$) $[M+H]^+$=132.

Intermediate 55: methyl 4-(1-methoxy-1-oxopentan-2-ylamino)-3-nitrobenzoate

Sodium bicarbonate (20.0 g, 238.08 mmol) was added to methyl 2-aminopentanoate hydrochloride (Intermediate 54, 15.57 g, 92.88 mmol) and methyl 4-fluoro-3-nitrobenzoate (9.0 g, 45.19 mmol) in THF (160 mL). The resulting mixture was stirred at room temperature for 18 hours. The solvent was removed under reduced pressure. The reaction mixture was diluted with EtOAc (150 mL), and washed sequentially with water (100 mL×1), saturated $NaHCO_3$ (100 mL×1) and saturated brine (100 mL×1). The organic layer was dried over $Na_2SO_4$, filtered and evaporated to afford methyl 4-(1-methoxy-1-oxopentan-2-ylamino)-3-nitrobenzoate (Intermediate 55, 14.09 g, 100%) as a yellow oil. $^1$H NMR (400 MHz, DMSO-$d_6$) δ 0.89 (3H, t), 1.26-1.41 (2H, m), 1.84-1.94 (2H, m), 3.73 (3H, s), 3.83 (3H, s), 4.68-4.75 (1H, m), 7.12 (1H, d), 8.00 (1H, d), 8.60 (1H, d), 8.63 (1H, d); m/z ($ES^+$) $[M+H]^+$=311.

Intermediate 56: methyl 3-oxo-2-propyl-1,2,3,4-tetrahydroquinoxaline-6-carboxylate $Pd(OH)_2$/C (20% wt, 1.58 g, 2.25 mmol) was added to methyl 4-((1-methoxy-1-oxopentan-2-yl)amino)-3-nitrobenzoate (Intermediate 55, 14.05 g, 45.28 mmol) in MeOH (300 mL). The resulting mixture was stirred at room temperature under $H_2$ for 30 hours. The reaction mixture was filtered. The precipitate was washed with DMF (100 mL) and the filtrate was evaporated to dryness to afford crude product. The crude product was washed with DCM (10 mL) and dried under vacuum to afford methyl 3-oxo-2-propyl-1,2,3,4-tetrahydroquinoxaline-6-carboxylate (Intermediate 56, 9.12 g, 81%) as a white solid. $^1$H NMR (400 MHz, DMSO-$d_6$) δ 0.87 (3H, t), 1.32-1.46 (2H, m), 1.57-1.64 (2H, m), 3.74 (3H, s), 3.88-3.93 (1H, m), 6.70 (1H, d), 6.83 (1H, d), 7.32 (1H, d), 7.40 (1H, dd), 10.38 (1H, s); m/z ($ES^+$) $[M+H]^+$=249.

Intermediate 57: methyl 3-oxo-2-propyl-3,4-dihydroquinoxaline-6-carboxylate

DDQ (9.42 g, 41.50 mmol) was added to methyl 3-oxo-2-propyl-1,2,3,4-tetrahydroquinoxaline-6-carboxylate (Intermediate 56, 9.12 g, 36.73 mmol) in 1,4-dioxane (200 mL). The resulting mixture was stirred at room temperature for 18 hours. The reaction mixture was diluted with saturated $NaHCO_3$ (200 mL). The resulting mixture was stirred at room temperature for 0.5 hour. The precipitate was collected by filtration, washed with water (1000 mL) and dried under vacuum to afford methyl 3-oxo-2-propyl-3,4-dihydroquinoxaline-6-carboxylate (Intermediate 57, 7.86 g, 87%) as an off-white solid. $^1$H NMR (400 MHz, DMSO-$d_6$) δ 0.98 (3H, t), 1.68-1.80 (2H, m), 2.75-2.83 (2H, m), 3.89 (3H, s), 7.73-7.85 (2H, m), 7.88 (1H, d), 12.45 (1H, s); m/z ($ES^+$) $[M+H]^+$=247.

Intermediate 58: 7-(hydroxymethyl)-3-propylquinoxalin-2 (1H)-one

A 1 M solution of DIBAL-H in THF (100 mL, 100.00 mmol) was added dropwise to methyl 3-oxo-2-propyl-3,4-dihydroquinoxaline-6-carboxylate (Intermediate 57, 7.81 g, 31.71 mmol) in THF (200 mL) at 0° C. The resulting mixture was stirred at room temperature for 18 hours. The reaction mixture was quenched with MeOH (5 mL) and saturated aqueous Monopotassium monosodium tartrate tetrahydrate solution (20 mL), the organic layer was evaporated to afford 7-(hydroxymethyl)-3-propylquinoxalin-2(1H)-one (Intermediate 58, 1.2 g, 17.34%) as a white solid. $^1$H NMR (400 MHz, DMSO-$d_6$) δ 0.97 (3H, t), 1.36-1.77 (2H, m), 2.71-2.79 (2H, m), 4.59 (2H, s), 5.39 (1H, s), 7.18 (1H, dd), 7.27 (1H, d), 7.65 (1H, d), 12.30 (1H, s); m/z ($ES^+$) $[M+H]^+$=219.

Intermediate 59: 7-(bromomethyl)-3-propylquinoxalin-2 (1H)-one

33% HBr in AcOH (74.6 μl, 1.37 mmol) was added to 7-(hydroxymethyl)-3-propylquinoxalin-2(1H)-one (Intermediate 58, 300 mg, 1.37 mmol). The resulting mixture was stirred at 80° C. for 1 hour. The solvent was removed under reduced pressure to afford 7-(bromomethyl)-3-propylquinoxalin-2(1H)-one (Intermediate 59, 600 mg, 155%) as a brown solid (the crude product was not pure and contained AcOH and other impurities. The product was used in the next step without further purification. The $^1$H NMR spectrum was not clean and was not interpreted; m/z ($ES^+$) $[M+H]^+$=282.

Synthesis Example 18: N-methyl-5-[4-[(3-oxo-2-propyl-4H-quinoxalin-6-yl)methyl]piperazin-1-yl]pyridine-2-carboxamide

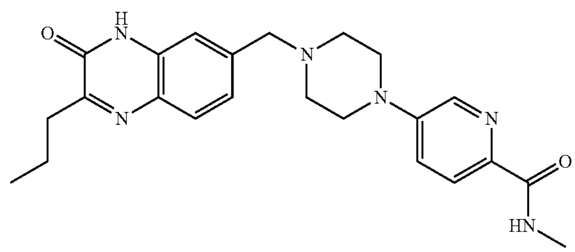

DIPEA (200 μL, 1.15 mmol) was added to 7-(bromomethyl)-3-propylquinoxalin-2(1H)-one (Intermediate 59, 200 mg, 0.71 mmol) and N-methyl-5-(piperazin-1-yl) picolinamide (Intermediate 13, 80 mg, 0.36 mmol) in NMP (3 mL). The resulting mixture was stirred at 80° C. for 1 hour. The solvent was removed under reduced pressure. The crude product was purified by preparative HPLC (Column: XBridge Shield RP18 OBD Column, 19×250 mm, 10 um; Mobile Phase A: Water (10 MMOL/L $NH_4HCO_3$, 0.1% $NH_3 \cdot H_2O$), Mobile Phase B: ACN; Flow rate: 20 mL/min; Gradient: 38 B to 50 B in 7 min; 254/220 nm; RT: 6.20. Fractions containing the desired compound were evaporated to dryness to afford N-methyl-5-[4-[(3-oxo-2-propyl-4H-quinoxalin-6-yl)methyl]piperazin-1-yl]pyridine-2-carboxamide (Synthesis Example 18, 71.0 mg, 46.5%) as a white solid. 1H NMR (400 MHz, DMSO-$d_6$) δ 0.97 (3H, t), 1.66-1.80 (2H, m), 2.55-2.61 (4H, m), 2.73-2.85 (5H, m), 3.33-3.40 (4H, m), 3.62 (2H, s), 7.19-7.31 (2H, m), 7.40 (1H, dd), 7.68 (1H, d), 7.83 (1H, d), 8.27 (1H, d), 8.35-8.45 (1H, m), 12.26 (1H, s); m/z ($ES^+$) $[M+H]^+$=421.

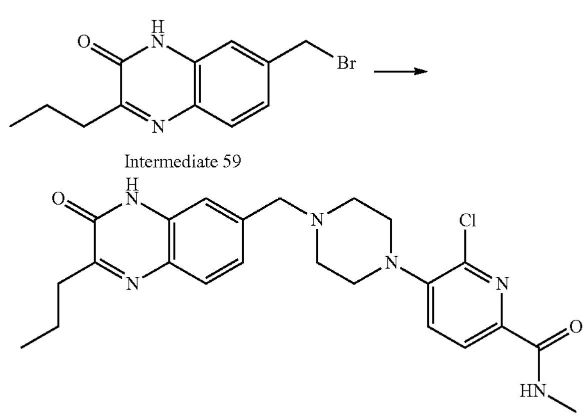

Intermediate 59

Example 19

Synthesis Example 19: 6-chloro-N-methyl-5-[4-[(3-oxo-2-propyl-4H-quinoxalin-6-yl)methyl]piperazin-1-yl]pyridine-2-carboxamide

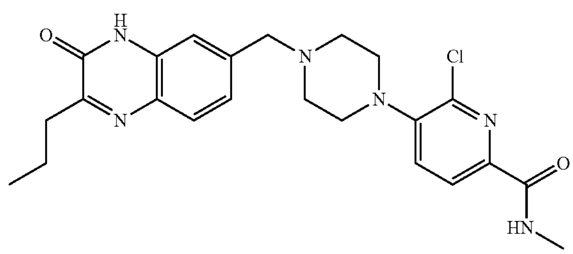 [SMILES: CCCc1nc2ccc(CN3CCN(c4ccc(C(=O)NC)nc4Cl)CC3)cc2[nH]c1=O]

DIPEA (200 μL, 1.15 mmol) was added to 7-(bromomethyl)-3-propylquinoxalin-2(1H)-one (Intermediate 59, 200 mg, 0.71 mmol) and 6-chloro-N-methyl-5-(piperazin-1-yl) picolinamide (Intermediate 48, 80 mg, 0.31 mmol) in NMP (3 mL). The resulting mixture was stirred at 80° C. for 1 hour. The solvent was removed under reduced pressure. The crude product was purified by preparative HPLC (Column: XBridge Shield RP18 OBD Column, 19×250 mm, 10 um; Mobile Phase A: Water (0.1% $HCO_2H$), Mobile Phase B: ACN; Flow rate: 20 mL/min; Gradient: 18 B to 30 B in 7 min; 254/220 nm; RT: 5.93. Fractions containing the desired compound were evaporated to dryness to afford 6-chloro-N-methyl-5-[4-[(3-oxo-2-propyl-4H-quinoxalin-6-yl) methyl]piperazin-1-yl]pyridine-2-carboxamide (Synthesis Example 19, 52.0 mg, 36.4%) as a white solid. 1H NMR (400 MHz, DMSO-$d_6$) δ 0.97 (3H, t), 1.66-1.79 (2H, m), 2.55-2.65 (4H, m), 2.71-2.85 (5H, m), 3.06-3.12 (4H, m), 3.64 (2H, s), 7.20-7.32 (2H, m), 7.64-7.72 (2H, m), 7.94 (1H, d), 8.40-8.50 (1H, m), 12.27 (1H, s); m/z ($ES^+$) $[M+H]^+$=455.

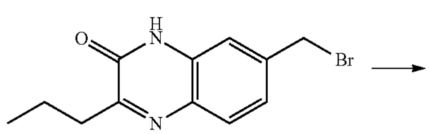

Intermediate 59

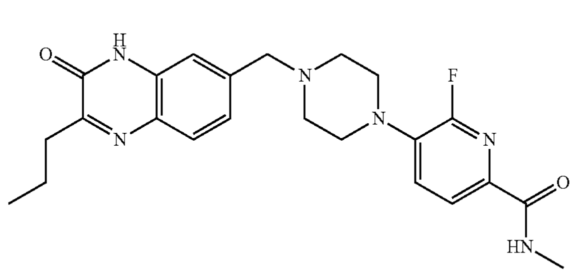

Example 20

Synthesis Example 20: 6-fluoro-N-methyl-5-[4-[(3-oxo-2-propyl-4H-quinoxalin-6-yl)methyl]piperazin-1-yl]pyridine-2-carboxamide

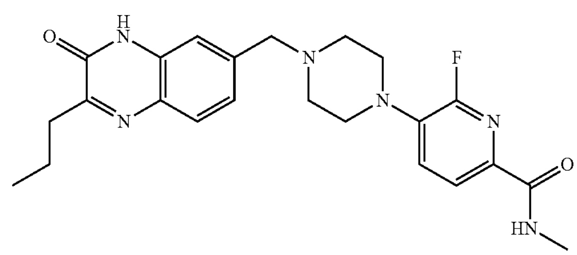 [SMILES: CCCc1nc2ccc(CN3CCN(c4ccc(C(=O)NC)nc4F)CC3)cc2[nH]c1=O]

DIPEA (500 μl, 2.86 mmol) was added to 7-(bromomethyl)-3-propylquinoxalin-2(1H)-one (Intermediate 59, 200 mg, 0.71 mmol) and 6-fluoro-N-methyl-5-(piperazin-1-yl) picolinamide, 2 HCl (Intermediate 23, 100 mg, 0.32 mmol) in NMP (3 mL). The resulting mixture was stirred at 80° C. for 1 hour. The solvent was removed under reduced pressure. The crude product was purified by preparative HPLC (Column: SunFire C18 OBD Prep Column, 100 Å, 5 μm, 19 mm×250 mm; Mobile Phase A: Water (0.1% $HCO_2H$), Mobile Phase B: ACN; Flow rate: 25 mL/min; Gradient: 10 B to 20 B in 13 min; 254/220 nm; RT: 12.13. Fractions containing the desired compound were evaporated to dryness to afford 6-fluoro-N-methyl-5-[4-[(3-oxo-2-propyl-4H-quinoxalin-6-yl)methyl]piperazin-1-yl]pyridine-2-carboxamide (Synthesis Example 20, 71.0 mg, 50.4%) as a white solid. $^1H$ NMR (400 MHz, DMSO-$d_6$) δ 0.97 (3H, t), 1.66-1.78 (2H, m), 2.54-2.60 (4H, m), 2.71-2.83 (5H, m), 3.14-3.25 (4H, m), 3.62 (2H, s), 7.19-7.33 (2H, m), 7.57 (1H, dd), 7.68 (1H, d), 7.85 (1H, dd), 8.37-5.43 (1H, m), 12.27 (1H, s); $^{19}F$ NMR (376 MHz, DMSO-$d_6$) δ −72.51; m/z ($ES^+$) $[M+H]^+$=439.

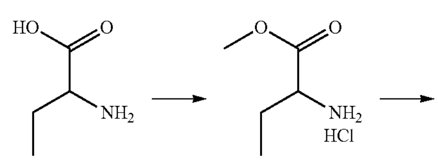

Intermediate 60

Intermediate 61

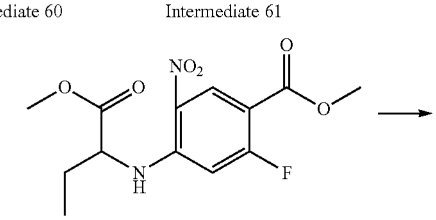

Intermediate 62

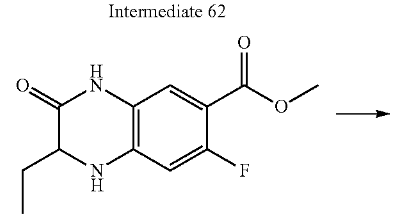

Intermediate 63

-continued

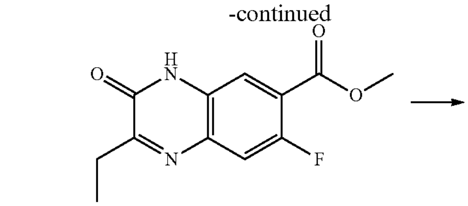

Intermediate 64

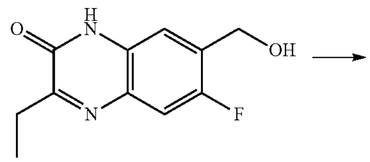

Intermediate 65

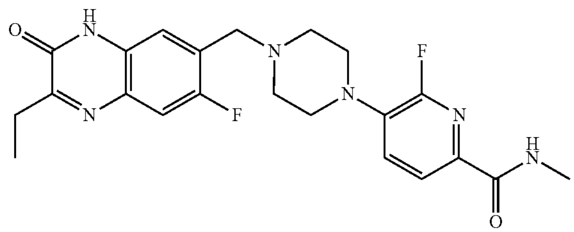

Example 21

Intermediate 61: methyl 2-aminobutanoate hydrochloride $SOCl_2$ (17 mL, 232.94 mmol) was added dropwise to 2-aminobutanoic acid (Intermediate 60, 10.0 g, 96.97 mmol) in MeOH (100 mL) at 0° C. The resulting mixture was stirred at room temperature for 18 hours. The solvent was removed under reduced pressure to afford methyl 2-aminobutanoate hydrochloride (Intermediate 61, 14.84 g, 100%) as a white solid. $^1$H NMR (400 MHz, DMSO-$d_6$) δ 0.91 (3H, t), 1.75-1.95 (2H, m), 3.73 (3H, s), 3.93 (1H, t), 8.72 (3H, s); m/z ($ES^+$) $[M+H]^+$=118.

Intermediate 62: methyl 2-fluoro-4-(1-methoxy-1-oxobutan-2-ylamino)-5-nitrobenzoate DIPEA (4.02 mL, 23.03 mmol) was added to methyl 2,4-difluoro-5-nitrobenzoate (1.0 g, 4.61 mmol) and methyl 2-aminobutanoate hydrochloride (Intermediate 61, 0.707 g, 4.61 mmol) in NMP (10 mL). The resulting mixture was stirred at rt for 5 hours. The crude product was purified by reverse phase chromatography, elution gradient 5 to 80% MeCN in water (0.1% $NH_4HCO_3$). Pure fractions were evaporated to dryness to afford methyl 2-fluoro-4-(1-methoxy-1-oxobutan-2-ylamino)-5-nitrobenzoate (Intermediate 62, 1.2 g, 83%) as a black solid. $^1$H NMR (400 MHz, DMSO-$d_6$) δ 0.88 (3H, t), 1.78-2.03 (2H, m), 3.75 (3H, s), 3.83 (3H, s), 4.73-4.80 (1H, m), 7.06 (1H, d), 8.66-8.72 (2H, m); m/z ($ES^+$) $[M+H]^+$=315.

Intermediate 63: methyl 2-ethyl-7-fluoro-3-oxo-1,2,3,4-tetrahydroquinoxaline-6-carboxylate Methyl 2-fluoro-4-((1-methoxy-1-oxobutan-2-yl)amino)-5-nitrobenzoate (Intermediate 62, 1.15 g, 3.66 mmol) was added to 20 wt % $Pd(OH)_2$ (500 mg, 0.71 mmol) in MeOH (300 mL) and ethyl acetate (50 mL) under hydrogen. The resulting mixture was stirred at room temperature for 3 days.

The reaction did not go to completion. The reaction mixture was filtered. The organic layer was evaporated to afford crude product, methyl 2-ethyl-7-fluoro-3-oxo-1,2,3,4-tetrahydroquinoxaline-6-carboxylate (Intermediate 63, 0.780 g, 85%), as a brown gum. The crude product was used in the next step directly without further purification. The crude product was not clean, and the 1HNMR spectrum was not interpreted; m/z ($ES^+$) $[M+H]^+$=253.

Intermediate 64: methyl 2-ethyl-7-fluoro-3-oxo-3,4-dihydroquinoxaline-6-carboxylate Methyl 2-ethyl-7-fluoro-3-oxo-1,2,3,4-tetrahydroquinoxaline-6-carboxylate (Intermediate 63, 760 mg, 3.01 mmol) was added to DDQ (821 mg, 3.62 mmol) in DCM (20 mL). The resulting mixture was stirred at room temperature for 2 hours. The reaction went to completion. The resulting mixture was concentrated under reduced pressure to obtain a brown solid. Aq $NaHCO_3$ saturated solution (10 mL) was added to the solid and stirred at room temperature for 1 hour. The precipitate was filtered and rinsed with additional aq $NaHCO_3$ solution (10 mL×5). The solid was dried under vacuum to afford methyl 2-ethyl-7-fluoro-3-oxo-3,4-dihydroquinoxaline-6-carboxylate (Intermediate 64, 750 mg, 99%) as a brown solid. $^1$H NMR (300 MHz, DMSO-$d_6$) δ 1.20 (3H, t), 2.82 (2H, q), 3.87 (3H, s), 7.65 (1H, d), 7.76 (1H, d), 12.42 (1H, s); m/z ($ES^+$) $[M+H]^+$=251.

Intermediate 65: 3-ethyl-6-fluoro-7-(hydroxymethyl)quinoxalin-2(1H)-one

A 1 M solution of diisobutylaluminum hydride in THF (15.35 mL, 15.35 mmol) was added portionwise to methyl 2-ethyl-7-fluoro-3-oxo-3,4-dihydroquinoxaline-6-carboxylate (Intermediate 64, 640 mg, 2.56 mmol) in THF (300 mL). The resulting mixture was stirred at room temperature for 16 hours. The reaction went to completion. The reaction mixture was quenched with saturated potassium sodium tartrate aqueous solution (20 mL) and MeOH (10 mL) at 0° C. The resulting mixture was stirred for 1 hour at room temperature. The reaction mixture was filtered and washed with THF (50 mL×3). The organic layer was evaporated to dryness to afford the crude product. The crude product was purified by reverse phase chromatography, elution gradient 5 to 60% MeOH in water (0.4% $HCO_2H$). Pure fractions were evaporated to dryness to afford 3-ethyl-6-fluoro-7-(hydroxymethyl)quinoxalin-2(1H)-one (Intermediate 65, 110 mg, 19.37%) as an off-white solid. $^1$H NMR (400 MHz, DMSO-$d_6$) δ 1.21 (3H, t), 2.80 (2H, q), 4.63 (2H, d), 5.49 (1H, t), 7.41 (1H, d), 7.49 (1H, d), 12.36 (1H, s); m/z ($ES^+$) $[M+H]^+$=223.

Synthesis Example 21: 5-[4-[(2-ethyl-7-fluoro-3-oxo-4H-quinoxalin-6-yl)methyl]piperazin-1-yl]-6-fluoro-N-methyl-pyridine-2-carboxamide

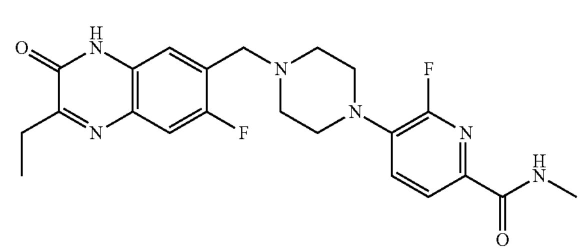 [SMILES: CCc1nc2cc(F)c(CN3CCN(c4ccc(C(=O)NC)nc4F)CC3)cc2[nH]c1=O]

3-ethyl-6-fluoro-7-(hydroxymethyl)quinoxalin-2(1H)-one (Intermediate 65, 50 mg, 0.23 mmol) was added to 33% HBr in the AcOH (2 mL, 12.15 mmol). The resulting mixture was stirred at 80° C. for 2 hours. The reaction mixture was evaporated under vacuum to afford 7-(bromomethyl)-3-ethyl-6-fluoroquinoxalin-2(1H)-one (crude product). The product was used in the next step directly without further purification. DIPEA (0.196 mL, 1.13 mmol) was added to 7-(bromomethyl)-3-ethyl-6-fluoroquinoxalin-2(1H)-one and 6-fluoro-N-methyl-5-(piperazin-1-yl)picolinamide (Intermediate 23, 70 mg, 0.29 mmol) in NMP (2 mL). The resulting mixture was stirred at 80° C. for 2 hours. The resulting mixture was purified by preparative HPLC (Column: Sunfire prep C18 column, 30×150 mm, 5 um; Mobile Phase A: Water (0.1% $HCO_2H$), Mobile Phase B: ACN; Flow rate: 60 mL/min; Gradient: 10 B to 35 B in 8 min; 254/220 nm; RT: 7.37. Fractions containing the desired compound were evaporated to dryness to afford 5-[4-[(2-ethyl-7-fluoro-3-oxo-4H-quinoxalin-6-yl)methyl]piperazin-1-yl]-6-fluoro-N-methyl-pyridine-2-carboxamide (Synthesis Example 21, 55.0 mg, 53.7%) as an off-white solid. $^1H$ NMR (400 MHz, DMSO-$d_6$) δ 1.21 (3H, t), 2.61 (4H, m), 2.73-2.85 (5H, m), 3.18 (4H, m), 3.68 (2H, s), 7.38 (1H, d), 7.51-7.61 (2H, m), 7.84 (1H, dd), 8.13 (0.29H, s), 8.38 (1H, m), 12.29 (1H, s); $^{19}F$ NMR (376 MHz, DMSO-$d_6$) δ −72.53, −124.31; m/z (ES$^+$) $[M+H]^+$=443.

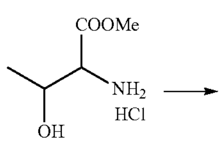

Intermediate 66

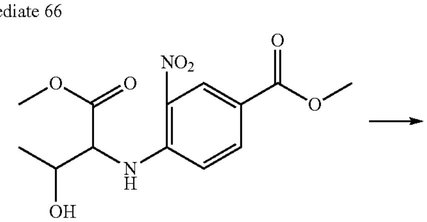

Intermediate 67

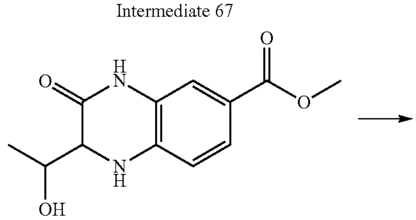

Intermediate 68

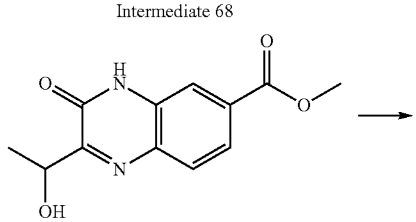

Intermediate 69

-continued

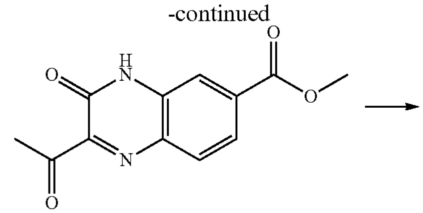

Intermediate 70

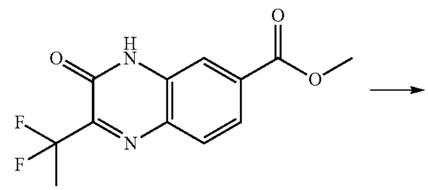

Intermediate 71

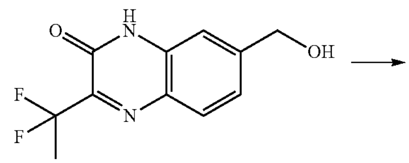

Intermediate 72

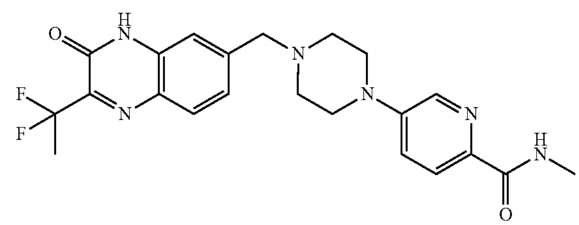

Example 22

Intermediate 67: methyl 4-(3-hydroxy-1-methoxy-1-oxobutan-2-ylamino)-3-nitrobenzoate DIPEA (8.77 mL, 50.22 mmol) was added to methyl 4-fluoro-3-nitrobenzoate (2.0 g, 10.04 mmol) and methyl 2-amino-3-hydroxybutanoate hydrochloride (Intermediate 66, 2.04 g, 12.05 mmol) in DMF (20 mL). The resulting mixture was stirred at rt for 16 hours. The reaction mixture was diluted with EtOAc (100 mL), and washed sequentially with saturated aqueous $NH_4Cl$ solution (100 mL×1), and brine (100 mL×4). The organic layer was dried over $Na_2SO_4$, filtered and evaporated to afford desired product, methyl 4-((3-hydroxy-1-methoxy-1-oxobutan-2-yl)amino)-3-nitrobenzoate (Intermediate 67, 2.9 g, 92%), as a yellow solid. $^1H$ NMR (400 MHz, DMSO-$d_6$) δ 1.15-1.27 (3H, m), 3.64-3.74 (3H, m), 3.83 (3H, s), 4.08-4.44 (1H, m), 4.61-4.72 (1H, m), 5.39-5.60 (1H, m), 7.03-7.15 (1H, m), 7.90-8.03 (1H, m), 8.62-8.69 (1H, m), 8.73-8.89 (1H, m); m/z (ES$^+$) $[M+H]^+$=313.

Intermediate 68: methyl 2-(1-hydroxyethyl)-3-oxo-1,2,3,4-tetrahydroquinoxaline-6-carboxylate 20% $Pd(OH)_2/C$ (0.648 g, 0.92 mmol) was added to methyl 4-((3-hydroxy-1-methoxy-1-oxobutan-2-yl)amino)-3-nitrobenzoate (Intermediate 67, 2.88 g, 9.22 mmol) in MeOH (300 mL) under hydrogen. The resulting mixture was stirred at room temperature for 16 hours. The reaction went to completion. The reaction mixture was filtered through celite. The organic layer was evaporated to afford methyl 2-(1-hydroxyethyl)-3-oxo-1,2,3,4-tetrahydroquinoxaline-6-carboxylate (Intermediate 68, 2.290 g, 99%) as a grey solid. $^1$H NMR (400 MHz, DMSO-$d_6$) 1.07 (3H, m), 2.81 (1H, d), 3.72 (1H, m), 3.74 (3H, s), 4.78 (1H, d), 6.70-6.86 (2H, m), 7.27 (1H, d), 7.37 (1H, dd), 10.38 (1H, d); m/z (ES$^+$) $[M+H]^+$=251.

Intermediate 69: methyl 2-(1-hydroxyethyl)-3-oxo-3,4-dihydroquinoxaline-6-carboxylate DDQ (2.265 g, 9.98 mmol) was added to methyl 2-(1-hydroxyethyl)-3-oxo-1,2,3,4-tetrahydroquinoxaline-6-carboxylate (Intermediate 68, 2.27 g, 9.07 mmol) in DCM (100 mL). The resulting mixture was stirred at room temperature for 1 hour. The reaction went to completion. The reaction mixture was concentrated under reduced pressure to obtain a brown solid. Aq $NaHCO_3$ saturated solution (100 mL) was added to the solid and stirred at room temperature for 1 hour. The precipitate was filtered and rinsed with additional aq $NaHCO_3$ solution (30 mL×3). The solid was dried under vacuum to afford methyl 2-(1-hydroxyethyl)-3-oxo-3,4-dihydroquinoxaline-6-carboxylate (Intermediate 69, 2.24 g, 99%) as a grey solid. $^1$H NMR (400 MHz, DMSO-$d_6$) δ 1.40 (3H, d), 3.88 (3H, s), 4.94 (1H, q), 7.69 (1H, dd), 7.77 (1H, d), 7.90 (1H, d) (2 protons are not shown); m/z (ES$^+$) $[M+H]^+$=249.

Intermediate 70: methyl 2-acetyl-3-oxo-3,4-dihydroquinoxaline-6-carboxylate

Dess-martin periodinane (2.56 g, 6.04 mmol) was added to methyl 2-(1-hydroxyethyl)-3-oxo-3,4-dihydroquinoxaline-6-carboxylate (Intermediate 69, 1.0 g, 4.03 mmol) in DCM (30 mL). The resulting mixture was stirred at room temperature for 3 hours. The reaction mixture was evaporated to afford the crude product. The crude product was purified by reverse phase chromatography, elution gradient 5 to 30% MeCN in water (0.4% $HCO_2H$). Pure fractions were evaporated to dryness to afford methyl 2-acetyl-3-oxo-3,4-dihydroauinoxaline-6-carboxylate (Intermediate 70, 0.62 g, 62.5%) as a pale yellow solid. $^1$H NMR (400 MHz, DMSO-$d_6$) δ 2.58 (3H, s), 3.91 (3H, s), 7.84 (1H, dd), 7.91-8.03 (2H, m), 12.86 (1H, s); m/z (ES$^+$) $[M+H]^+$=247.

Intermediate 71: methyl 2-(1,1-difluoroethyl)-3-oxo-3,4-dihydroquinoxaline-6-carboxylate BAST (1.35 mL, 7.31 mmol) was added to methyl 2-acetyl-3-oxo-3,4-dihydroquinoxaline-6-carboxylate (Intermediate 70, 600 mg, 2.44 mmol) in DCM (20 mL). The resulting mixture was stirred at room temperature for 16 hours. The reaction mixture was evaporated to afford crude product. The crude product was purified by reverse phase chromatography, elution gradient 5 to 30% MeCN in water (0.4% $HCO_2H$). Pure fractions were evaporated to dryness to afford methyl 2-(1,1-difluoroethyl)-3-oxo-3,4-dihydroquinoxaline-6-carboxylate (Intermediate 71, 174 mg, 26.6%) as an off-white solid. 1H NMR (400 MHz, DMSO-d6) δ 2.07 (3H, t), 3.91 (3H, s), 7.84 (1H, dd), 7.92-7.99 (2H, m), 12.90 (1H, s); $^{19}$F NMR (376 MHz, DMSO-$d_6$) δ −93.26; m/z (ES$^+$) $[M+H]^+$=269.

Intermediate 72: 3-(1,1-difluoroethyl)-7-(hydroxymethyl) quinoxalin-2(1H)-one

A solution of 1 M diisobutylaluminum hydride in THF (2.39 mL, 2.39 mmol) was added to methyl 2-(1,1-difluoroethyl)-3-oxo-3,4-dihydroquinoxaline-6-carboxylate (Intermediate 71, 160 mg, 0.60 mmol) in THF (50 mL) at 0° C. The resulting mixture was stirred at room temperature for 16 hours. The reaction mixture was quenched with saturated potassium sodium tartrate aqueous solution (3 mL) and MeOH (1 mL) at 0° C. The resulting mixture was stirred for 1 hour. The reaction mixture was filtered and washed with THF (10 mL×3). The organic layer was evaporated to afford crude product, 3-(1,1-difluoroethyl)-7-(hydroxymethyl) quinoxalin-2(1H)-one (Intermediate 72, 120 mg, 84%). The product was used in the next step directly without further purification. 1H NMR (400 MHz, DMSO-$d_6$) δ 2.06 (3H, t), 4.63 (2H, s), 5.47 (1H, s), 7.26 (1H, dd), 7.35 (1H, d), 7.78 (1H, d), 12.75 (1H, br s); m/z (ES+) $[M+H]^+$=241.

Synthesis Example 22: 5-[4-[[2-(1,1-difluoroethyl)-3-oxo-4H-quinoxalin-6-yl]methyl]piperazin-1-yl]-N-methyl-pyridine-2-carboxamide

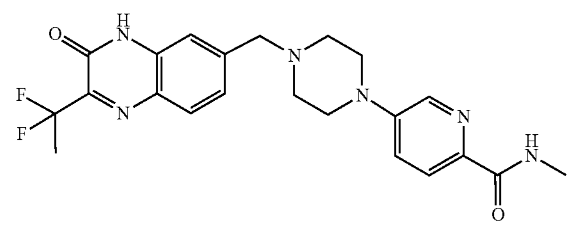 [SMILES: CNC(=O)c1ccc(N2CCN(Cc3ccc4nc(C(C)(F)F)c(=O)[nH]c4c3)CC2)cn1]

3-(1,1-difluoroethyl)-7-(hydroxymethyl) quinoxalin-2(1H)-one (Intermediate 72, 60 mg, 0.25 mmol) was added to 33% HBr in acetic acid (2 mL, 12.15 mmol). The resulting mixture was stirred at 80° C. for 2 hours. The reaction mixture was evaporated under vacuum to afford 7-(bromomethyl)-3-(1,1-difluoroethyl)quinoxalin-2(1H)-one (crude product). The product was used in the next step directly without further purification. DIPEA (0.218 mL, 1.25 mmol) was added to 7-(bromomethyl)-3-(1,1-difluoroethyl)quinoxalin-2(1H)-one (crude product) and N-methyl-5-(piperazin-1-yl)picolinamide (Intermediate 13, 60 mg, 0.27 mmol) in NMP (3 mL). The resulting mixture was stirred at 80° C. for 1 hour. The reaction mixture was concentrated and purified by preparative HPLC (Column: XBridge Shield RP18 OBD Column, 30×150 mm, 5 um; Mobile Phase A: Water (0.05% $NH_3H_2O$), Mobile Phase B: ACN; Flow rate: 60 mL/min; Gradient: 13 B to 33 B in 7 min; 254; 220 nm; RT: 5.70. Fractions containing the desired compound were evaporated to dryness to afford 5-[4-[[2-(1,1-difluoroethyl)-3-oxo-4H-quinoxalin-6-yl]methyl]piperazin-1-yl]-N-methyl-pyridine-2-carboxamide (Synthesis Example 22, 47.8 mg, 43.2%) as an yellow solid. $^1$H NMR (400 MHz, DMSO-$d_6$) δ 2.06 (3H, t), 2.52-2.62 (4H, m), 2.78 (3H, d), 3.30-3.40 (4H, m), 3.67 (2H, s), 7.32-7.42 (3H, m), 7.80-7.86 (2H, m), 8.27 (1H, d), 8.34-8.42 (1H, m), 12.70 (1H, s); $^{19}$F NMR (376 MHz, DMSO-$d_6$) δ −92.74; m/z (ES$^+$) $[M+H]^+$=443.

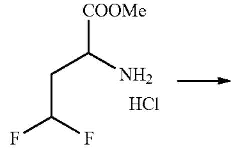

Intermediate 73

-continued

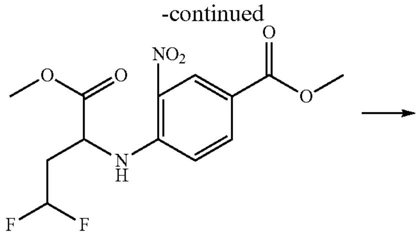

Intermediate 74

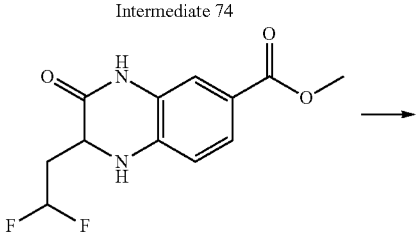

Intermediate 75

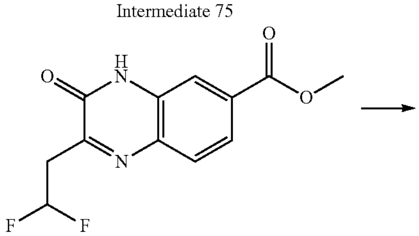

Intermediate 76

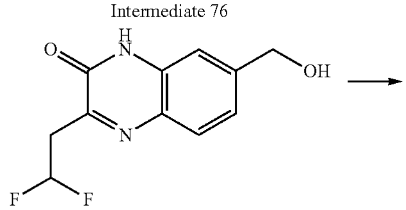

Intermediate 77

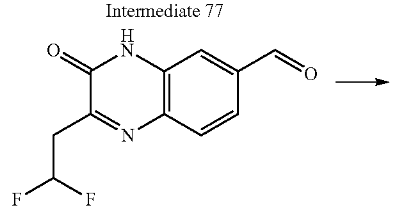

Intermediate 78

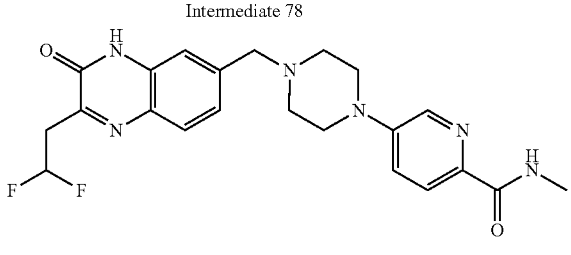

Example 23

Intermediate 74: methyl 4-(4,4-difluoro-1-methoxy-1-oxobutan-2-ylamino)-3-nitrobenzoate DIPEA (8.77 mL, 50.22 mmol) was added to methyl 4-fluoro-3-nitrobenzoate (2.0 g, 10.04 mmol) and methyl 2-amino-4,4-difluorobutanoate hydrochloride (Intermediate 73, 2.0 g, 10.55 mmol) in DMF (20 mL). The resulting mixture was stirred at 40° C. for 8 hours. The reaction mixture was diluted with EtOAc (100 mL), and washed sequentially with saturated $NH_4Cl$ (100 mL×1), and brine (100 mL×4). The organic layer was dried over $Na_2SO_4$, filtered and evaporated to afford desired product, methyl 4-((4,4-difluoro-1-methoxy-1-oxobutan-2-yl)amino)-3-nitrobenzoate (Intermediate 74, 2.5 g, 74.9%), as a yellow solid. $^1H$ NMR (300 MHz, DMSO-$d_6$) δ 2.50-2.76 (2H, m), 3.71 (3H, s), 3.82 (3H, s), 4.95 (1H, q), 6.22 (1H, tt), 7.18 (1H, d), 7.99 (1H, dd), 8.63 (1H, d), 8.66 (1H, d); m/z ($ES^+$) $[M+H]^+$=333.

Intermediate 75: methyl 2-(2,2-difluoroethyl)-3-oxo-1,2,3,4-tetrahydroquinoxaline-6-carboxylate 20% $Pd(OH)_2$/C (0.465 g, 0.66 mmol) was added to methyl 4-((4,4-difluoro-1-methoxy-1-oxobutan-2-yl)amino)-3-nitrobenzoate (Intermediate 74, 2.2 g, 6.62 mmol) in MeOH (300 mL) under hydrogen. The resulting mixture was stirred at room temperature for 16 hours. The reaction mixture was filtered through celite. The filtrate was evaporated to afford methyl 2-(2,2-difluoroethyl)-3-oxo-1,2,3,4-tetrahydroquinoxaline-6-carboxylate (Intermediate 75, 1.64 g, 92%) as a yellow solid. $^1H$ NMR (400 MHz, DMSO-$d_6$) δ 2.24-2.32 (2H, m), 3.76 (3H, s), 4.10-4.18 (1H, m), 6.27 (1H, tt), 6.73 (1H, d), 6.89 (1H, s), 7.37 (1H, d), 7.44 (1H, dd), 10.58 (1H, s); m/z ($ES^+$) $[M+H]^+$=271.

Intermediate 76: methyl 2-(2,2-difluoroethyl)-3-oxo-3,4-dihydroquinoxaline-6-carboxylate DDQ (1.478 g, 6.51 mmol) was added to methyl 2-(2,2-difluoroethyl)-3-oxo-1,2,3,4-tetrahydroquinoxaline-6-carboxylate (Intermediate 75, 1.6 g, 5.92 mmol) in DCM (100 mL). The resulting mixture was stirred at room temperature for 3 hours. The resulting mixture was removed under reduced pressure to obtain a brown solid. Aq $NaHCO_3$ saturated solution (100 mL) was added to the solid and stirred at room temperature for 1 hour. The precipitate was filtered and rinsed with additional aq $NaHCO_3$ solution (30 mL×3). The solid was dried under vacuum to afford methyl 2-(2,2-difluoroethyl)-3-oxo-3,4-dihydroquinoxaline-6-carboxylate (Intermediate 76, 1.58 g, 99%) as an off-white solid. $^1H$ NMR (400 MHz, DMSO-$d_6$) 3.46 (2H, td), 3.90 (3H, s), 6.57 (1H, t), 7.79-7.92 (3H, m), 12.68 (1H, s); m/z ($ES^+$) $[M+H]^+$=269.

Intermediate 77: 3-(2,2-difluoroethyl)-7-(hydroxymethyl) quinoxalin-2(1H)-one

A 1 M solution of diisobutylaluminum hydride in THF (22.37 mL, 22.37 mmol) was added portionwise to methyl 2-(2,2-difluoroethyl)-3-oxo-3,4-dihydroquinoxaline-6-carboxylate (Intermediate 76, 1.0 g, 3.73 mmol) in THF (100 mL) at 0° C. The resulting mixture was stirred at room temperature for 16 hours. The reaction mixture was quenched with saturated potassium sodium tartrate aqueous solution (20 mL) and MeOH (10 mL) at 0° C. The resulting mixture was stirred for 1 hour. The reaction mixture was filtered and washed with THF (30 mL×3). The organic layer was evaporated to afford 3-(2,2-difluoroethyl)-7-(hydroxymethyl)quinoxalin-2(1H)-one (0.72 g, 80%) as a red solid (crude product). The crude product was purified by reverse phase chromatography, elution gradient 5 to 60% MeOH in water (0.4% $HCO_2H$). Pure fractions were evaporated to dryness to afford 3-(2,2-difluoroethyl)-7-(hydroxymethyl)quinoxalin-2(1H)-one (Intermediate 77, 500 mg, 69.4%) as a red solid. $^1H$ NMR (300 MHz, DMSO-$d_6$)

δ 3.42 (2H, td), 4.61 (2H, s), 5.42 (1H, brs), 6.56 (1H, tt), 7.23 (1H, dd), 7.32 (1H, d), 7.71 (1H, d), 12.55 (1H, s); m/z ($ES^+$) $[M+H]^+$=241.

Intermediate 78: 2-(2,2-difluoroethyl)-3-oxo-3,4-dihydroquinoxaline-6-carbaldehyde Dess-Martin periodinane (530 mg, 1.25 mmol) was added to 3-(2,2-difluoroethyl)-7-(hydroxymethyl) quinoxalin-2(1H)-one (Intermediate 77, 200 mg, 0.83 mmol) in DCM (5 mL). The resulting mixture was stirred at room temperature for 2 hours. The resulting mixture was evaporated to afford crude product. The crude product was purified by reverse phase chromatography, elution gradient 5 to 30% MeCN in water (0.4% $HCO_2H$). Pure fractions were evaporated to dryness to afford 2-(2,2-difluoroethyl)-3-oxo-3,4-dihydro-quinoxaline-6-carbaldehyde (Intermediate 78, 160 mg, 81%) as a yellow solid. $^1H$ NMR (400 MHz, DMSO-$d_6$) δ 3.47 (2H, td), 6.58 (1H, tt), 7.77-7.85 (2H, m), 7.90-7.98 (1H, m), 10.09 (1H, s), 12.79 (1H, s); m/z ($ES^+$) $[M+H]^+$=239.

Synthesis Example 23: 5-[4-[[2-(2,2-difluoroethyl)-3-oxo-4H-quinoxalin-6-yl]methyl]piperazin-1-yl]-N-methyl-pyridine-2-carboxamide

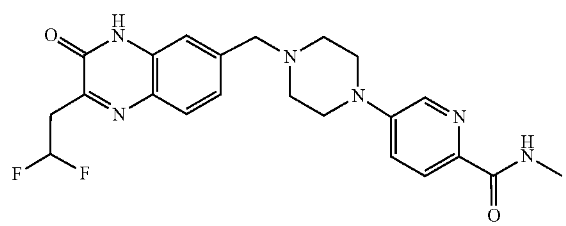 [SMILES: CNC(=O)c1ccc(N2CCN(Cc3ccc4nc(CC(F)F)c(=O)[nH]c4c3)CC2)cn1]

Titanium isopropoxide (65.6 mg, 0.23 mmol) was added to 2-(2,2-difluoroethyl)-3-oxo-3,4-dihydroquinoxaline-6-carbaldehyde (Intermediate 78, 55 mg, 0.23 mmol) and N-methyl-5-(piperazin-1-yl)picolinamide (Intermediate 13, 60 mg, 0.23 mmol) in THF (2 mL). The resulting mixture was stirred at room temperature for 2 minutes. Sodium triacetoxyborohydride (196 mg, 0.92 mmol) was added. The resulting mixture was stirred at room temperature for 1 hour. The reaction mixture was quenched with MeOH (0.1 mL). The reaction mixture was evaporated to afford crude product which was purified by preparative HPLC (Column: XBridge Shield RP18 OBD Column, 30×150 mm, 5 um; Mobile Phase A: Water (0.05% $NH_3H_2O$), Mobile Phase B: ACN; Flow rate: 60 mL/min; Gradient: 13 B to 33 B in 7 min; 254; 220 nm; RT: 5.70. Fractions containing the desired compound were evaporated to dryness to afford 5-[4-[[2-(2,2-difluoroethyl)-3-oxo-4H-quinoxalin-6-yl]methyl]piperazin-1-yl]-N-methyl-pyridine-2-carboxamide (Synthesis Example 23, 8.76 mg, 8.57%) as a yellow solid. $^1H$ NMR (400 MHz, DMSO-$d_6$) δ 2.56 (4H, m), 2.78 (3H, d), 3.32-3.48 (6H, m), 3.64 (2H, s), 6.55 (1H, tt), 7.27-7.33 (2H, m), 7.39 (1H, dd), 7.73 (1H, d), 7.83 (1H, d), 8.26 (1H, d), 8.37 (1H, m), 12.49 (1H, s); $^{19}F$ NMR (376 MHz, DMSO-$d_6$) δ −114.29; m/z ($ES^+$) $[M+H]^+$=443.

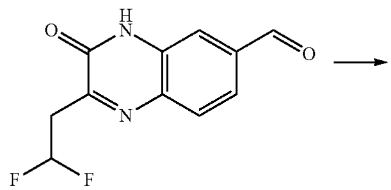

Intermediate 78

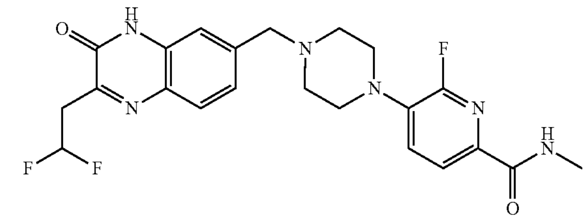

Example 24

Synthesis Example 24: 5-[4-[[2-(2,2-difluoroethyl)-3-oxo-4H-quinoxalin-6-yl]methyl]piperazin-1-yl]-6-fluoro-N-methyl-pyridine-2-carboxamide

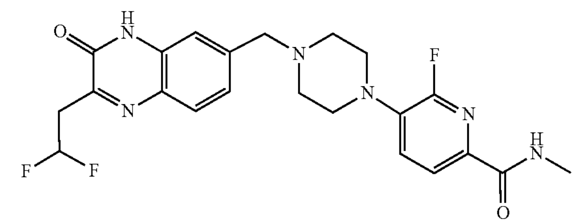 [SMILES: CNC(=O)c1ccc(N2CCN(Cc3ccc4nc(CC(F)F)c(=O)[nH]c4c3)CC2)c(F)n1]

Titanium isopropoxide (59.7 mg, 0.21 mmol) was added to 2-(2,2-difluoroethyl)-3-oxo-3,4-dihydroquinoxaline-6-carbaldehyde (Intermediate 78, 50 mg, 0.21 mmol) and 6-fluoro-N-methyl-5-(piperazin-1-yl)picolinamide (Intermediate 23, 50.0 mg, 0.21 mmol) in THF (2 mL). The resulting mixture was stirred at room temperature for 2 minutes. Sodium triacetoxyborohydride (178 mg, 0.84 mmol) was added. The resulting mixture was stirred at room temperature for 1 hour. The reaction went to completion. The reaction mixture was quenched with MeOH (0.1 mL). The reaction mixture was evaporated to afford crude product. The crude product was purified by preparative HPLC (Column: Sunfire prep C18 column, 30×150, 5 um; Mobile Phase A: Water (0.1% $HCO_2H$), Mobile Phase B: ACN; Flow rate: 60 mL/min; Gradient: 2 B to 27 B in 7 min; 254/220 nm; RT: 6.78. Fractions containing the desired compound were evaporated to dryness to afford 5-[4-[[2-(2,2-difluoroethyl)-3-oxo-4H-quinoxalin-6-yl]methyl]piperazin-1-yl]-6-fluoro-N-methyl-pyridine-2-carboxamide (Synthesis Example 24, 21.72 mg, 22.13%) as a yellow solid. $^1H$ NMR (400 MHz, DMSO-$d_6$) δ 2.54-2.61 (4H, m), 2.76 (3H, d), 3.14-3.22 (4H, m), 3.41 (2H, td), 3.64 (2H, s), 6.39-6.71 (1H, m), 7.26-7.33 (2H, m), 7.57 (1H, dd), 7.73 (1H, d), 7.82-7.86 (1H, m), 8.13 (0.16H, s), 8.37 (1H, m), 12.49 (1H, s); $^{19}F$ NMR (376 MHz, DMSO-$d_6$) δ −72.52, −114.29; m/z ($ES^+$) $[M+H]^+$=461.

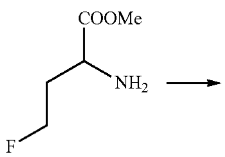

Intermediate 79

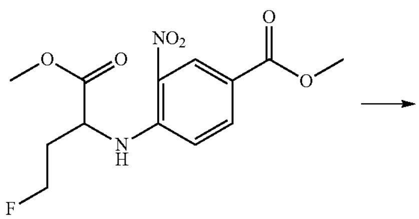

Intermediate 80

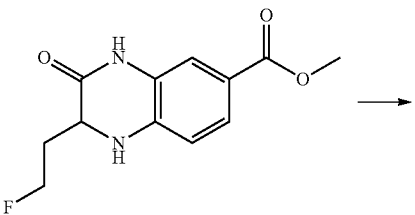

Intermediate 81

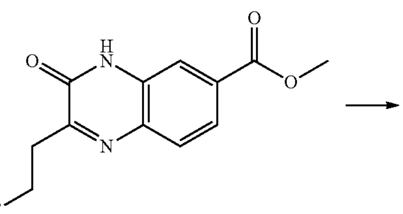

Intermediate 82

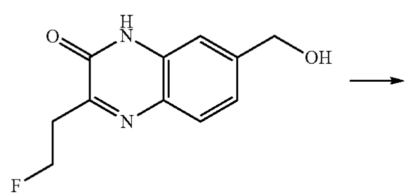

Intermediate 83

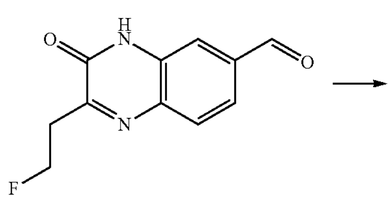

Intermediate 84

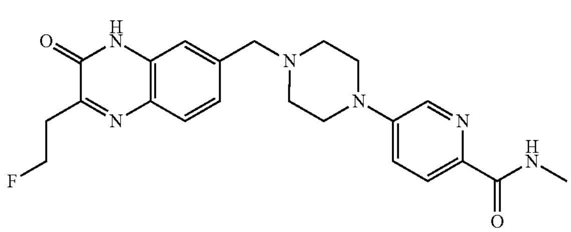

Example 25

Intermediate 80: methyl 4-(4-fluoro-1-methoxy-1-oxobutan-2-ylamino)-3-nitrobenzoate DIPEA (8.77 mL, 50.22 mmol) was added to methyl 4-fluoro-3-nitrobenzoate (2.0 g, 10.04 mmol) and methyl 2-amino-4-fluorobutanoate hydrochloride (Intermediate 79, 1.81 g, 10.55 mmol) in DMF (20 mL). The resulting mixture was stirred at 40° C. for 8 hours. The reaction mixture was diluted with EtOAc (100 mL), and washed sequentially with saturated $NH_4Cl$ (100 mL×1), and brine (100 mL×4). The organic layer was dried over $Na_2SO_4$, filtered and evaporated to afford desired product, methyl 4-((4-fluoro-1-methoxy-1-oxobutan-2-yl)amino)-3-nitrobenzoate (Intermediate 80, 2.5 g, 79%), as a yellow solid. 1H NMR (300 MHz, DMSO-$d_6$) δ 2.25-2.35 (1H, m), 2.35-2.45 (1H, m), 3.71 (3H, s), 3.82 (3H, s), 4.36-4.58 (1H, m), 4.56-4.74 (1H, m), 4.84 (1H, q), 7.14 (1H, d), 7.99 (1H, dd), 8.63 (1H, d), 8.67 (1H, d); m/z ($ES^+$) $[M+H]^+$=315.

Intermediate 81: methyl 2-(2-fluoroethyl)-3-oxo-1,2,3,4-tetrahydroquinoxaline-6-carboxylate 20% $Pd(OH)_2$/C (0.547 g, 0.78 mmol) was added to methyl 4-((4-fluoro-1-methoxy-1-oxobutan-2-yl)amino)-3-nitrobenzoate (Intermediate 80, 2.45 g, 7.80 mmol) in MeOH (300 mL) under hydrogen. The resulting mixture was stirred at room temperature for 16 hours. The reaction went to completion. The reaction mixture was filtered through celite. The filtrate was evaporated to afford methyl 2-(2-fluoroethyl)-3-oxo-1,2,3,4-tetrahydroquinoxaline-6-carboxylate (Intermediate 81, 1.9 g, 97%) as a grey solid. $^1H$ NMR (400 MHz, DMSO-$d_6$) δ1.91-2.19 (2H, m), 3.75 (3H, s), 4.03 (1H, m), 4.49-4.73 (2H, m), 6.73 (1H, d), 6.91 (1H, d), 7.35 (1H, d), 7.42 (1H, dd), 10.46 (1H, s); m/z ($ES^+$) $[M+H]^+$=253.

Intermediate 82: methyl 2-(2-fluoroethyl)-3-oxo-3,4-dihydroquinoxaline-6-carboxylate DDQ (1.83 g, 8.07 mmol) was added to methyl 2-(2-fluoroethyl)-3-oxo-1,2,3,4-tetrahydroquinoxaline-6-carboxylate (Intermediate 81, 1.85 g, 7.33 mmol) in DCM (100 mL). The resulting mixture was stirred at room temperature for 3 hours. The resulting mixture was removed under reduced pressure to obtain a brown solid. Aq·$NaHCO_3$ saturated solution (100 mL) was added to the solid and stirred at room temperature for 1 hour. The precipitate was filtered and rinsed with additional aq $NaHCO_3$ solution (30 mL×3). The solid was dried under vacuum to afford methyl 2-(2-fluoroethyl)-3-oxo-3,4-dihydroauinoxaline-6-carboxylate (Intermediate 82, 1.8 g, 98%) as a grey solid. $^1H$ NMR (400 MHz, DMSO-$d_6$) δ 3.23 (2H, dt), 3.89 (3H, s), 4.90 (2H, dt), 7.76-7.85 (2H, m), 7.88 (1H, d), 12.55 (1H, s); m/z ($ES^+$) $[M+H]^+$=251.

Intermediate 83: 3-(2-fluoroethyl)-7-(hydroxymethyl) quinoxalin-2(1H)-one

1 M solution of diisobutylaluminum hydride in THF (15.99 mL, 15.99 mmol) was added portionwise to methyl 2-(2-fluoroethyl)-3-oxo-3,4-dihydroquinoxaline-6-carboxylate (Intermediate 82, 1.0 g, 4.00 mmol) in THF (100 mL) at 0° C. The resulting mixture was stirred at room temperature for 16 hours. The reaction mixture was quenched with saturated potassium sodium tartrate aqueous solution (20 mL) and MeOH (10 mL) at 0° C. The resulting mixture was stirred for 1 hour. The reaction mixture was filtered and washed with THF (30 mL×3). The organic layer was evaporated to afford crude product. The crude product was purified by reverse phase chromatography, elution gradient 5 to 60% MeOH in water (0.4% $HCO_2H$). Pure fractions were evaporated to dryness to afford 3-(2-fluoroethyl)-7-(hydroxymethyl) quinoxalin-2(1H)-one (Intermediate 83, 0.49 g, 55.2%) as a brown solid. $^1H$ NMR (300 MHz, DMSO-$d_6$) δ 3.20 (2H, dt), 4.60 (2H, d), 4.90 (2H, dt), 5.41 (1H, t), 7.21 (1H, dd), 7.30 (1H, d), 7.68 (1H, d), 12.42 (1H, s); m/z (ES$^+$) $[M+H]^+$=223.

Intermediate 84: 2-(2-fluoroethyl)-3-oxo-3,4-dihydroauinoxaline-6-carbaldehyde

Dess-Martin periodinane (229 mg, 0.54 mmol) was added to 3-(2-fluoroethyl)-7-(hydroxymethyl)quinoxalin-2(1H)-one (Intermediate 83, 100 mg, 0.45 mmol) in DCM (3 mL). The resulting mixture was stirred at room temperature for 2 hours. The reaction mixture was evaporated to afford crude product. The crude product was purified by reverse phase chromatography, elution gradient 5 to 30% MeCN in water (0.4% $HCO_2H$). Pure fractions were evaporated to dryness to afford 2-(2-fluoroethyl)-3-oxo-3,4-dihydroquinoxaline-6-carbaldehyde (Intermediate 84, 93 mg, 94%) as a yellow solid. $^1H$ NMR (300 MHz, DMSO-$d_6$) δ 3.20-3.28 (2H, m), 4.90 (2H, dt), 7.74-7.80 (2H, m), 7.91 (1H, d), 10.06 (1H, s), 12.66 (1H, s); m/z (ES+) $[M+H]^+$=221.

Synthesis Example 25: 5-[4-[[2-(2-fluoroethyl)-3-oxo-4H-quinoxalin-6-yl]methyl]piperazin-1-yl]-N-methyl-pyridine-2-carboxamide

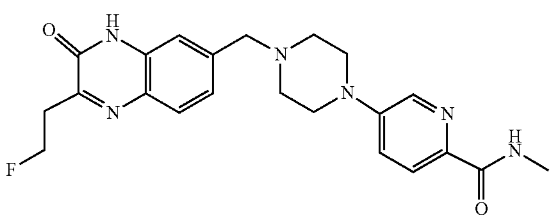 [SMILES: CNC(=O)c1ccc(N2CCN(Cc3ccc4nc(CCF)c(=O)[nH]c4c3)CC2)cn1]

Titanium isopropoxide (64.5 mg, 0.23 mmol) was added to 2-(2-fluoroethyl)-3-oxo-3,4-dihydroquinoxaline-6-carbaldehyde (Intermediate 84, 50 mg, 0.23 mmol) and N-methyl-5-(piperazin-1-yl)picolinamide (Intermediate 13, 50.0 mg, 0.23 mmol) in THF (3 mL). The resulting mixture was stirred at room temperature for 2 minutes. Sodium triacetoxyborohydride (192 mg, 0.91 mmol) was added. The resulting mixture was stirred at room temperature for 2 hours. This was repeated in another batch, and two batches were combined for the purification. The combined reaction mixture was purified by preparative HPLC (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 20 B to 35 B in 7 min; 254/210 nm; RT: 6.38. Fractions containing the desired compound were evaporated to dryness to afford 5-[4-[[2-(2-fluoroethyl)-3-oxo-4H-quinoxalin-6-yl]methyl]piperazin-1-yl]-N-methyl-pyridine-2-carboxamide (Synthesis Example 25, 4.83 mg, 2.54%) as a white solid. $^1H$ NMR (400 MHz, DMSO-$d_6$) δ 2.53-2.59 (4H, m), 2.78 (3H, d), 3.17 (1H, t), 3.23 (1H, t), 3.32-3.38 (4H, m), 3.63 (2H, s), 4.83 (1H, t), 4.95 (1H, t), 7.25-7.32 (2H, m), 7.39 (1H, dd), 7.71 (1H, d), 7.83 (1H, d), 8.26 (1H, d), 8.37 (1H, d), 12.36 (1H, s); $^{19}F$ NMR (376 MHz, DMSO-d6) 5-217.70; m/z (ES$^+$) $[M+H]^+$= 425.

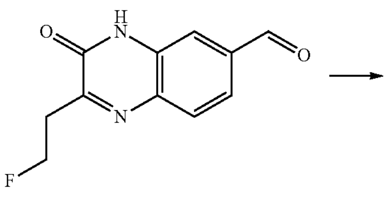

Intermediate 84

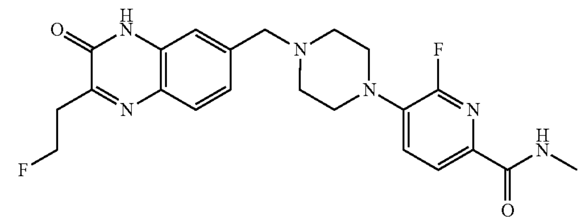

Example 26

Synthesis Example 26: 6-fluoro-5-[4-[[2-(2-fluoroethyl)-3-oxo-4H-quinoxalin-6-yl]methyl]piperazin-1-yl]-N-methyl-pyridine-2-carboxamide

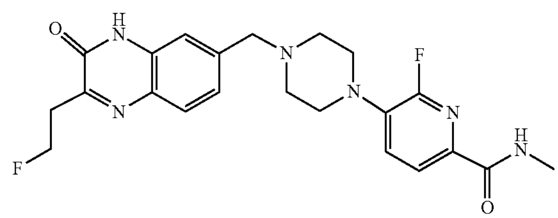 [SMILES: CNC(=O)c1ccc(N2CCN(Cc3ccc4nc(CCF)c(=O)[nH]c4c3)CC2)c(F)n1]

Titanium isopropoxide (90 mg, 0.32 mmol) was added to 2-(2-fluoroethyl)-3-oxo-3,4-dihydroquinoxaline-6-carbaldehyde (Intermediate 84, 70 mg, 0.32 mmol) and 6-fluoro-N-methyl-5-(piperazin-1-yl)picolinamide (Intermediate 23, 76 mg, 0.32 mmol) in THF (3 mL). The resulting mixture was stirred at room temperature for 2 minutes. Sodium triacetoxyborohydride (269 mg, 1.27 mmol) was added. The resulting mixture was stirred at room temperature for 1 hour. The reaction mixture was quenched with MeOH (0.1 mL). The reaction mixture was evaporated to afford crude product. The crude product was purified by preparative HPLC (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 28 B to 35 B in 8 min; 254/210 nm; RT: 7 Fractions containing the desired compound were evaporated to dryness to afford crude product. The crude product was further purified by preparative HPLC (Column: Xselect CSH OBD Column 30*150 mm 5 um, n; Mobile Phase A: Water (0.1% $HCO_2H$), Mobile Phase B: ACN; Flow rate: 60 mL/min; Gradient: 5 B to 20 B in 7 min; 254; 220 nm; RT: 6.83. Fractions containing the desired compound were evaporated to dryness to afford 6-fluoro-5-[4-[[2-(2-fluoroethyl)-3-oxo-4H-quinoxalin-6-yl]methyl]piperazin-1-yl]-N-methyl-pyridine-2-carboxamide (Synthesis Example 26, 3.79 mg, 2.65%) as a yellow solid. 1H NMR (400 MHz, DMSO-$d_6$)

δ 2.55-2.60 (4H, m), 2.76 (3H, d), 3.14-3.25 (6H, m), 3.63 (2H, s), 4.89 (2H, dt), 7.24-7.31 (2H, m), 7.57 (1H, dd), 7.70 (1H, d), 7.84 (1H, d), 8.24 (0.174H, s), 8.38 (1H, d), 12.37 (1H, s); $^{19}F$ NMR (376 MHz, DMSO-$d_6$) δ −72.51, −217.71; ($ES^+$) $[M+H]^+$=443.

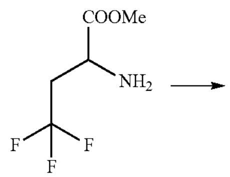

Intermediate 85

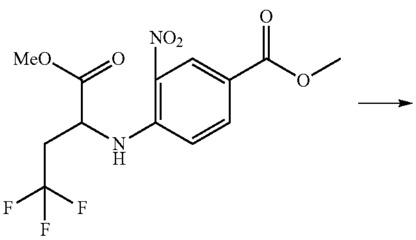

Intermediate 86

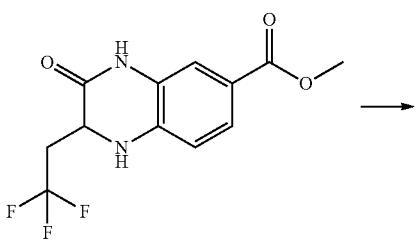

Intermediate 87

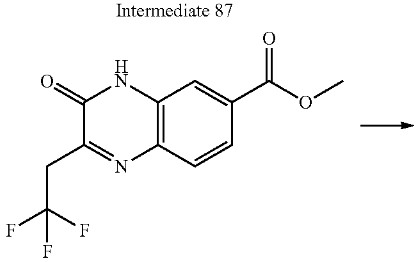

Intermediate 88

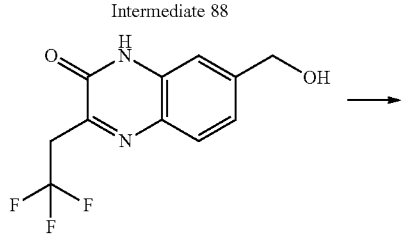

Intermediate 89

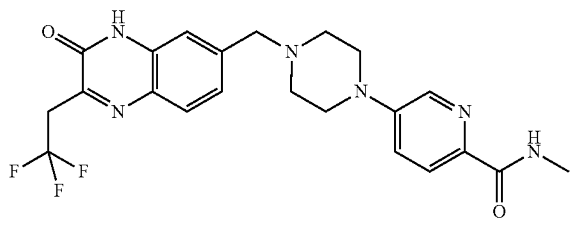

Example 27

Intermediate 86: methyl 3-nitro-4-(4,4,4-trifluoro-1-methoxy-1-oxobutan-2-ylamino)benzoate DIPEA (8.77 mL, 50.22 mmol) was added to methyl 4-fluoro-3-nitrobenzoate (2.0 g, 10.04 mmol) and methyl 2-amino-4,4,4-trifluorobutanoate hydrochloride (Intermediate 85, 2.2 g, 10.55 mmol) in DMF (20 mL). The resulting mixture was stirred at 50° C. for 10 hours. The reaction mixture was diluted with EtOAc (100 mL), and washed sequentially with saturated aqueous $NH_4Cl$ (100 mL×1), and brine (100 mL×4). The organic layer was dried over $Na_2SO_4$, filtered and evaporated to afford desired product, methyl 3-nitro-4-((4,4,4-trifluoro-1-methoxy-1-oxobutan-2-yl)amino)benzoate (Intermediate 86, 3.0 g, 85%), as a yellow solid. $^1H$ NMR (400 MHz, DMSO-$d_6$) δ 2.99-3.28 (2H, m), 3.73 (3H, s), 3.84 (3H, s), 5.18 (1H, td), 7.28 (1H, d), 8.01 (1H, dd), 8.65 (1H, d), 8.71 (1H, d); m/z ($ES^+$) $[M+H]^+$=351.

Intermediate 87: methyl 3-oxo-2-(2,2,2-trifluoroethyl)-1,2,3,4-tetrahydroquinoxaline-6-carboxylate 20% $Pd(OH)_2$/C (0.601 g, 0.86 mmol) was added to methyl 3-nitro-4-((4,4,4-trifluoro-1-methoxy-1-oxobutan-2-yl)amino)benzoate (Intermediate 86, 3.0 g, 8.57 mmol) in MeOH (300 mL) under hydrogen. The resulting mixture was stirred at room temperature for 16 hours. The reaction mixture was filtered through celite. The filtrate was evaporated to dryness to afford methyl 3-oxo-2-(2,2,2-trifluoroethyl)-1,2,3,4-tetrahydroquinoxaline-6-carboxylate (Intermediate 87, 2.3 g, 93%) as an off-white solid. $^1H$ NMR (400 MHz, DMSO-$d_6$) δ 2.64-2.83 (2H, m), 3.76 (3H, s), 4.32-4.37 (1H, m), 6.78 (1H, d), 6.90 (1H, d), 7.37 (1H, d), 7.43 (1H, dd), 10.64 (1H, s); m/z ($ES^+$) $[M+H]^+$=289.

Intermediate 88: methyl 3-oxo-2-(2,2,2-trifluoroethyl)-3,4-dihydroquinoxaline-6-carboxylate DDQ (1.975 g, 8.70 mmol) was added to methyl 3-oxo-2-(2,2,2-trifluoroethyl)-1,2,3,4-tetrahydroquinoxaline-6-carboxylate (Intermediate 87, 2.28 g, 7.91 mmol) in DCM (100 mL). The resulting mixture was stirred at room temperature for 3 hours. The resulting mixture was removed under reduced pressure to obtain a brown solid. Aq·$NaHCO_3$ saturated solution (100 mL) was added to the solid and stirred at room temperature for 1 hour. The precipitate was filtered and rinsed with additional aq $NaHCO_3$ solution (30 mL×3). The solid was dried under vacuum to afford methyl 3-oxo-2-(2,2,2-trifluoroethyl)-3,4-dihydroquinoxaline-6-carboxylate (Intermediate 88, 2.2 g, 97%) as a brown solid. $^1H$ NMR (400 MHz, DMSO-$d_6$) δ 3.88-3.98 (5H, m), 7.81 (1H, dd), 7.86-7.94 (2H, m), 12.75 (1H, s); m/z ($ES^+$) $[M+H]^+$=287.

Intermediate 89: 7-(hydroxymethyl)-3-(2,2,2-trifluoroethyl) quinoxalin-2(1H)-one A 1 M solution of diisobutylaluminum hydride in THF (20.96 mL, 20.96 mmol) was added portionwise to methyl 3-oxo-2-(2,2,2-trifluoroethyl)-3,4-dihydroquinoxaline-6-carboxylate (Intermediate 88, 1.0 g, 3.49 mmol) in THF (100 mL) at 0° C. The resulting mixture was stirred at room temperature for 16 hours. The reaction mixture was quenched with saturated potassium sodium tartrate aqueous solution (20 mL) and MeOH (10 mL) at 0° C. The resulting mixture was stirred for 1 hour. The reaction mixture was filtered and washed with THF (30 mL×3). The organic layer was evaporated to afford an off-white solid that was purified by flash silica chromatography, elution gradient 5 to 55% MeOH in water (0.4% $HCO_2H$). Pure fractions were evaporated to dryness to afford 7-(hydroxymethyl)-3-(2,2,2-trifluoroethyl) quinoxalin-2(1H)-one (Intermediate 89, 650 mg, 72.2%) as a yellow solid. 1H NMR (300 MHz, DMSO-$d_6$) δ 3.88 (2H, q), 4.62 (2H, d), 5.45 (1H, t), 7.24 (1H, dd), 7.33 (1H, d), 7.73 (1H, d), 12.62 (1H, s); m/z ($ES^+$) $[M+H]^+$=259.

Synthesis Example 27: N-methyl-5-[4-[[3-oxo-2-(2,2,2-trifluoroethyl)-4H-quinoxalin-6-yl]methyl]piperazin-1-yl]pyridine-2-carboxamide

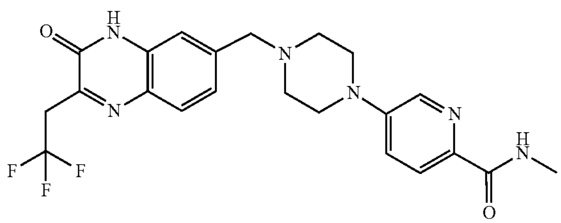 [SMILES: CNC(=O)c1ccc(N2CCN(Cc3ccc4nc(CC(F)(F)F)c(=O)[nH]c4c3)CC2)cn1]

7-(hydroxymethyl)-3-(2,2,2-trifluoroethyl)quinoxalin-2(1H)-one (Intermediate 89, 50 mg, 0.19 mmol) was added to 33% HBr in AcOH (2 mL, 12.15 mmol). The resulting mixture was stirred at 80° C. for 2 hours. The reaction mixture was evaporated under vacuum to afford 7-(bromomethyl)-3-(2,2,2-trifluoroethyl) quinoxalin-2(1H)-one (crude product). The product was used in the next step directly without further purification. DIPEA (0.169 mL, 0.97 mmol) was added to 7-(bromomethyl)-3-(2,2,2-trifluoroethyl)quinoxalin-2(1H)-one (crude product) and N-methyl-5-(piperazin-1-yl)picolinamide (Intermediate 13, 50 mg, 0.23 mmol) in NMP (2 mL). The resulting mixture was stirred at 80° C. for 1 hour. The reaction mixture was concentrated purified by preparative HPLC (Column: Sunfire prep C18 column, 30×150, 5 um; Mobile Phase A: Water (0.1% $HCO_2H$), Mobile Phase B: ACN; Flow rate: 60 mL/min; Gradient: 10 B to 25 B in 7 min; 254/220 nm; RT: 6.57. Fractions containing the desired compound were evaporated to dryness to afford N-methyl-5-[4-[[3-oxo-2-(2,2,2-trifluoroethyl)-4H-quinoxalin-6-yl]methyl]piperazin-1-yl]pyridine-2-carboxamide (Synthesis Example 27, 41.5 mg, 46.6%) as an off-white solid. $^1H$ NMR (400 MHz, DMSO-$d_6$) δ 2.56 (4H, m), 2.78 (3H, d), 3.35 (4H, m), 3.65 (2H, s), 3.88 (2H, q), 7.29-7.42 (3H, m), 7.79 (2H, m), 8.25-8.30 (1H, m), 8.38 (1H, m), 12.60 (1H, br s); $^{19}F$ NMR (376 MHz, DMSO-$d_6$) δ −61.53; m/z ($ES^+$) $[M+H]^+$=461.

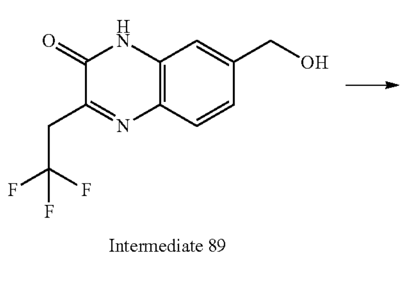

Intermediate 89

-continued

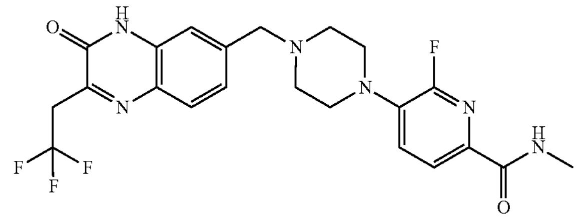

Example 28

Synthesis Example 28: 6-fluoro-N-methyl-5-[4-[[3-oxo-2-(2,2,2-trifluoroethyl)-4H-quinoxalin-6-yl]methyl]piperazin-1-yl]pyridine-2-carboxamide

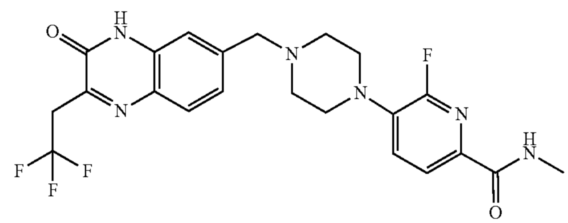 [SMILES: CNC(=O)c1ccc(N2CCN(Cc3ccc4nc(CC(F)(F)F)c(=O)[nH]c4c3)CC2)c(F)n1]

7-(hydroxymethyl)-3-(2,2,2-trifluoroethyl)quinoxalin-2(1H)-one (Intermediate 89, 60 mg, 0.23 mmol) was added to 33% HBr in AcOH (2 mL, 12.15 mmol). The resulting mixture was stirred at 80° C. for 2 hours. The reaction mixture was evaporated under vacuum to afford 7-(bromomethyl)-3-(2,2,2-trifluoroethyl) quinoxalin-2(1H)-one (crude product). The product was used in the next step directly without further purification. DIPEA (0.203 mL, 1.16 mmol) was added to 7-(bromomethyl)-3-(2,2,2-trifluoroethyl)quinoxalin-2(1H)-one (crude product) and 6-fluoro-N-methyl-5-(piperazin-1-yl)picolinamide (Intermediate 23, 60 mg, 0.25 mmol) in NMP (2 mL). The resulting mixture was stirred at 80° C. for 2 hours. The resulting mixture was purified by preparative HPLC (Column: Sunfire prep C18 column, 30×150, 5 um; Mobile Phase A: Water (0.1% $HCO_2H$), Mobile Phase B: ACN; Flow rate: 60 mL/min; Gradient: 12 B to 30 B in 7 min; 254/220 nm; RT: 6.25. Fractions containing the desired compound were evaporated to dryness to afford 6-fluoro-N-methyl-5-[4-[[3-oxo-2-(2,2,2-trifluoroethyl)-4H-quinoxalin-6-yl]methyl]piperazin-1-yl]pyridine-2-carboxamide (Synthesis Example 28, 49.0 mg, 43.3%) as an off-white solid. $^1H$ NMR (400 MHz, DMSO-$d_6$) δ 2.53-2.63 (4H, m), 2.76 (3H, d), 3.15-3.22 (4H, m), 3.65 (2H, s), 3.88 (2H, q), 7.28-7.35 (2H, m), 7.57 (1H, dd), 7.76 (1H, d), 7.84 (1H, dd), 8.17 (0.185H, s), 8.38 (1H, m), 12.57 (1H, s); $^{19}F$ NMR (376 MHz, DMSO-$d_6$) δ −61.54, −72.52; m/z ($ES^+$) $[M+H]^+$=479.

Synthesis Example 29: 6-(difluoromethyl)-5-[4-[(7-ethyl-6-oxo-5H-1,5-naphthyridin-3-yl)methyl]piperazin-1-yl]-N-methyl-pyridine-2-carboxamide

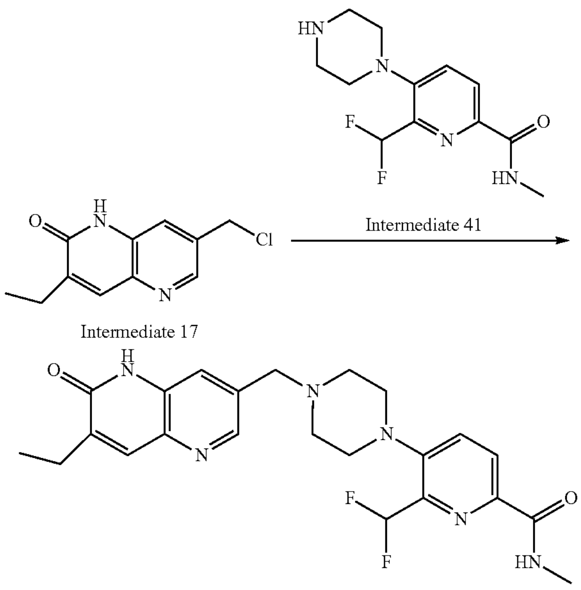

Intermediate 17

Example 29

DIPEA (330 μl, 1.89 mmol) was added to a stirred solution of 7-(chloromethyl)-3-ethyl-1,5-naphthyridin-2(1H)-one, HCl (Intermediate 17, 70 mg, 0.27 mmol), sodium iodide (4.05 mg, 0.03 mmol) and 6-(difluoromethyl)-N-methyl-5-piperazin-1-yl-pyridine-2-carboxamide, 2HCl (Intermediate 41,102 mg, 0.30 mmol) in acetonitrile (2.4 mL) at 20° C. and the resulting solution was stirred at 50° C. for 3 hours. Solvent was removed under vacuum and 50 mL water followed by 3 mL sat $NaHCO_3$ was added. Mixture was extracted with ethyl acetate. After concentration, the resulting residue was purified by flash silica chromatography, elution gradient 0 to 30% MeOH in DCM. Product fractions were concentrated under reduced pressure to dryness to afford 6-(difluoromethyl)-5-[4-[(7-ethyl-6-oxo-5H-1,5-naphthyridin-3-yl)methyl]piperazin-1-yl]-N-methyl-pyridine-2-carboxamide (Synthesis Example 29, 52.0 mg, 42%) as a pale yellow solid. $^1H$ NMR (500 MHz, DMSO-$d_6$) 1.19 (3H, t), 2.54-2.58 (2H, m), 2.63 (4H, br s), 2.84 (3H, d), 3.03 (4H, br t), 3.68 (2H, s), 7.14 (1H, t), 7.62 (1H, d), 7.76 (1H, s), 7.86 (1H, d), 8.10 (1H, d), 8.32-8.45 (2H, m), 11.86 (1H, s); m/z ($ES^+$) $[M+H]^+$=457.

Synthesis Example 30: 5-[4-[(7-ethyl-6-oxo-5H-1,5-naphthyridin-3-yl)methyl]piperazin-1-yl]-N-methyl-6(trifluoromethyl)pyridine-2-carboxamide

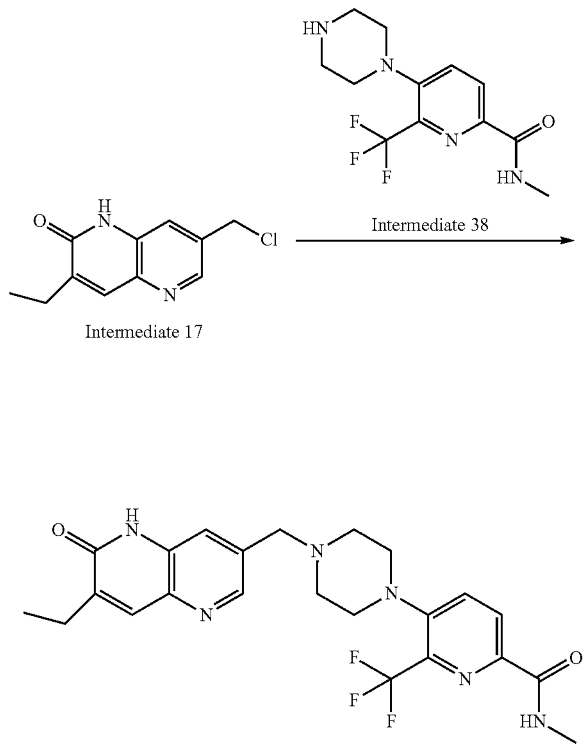

Intermediate 17

Example 30

DIPEA (330 μl, 1.89 mmol) was added to a stirred solution of 7-(chloromethyl)-3-ethyl-1,5-naphthyridin-2(1H)-one, HCl (Intermediate 17, 70 mg, 0.27 mmol), sodium iodide (4.05 mg, 0.03 mmol) and N-methyl-5-piperazin-1-yl-6-(trifluoromethyl)pyridine-2-carboxamide, 2HCl (Intermediate 38,107 mg, 0.30 mmol) in acetonitrile (2.4 mL) at 20° C. and the resulting solution was stirred at 50° C. for 3 hours. Solvent was removed under vacuum and 50 mL water followed by 3 mL sat $NaHCO_3$ was added. Mixture was extracted with ethyl acetate. After concentration, the resulting residue was purified by flash silica chromatography, elution gradient 0 to 30% MeOH in DCM. Product fractions were concentrated under reduced pressure to dryness to afford 5-[4-[(7-ethyl-6-oxo-5H-1,5-naphthyridin-3-yl)methyl]piperazin-1-yl]-N-methyl-6 (trifluoromethyl)pyridine-2-carboxamide (Synthesis Example 30, 58.0 mg, 45%) as a pale yellow solid. $^1H$ NMR (500 MHz, DMSO-$d_6$) 1.19 (3H, t), 2.54-2.62 (6H, m), 2.83 (3H, d), 3.04 (4H, br t), 3.67 (2H, s), 7.62 (1H, d), 7.75 (1H, s), 8.04 (1H, d), 8.19 (1H, d), 8.31-8.48 (2H, m), 11.85 (1H, s); m/z ($ES^+$) $[M+H]^+$=475.

Synthesis Example 31: 5-[4-[(7-ethyl-6-oxo-5H-1,5-naphthyridin-3-yl)methyl]piperazin-1-yl]-N,6-dimethyl-pyridine-2-carboxamide

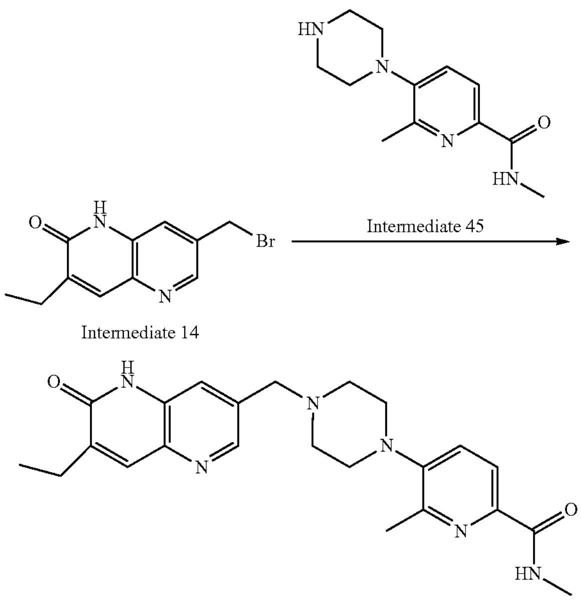

Intermediate 14

Example 31

DIPEA (0.366 mL, 2.10 mmol) was added to a stirred solution of 7-(bromomethyl)-3-ethyl-1,5-naphthyridin-2(1H)-one (Intermediate 14, 80 mg, 0.30 mmol) and N,6-dimethyl-5-piperazin-1-yl-pyridine-2-carboxamide, 2HCl (Intermediate 45, 101 mg, 0.33 mmol) in acetonitrile (2 mL) at 20° C. and the resulting solution was stirred at 70° C. for 3 hours. Solvent was removed under vacuum and 50 mL water followed by 3 mL sat $NaHCO_3$ was added. Mixture was extracted with ethyl acetate. After concentration, the resulting residue was purified by flash silica chromatography, elution gradient 0 to 30% MeOH in DCM. Product fractions were concentrated under reduced pressure to dryness to afford 5-[4-[(7-ethyl-6-oxo-5H-1,5-naphthyridin-3-yl)methyl]piperazin-1-yl]-N,6-dimethyl-pyridine-2-carboxamide (Synthesis Example 31, 36.0 mg, 29%) as a pale yellow solid. $^1H$ NMR (500 MHz, DMSO-$d_6$) 1.19 (3H, t), 2.50 (3H, s), 2.54-2.57 (2H, m), 2.57-2.64 (4H, m), 2.81 (3H, d), 2.96 (4H, br s), 3.68 (2H, s), 7.49 (1H, d), 7.63 (1H, d), 7.76 (1H, s), 7.80 (1H, d), 8.35-8.47 (2H, m), 11.85 (1H, br s); m/z ($ES^+$) $[M+H]^+$=421.

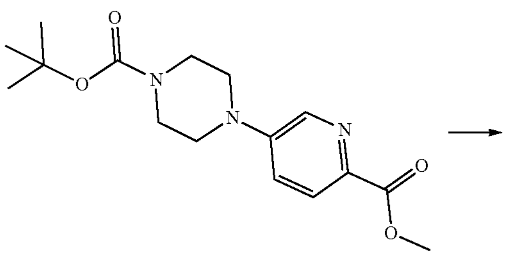

Intermediate 15

-continued

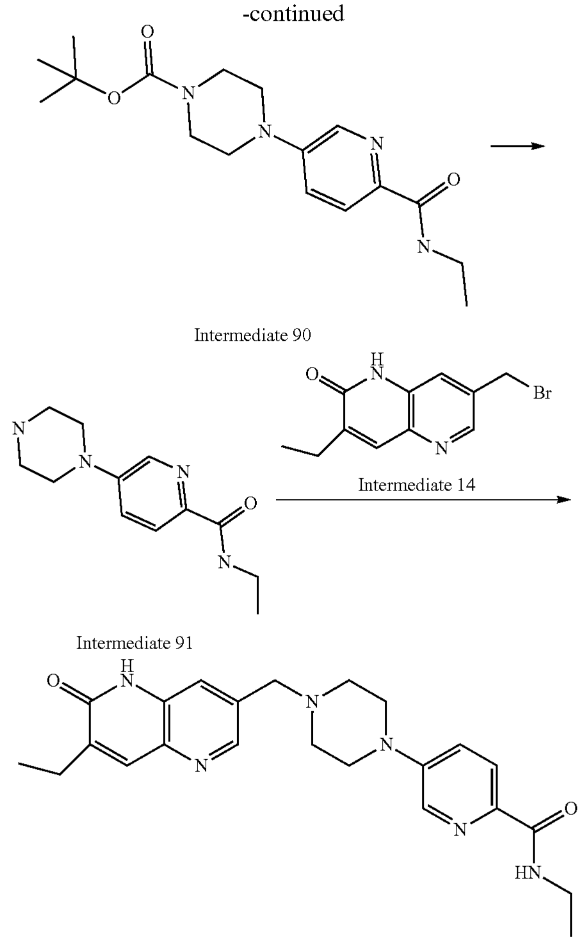

Intermediate 90

Intermediate 91

Example 32

Intermediate 90: tert-butyl 4-[6-(ethylcarbamoyl)-3-pyridyl]piperazine-1-carboxylate Ethanamine in methanol (7M, 7.78 mL, 15.56 mmol) was added to solution of tert-butyl 4-(6-(methoxycarbonyl)pyridin-3-yl)piperazine-1-carboxylate (Intermediate 15, 500 mg, 1.56 mmol) and the resulting solution was stirred at 50° C. for 18 hours. Solvent was removed under vacuum and sample was dried further to afford tert-butyl 4-[6-(ethylcarbamoyl)-3-pyridyl]piperazine-1-carboxylate (Intermediate 90, 0.495 g, 95%). $^1H$ NMR (500 MHz, DMSO-d6) 1.11 (3H, t), 1.43 (9H, s), 3.27-3.32 (6H, m), 3.44-3.52 (4H, m), 7.42 (1H, dd), 7.85 (1H, d), 8.28 (1H, d), 8.44 (1H, br t).

Intermediate 91: N-ethyl-5-piperazin-1-yl-pyridine-2-carboxamide

HCl in dioxane (0.473 mL, 15.58 mmol) was added slowly to a stirred solution of tert-butyl 4-(6-(ethylcarbamoyl)pyridin-3-yl)piperazine-1-carboxylate (Intermediate 90, 521 mg, 1.56 mmol), in methanol (10 mL). The resulting solution was stirred at rt for 17 hours. Reaction was concentrated and the solid was dried to give N-ethyl-5-piperazin-1-yl-pyridine-2-carboxamide, 2HCl (Intermediate 91, 421 mg, 88%); m/z ($ES^+$) $[M+H]^+$=235.

Synthesis Example 32: N-ethyl-5-[4-[(7-ethyl-6-oxo-5H-1,5-naphthyridin-3-yl)methyl]piperazin-1-yl]pyridine-2-carboxamide

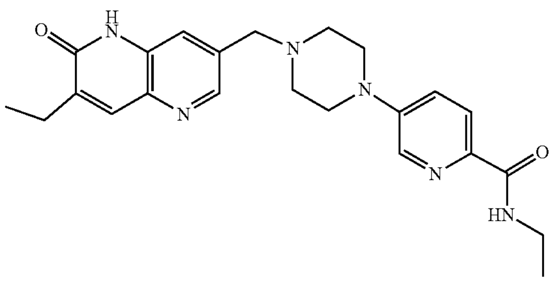 [SMILES: CCNC(=O)c1ccc(N2CCN(Cc3cnc4cc(CC)c(=O)[nH]c4c3)CC2)cn1]

DIPEA (0.320 mL, 1.83 mmol) was added to a stirred solution of 7-(bromomethyl)-3-ethyl-1,5-naphthyridin-2(1H)-one (Intermediate 14, 70 mg, 0.26 mmol), and N-ethyl-5-piperazin-1-yl-pyridine-2-carboxamide, 2HCl (Intermediate 91, 89 mg, 0.29 mmol) in acetonitrile (2 mL) at 20° C. and the resulting solution was stirred at 70° C. for 3 hours. Solvent was removed under vacuum and 50 mL water followed by 3 mL sat $NaHCO_3$ was added. Mixture was extracted with ethyl acetate. After concentration, the crude product was purified by reverse phase chromatography (column: XbridC18), elution gradient 20 to 50% MeCN in water (with 0.2% $NH_4OH$). Pure fractions were evaporated to dryness to afford N-ethyl-5-[4-[(7-ethyl-6-oxo-5H-1,5-naphthyridin-3-yl)methyl]piperazin-1-yl]pyridine-2-carboxamide (Synthesis Example 32, 28.0 mg, 25%) as white solid. $^1H$ NMR (500 MHz, DMSO-$d_6$) 1.10 (3H, t), 1.19 (3H, t), 2.52-2.55 (2H, m), 2.55-2.59 (4H, m), 3.26-3.30 (2H, m), 3.34 (4H, br d), 3.66 (2H, s), 7.40 (1H, dd), 7.63 (1H, s), 7.76 (1H, s), 7.83 (1H, d), 8.27 (1H, d), 8.36-8.46 (2H, m), 11.74-11.94 (1H, m); m/z ($ES^+$) $[M]^+$=420.

Synthesis Example 4—Form A

In Synthesis Example 4, 5-[4-[(7-ethyl-6-oxo-5H-1,5-naphthyridin-3-yl)methyl]piperazin-1-yl]-N-methyl-pyridine-2-carboxamide was obtained as a partially crystalline solid by evaporating a methanol/dichloromethane solution under reduced pressure. The crystalline material so-obtained was characterised as crystalline Form A.

In the case of poor crystallinity, crystalline Form A was obtainable by suspending 20 mg of the crude sample in 0.20 ml of water, methanol, ethanol, acetone, acetonitrile, tetrahydrofuran, ethyl acetate or other solvent for 1 day at the ambient temperature or 50° C. Form A was analysed by XRPD and the results are shown in FIG. 16A and tabulated below:

XRPD Peaks for Form A

| Angle (2θ ± 0.2°) | Intensity (%) |
|---|---|
| 8.3 | 100.0 |
| 12.4 | 30.9 |
| 19.4 | 26.5 |
| 20.4 | 25.8 |
| 26.3 | 19.2 |
| 21.2 | 17.4 |
| 20.8 | 14.8 |
| 22.8 | 14.1 |
| 16.8 | 14.0 |
| 10.2 | 13.2 |
| 18.4 | 10.8 |
| 11.4 | 9.9 |
| 28.1 | 8.4 |
| 18.0 | 8.4 |
| 25.2 | 8.2 |
| 24.9 | 6.7 |
| 16.5 | 6.4 |
| 17.3 | 5.3 |
| 22.1 | 4.0 |
| 29.3 | 3.3 |
| 24.3 | 2.7 |
| 30.3 | 2.5 |
| 38.2 | 2.0 |
| 33.9 | 1.4 |
| 14.2 | 1.4 |
| 13.7 | 1.4 |
| 33.0 | 1.3 |
| 36.5 | 1.2 |
| 39.2 | 1.2 |

Form A is characterized in providing at least one of the following 26 values measured using CuKα radiation: 8.3, 12.4, and 19.4°.

Form A was analyzed by thermal techniques. DSC analysis indicated that Form A has a melting point with an onset at 254° C. and a peak at 255° C. A representative DSC trace of Form A is shown in FIG. 16B.

Biological Assays (PARP1 Selective Inhibitor)

The following test procedures may be employed to determine the inhibitory properties of PARP1 selective inhibitor compounds described herein.

PARP Fluorescence Anisotropy Binding Assays

Recombinant full length 6HIS tagged PARP1 protein was diluted to 6 nM with 50 mM Tris pH 8, 0.001% Triton X100, 10 mM $MgCl_2$, 150 mM NaCl and incubated for four hours with an equivalent volume of 2 nM fluorescent probe diluted with 50 mM Tris pH 8, 0.001% Triton X100, 10 mM $MgCl_2$, 150 mM NaCl. The final DMSO concentration of the probe was kept below 1% (v/v).

Recombinant full length PARP2 protein was diluted to 6 nM with 50 mM Tris pH 8, 0.001% Triton X100, 10 mM $MgCl_2$, 150 mM NaCl and incubated for four hours with an equivalent volume of 2 nM fluorescent probe diluted with 50 mM Tris pH 8, 0.001% Triton X100, 10 mM $MgCl_2$, 150 mM NaCl. The final DMSO concentration of the probe was kept below 1% (v/v).

Recombinant full length PARP3 protein was diluted to 100 nM with 50 mM Tris pH 8, 0.001% Triton X100, 10 mM $MgCl_2$, 150 mM NaCl and incubated for four hours with an equivalent volume of 6 nM fluorescent probe diluted with 50 mM Tris pH 8, 0.001% Triton X100, 10 mM $MgCl_2$, 150 mM NaCl. The final DMSO concentration of the probe was kept below 1% (v/v).

Recombinant PARP5a binding domain was diluted to 160 nM with 50 mM Tris pH 8, 0.001% Triton X100, 10 mM $MgCl_2$, 150 mM NaCl and incubated for four hours with an equivalent volume of 6 nM fluorescent probe diluted with 50 mM Tris pH 8, 0.001% Triton X100, 10 mM $MgCl_2$, 150 mM NaCl. The final DMSO concentration of the probe was kept below 1% (v/v).

Recombinant full length GST tagged PARP6 protein was diluted to 160 nM with 50 mM Tris pH 8, 0.001% Triton X100, 10 mM $MgCl_2$, 150 mM NaCl and incubated for four hours with an equivalent volume of 6 nM fluorescent probe diluted with 50 mM Tris pH 8, 0.001% Triton X100, 10 mM $MgCl_2$, 150 mM NaCl. The final DMSO concentration of the probe was kept below 1% (v/v).

Fluorescence anisotropy of the probe when bound to the proteins was measured using a BMG Pherastar FS© in the presence of test compounds or solvent control and the effect on anisotropy determined. % inhibition values for different test compound concentrations were calculated and fitted to a four parameter logistic plot in order to determine the $IC_{50}$ value. Where necessary, the compound $K_i$ can be determined from the $IC_{50}$ value using a Munson Rodbard equation defined in *Anal. Biochem.* 1980 Sep. 1; 107(1):220-39 and is based on the known $K_D$ of the probe binding to the relevant PARP protein.

hERG Electrophysiological Assay

Electrophysiological recordings (all performed at RT) from stably transfected CHO hKv11.1 cells were obtained using the Nanion Syncropatch 768PE. Test compounds, vehicle or positive controls were added with 6 compound plates each at a different concentration to allow cumulative dosing onto cells (10 mM, 3.167 mM, 1 mM, 0.3167 mM, 0.1 mM, 0.03167 mM). 600 ▯1 of compound is resuspended into 90 μl of reference buffer (in mM, NaCl 80, KCL 4, CaCl 5, MgCl 1, NMDG Cl 60, D-Glucose monohydrate 5, HEPES 10 (pH7.4 HCL, 298 mOsm) for a final compound concentration of 39.6 μM, 13.2 μM, 4.4 μM, 1.46 μM, 0.48 μM, 0.16 μM. For each Nanion Syncropatch 768PE run, the current amplitude in each cell in the presence of extracellular solution (in mM, NaCl 80, KCL 4, CaCl 5, MgCl 1, NMDG Cl 60, D-Glucose monohydrate 5, HEPES 10 (pH7.4 HCL, 298 mOsm) is measured with all liquid additions performed using the Syncropatch liquid handling system. Add 40 μL external solution (in mM, HBPS, $CaCl_2$) 2, MgCl2 1 (pH7.4, NaOH) to 384 well multihole medium resistance recording chip and perfuse internal buffer (in mM, KF 130, KCl 20, MgCl2 1, EGTA 10, HEPES 10, Escin 25 (all Sigma-Aldrich; pH 7.2-7.30 using 10 M KOH, 320 mOsm) to the underside of plate. Dispense 20 μL of cells at a density of 1e6 cells/ml maintained at ~9° C. into each well of the chip followed by 20 μL of seal enhancer (in mM, NaCl 80, KCl 3, CaCl 10, HEPES 10, MgCl 1 (pH7.4 NaOH). Perform wash step leaving a residual volume of 40 μL. Dispense 40 μL of reference buffer to establish a stable baseline prior to the addition of test compounds, with a removal step of 40 μL after 3 min, repeat this step. Dispense 40 μL of compound concentration 1 (0.16 μM), 'real time' recordings for 3 min exposure prior to removal of 40 μL. This step is repeated for 5 further subsequent compound plates to generate cumulative curve analysis. All data is leak subtracted, 2 pulses to −80 mV 100 ms with 100 ms delay. Outward K+ currents are then evoked by a voltage step to +60 mV from a holding potential of −90 mV, Each pulse is delivered at a frequency of 2 Hz with a 15 s pulse interval.

PARP Proliferation Assay (4 Day Compound Dosing)

DLD1 and BRCA2 (−/−) DLD1 cells were harvested to a density of 1.875E4 cells/ml and 6.25E4 cells/ml respectively in complete media, 40 μL/well seeded into 384-well plates (Greiner, Kremsmunster, Austria; 781090) using a Multidrop Combi then incubated at 37° C., 5% $CO_2$ overnight. Next day (Day 1) using a Multidrop Combi add sytox green (5 ul, 2 uM) and saponin (10 ul, 0.25% stock) to a day 0 plate, seal the plate using a black adhesive lid and incubate for >3 hrs at RT. Cells were imaged using Cell Insight (Thermo Fisher) fitted with a 4× objective. Test compounds are added using an Echo 555 and placed in incubator maintained at 37° C., 5% $CO\cdot_2$ and incubated for 4 days. On Day 5 add sytox green (5 ul, 2 uM) and then saponin (10 ul, 0.25% stock) to plates, seal the plate using a black adhesive lid and incubate for >3 hrs at RT. Read all cells on the Cell Insight with 4× Objective. The rate of proliferation is determined in Genedata by assessing the total cell number output from the Cell Insight for Day 0 and Day 5 plates.

| Synth. Example No. | PARP1 IC50 (μM) | PARP2 IC50 (μM) | PARP3 IC50 (μM) | PARP5a IC50 (μM) | PARP6 IC50 (μM) | BRCA2 −/− DLD-1 prolif 4 d IC50 (μM) | WT DLD-1 prolif 4 d IC50 (μM) | hERG IC50 (μM) |
|---|---|---|---|---|---|---|---|---|
| 1 | 0.003 | 1.7 | 4 | >100 | 34 | 0.010 | >30 | >40 |
| 2 | 0.004 | 0.88 | 9.9 | 20 | 14 | 0.008 | >30 | >40 |
| 3 | 0.005 | 1.3 | 12 | >100 | 14 | 0.004 | >30 | 22 |
| 4 | 0.004 | >1.5 | 4.7 | >100 | 19 | >0.017 | >30 | >40 |
| 5 | 0.002 | 0.65 | 7.1 | >100 | 23 | 0.006 | >30 | >40 |
| 6 | 0.003 | 0.84 | 9.3 | >100 | 8.2 | 0.006 | >30 | >40 |
| 7 | 0.002 | 1.3 | 2.6 | 94 | 22 | 4.14 | | |
| 8 | 0.003 | 11 | 55 | 93 | 18 | 0.011 | >19 | >40 |
| 9 | 0.009 | 22 | >100 | >100 | 47 | 0.010 | 17 | >40 |
| 10 | 0.005 | 17 | 48 | 56 | 26 | 0.006 | >30 | >40 |
| 11 | 0.005 | 4 | 13 | >100 | 22 | 0.184 | >30 | >40 |
| 12 | 0.004 | 1.6 | 19 | 89 | 11 | 0.008 | >30 | >40 |
| 13 | 0.007 | 8.5 | 30 | >100 | 30 | 0.005 | >26 | >40 |
| 14 | 0.004 | 2.9 | 30 | 50 | 11 | 0.006 | >30 | >40 |
| 15 | 0.011 | 3.6 | 35 | >100 | 80 | 0.090 | >30 | >40 |
| 16 | 0.007 | 3.3 | 74 | 61 | 31 | 0.018 | >22 | >40 |
| 17 | 0.007 | 1.7 | 96 | >100 | 59 | 0.020 | >30 | >40 |
| 18 | 0.031 | 17 | >100 | >100 | >29 | 4.90 | >30 | 5.2 |
| 19 | 0.015 | >100 | >100 | >100 | >29 | 0.015 | >30 | 21 |
| 20 | 0.014 | 28 | >100 | >100 | >100 | 0.016 | >24 | 38 |
| 21 | 0.004 | 9.5 | >100 | >100 | 33 | 0.016 | >30 | >40 |
| 22 | 0.006 | 1 | 2.6 | 26 | 16 | 0.012 | >30 | >40 |
| 23 | 0.004 | 4.4 | 60 | 60 | >100 | | 4.2 | 36 |
| 24 | 0.003 | 5.1 | >100 | 93 | >100 | 0.010 | 14 | 37 |
| 25 | 0.002 | 6 | 43 | >100 | >100 | | >25 | >40 |
| 26 | 0.005 | 6.7 | >100 | >100 | >100 | 0.005 | 23 | >40 |

-continued

| Synth. Example No. | PARP1 IC50 (μM) | PARP2 IC50 (μM) | PARP3 IC50 (μM) | PARP5a IC50 (μM) | PARP6 IC50 (μM) | BRCA2 −/− DLD-1 prolif 4 d IC50 (μM) | WT DLD-1 prolif 4 d IC50 (μM) | hERG IC50 (μM) |
|---|---|---|---|---|---|---|---|---|
| 27 | 0.007 | 16 | >100 | 71 | >100 | 10.3 | >10 | 26 |
| 28 | 0.006 | 14 | >100 | >29 | >100 | 0.027 | >30 | >40 |
| 29 | 0.004 | 6.1 | 9.9 | >100 | 14 | 0.007 | >30 | >40 |
| 30 | 0.003 | 7.6 | 4.5 | >100 | 10 | 0.004 | >30 | >40 |
| 31 | 0.005 | 3 | 2.6 | >100 | 28 | | | >40 |
| 32 | 0.003 | 2.1 | 1.9 | >100 | 10 | | | >40 |

Example 1: Production of Antibody-Drug Conjugate

In accordance with a production method described in WO2015/115091 and using an anti-HER2 antibody (an antibody comprising a heavy chain consisting of an amino acid sequence represented by SEQ ID NO: 11 (amino acid residues 1 to 449 of SEQ ID NO: 1) and a light chain consisting of an amino acid sequence consisting of all amino acid residues 1 to 214 of SEQ ID NO: 2), an anti-HER2 antibody-drug conjugate in which a drug-linker represented by the following formula:

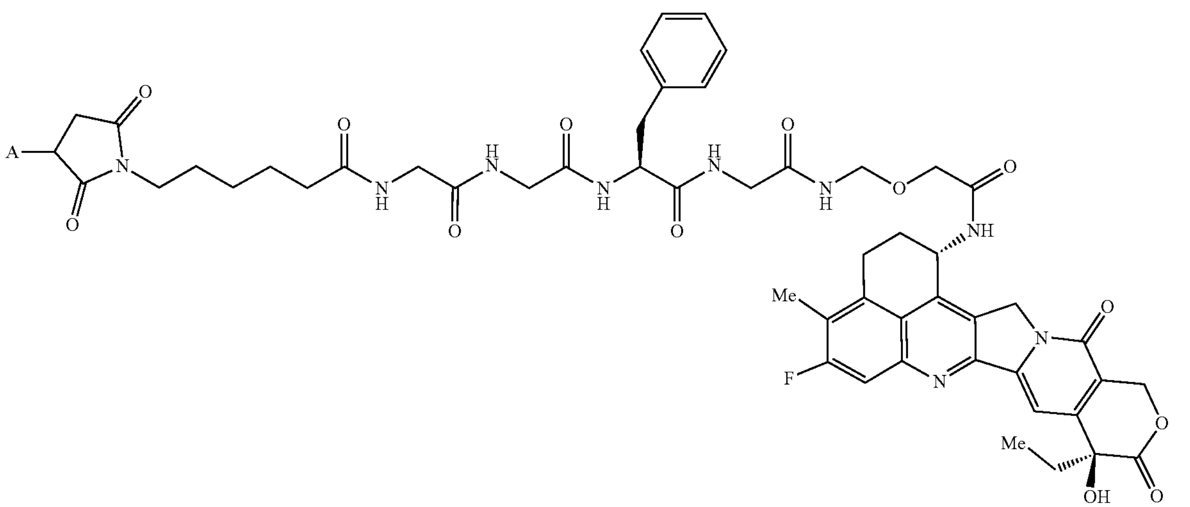

wherein A represents the connecting position to an antibody, is conjugated to the anti-HER2 antibody via a thioether bond was produced (DS-8201: trastuzumab deruxtecan). The DAR of the antibody-drug conjugate is 7.7 or 7.8.

Example 2: Production of PARP1 Selective Inhibitor

In accordance with a production method described herein, a PARP1 selective inhibitor of formula (I) is prepared. Specifically, 5-[4-[(7-ethyl-6-oxo-5H-1,5-naphthyridin-3-yl)methyl]piperazin-1-yl]-N-methyl-pyridine-2-carboxamide:

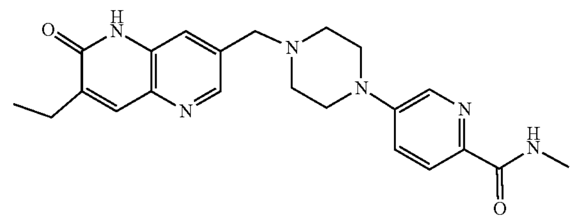

(AZD5305)

can be prepared according to Synthesis Example 4 herein (Example 4 of WO2021/013735).

Example 3: Antitumor Test

Combination of antibody-drug conjugate DS-8201 (trastuzumab deruxtecan (Enhertu®)) with PARP1 selective inhibitor AZD5305 (5-[4-[(7-ethyl-6-oxo-5H-1,5-naphthyridin-3-yl)methyl]piperazin-1-yl]-N-methyl-pyridine-2-carboxamide)

Method:

A high-throughput combination screen was run, in which 27 breast cancer cell lines with diverse HER2 expression and one gastric cell line with high HER2 expression (Table 1) were treated with combinations of DS-8201 and AZD5305 (PARP1 selective inhibitor).

TABLE 1

| Cell Line | HER2 Status | Cancer Type |
|---|---|---|
| NCI-N87 | Amp (High) | Gastric |
| SKBR3 | Amp (High) | Breast |
| AU565 | Amp (High) | Breast |
| HCC1569 | Amp (High) | Breast |
| HCC1187 | Low | Breast |
| HCC1954 | Amp (High) | Breast |
| KPL-4 | Amp (High) | Breast |
| HCC38 | Amp (Low) | Breast |
| MCF7 (ER+) | Del (null) | Breast |
| MDA-MB-157 | Low | Breast |
| HCC1419 | Amp (High) | Breast |
| ZR-75-30 | Amp (High) | Breast |
| ZR-75-1 (ER+) | Low | Breast |
| HCC1395 | Low | Breast |
| BT474 (ER+) | Amp (High) | Breast |
| EFM-19 (ER+) | Low | Breast |
| HCC1937 | null | Breast |
| BT-549 | Del (null) | Breast |
| MDA-MB-453 | Low | Breast |
| MDA-MB-361 | Amp (Low) | Breast |
| CAL-51 | Low | Breast |
| MDA-MB-468 | Amp (Low) | Breast |
| T-47D (ER+) | Low | Breast |
| HCC1143 | Low | Breast |
| JIMT1 | Amp (Low) | Breast |
| CAMA1 (ER+) | Low | Breast |
| MDA-MB-231 | Low | Breast |
| HCC70 | Low | Breast |

The readout of the screen was a 7-day CellTiter-Glo cell viability assay, conducted as a 6×6 dose response matrix (5-point log serial dilution for DS-8201, and half log serial dilution for AZD5305). Maximum concentration was 3 μM for AZD5305 and 10 μg/ml for DS-8201. In addition, trastuzumab and exatecan (DNA topoisomerase I inhibitor) were also screened in parallel with AZD5305, to help deconvolute the mechanism of action of effective combinations. Combination activity was assessed based on a combination of the ΔEmax and Loewe synergy scores.

Results:

Results are shown for HER2 high cell lines (KPL4, NCI-N87, SKBR3, HCC1954, HCC1569, AU565) in FIGS. 12A and 12B and Table 2, and for HER2 low cell lines (MDA-MB-468, MDA-MB-157, HCC1187, T47D, HCC38) in FIGS. 13A and 13B and Table 3.

FIGS. 12A and 13A show matrices of measured cell viability signals. X axes represent drug A (DS-8201), and Y axes represent drug B (AZD5305). Values in the box represent the ratio of cells treated with drug A+B compared to DMSO control at day 7. All values are normalised to cell viability values at day 0. Values between 0 and 100 represent % growth inhibition and values above 100 represent cell death.

FIGS. 12B and 13B show Loewe excess matrices. Values in the box represent excess values calculated by the Loewe additivity model.

Tables 2 and 3 show HSA synergy and Loewe additivity scores:

TABLE 2

| Cell line | KPL4 | NCI-N87 | SKBR3 | HCC1954 | HCC1569 | AU565 |
|---|---|---|---|---|---|---|
| HSA synergy score | 68.2 | 70.95 | 20.33 | 9.9 | 38.6 | 32.77 |
| Loewe synergy score | 68.2 | 70.95 | 20.33 | 9.9 | 38.6 | 32.77 |

TABLE 3

| Cell line | MDA-MB-468 | MDA-MB-157 | HCC1187 | T47D | HCC38 |
|---|---|---|---|---|---|
| HSA synergy score | 11.6 | 7.04 | 52.7 | 12.33 | 8.9 |
| Loewe synergy score | 11.6 | 6.5 | 52.7 | 12.33 | 8.8 |

Notes:

Loewe Dose Additivity predicts the expected response if the two compounds act on the same molecular target by means of the same mechanism. It calculates additivity based on the assumption of zero interaction between the compounds and it is independent from the nature of the dose-response relationship.

HSA (Highest Single Agent) [Berenbaum 1989] quantifies the higher of the two single compound effects at their corresponding concentrations. The combined effect is compared with the effect of each single agent at the concentration used in the combination. Excess over the highest single agent effect indicates cooperativity. HSA does not require the compounds to affect the same target.

Excess Matrix: For each well in the concentration matrix, the measured or fitted values are compared to the predicted non-synergistic values for each concentration pair. The predicted values are determined by the chosen model. Differences between the predicted and observed values may indicate synergy or antagonism, and are shown in the Excess Matrix. Excess Matrix values are summarized by the combination scores Excess Volume and Synergy Score.

FIG. 14 shows combination Emax and Loewe synergy scores in various cell lines treated with DS-8201 combined with AZD5305.

As seen from FIGS. 12A and 12B, and Table 2, AZD5305 interacted synergistically with DS-8201 and also increased cell death in HER2+ breast and gastric cell lines. As seen from FIGS. 13A and 13B, and Table 3, AZD5305 interacted synergistically with DS-8201 and also increased cell death in HER2 low breast cancer cell lines at Emax (3 μM AZD5305 and 10 μg/ml DS-8201). As seen from FIG. 14, in eleven cell lines, including HER2 low breast cancer cell lines, treatment with DS-8201 combined with AZD5305 resulted in high combination Emax (>100) and high Loewe synergy scores (>5).

Example 4: Antitumor Test

Combination of antibody-drug conjugate DS-8201 (trastuzumab deruxtecan (Enhertu®)) with PARP1 selective inhibitor AZD5305 (5-[4-[(7-ethyl-6-oxo-5H-1,5-naphthyridin-3-yl)methyl]piperazin-1-yl]-N-methyl-pyridine-2-carboxamide)

Method:

Cells grown in their respective conditions were plated in 96-well plates at optimal density to allow linear proliferation for the duration of the assay (4 to 8 days). Immediately after plating, the cells were dosed with the indicated compounds for a total volume of 200 μL/well and placed in the incubator. Combinations were conducted as a 6×8 concentration response matrix for each combination. At the endpoint, the cells were fixed in 2% PFA for 20 minutes at room temperature. In order to obtain the number of cells at the start of treatment, one additional plate was used for each experiment and fixed after cells attached. The cells were then permeabilised in 0.5% Triton-X100 in PBS for 10 minutes. After a PBS wash, the cells were blocked in 5% FBS in PBS 1 h at RT and incubated with primary antibodies in 5% FBS+0.05% triton overnight at 4° C. After 3 washes in PBS cells were incubated with secondary antibodies in 5% FBS+0.05% triton with Hoechst33258 for 1 h at room temperature. After 3 washes in PBS, the cells were scanned with a Cellinsight instrument with a 10× objective and 9 fields/well. Images were analysed using Columbus for cell count based on nuclear Hoechst staining. The total cell count/well was used to calculate the relative growth in each well compared to solvent control. To calculate the synergy scores, the growth inhibition data were analysed using Combenefit software (Di Veroli, G. Y., et al., *Combenefit: an interactive platform for the analysis and visualization of drug combinations*. Bioinformatics, 2016, 32(18): p. 2866-8).

Results:

Results are shown for a HER2 high cell line (KPL4) and two HER2 low cell lines (JIMT1, MDA-MB-468) in FIGS. 15A and 15B.

FIG. 15A shows cell count matrices, in which Y axes represent drug A (DS-8201), and X axes represent drug B (AZD5305). Values in the box represent relative total cell (nuclear) counts as percentage of DMSO vehicle control.

FIG. 15B shows matrices, in which Y axes represent drug A (DS-8201), and X axes represent drug B (AZD5305), and the values in the box represent calculated Loewe synergy scores.

The results in Examples 3 and 4 demonstrate that selective PARP1 inhibition using AZD5305 enhances the antitumor efficacy of DS-8201 in both high and low HER2-expressing cell lines in vitro. In Example 3, AZD5305 in combination with DS-8201 showed combination benefit in five HER2+ breast cancer cell lines, one HER2+ gastric cancer cell line (FIGS. 12A, 12B, 14 and Table 2) and five HER2 low breast cancer cell lines (FIGS. 13A, 13B and 14, and Table 3). In Example 4, AZD5305 in combination with DS-8201 showed synergistic activity in HER2-high (KPL4) and HER2-low (JIMT-1, MDA-MB-468) cell lines (FIGS. 15A and 15B).

Example 5: Antitumor Test—In Vivo

Combination of antibody-drug conjugate DS-8201 (trastuzumab deruxtecan (Enhertu®)) with PARP1 selective inhibitor AZD5305 (5-[4-[(7-ethyl-6-oxo-5H-1,5-naphthyridin-3-yl)methyl]piperazin-1-yl]-N-methyl-pyridine-2-carboxamide)

Method:

Female Nude mice (Charles River) aged 5-8 weeks were used, following 7 days acclimatisation before entry into the study. $1\times10^7$ NCI-N87 tumour cells (1:1 in Matrigel) were implanted subcutaneously onto the flank of the female Nude mice. When tumours reached approximately 150 $mm^3$, similar-sized tumours were randomly assigned to treatment groups as shown in Table 4:

TABLE 4

| Treatment | Dose | Route of administration | Dosing Schedule (28 days) |
|---|---|---|---|
| Vehicle | — | IV + PO | Single dose + QD |
| DS-8201 | 3 mg/kg | IV | Single dose |
| DS-8201 | 1 mg/kg | IV | Single dose |
| AZD5305 | 1 mg/kg | PO | QD |
| DS-8201 + AZD5305 | 1 mg/kg or 3 mg/kg + 1 mg/kg | IV + PO | Single dose + QD |

PO: oral (per os) dosing
QD: once per day (quaque die) dosing

The dose of compound for each animal was calculated based on the individual body weight on the day of dosing. DS-8201 and AZD5305 were dosed on the same day, with DS-8201 being administered approximately 1 hour post the PO dose of AZD5305. DS-8201 was administered as a single dose at 1 mg/kg or 3 mg/kg on day 1, and AZD5305 was administered at 1 mg/kg QD for 28 days. Duration of dosing was for 28 days.

Formulation of DS-8201 at 3 mg/kg and 1 mg/kg

The dosing solutions for DS-8201 were prepared on the day of dosing by diluting the DS-8201 stock (20.1 mg/ml) in 25 mM histidine buffer, 9% sucrose (pH5.5) to 0.6 mg/ml, and 0.2 mg/ml for the 3 mg/kg and 1 mg/kg dosing solutions, respectively. Each dosing solution was mixed well using a pipette before administration via IV injection at a dosing volume of 5 ml/kg.

Formulation of AZD5305 at 1 mg/kg

To formulate for a 1 mg/kg dosing solution, a concentration of 0.1 mg/ml AZD5305 was prepared which resulted in a dosing volume of 10 ml/kg for PO dosing. A total of 49 ml of vehicle was required. A volume of 15 μl of 1M HCl was added to the compound and mixed well by vortexing. A volume of 1 ml of sterile water was added to the Eppendorf tube and mixed well with the compound using a pellet pestle. The compound was sonicated for approximately 5 minutes then the contents transferred to a glass bottle. A volume of 1 ml sterile water was used to rinse the Eppendorf tube of any remaining compound and was then transferred to the glass bottle. The remaining volume of sterile water (37.2 ml; a total of 80% of the total vehicle volume) was added to the glass bottle and mixed well using a magnetic stirrer. The pH of the dosing solution was adjusted to pH 3.74 then the remaining vehicle (9.772 ml of sterile water) was added to the glass bottle and mixed well using a magnetic stirrer. The dosing solution was protected from light and a small aliquot was taken daily for dosing. All remaining dosing solution was kept for up to 7 days in the fridge. The final dosing matrix for 1 mg/kg AZD5305 was a clear solution.

Measurements

Tumour growth inhibition (TGI) was calculated as follows:

$$TGI\ \%=\{1-(MTV\ treated/MTV\ control)\}*100$$

where MTV=mean tumor volume.

Statistical significance was evaluated using one-tailed t-test of (log(relative tumour volume)=log(final vol/start vol)) at the day of final measure, comparing to vehicle control.

Results

Tumour volumes for treatments with DS-8201 or AZD5305 alone or with DS-8201 in combination with AZD5305 are shown in FIG. 17. Data represents change in tumour volume over time for treatment groups. The dotted line in FIG. 17 represents end of dosing periods. For full dose and schedule information, refer to Table 4 above. Values shown are mean±SEM; n=10 initially for vehicle-treated mice and n=8 for all other treatment groups.

TGI responses (Day 41 TGI %) following treatment with DS-8201 or AZD5305 alone or with DS-8201 in combination with AZD5305, in NCI-N87 xenograft, are shown in Table 5:

TABLE 5

| Treatment group | TGI % day 41 | p-value vs vehicle | Significance |
|---|---|---|---|
| DS-8201 3 mg/kg | 62% | 0.00071 | *** |
| DS-8201 1 mg/kg | 25% | 0.025 | †ns |
| AZD5305 1 mg/kg | 40% | <0.0001 | †ns |
| DS-8201 1 mg/kg + AZD5305 1 mg/kg | 55% | <0.0001 | ** |
| DS-8201 3 mg/kg + AZD5305 1 mg/kg | 90% | <0.0001 | **** |

†not significant

Monotherapy with DS-8201 at 3 mg/kg showed TGI value of 62% at day 41 post treatment. At 1 mg/kg DS-8201 showed a TGI of 25% at day 41 post treatment. AZD5305 monotherapy achieved a TGI of 40% at day 41 post treatment. Combination treatment of AZD5305 with DS-8201 at 1 mg/kg resulted in a TGI of 55% at 41 days post treatment. Combination therapy using higher DS-8201 3 mg/kg dose with AZD5305 achieved significant TGI of 90% at day 41 post treatment and showed better response than either respective monotherapies.

Treatment groups were generally well tolerated (two outlier animals taken off study due to body weight loss>15%) and average bodyweights of all treatment groups remained stable during the study.

Example 6

Combination dosing of antibody-drug conjugate DS-8201 (trastuzumab deruxtecan (Enhertu®)) with PARP1 selective inhibitor AZD5305 (5-[4-[(7-ethyl-6-oxo-5H-1,5-naphthyridin-3-yl)methyl]piperazin-1-yl]-N-methyl-pyridine-2-carboxamide) in HER2 high, HER2 low, and HER2 mutant-expressing cell lines in vitro Method:

A high-throughput combination screen was run, in which four lung cancer cell lines with diverse HER2 expression (Table 6) and a HER2 mutant cancer cell line (Table 7) were screened with combinations of DS-8201 and AZD5305.

TABLE 6

| Cell line | HER2 receptors per cell by flow cytometry | IHC Dako H2L H-score | Cancer Type |
|---|---|---|---|
| HCC1171 | 146050 ± 654 | 200 | NSCLC adenocarcinoma |
| NCIH1573 | 51090 ± 165 | 100 | NSCLC adenocarcinoma |
| NCIH2170 | 2472499 ± 21851 | 300 | NSCLC squamous |
| Calu6 | 12935 ± 200 | 0 | NSCLC adenocarcinoma |

TABLE 7

| Cell line | HER2 receptors per cell by flow cytometry | HER2 Mutation | Cancer Type |
|---|---|---|---|
| 5637 | 27497 ± 14 | p.S310F | Urinary tract |

The readout of the screen was a 7-day CellTiter-Glo cell viability assay, conducted as a 6×6 dose response matrix (DS-8201 and AZD5305 each at half-log serial dilutions for each combination). Maximum concentration was 3.33 or 10 μM for AZD5305 and 100 μg/ml for DS-8201. Combination activity was assessed based on a combination of the ΔEmax and Loewe synergy scores.

Results:

Results are shown for HER2+, HER2 low, HER2 low/null NSCLC cell lines (HCC1171, NCIH1573, NCIH2170, Calu6) in FIGS. 18A, 18B and 18C, and Table 8, and for a HER2 mutant cell line (5637) in FIGS. 19A, 19B and 19C, and Table 9.

FIGS. 18A and 19A show matrices of measured cell viability signals. X axes represent drug A (DS-8201), and Y axes represent drug B (AZD5305). Values in the box represent the ratio of cells treated with drug A+B compared to DMSO control at day 7. All values are normalised to cell viability values at day 0. Values between 0 and 100 represent % growth inhibition and values above 100 represent cell death.

FIGS. 18B and 19B show Loewe excess matrices. Values in the box represent excess values calculated by the Loewe additivity model.

FIGS. 18C and 19C show HSA excess matrices. Values in the box represent excess values calculated by the HSA (Highest Single Agent) model.

Tables 8 and 9 show HSA synergy and Loewe additivity scores:

TABLE 8

| Cell line (NSCLC) | HCC1171 | NCIH1573 | NCIH2170 | Calu6 |
|---|---|---|---|---|
| HSA Synergy Score | 6.2 | 6.14 | 33.99 | 10.55 |
| Loewe Synergy Score | 6.2 | 5.4 | 33.99 | 10.55 |

TABLE 9

| Cell line (Urinary tract) | 5637 |
|---|---|
| HSA Synergy Score | 11.2 |
| Loewe Synergy Score | 11.2 |

As seen from FIGS. 18A, 18B and 18C, and Table 8, AZD5305 interacted synergistically with DS-8201 and also increased cell death in HER2+ cell line NCIH2170 at Emax (0.125 μM AZD5305 and 100 μg/ml DS-8201), in HER2 low cell line HCC1171 at Emax (0.125 μM AZD5305 and 100 μg/ml DS-8201) and in HER2 low/null cell line Calu6 at Emax (1.25 μM AZD5305 and 100 μg/ml DS-8201). Combination activity was observed even where single agent activity was absent or low. Although synergy was observed in cell line NCIH1573, there was no cell death.

As seen from FIGS. 19A, 19B and 19C, and Table 9, AZD5305 interacted synergistically with DS-8201 and also increased cell death in HER2 mutant cell line 5637 at Emax (1.25 μM AZD5305 and 100 μg/ml DS-8201).

Combination activity was observed even where AZD5305 as single agent was not active.

The foregoing written specification is considered to be sufficient to enable one skilled in the art to practice the embodiments. The foregoing description and Examples detail certain embodiments and describe the best mode contemplated by the inventors. It will be appreciated, however, that no matter how detailed the foregoing may appear in text, the embodiments may be practiced in many ways and the claims include any equivalents thereof.

Free Text of Sequence Listing

SEQ ID NO: 1—Amino acid sequence of a heavy chain of an anti-HER2 antibody

SEQ ID NO: 2—Amino acid sequence of a light chain of an anti-HER2 antibody

SEQ ID NO: 3—Amino acid sequence of a heavy chain CDRH1 [=amino acid residues 26 to 33 of SEQ ID NO: 1]

SEQ ID NO: 4—Amino acid sequence of a heavy chain CDRH2 [=amino acid residues 51 to 58 of SEQ ID NO: 1]

SEQ ID NO: 5—Amino acid sequence of a heavy chain CDRH3 [=amino acid residues 97 to 109 of SEQ ID NO: 1]

SEQ ID NO: 6—Amino acid sequence of a light chain CDRL1 [=amino acid residues 27 to 32 of SEQ ID NO: 2]

SEQ ID NO: 7—Amino acid sequence comprising amino acid sequence of a light chain CDRL2 (SAS) [=amino acid residues 50 to 56 of SEQ ID NO: 2]

SEQ ID NO: 8—Amino acid sequence of a light chain CDRL3 [=amino acid residues 89 to 97 of SEQ ID NO: 2]

SEQ ID NO: 9—Amino acid sequence of a heavy chain variable region [=amino acid residues 1 to 120 of SEQ ID NO: 1]

SEQ ID NO: 10—Amino acid sequence of a light chain variable region [=amino acid residues 1 to 107 of SEQ ID NO: 2]

SEQ ID NO: 11—Amino acid sequence of a heavy chain [=amino acid residues 1 to 449 of SEQ ID NO: 1]

The invention claimed is:

1. A pharmaceutical product comprising an anti-HER2 antibody-drug conjugate and a PARP1 selective inhibitor for administration in combination, wherein the anti-HER2 antibody-drug conjugate is an antibody-drug conjugate comprising a drug-linker conjugated to an anti-HER2 antibody in which the drug-linker is represented by the following formula:

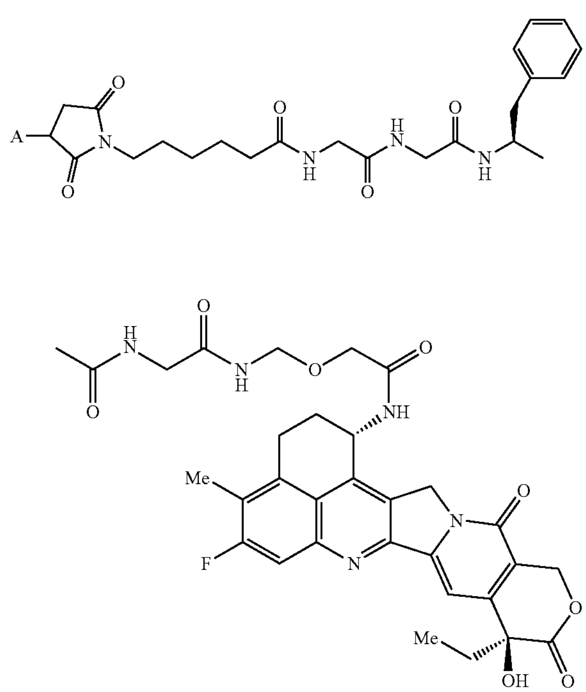

wherein A represents the connecting position to the anti-HER2 antibody, and the drug-linker is conjugated to the anti-HER2 antibody via a thioether bond;

wherein the PARP1 selective inhibitor is a compound represented by the following formula (I):

(I)

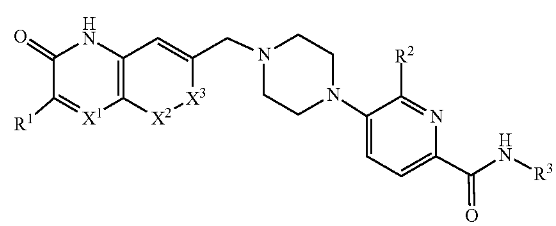

wherein:

$X^1$ and $X^2$ are each independently selected from N and C(H), $X^3$ is independently selected from N and C($R^4$), wherein $R^4$ is H or fluoro, $R^1$ is $C_{1-4}$ alkyl or $C_{1-4}$ fluoroalkyl, $R^2$ is independently selected from H, halo, $C_{1-4}$ alkyl, and $C_{1-4}$ fluoroalkyl, and $R^3$ is H or $C_{1-4}$ alkyl, or a pharmaceutically acceptable salt thereof provided that:

when $X^1$ is N, then $X^2$ is C(H), and $X^3$ is C($R^4$), when $X^2$ is N, then $X^1$ is C(H), and $X^3$ is C($R^4$), and when $X^3$ is N, then $X^1$ and $X^2$ are both C(H); and wherein the anti-HER2 antibody is an antibody comprising a heavy chain comprising a CDRH1 consisting of an amino acid sequence represented by SEQ ID NO: 3, a CDRH2 consisting of an amino acid sequence represented by SEQ ID NO: 4, and a CDRH3 consisting of an amino acid sequence represented by SEQ ID NO: 5, and a light chain comprising a CDRL1 consisting of an amino acid sequence represented by SEQ ID NO: 6, a CDRL2 consisting of an amino acid sequence consisting of amino acid residues 1 to 3 of SEQ ID NO: 7, and a CDRL3 consisting of an amino acid sequence represented by SEQ ID NO: 8.

2. The pharmaceutical product according to claim 1 wherein, in formula (I), $R^3$ is $C_{1-4}$ alkyl.

3. The pharmaceutical product according to claim 1 wherein, in formula (I), $R^3$ is methyl.

4. The pharmaceutical product according to claim 1 wherein, in formula (I), $R^1$ is ethyl.

5. The pharmaceutical product according to claim 1, wherein the PARP1 selective inhibitor is a compound represented by the following formula (Ia):

(Ia)

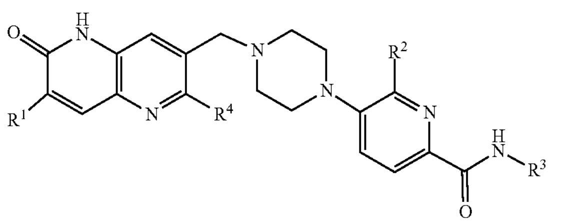

wherein $R^1$ is $C_{1-4}$ alkyl, $R^2$ is selected from H, halo, $C_{1-4}$ alkyl, and $C_{1-4}$ fluoroalkyl, $R^3$ is H or $C_{1-4}$ alkyl, and $R^4$ is H, or a pharmaceutically acceptable salt thereof.

6. The pharmaceutical product according to claim 5 wherein, in formula (Ia), $R^2$ is H or halo.

7. The pharmaceutical product according to claim 5 wherein, in formula (Ia), $R^1$ is ethyl, $R^2$ is selected from H, chloro and fluoro, and $R^3$ is methyl.

8. The pharmaceutical product according to claim 1, wherein the PARP1 selective inhibitor is AZD5305 represented by the following formula:

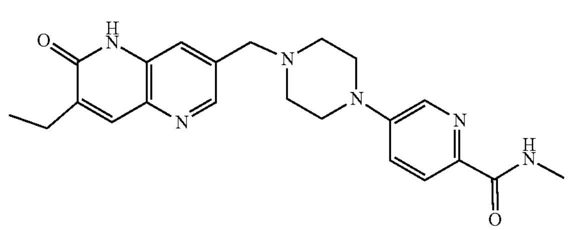 [SMILES: CCc1cc2ncc(CN3CCN(c4ccc(C(=O)NC)nc4)CC3)cc2[nH]c1=O]

or a pharmaceutically acceptable salt thereof.

9. The pharmaceutical product according to claim 1, wherein the anti-HER2 antibody is an antibody comprising a heavy chain comprising a heavy chain variable region consisting of an amino acid sequence represented by SEQ ID NO: 9 and a light chain comprising a light chain variable region consisting of an amino acid sequence represented by SEQ ID NO: 10.

10. The pharmaceutical product according to claim 1, wherein the anti-HER2 antibody is an antibody comprising a heavy chain consisting of an amino acid sequence represented by SEQ ID NO: 1 and a light chain consisting of an amino acid sequence represented by SEQ ID NO: 2.

11. The pharmaceutical product according to claim 1, wherein the anti-HER2 antibody is an antibody comprising a heavy chain consisting of an amino acid sequence represented by SEQ ID NO: 11 and a light chain consisting of an amino acid sequence represented by SEQ ID NO: 2.

12. The pharmaceutical product according to claim 1, wherein the anti-HER2 antibody-drug conjugate is represented by the following formula:

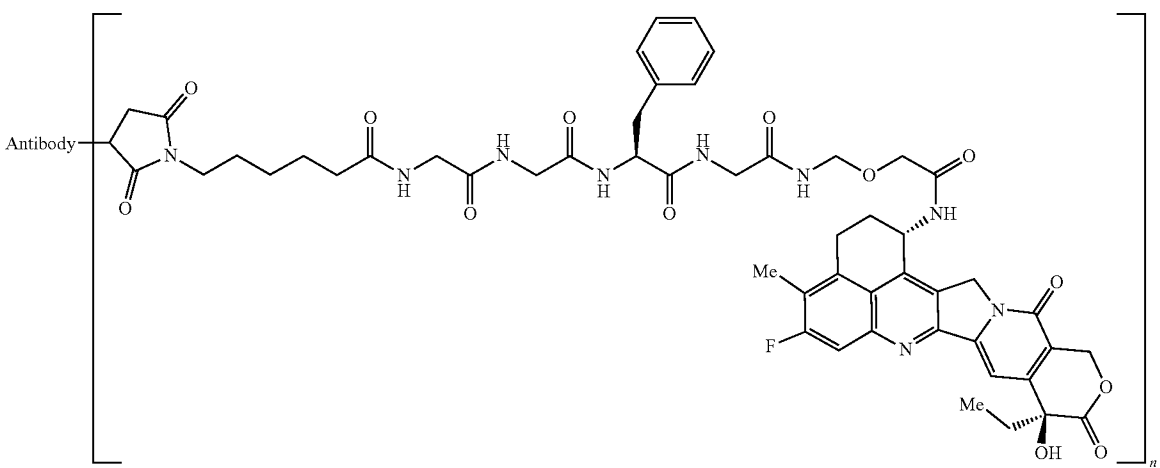

wherein 'Antibody' indicates the anti-HER2 antibody conjugated to the drug-linker via a thioether bond, and n indicates an average number of units of the drug-linker conjugated per antibody molecule in the antibody-drug conjugate, wherein n is in the range of from 7 to 8.

13. The pharmaceutical product according to claim 1, wherein the anti-HER2 antibody-drug conjugate is trastuzumab deruxtecan (DS-8201).

14. The pharmaceutical product according to claim 1, wherein the product is a composition comprising the anti-HER2 antibody-drug conjugate and the PARP1 selective inhibitor, for simultaneous administration.

15. The pharmaceutical product according to claim 1, wherein the product is a combined preparation comprising the anti-HER2 antibody-drug conjugate and the PARP1 selective inhibitor, for sequential or simultaneous administration.

16. A method of treating a HER2 expressing cancer comprising administering an anti-HER2 antibody-drug conjugate and a PARP1 selective inhibitor as defined in claim 1 in combination to a subject in need thereof.

17. The method according to claim 16, wherein the HER2 expressing cancer is at least one selected from the group consisting of breast cancer, gastric cancer, colorectal cancer, lung cancer, esophageal cancer, head-and-neck cancer, esophagogastric junction adenocarcinoma, biliary tract cancer, Paget's disease, pancreatic cancer, ovarian cancer, uterine carcinosarcoma, urothelial cancer, prostate cancer, bladder cancer, gastrointestinal stromal tumor, digestive tract stromal tumor, uterine cervix cancer, squamous cell carcinoma, peritoneal cancer, liver cancer, hepatocellular cancer, corpus uteri carcinoma, kidney cancer, vulval cancer, thyroid cancer, penis cancer, leukemia, malignant lymphoma, plasmacytoma, myeloma, glioblastoma multiforme, osteosarcoma, sarcoma, and melanoma.

18. The method according to claim 16, wherein the HER2 expressing cancer is breast cancer.

19. The method according to claim 18, wherein the breast cancer has a HER2 status score of IHC 3+.

20. The method according to claim 18, wherein the breast cancer is HER2 low-expressing breast cancer.

21. The method according to claim 18, wherein the breast cancer has a HER2 status score of IHC 2+.

22. The method according to claim 18, wherein the breast cancer has a HER2 status score of IHC 1+.

23. The method according to claim 18, wherein the breast cancer has a HER2 status score of IHC>0 and <1+.

24. The method according to claim 18, wherein the breast cancer is triple-negative breast cancer.

25. The method according to claim 16, wherein the HER2 expressing cancer is gastric cancer.

26. The method according to claim 16, wherein the HER2 expressing cancer is colorectal cancer.

27. The method according to claim 16, wherein the HER2 expressing cancer is lung cancer.

28. The method according to claim 27, wherein the lung cancer is non-small cell lung cancer.

29. The method according to claim 16, wherein the HER2 expressing cancer is pancreatic cancer.

30. The method according to claim 16, wherein the HER2 expressing cancer is ovarian cancer.

31. The method according to claim 16, wherein the HER2 expressing cancer is prostate cancer.

32. The method according to claim 16, wherein the HER2 expressing cancer is kidney cancer.

33. The method according to claim 16, wherein the method comprises administering the anti-HER2 antibody-drug conjugate and the PARP1 selective inhibitor sequentially.

34. The method according to claim 16, wherein the method comprises administering the anti-HER2 antibody-drug conjugate and the PARP1 selective inhibitor simultaneously.

* * * * *

SEQUENCE LISTING

```
<160> NUMBER OF SEQ ID NOS: 11

<210> SEQ ID NO 1
<211> LENGTH: 450
<212> TYPE: PRT
<213> ORGANISM: Artificial Sequence
<220> FEATURE:
<223> OTHER INFORMATION: Heavy chain of humanized anti-HER2 antibody

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

-continued

```
Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 2
<211> LENGTH: 214
<212> TYPE: PRT
<213> ORGANISM: Artificial Sequence
<220> FEATURE:
<223> OTHER INFORMATION: Light chain of humanized anti-HER2 antibody

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

-continued

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 3
<211> LENGTH: 8
<212> TYPE: PRT
<213> ORGANISM: Artificial Sequence
<220> FEATURE:
<223> OTHER INFORMATION: CDRH1 of heavy chain of humanized anti-HER2 antibody

<400> SEQUENCE: 3

Gly Phe Asn Ile Lys Asp Thr Tyr
1 5

<210> SEQ ID NO 4
<211> LENGTH: 8
<212> TYPE: PRT
<213> ORGANISM: Artificial Sequence
<220> FEATURE:
<223> OTHER INFORMATION: CDRH2 of heavy chain of humanized anti-HER2 antibody

<400> SEQUENCE: 4

Ile Tyr Pro Thr Asn Gly Tyr Thr
1 5

<210> SEQ ID NO 5
<211> LENGTH: 13
<212> TYPE: PRT
<213> ORGANISM: Artificial Sequence
<220> FEATURE:
<223> OTHER INFORMATION: CDRH3 of heavy chain of humanized anti-HER2 antibody

<400> SEQUENCE: 5

Ser Arg Trp Gly Gly Asp Gly Phe Tyr Ala Met Asp Tyr
1 5 10

<210> SEQ ID NO 6
<211> LENGTH: 6
<212> TYPE: PRT
<213> ORGANISM: Artificial Sequence
<220> FEATURE:
<223> OTHER INFORMATION: CDRL1 of light chain of humanized anti-HER2 antibody

<400> SEQUENCE: 6

Gln Asp Val Asn Thr Ala
1 5

<210> SEQ ID NO 7
<211> LENGTH: 7
<212> TYPE: PRT
<213> ORGANISM: Artificial Sequence
<220> FEATURE:
<223> OTHER INFORMATION: Sequence comprising CDRL2 of light chain of humanized anti-HER2 antibody

<400> SEQUENCE: 7

Ser Ala Ser Phe Leu Tyr Ser
1 5

<210> SEQ ID NO 8
<211> LENGTH: 9
<212> TYPE: PRT
<213> ORGANISM: Artificial Sequence
<220> FEATURE:
<223> OTHER INFORMATION: CDRL3 of light chain of humanized anti-HER2 antibody

<400> SEQUENCE: 8

Gln Gln His Tyr Thr Thr Pro Pro Thr
1 5

<210> SEQ ID NO 9
<211> LENGTH: 120
<212> TYPE: PRT
<213> ORGANISM: Artificial Sequence
<220> FEATURE:
<223> OTHER INFORMATION: Variable region of heavy chain of humanized anti-HER2 antibody

<400> SEQUENCE: 9

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser
115 120

<210> SEQ ID NO 10
<211> LENGTH: 107
<212> TYPE: PRT
<213> ORGANISM: Artificial Sequence
<220> FEATURE:
<223> OTHER INFORMATION: Variable region of light chain of humanized anti-HER2 antibody

<400> SEQUENCE: 10

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro 65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys
100 105

<210> SEQ ID NO 11
<211> LENGTH: 449
<212> TYPE: PRT
<213> ORGANISM: Artificial Sequence
<220> FEATURE:
<223> OTHER INFORMATION: Heavy chain of humanized anti-HER2 antibody

<400> SEQUENCE: 11

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu

-continued

```
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```